(12) United States Patent
Ibrahim et al.

(10) Patent No.: US 8,912,204 B2
(45) Date of Patent: Dec. 16, 2014

(54) COMPOUNDS AND METHODS FOR KINASE MODULATION, AND INDICATIONS THEREFOR

(75) Inventors: Prabha N. Ibrahim, Mountain View, CA (US); Ryan Bremer, Oakland, CA (US); Jiazhong Zhang, Foster City, CA (US); Marika Nespi, Berkeley, CA (US); Hanna Cho, San Francisco, CA (US)

(73) Assignee: Plexxikon Inc., Berkeley, CA (US)

( * ) Notice: Subject to any disclaimer, the term of this patent is extended or adjusted under 35 U.S.C. 154(b) by 187 days.

(21) Appl. No.: 13/411,919

(22) Filed: Mar. 5, 2012

(65) Prior Publication Data

US 2012/0165329 A1 Jun. 28, 2012

Related U.S. Application Data

(62) Division of application No. 12/467,194, filed on May 15, 2009, now Pat. No. 8,158,636.

(60) Provisional application No. 61/054,451, filed on May 19, 2008.

(51) Int. Cl.
*A01N 43/90* (2006.01)
*A61K 31/519* (2006.01)
*C07D 487/00* (2006.01)
*C07D 487/04* (2006.01)

(52) U.S. Cl.
CPC .................................. *C07D 487/04* (2013.01)
USPC ........................................ 514/265.1; 544/280

(58) Field of Classification Search
None
See application file for complete search history.

(56) References Cited

U.S. PATENT DOCUMENTS

| | | | |
|---|---|---|---|
| 7,271,262 B2 | 9/2007 | La Greca et al. | |
| 2004/0077595 A1 | 4/2004 | Cheng et al. | |
| 2007/0032519 A1 | 2/2007 | Zhang et al. | |
| 2009/0076046 A1 | 3/2009 | Zhang et al. | |

FOREIGN PATENT DOCUMENTS

| | | |
|---|---|---|
| WO | WO 2004/056830 | 7/2004 |
| WO | WO 2005/116035 | 12/2005 |
| WO | WO 2007/002433 | 1/2007 |
| WO | WO 2007/013896 | 2/2007 |

OTHER PUBLICATIONS

U.S. Appl. No. 10/473,347, filed Sep. 1, 2009, Wei Shao.
Bagshawe, Kenneth D., Antibody-Directed Enzyme Prodrug Therapy: A Review, Drug Development Research 34:220-230 (1995).
Banker and Rhodes editors, Modern Pharmaceutics, 3rd edition, revised and expanded. "Prodrugs," p. 596. 1996.
Bertolini, et al., "A New Rational Hypothesis for the Pharmacophore of the Active Metabolite of Leflunomide, a Potent Immunosuppressive Drug," J. Med. Chem., (1997), 40:2011-2016.
Bjorntorp, Per, Neuroendocrine Perturbations as a Cause of Insulin Resistance, Diabetes Metab Res Rev 15:427-441 (1999).
Bouzakri, Karim and Zierath, Juleen R., MAP4K4 Gene Silencing in Human Skeletal Muscle Prevents Tumor Necrosis Factor-a-induced Insulin Resistance, J. of Biological Chemistry 282:7783-7789 (2007).
Broudy, Virginia C., Stem Cell Factor and Hematopoiesis, Blood 90:1345-1364 (1997).
Clohisy et al., Review of Cellular Mechanisms of Tumor Osteolysis, Clinical Orthopaedics and Related Research 373:104-114 (2000).
Collins et al., A small interfering RNA screen for modulators of tumor cell motility identifies MAP4K4 as a promigratory kinase, PNAS, 103(10):3775-3780 (2006).
Coulie et al., Recombinant Human Neurotrophic Factors Accelerate Colonic Transit and Relieve Constipation in Humans, Gastroenterology 119:41-50 (2000).
Dorwald, Side Reactions in Organic Synthesis: A Guide to Successful Synthesis Design. Wiley-VCH, Preface p. IX, 2005.
Douma et al., Suppression of anoikis and induction of metastasis by the neurotrophic receptor TrkB, Nature 430:1034-1039 (2004).
Dumas, Protein kinase inhibitors: emerging pharmacophores 1997-2000. Exp. Opin. Ther. Patents, 11(3): 405-429, 2001.
Engelman et al., Effective use of PI3K and MEK inhibitors to treat mutant Kras G12D and PIK3CA H1047R murine lung cancers, Nature Medicine 14(12):1351-1356 (2008).

(Continued)

*Primary Examiner* — Jeffrey H Murray
(74) *Attorney, Agent, or Firm* — Sheppard Mullin Richter & Hampton LLP

(57) ABSTRACT

Compounds of Formula I:

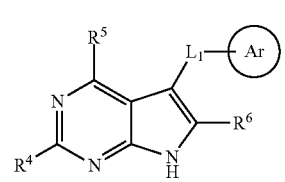

Formula I and salts thereof, formulations thereof, conjugates thereof, derivatives thereof, forms thereof and uses thereof are described. In certain aspects and embodiments, the described compounds or salts thereof, formulations thereof, conjugates thereof, derivatives thereof, forms thereof are active on at least one of Fms protein kinase or Kit protein kinase. Also described are methods of use thereof to treat diseases and conditions, including diseases and conditions associated with activity of Fms protein kinases and/or Kit protein kinases, including rheumatoid arthritis, osteoarthritis, osteoporosis, peri-prosthetic osteolysis, systemic sclerosis, demyelinating disorders, multiple sclerosis, Charcot Marie Tooth syndrome, amyotrophic lateral sclerosis, Alzheimer's disease, Parkinson's disease, ulcerative colitis, Crohn's disease, immune thrombocytopenic purpura, myelopreparation for autologous transplantation, transplant rejection, nephritis, nephropathy, type I diabetes, acute pain, inflammatory pain, neuropathic pain, breast cancer, prostate cancer, pancreatic cancer, lung cancer, ovarian cancer, gliomas, glioblastomas, neurofibromatosis, osteolytic bone metastases, and giant cell tumors.

15 Claims, No Drawings

(56) References Cited

OTHER PUBLICATIONS

Feng et al., Tyrosines 559 and 807 in the Cytoplasmic Tail of the Macrophage Colony-Stimulating Factor Receptor Play Distinct Roles in Osteoclast Differentiation and Function, Endocrinology 143(12):4858-4874 (2002).
Final Office Action dated Jun. 24, 2011 in U.S. Appl. No. 12/467,194.
Flanagan, Adrienne M. And Lader, Charlotte S., Update on the biologic effects of macrophage colony-stimulating factor, Current Opinion in Hematology, Lippincott-Raven Publishers 5:181-185 (1998).
Garzya et al., Indium(III)-catalysed aryl sulfonylation reactions, Tetrahedron Letters 45:1499-1501 (2004).
Girgis et al., The Synthesis of 5-Azaindoles by Substitution-Rearrangement of 7-Azaindoles upon Treatment with Certain Primary Amines J. Heterocyclic Chem. 26:317 (1989).
Halvorson et al., A Blocking Antibody to Nerve Growth Factor Attenuates Skeletal Pain Induced by Prostate Tumor Cells Growing in Bone, Cancer Res 65(20):9426-9435 (2005).
International Search Report dated Feb. 18, 2010 for PCT Patent Application No. PCT/US2009/044151.
Isbel et al., Local macrophage proliferation correlates with increased renal M-CSF expression in human glomulonephritis, Nephrol Dial Transplant 15:1635-1647 (2001).
Kassel et al., Local increase in the number of mast cells and expression of nerve growth factor in the bronchus of asthmatic patients after repeated inhalation of allergen at low-dose, Clinical and Experimental Allergy 31:1432-1440 (2001).
Kodama et al., Congenital Osteoclast Deficiency in Osteopetrotic (op/op) Mice is Cured by Injections of Macrophage Colony-stimulating Factor, J. Exp. Med. The Rockefeller Universitiy Press 173:269-272 (1991).
Le Meur et al., Macrophage accumulation at a site of renal inflammation is dependent on the M-CSF/c-fms pathway, J. Leuk. Bio. 72:530-537 (2002).
Libby, Inflammation in atherosclerosis, Nature, 420:19-26 (2002).
Loveland, K. L. and Schlatt, S., Stem cell factor and c-kit in the mammalian testis: lessons originating from Mother Nature's gene knockouts, Journal of Endocrinology 153:337-344 (1997).
Lyman, S. D. and Jacobsen, S. E. W., c-kit Ligand and Flt3 Ligand: Stem/Progenitor Cell Factors With Overlapping Yet Distinct Activities, 91:1101-1134 (1998).
Machida et al., Mitogen-activated Protein Kinase Kinase Kinase Kinase 4 as a Putative Effector of Rap2 to Activate the c-Jun N-terminal Kinase, Journal of Biological Chemistry, 279(16):15711-15714 (2004).
Mack et al., Functional identification of kinases essential for T-cell activation through a genetic suppression screen, Immunology Letters 96:129-145 92005).
Matayoshi et al, Actions of brain-derived neurotrophic factor on spinal nociceptive transmission during inflammation in the rat, J Physiol. 569:685-695 (2005).
Miyaura, N. and Suzuki, A., Palladium-Catalyzed Cross-Coupling Reactions of Organoboron Compounds, Chem. Rev. 95:2457-2483 (1995).
Motoyoshi, Kazuo, Biological activities and clinical application of M-CSF, International Journal of Hematology 67:109-122 (1998).
Nakagawara et al., Expression and Function of TRK-B and BDNF in Human Neuroblastomas, Molecular and Cellular Biology, 14(1):759-767 (1994).
Nassenstein et al., The Neurotrophins Nerve Growth Factor, Brain-derived Neurotrophic Factor, Neurotrophin-4 Are Survival and Activation Factors for Eosinophils in Patients with Allergic Bronchial Asthma, J. Exp. Med., The Rockefeller University Press, 198(3):455-467 (2003).
Non-Final Office Action dated Feb. 3, 2011 in U.S. Appl. No. 12/467,194.
Notice of Allowance and Fees Due dated Dec. 6, 2011 in U.S. Appl. No. 12/467,194.
Ochs et al., A phase I/II trial of recombinant methionyl human brain derived neurotrophic factor administered by intrathecal infusion to patients with amyotrophic lateral sclerosis, ALS and other motor neuron disorders, 1:201-206 (2000).
Petty et al., The Effect of Systemically Administered Recombinant Human Nerve Growth Factor in Healthy Human Subjects, Ann Neurol 36(2):244-246 (1994).
Pignon, J.-M., C-kit mutations and mast cell disorders A model of activating mutations of growth factor receptors, Hematol. Cell Ther. 39:114-116 (1997).
Prien, Target-family-oriented focused libraries for kinases—Conceptual design aspects and commercial availability. ChemBioChem, 6:500-505, 2005.
Qiao et al., Role of Macrophage Colony-Stimulating Factor in Atherosclerosis, Studies of Osteopetrotic Mice, Am. J. Pathol. 150:1687-1699 (1997).
Rajavashisth et al, Heterozygous Osteopetrotic (op) Mutation Reduces Atherosclerosis in LDL Receptor-deficient Mice, J. Clin. Invest. 101(12):2702-2710 (1998).
Ridge et al., FMS mutations in myelodysplastic, leukemic, and normal subjects, Proc. Natl. Acad. Sci. USA, 87:1377-1380 (1990).
Robinson, W.A., Stanley, E.R. And Metcalf, D., Brief Report: Stimulation of Bone Marrow Colony Growth In Vitro by Human Urine, Blood 33:396-399 (1969).
Rodan, Gideon A. and Martin, T. John, Therapeutic Approaches to Bone Diseases, Science 289:1508-1514 (2000).
Sclabas et al., Overexpression of Tropomysin-Related Kinase B in Metastatic Human Pancreatic Cancer Cells, Clinical Cancer Research, 11:440-449 (2005).
Shan et al., Prodrug Strategies Based on Intramolecular Cyclization Reactions, 86(7):765-767 (1997).
Shibata et al., Alveolar macrophage deficiency in osteopetroitic mice deficient in macrophage colony-stimulating factor is spontaneously corrected with age and associated with matrix metalloproteinase expression and emphysema, Blood 98(9):2845-2852 (2001).
Tang et al., An RNA interference-based screen identifies MAP4K4/NIK as a negative regulator of PPAR, PNAS 103(7):2087-2092 (2006).
Teitelbaum, Steven L., Bone Resorption by Osteoclasts, Science 289:1504-1508 (2000).
Tsujimura, Tohru, Role of c-kit receptor tyrosine kinase in the development survival and neoplastic transformation of mast cells, Pathology International 46:933-938 (1996).
Vilagoftis, M. D., H., Worobec, M.D., A. S. and Metcalfe, MD, D. D., the protooncogene c-kit and c-kit ligand in human disease, J. Allergy Clin. Immunol 100:435-440 (1997).
Viskochil, David H., It takes two to tango: mast cell and Schwann cell interactions in neurofibromas, J. Clin. Invest. 112:1791-1793 (2003).
Wild et al., Antibodies to Nerve Growth Factor Reverse Established Tactile allodynia in rodent Models of Neuropathic Pain without Tolerance, J. Pharmacology and Experimental Therapeutics 322:282-267 (2007).
Wolff, editor. Burger's Medicinal Chemistry and Drug Discovery, ZFifth edition, vol. 1: Principles and Practice. p. 975-977. 1995.
Wright et al., The STE20 Kinase HGK is Broadly Expressed in Human Tumor Cells and Can Modulate Cellular Transformation, Invasion, and Adhesion Molecular and Cellular Biology 23(6):2068-2082 (2003).
Yang et al., Identification of Brain-Derived Neurotrophic Factor as a Novel Functional Protein in Hepatocellular Carcinoma, Cancer Res. 65(1):219-225 (2005).
Yang, et al., Neurofibromin-Deficient Schwann Cells Secrete a Potent Migratory Stimulus for NF1+/− Mast Cells, J Clin Invest., 112:1851-1861 (2003).
Yao et al., A Novel Human STE20-related Protein Kinase, HGK, That Specifically Activates the c-Jun N-terminal Kinase Signaling Pathway, Journal of Biological Chemistry, 274(4):2118-2125 (1999).

COMPOUNDS AND METHODS FOR KINASE MODULATION, AND INDICATIONS THEREFOR

CROSS-REFERENCE TO RELATED APPLICATIONS

This application is a divisional of U.S. application Ser. No. 12/467,194 filed May 15, 2009, which claims the benefit under 35 U.S.C. §119(e) of U.S. Provisional Patent Application No. 61/054,451, filed May 19, 2008, which are incorporated herein by reference in their entireties and for all purposes.

FIELD OF THE INVENTION

Disclosed are novel compounds and uses thereof. In certain embodiments disclosed compounds are kinase inhibitors.

SUMMARY OF THE INVENTION

In certain aspects and embodiments disclosed herein, compounds are provided, as well as various salts thereof, formulations thereof, conjugates thereof, derivatives thereof, forms thereof and uses thereof. Also contemplated in accordance with the present invention are methods for the use of the compounds in treating diseases and conditions associated with regulation of the activity of one or more protein kinases in general, including, but not limited to, Abl, Akt1, Akt2, Akt3, ALK, Alk5, A-Raf, B-Raf, Brk, Btk, Cdk2, CDK4, CDK5, CDK6, CHK1, c-Raf-1, Csk, EGFR, EphA1, EphA2, EphB2, EphB4, Erk2, Fak, FGFR1, FGFR2, FGFR3, FGFR4, Flt1, Flt3, Flt4, Fms, Frk, Fyn, Gsk3α, Gsk3β, HCK, Her2/Erbb2, Her4/Erbb4, IGF1R, IKK beta, Irak4, Itk, Jak1, Jak2, Jak3, Jnk1, Jnk2, Jnk3, Kdr, Kit, Lck, Lyn, MAP2K1, MAP2K2, MAP4K4, MAPKAPK2, Met, Mnk1, MLK1, mTOR, p38, PDGFRA, PDGFRB, PDPK1, PI3Kα, PI3Kβ, PI3Kδ, PI3Kγ, Pim1, Pim2, Pim3, PKC alpha, PKC beta, PKC theta, Plk1, Pyk2, Ret, ROCK1, ROCK2, Ron, Src, Stk6, Syk, TEC, Tie2, TrkA, TrkB, Yes, and/or Zap70, including any mutations of these kinases. Thus, the use of compounds for therapeutic methods involving modulation of protein kinases are provided. In certain embodiments, the compounds are active on one or more kinases, including Fms, Kit, MAP4K4, TrkA, and/or TrkB, including any mutations thereof. In certain embodiments, the compounds are used for therapeutic methods involving modulation of one or more protein kinases selected from the group consisting of Fms, Kit, MAP4K4, TrkA, and TrkB, including treatment of a variety of indications, including, but not limited to, rheumatoid arthritis, osteoarthritis, osteoporosis, peri-prosthetic osteolysis, systemic sclerosis, demyelinating disorders, multiple sclerosis, Charcot Marie Tooth syndrome, amyotrophic lateral sclerosis, Alzheimer's disease, Parkinson's disease, ulcerative colitis, Crohn's disease, immune thrombocytopenic purpura, myelopreparation for autologous transplantation, transplant rejection, nephritis, nephropathy, type I diabetes, acute pain, inflammatory pain, neuropathic pain, breast cancer, prostate cancer, pancreatic cancer, lung cancer, ovarian cancer, gliomas, glioblastomas, neurofibromatosis, osteolytic bone metastases, and giant cell tumors. In some embodiments, compounds are of Formula I, Formula Ia or Formula Ib as described below.

In a first aspect, compounds having the structure according to the following Formula I are provided:

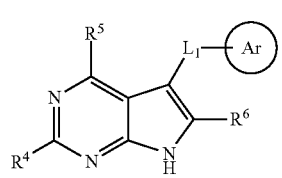

Formula I or a salt, a prodrug, a tautomer or a stereoisomer thereof, wherein:

$L_1$ is selected from the group consisting of —C($R^7R^8$)—, —C(O)—, —C(S)—, —N($R^9$)—, —O—, —S—, —S(O)—, and —S(O)$_2$—;

Ar is selected from the group consisting of:

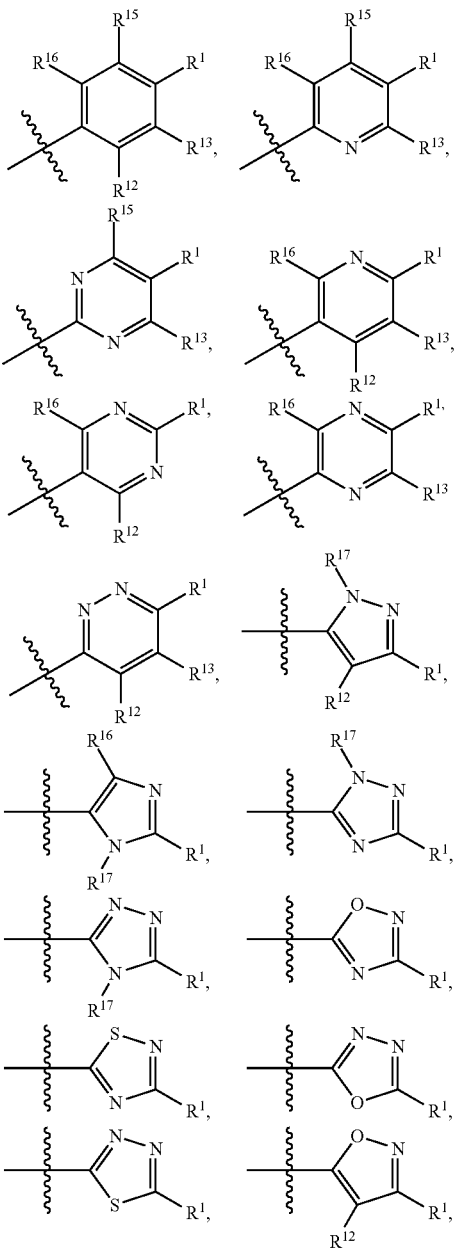

-continued

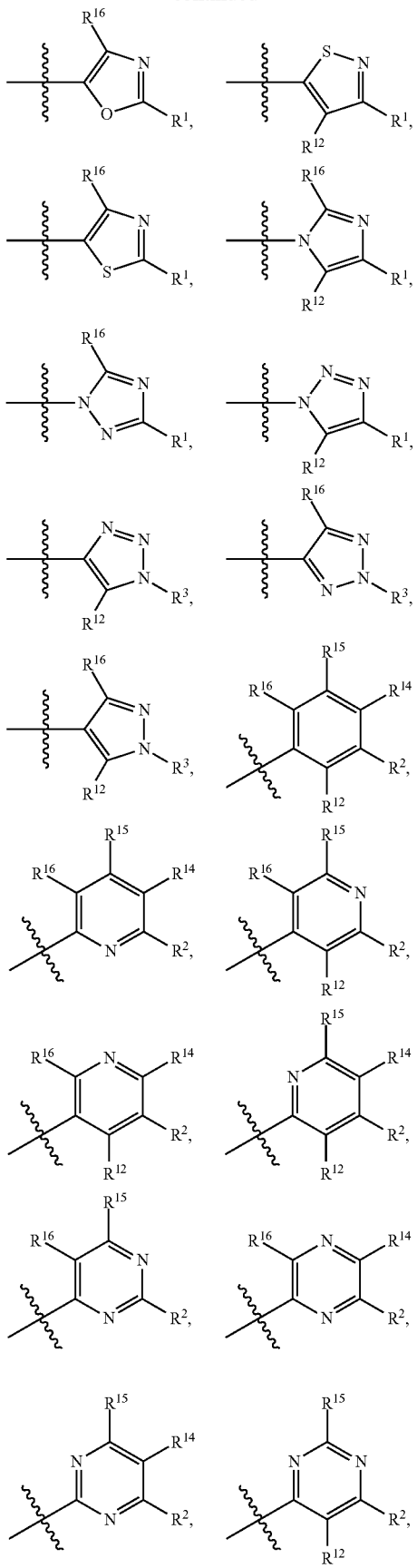

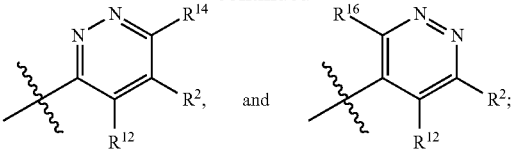

wherein indicates the point of attachment of Ar to $L_1$ of Formula I;

$R^1$ is selected from the group consisting of
—[C($R^{10}R^{11}$)]$_r$—$R^{19}$, —[C($R^{10}R^{11}$)]$_p$—N($R^{18}$)—[C($R^{10}R^{11}$)]$_q$—$R^{19}$, —[C($R^{10}R^{11}$)]$_p$—C(O)—[C($R^{10}R^{11}$)]$_q$—$R^{19}$, —[C($R^{10}R^{11}$)$_2$]$_a$—$R^{21}$, —[C($R^{10}R^{11}$)]$_p$—S—[C($R^{10}R^{11}$)]$_q$—$R^{19}$,
—[C($R^{10}R^{11}$)]$_p$—C(O)—[C($R^{10}R^{11}$)]$_q$—$R^{19}$, —[C($R^{10}R^{11}$)]$_p$—C(S)—[C($R^{10}R^{11}$)]—$R^{19}$,
—[C($R^{10}R^{11}$)]$_p$—S(O)—[C($R^{10}R^{11}$)]$_q$—$R^{19}$, —[C($R^{10}R^{11}$)]$_p$—S(O)$_2$—[C($R^{10}R^{11}$)]$_q$—$R^{19}$, —[C($R^{10}R^{11}$)]$_p$—C(O)—N($R^{18}$)—[C($R^{10}R^{11}$)]$_q$—$R^{19}$,
—[C($R^{10}R^{11}$)]$_p$—C(S)—N($R^{18}$)—[C($R^{10}R^{11}$)]$_q$—$R^{19}$, —[C($R^{10}R^{11}$)]$_p$—S(O)—N($R^{18}$)—[C($R^{10}R^{11}$)]$_q$—$R^{19}$, —[C($R^{10}R^{11}$)]$_q$—$R^{19}$, —[C($R^{10}R^{11}$)]$_p$—N($R^{18}$)—C(O)—[C($R^{10}R^{11}$)]$_q$—$R^{19}$, —[C($R^{10}R^{11}$)]$_p$—N($R^{18}$)—C(S)—[C($R^{10}R^{11}$)]$_q$—$R^{19}$,
—[C($R^{10}R^{11}$)]$_p$—N($R^{18}$)—S(O)—[C($R^{10}R^{11}$)]$_q$—$R^{19}$, —[C($R^{10}R^{11}$)]$_p$—N($R^{18}$)—S(O)$_2$—[C($R^{10}R^{11}$)]$_q$—$R^{19}$, —[C($R^{10}R^{11}$)]$_p$—N($R^{18}$)—C(O)—N($R^{18}$)—[C($R^{10}R^{11}$)]—$R^{19}$, —[C($R^{10}R^{11}$)]$_p$—N($R^{18}$)—C(S)—N($R^{18}$)—[C($R^{10}R^{11}$)]$_q$—$R^{19}$, —[C($R^{10}R^{11}$)]$_p$—N($R^{18}$)—S(O)$_2$—N($R^{18}$)—[C($R^{10}R^{11}$)]$_q$—$R^{19}$, —N($R^{18}$)—$R^{20}$, —N($R^{18}$)—C(O)—$R^{20}$, —N($R^{18}$)—C(S)—$R^{20}$, —N($R^{18}$)—S(O)—$R^{20}$, —N($R^{18}$)—S(O)$_2$—$R^{20}$, —N($R^{18}$)—C(O)—N($R^{18}$)—$R^{20}$, —N($R^{18}$)—C(S)—N($R^{18}$)—$R^{20}$, and —N($R^{18}$)—S(O)$_2$—N($R^{18}$)—$R^{20}$;

$R^2$ is selected from the group consisting of
—[C($R^{10}R^{11}$)]$_r$—$R^{19}$, —[C($R^{10}R^{11}$)]$_p$—N($R^{18}$)—[C($R^{10}R^{11}$)]$_q$—$R^{19}$, —[C($R^{10}R^{11}$)]$_p$—O—[C($R^{10}R^{11}$)]$_q$—$R^{19}$, —[O—[C($R^{10}R^{11}$)$_2$]$_a$—$R^{21}$, [C($R^{10}R^{11}$)]$_p$—S—[C($R^{10}R^{11}$)]$_q$—$R^{19}$,
—[C($R^{10}R^{11}$)]$_p$—C(O)—[C($R^{10}R^{11}$)]$_q$—$R^{19}$, —[C($R^{10}R^{11}$)]$_p$—C(S)—[C($R^{10}R^{11}$)]$_q$—$R^{19}$, —[C($R^{10}R^{11}$)]$_p$—S(O)—[C($R^{10}R^{11}$)]$_q$—$R^{19}$, —[C($R^{10}R^{11}$)]$_p$—S(O)$_2$—[C($R^{10}R^{11}$)]$_q$—$R^{19}$, —[C($R^{10}R^{11}$)]$_p$—C(O)—N($R^{18}$)—[C($R^{10}R^{11}$)]$_q$—$R^{19}$,
—[C($R^{10}R^{11}$)]$_p$—C(S)—N($R^{18}$)—[C($R^{10}R^{11}$)]$_q$—$R^{19}$, —[C($R^{10}R^{11}$)]$_p$—S(O)—N($R^{18}$)—[C($R^{10}R^{11}$)]$_q$—$R^{19}$, —[C($R^{10}R^{11}$)]$_q$—$R^{19}$, —[C($R^{10}R^{11}$)]$_p$—S(O)—N($R^{18}$)—[C($R^{10}R^{11}$)]$_q$—$R^{19}$, and —N($R^{18}$)—$R^{20}$;

$R^3$ is selected from the group consisting of
—[C($R^{10}R^{11}$)]$_r$—$R^{19}$, —[C($R^{10}R^{11}$)]$_s$—N($R^{18}$)—[C($R^{10}R^{11}$)]$_q$—$R^{19}$, —[C($R^{10}R^{11}$)]$_s$—O—[C($R^{10}R^{11}$)]$_q$—$R^{19}$, —[C($R^{10}R^{11}$)]$_s$—S—[C($R^{10}R^{11}$)]$_q$—$R^{19}$, —[C($R^{10}R^{11}$)]$_p$—C(O)—[C($R^{10}R^{11}$)]$_q$—$R^{19}$, —[C($R^{10}R^{11}$)]$_p$—C(S)—[C($R^{10}R^{11}$)]$_q$—$R^{19}$, —[C($R^{10}R^{11}$)]$_p$—S(O)—[C($R^{10}R^{11}$)]$_q$—$R^{19}$, —[C($R^{10}R^{11}$)]$_p$—S(O)$_2$—[C($R^{10}R^{11}$)]$_q$—$R^{19}$, —[C($R^{10}R^{11}$)]$_p$—C(O)—N($R^{18}$)—

$[C(R^{10}R^{11})]_q$—$R^{19}$, —$[C(R^{10}R^{11})]_p$—C(S)—N($R^{18}$)—$[C(R^{10}R^{11})]_q$—$R^{19}$, —$[C(R^{10}R^{11})]_s$—S(O)—N($R^{18}$)—$[C(R^{10}R^{11})]_q$—$R^{19}$, —$[C(R^{10}R^{11})]_p$—S(O)$_2$—N($R^{18}$)—$[C(R^{10}R^{11})]_q$—$R^{19}$, —$[C(R^{10}R^{11})]_s$—N($R^{18}$)—C(O)—$[C(R^{10}R^{11})]_q$—$R^{19}$, —$[C(R^{10}R^{11})]_s$—N($R^{18}$)—C(S)—$[C(R^{10}R^{11})]_q$—$R^{19}$, —$[C(R^{10}R^{11})]_s$—N($R^{18}$)—S(O)—$[C(R^{10}R^{11})]_q$—$R^{19}$, —$[C(R^{10}R^{11})]_s$—N($R^{18}$)—S(O)$_2$—$[C(R^{10}R^{11})]_q$—$R^{19}$, —$[C(R^{10}R^{11})]_s$—N($R^{18}$)—C(O)—N($R^{18}$)—$[C(R^{10}R^{11})]_q$—$R^{19}$, —$[C(R^{10}R^{11})]_s$—N($R^{18}$)—C(S)—N($R^{18}$)—$[C(R^{10}R^{11})]_q$—$R^{19}$, and —$[C(R^{10}R^{11})]_s$—N($R^{18}$)—S(O)$_2$—N($R^{18}$)—$[C(R^{10}R^{11})]_q$—$R^{19}$;

a is 1 or 2;

p, q and r are independently 0, 1, 2, or 3;

s is 1, 2, or 3;

$R^4$ is selected from the group consisting of hydrogen, optionally substituted lower alkyl, optionally substituted lower alkenyl, optionally substituted lower alkynyl, optionally substituted cycloalkyl, optionally substituted heterocycloalkyl, optionally substituted aryl, optionally substituted heteroaryl, —CN, —NO$_2$, —O—$R^{22}$, —S—$R^{24}$, —N($R^{22}$)—$R^{23}$, —C(O)—$R^{24}$, —C(S)—$R^{24}$, —C(O)—N($R^{22}$)—$R^{23}$, —C(S)—N($R^{22}$)—$R^{23}$, —C(O)—N($R^{25}$)—O$R^{22}$, —C(S)—N($R^{25}$)—O$R^{22}$, —C(O)—N($R^{25}$)—S(O)$_2$—$R^{24}$, —C(S)—N($R^{25}$)—S(O)$_2$—$R^{24}$, —C(O)—O—$R^{22}$, —S(O)—$R^{24}$, —S(O)$_2$—$R^{24}$, —S(O)—N($R^{22}$)—$R^{23}$, —S(O)$_2$—N($R^{22}$)—$R^{23}$, —S(O)$_2$—N($R^{25}$)—C(O)$R^{24}$, —S(O)$_2$—N($R^{25}$)—C(S)$R^{24}$, —N($R^{25}$)—C(O)—$R^{24}$, —N($R^{25}$)—C(S)—$R^{24}$, —N($R^{25}$)—S(O)—$R^{24}$, —N($R^{25}$)—S(O)$_2$—$R^{24}$, —N($R^{25}$)—C(O)—N($R^{22}$)—$R^{23}$, —N($R^{25}$)—C(S)—N($R^{22}$)—$R^{23}$, and —N($R^{25}$)—S(O)$_2$—N($R^{22}$)—$R^{23}$;

$R^5$ is selected from the group consisting of hydrogen, optionally substituted lower alkyl, optionally substituted lower alkenyl, optionally substituted lower alkynyl, optionally substituted cycloalkyl, optionally substituted heterocycloalkyl, optionally substituted aryl, optionally substituted heteroaryl, —CN, —NO$_2$, —O—$R^{28}$, —S—$R^{28}$, —C(O)—$R^{28}$, —C(S)—$R^{28}$, —C(O)—N($R^{26}$)—$R^{27}$, —C(S)—N($R^{26}$)—$R^{27}$, —C(O)—N($R^{29}$)—O$R^{26}$, —C(S)—N($R^{29}$)—O$R^{26}$, —C(O)—N($R^{29}$)—S(O)$_2$—$R^{28}$, —C(S)—N($R^{29}$)—S(O)$_2$—$R^{28}$, —C(O)—O—$R^{26}$, —S(O)—$R^{28}$, —S(O)$_2$—$R^{28}$, —S(O)—N($R^{26}$)—$R^{27}$, —S(O)$_2$—N($R^{26}$)—$R^{27}$, —S(O)$_2$—N($R^{29}$)—C(O)$R^{28}$, —S(O)$_2$—N($R^{29}$)—C(S)$R^{28}$, —N($R^{29}$)—C(O)—$R^{28}$, —N($R^{29}$)—C(S)—$R^{28}$, —N($R^{29}$)—S(O)—$R^{28}$, —N($R^{29}$)—S(O)$_2$—$R^{28}$, —N($R^{29}$)—C(O)—N($R^{26}$)—$R^{27}$, —N($R^{29}$)—C(S)—N($R^{26}$)—$R^{27}$, and —N($R^{29}$)—S(O)$_2$—N($R^{26}$)—$R^{27}$;

$R^6$ is selected from the group consisting of hydrogen, halogen, optionally substituted lower alkyl, optionally substituted lower alkenyl, optionally substituted lower alkynyl, optionally substituted cycloalkyl, optionally substituted heterocycloalkyl, optionally substituted aryl, optionally substituted heteroaryl, —CN, —NO$_2$, —O—$R^{30}$, —S—$R^{32}$, —N($R^{30}$)—$R^{31}$, —C(O)—$R^{32}$, —C(S)—$R^{32}$, —C(O)—N($R^{30}$)—$R^{31}$, —C(S)—N($R^{30}$)—$R^{31}$, —C(O)—N($R^{33}$)—O$R^{30}$, —C(S)—N($R^{33}$)—O$R^{30}$, —C(O)—N($R^{33}$)—S(O)$_2$—$R^{32}$, —C(S)—N($R^{33}$)—S(O)$_2$—$R^{32}$, —C(O)—O—$R^{30}$, —S(O)—$R^{32}$, —S(O)$_2$—$R^{32}$, —S(O)—N($R^{30}$)—$R^{31}$, —S(O)$_2$—N($R^{30}$)—$R^{31}$, —S(O)$_2$—N($R^{33}$)—C(O)$R^{32}$, —S(O)$_2$—N($R^{33}$)—C(S)$R^{32}$, —N($R^{33}$)—C(O)—$R^{32}$, —N($R^{33}$)—C(S)—$R^{32}$, —N($R^{33}$)—S(O)—$R^{32}$, —N($R^{33}$)—S(O)$_2$—$R^{32}$, —N($R^{33}$)—C(O)—N($R^{30}$)—$R^{31}$, —N($R^{33}$)—C(S)—N($R^{30}$)—$R^{31}$, and —N($R^{33}$)—S(O)$_2$—N($R^{30}$)—$R^{31}$;

$R^7$, $R^8$, $R^{10}$, and $R^{11}$, at each occurrence, are independently selected from the group consisting of hydrogen, fluoro, —OH, —NH$_2$, lower alkyl, lower alkoxy, lower alkylthio, mono-alkylamino, di-alkylamino, and —N($R^{34}$)—$R^{35}$, wherein the alkyl chain(s) of lower alkyl, lower alkoxy, lower alkylthio, mono-alkylamino, or di-alkylamino are optionally substituted with one or more substituents selected from the group consisting of fluoro, —OH, —NH$_2$, lower alkoxy, fluoro substituted lower alkoxy, lower alkylthio, fluoro substituted lower alkylthio, mono-alkylamino, di-alkylamino, and cycloalkylamino; or $R^7$ and $R^8$, or any two of $R^{10}$ and $R^{11}$ on the same or different carbons, combine to form a 3-7 membered monocyclic cycloalkyl or 5-7 membered monocyclic heterocycloalkyl and any others of $R^{10}$ and $R^{11}$ are independently selected from the group consisting of hydrogen, fluoro, —OH, —NH$_2$, lower alkyl, lower alkoxy, lower alklylthio, mono-alkylamino, di-alkylamino, and —N($R^{34}$)—$R^{35}$, wherein the alkyl chain(s) of lower alkyl, lower alkoxy, lower alkylthio, mono-alkylamino, or di-alkylamino are optionally substituted with one or more substituents selected from the group consisting of fluoro, —OH, —NH$_2$, lower alkoxy, fluoro substituted lower alkoxy, lower alkylthio, fluoro substituted lower alkylthio, mono-alkylamino, di-alkylamino, and cycloalkylamino, and wherein the 3-7 membered monocyclic cycloalkyl or 5-7 membered monocyclic heterocycloalkyl are optionally substituted with one or more substituents selected from the group consisting of halogen, —OH, —NH$_2$, lower alkyl, fluoro substituted lower alkyl, lower alkoxy, fluoro substituted lower alkoxy, lower alkylthio, fluoro substituted lower alkylthio, mono-alkylamino, di-alkylamino, and cycloalkylamino;

$R^9$, $R^{25}$, $R^{29}$, and $R^{33}$ are independently selected from the group consisting of hydrogen, optionally substituted lower alkyl, optionally substituted cycloalkyl, optionally substituted heterocycloalkyl, optionally substituted aryl, optionally substituted heteroaryl, —C(O)—$R^{36}$, —C(S)—$R^{36}$, —S(O)—$R^{36}$, —S(O)$_2$—$R^{36}$, —C(O)—N(H)—$R^{36}$, —C(S)—N(H)—$R^{36}$, and —S(O)$_2$—N(H)—$R^{36}$;

$R^{12}$, $R^{13}$, $R^{14}$, $R^{15}$, and $R^{16}$ are independently selected from the group consisting of hydrogen, halogen, optionally substituted lower alkyl, —N($R^{37}$)—$R^{38}$, —O—$R^{37}$, and —S—$R^{39}$;

$R^{17}$ is hydrogen or optionally substituted lower alkyl;

$R^{18}$ at each occurrence is independently hydrogen, lower alkyl, or lower alkyl substituted with one or more substituents selected from the group consisting of fluoro, —OH, —NH$_2$, lower alkoxy, fluoro substituted lower alkoxy, lower alkylthio, fluoro substituted lower alkylthio, mono-alkylamino, fluoro substituted mono-alkylamino, di-alkylamino, fluoro substituted di-alkylamino, and —N($R^{34}$)—$R^{35}$;

$R^{19}$ is selected from the group consisting of optionally substituted cycloalkyl, optionally substituted heterocycloalkyl, optionally substituted aryl, and optionally substituted heteroaryl;

$R^{20}$ is selected from the group consisting of optionally substituted lower alkyl, optionally substituted lower alkenyl, and optionally substituted lower alkynyl;

$R^{21}$ is selected from the group consisting of hydrogen, optionally substituted lower alkyl, optionally substituted cycloalkyl, optionally substituted heterocycloalkyl, optionally substituted aryl, optionally substituted heteroaryl, and —O—$R^{40}$;

$R^{24}$, $R^{28}$ and $R^{32}$ are independently selected from the group consisting of optionally substituted lower alkyl, optionally substituted lower alkenyl, optionally substituted lower alkynyl, optionally substituted cycloalkyl, optionally substituted heterocycloalkyl, optionally substituted aryl, and optionally substituted heteroaryl;

$R^{22}$, $R^{23}$, $R^{26}$, $R^{27}$, $R^{30}$ and $R^{31}$ are independently selected from the group consisting of hydrogen, optionally substituted lower alkyl, optionally substituted lower alkenyl, optionally substituted lower alkynyl, optionally substituted cycloalkyl, optionally substituted heterocycloalkyl, optionally substituted aryl, and optionally substituted heteroaryl;

$R^{34}$ and $R^{35}$ at each occurrence combine with the nitrogen to which they are attached to form a 5-7 membered heterocycloalkyl optionally substituted with one or more substituents selected from the group consisting of fluoro, —OH, —$NH_2$, lower alkyl, fluoro substituted lower alkyl, lower alkoxy, fluoro substituted lower alkoxy, lower alkylthio, and fluoro substituted lower alkylthio;

$R^{36}$ at each occurrence is independently selected from the group consisting of optionally substituted lower alkyl, optionally substituted cycloalkyl, optionally substituted heterocycloalkyl, optionally substituted aryl, and optionally substituted heteroaryl;

$R^{37}$ and $R^{38}$ at each occurrence are independently hydrogen or optionally substituted lower alkyl; and $R^{39}$ and $R^{40}$ at each occurrence are independently optionally substituted lower alkyl.

In a second aspect, compounds of Formula I having the structure according to the following Formula Ia are provided:

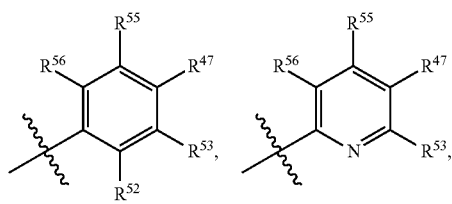

Formula Ia or a salt, a prodrug, a tautomer or a stereoisomer thereof, wherein:

$L_2$ is selected from the group consisting of —C($R^{44}R^{45}$)—, —C(O)—, —C(S)—, —N($R^{46}$)—, —O—, —S—, —S(O)—, and —S(O)$_2$—;

$Ar_1$ is selected from the group consisting of:

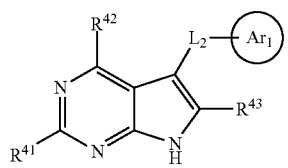

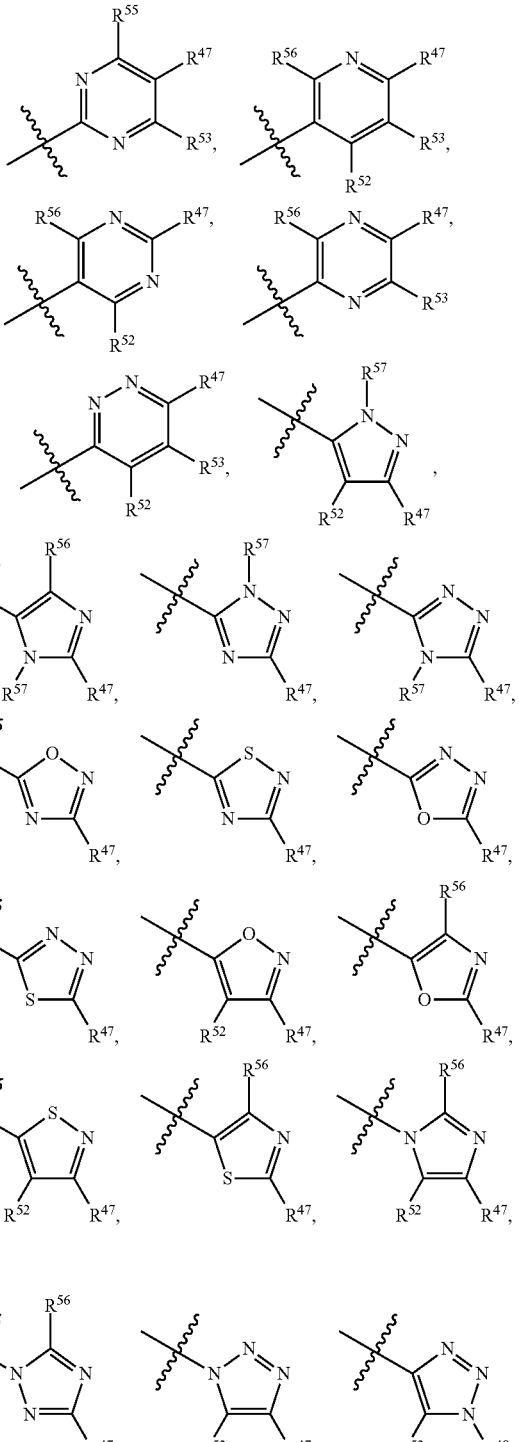

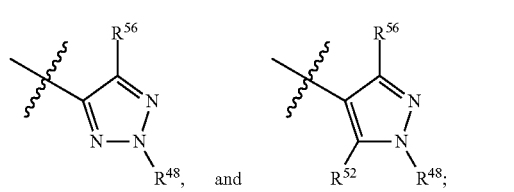

wherein

indicates the point of attachment of $Ar_1$ to $L_2$ of Formula Ia;

$R^{47}$ is selected from the group consisting of —$R^{58}$, —C($R^{49}R^{50}$)—$R^{58}$, —[C($R^{49}R^{50}$)]$_2$—$R^{58}$, —N($R^{51}$)—$R^{58}$, —N($R^{51}$)—C($R^{49}R^{50}$)—$R^{58}$, —N($R^{51}$)—[C($R^{49}R^{50}$)]$_2$—$R^{58}$, —N($R^{51}$)—[C($R^{49}R^{50}$)]$_3$—$R^{58}$, —C($R^{49}R^{50}$)—N($R^{51}$)—$R^{58}$, —O—, —O—[C($R^{49}R^{50}$)]$_2$—$R^{58}$, —O—[C($R^{49}R^{50}$)]$_2$—$R^{58}$, —O—[C($R^{49}R^{50}$)]$_3$—$R^{58}$, —C($R^{49}R^{50}$)—O—$R^{58}$, —S—$R^{58}$, —S—C($R^{49}R^{50}$)—$R^{58}$, —S—[C($R^{49}R^{50}$)]$_2$—$R^{58}$, —S—[C($R^{49}R^{50}$)]$_3$—$R^{58}$, —C($R^{49}R^{50}$)—S—$R^{58}$, —C(O)—N($R^{51}$)—$R^{58}$, —C(O)—N($R^{51}$)—C($R^{49}R^{50}$)—$R^{58}$, —C(O)—N($R^{51}$)—[C($R^{49}R^{50}$)]$_2$—$R^{58}$, —C(S)—N($R^{51}$)—$R^{58}$, —C(S)—N($R^{51}$)—C($R^{49}R^{50}$)—$R^{58}$, —C(S)—N($R^{51}$)—[C($R^{49}R^{50}$)]$_2$—$R^{58}$, —S(O)—N($R^{51}$)—$R^{58}$, —S(O)—N($R^{51}$)—C($R^{49}R^{50}$)—$R^{58}$, —S(O)—N($R^{51}$)—[C($R^{49}R^{50}$)]$_2$—$R^{58}$, —S(O)$_2$—N($R^{51}$)—$R^{58}$, —S(O)$_2$—N($R^{51}$)—C($R^{49}R^{50}$)—$R^{58}$, —S(O)$_2$—N($R^{51}$)—[C($R^{49}R^{50}$)]$_2$—$R^{58}$, —N($R^{51}$)—C(O)—$R^{58}$, —N($R^{51}$)—C(O)—C($R^{49}R^{50}$)—$R^{58}$, —N($R^{51}$)—C(O)—[C($R^{49}R^{50}$)]$_2$—$R^{58}$, —N($R^{51}$)—C(S)—$R^{58}$, —N($R^{51}$)—C(S)—C($R^{49}R^{50}$)—$R^{58}$, —N($R^{51}$)—C(S)—[C($R^{49}R^{50}$)]$_2$—$R^{58}$, —N($R^{51}$)—S(O)—$R^{58}$, —N($R^{51}$)—S(O)—C($R^{49}R^{50}$)—$R^{58}$, —N($R^{51}$)—S(O)—[C($R^{49}R^{50}$)]$_2$—$R^{58}$, —N($R^{51}$)—S(O)$_2$—$R^{58}$, —N($R^{51}$)—S(O)$_2$—C($R^{49}R^{50}$)—$R^{58}$, —N($R^{51}$)—S(O)$_2$—[C($R^{49}R^{50}$)]$_2$—$R^{58}$, —N($R^{51}$)—C(O)—N($R^{51}$)—$R^{58}$, —N($R^{51}$)—C(O)—N($R^{51}$)—C($R^{49}R^{50}$)—$R^{58}$, —N($R^{51}$)—C(O)—N($R^{51}$)—[C($R^{49}R^{50}$)]$_2$—$R^{58}$, —N($R^{51}$)—C(S)—N($R^{51}$)—$R^{58}$, —N($R^{51}$)—C(S)—N($R^{51}$)—C($R^{49}R^{50}$)—$R^{58}$, —N($R^{51}$)—C(S)—N($R^{51}$)—[C($R^{49}R^{50}$)]$_2$—$R^{58}$, —N($R^{51}$)—S(O)$_2$—N($R^{51}$)—$R^{58}$, —N($R^{51}$)—S(O)$_2$—N($R^{51}$)—C($R^{49}R^{50}$)—$R^{58}$, and —N($R^{51}$)—S(O)$_2$—N($R^{51}$)—[C($R^{49}R^{50}$)]$_2$—$R^{58}$;

$R^{48}$ is selected from the group consisting of —C($R^{49}R^{50}$)—$R^{58}$, —[C($R^{49}R^{50}$)]$_2$—$R^{58}$, —C($R^{49}R^{50}$)—N($R^{51}$)—$R^{58}$, —C($R^{49}R^{50}$)—O—$R^{58}$, —C($R^{49}R^{50}$)—S—$R^{58}$, —C(O)—N($R^{51}$)—$R^{58}$, —C(O)—N($R^{51}$)—C($R^{49}R^{50}$)—$R^{58}$, —C(O)—N($R^{51}$)—[C($R^{49}R^{50}$)]$_2$—$R^{58}$, —C(S)—N($R^{51}$)—$R^{58}$, —C(S)—N($R^{51}$)—C($R^{49}R^{50}$)—$R^{58}$, —C(S)—N($R^{51}$)—[C($R^{49}R^{50}$)]$_2$—$R^{58}$, —S(O)$_2$—N($R^{51}$)—$R^{58}$, —S(O)$_2$—N($R^{51}$)—C($R^{49}R^{50}$)—$R^{58}$, and —S(O)$_2$—N($R^{51}$)—[C($R^{49}R^{50}$)]$_2$—$R^{58}$;

$R^{41}$ is selected from the group consisting of hydrogen, —OH, —NH$_2$, —CN, —NO$_2$, —C(O)—OH, —S(O)—NH$_2$, —S(O)$_2$—NH$_2$, —C(O)—NH$_2$, —O—$R^{59}$, —S—$R^{59}$, —N($R^{60}$)—$R^{59}$, —N($R^{60}$)—C(O)—$R^{59}$, —N($R^{60}$)—S(O)—$R^{59}$, —N($R^{60}$)—S(O)$_2$—$R^{59}$, —C(O)—N($R^{60}$)—$R^{59}$, —C(O)—O—$R^{59}$, —C(O)—$R^{59}$, —S(O)—N($R^{60}$)—$R^{59}$, —S(O)$_2$—N($R^{60}$)—$R^{59}$, —S(O)—$R^{59}$, —S(O)$_2$—$R^{59}$, lower alkyl, cycloalkyl, heterocycloalkyl, aryl and heteroaryl, wherein lower alkyl is optionally substituted with one or more substituents selected from the group consisting of fluoro, lower alkoxy, fluoro substituted lower alkoxy, lower alkylthio, fluoro substituted lower alkylthio, mono-alkylamino, di-alkylamino, cycloalkyl, heterocycloalkyl, aryl, and heteroaryl, wherein cycloalkyl, heterocycloalkyl, aryl, and heteroaryl as $R^{41}$ or as substituents of lower alkyl are optionally substituted with one or more substituents selected from the group consisting of —OH, —NH$_2$, —CN, —NO$_2$, —C(O)—OH, —S(O)—NH$_2$, —S(O)$_2$—NH$_2$, —C(O)—NH$_2$, —O—$R^{61}$, —S—$R^{61}$, —N($R^{60}$)—$R^{61}$, —N($R^{60}$)—C(O)—$R^{61}$, —N($R^{60}$)—S(O)—$R^{61}$, —N($R^{60}$)—S(O)$_2$—$R^{61}$, —C(O)—$R^{61}$, —S(O)—$R^{61}$, —S(O)$_2$—$R^{61}$, —C(O)—O—$R^{61}$, —C(O)—N($R^{60}$)—$R^{61}$, —S(O)—N($R^{6}$)—$R^{61}$, —S(O)$_2$—N($R^{60}$)—$R^{61}$ halogen, lower alkyl, fluoro substituted lower alkyl, and cycloalkylamino;

$R^{42}$ is selected from the group consisting of hydrogen, —CN, —NO$_2$, —C(O)—OH, —S(O)—NH$_2$, —S(O)$_2$—NH$_2$, —C(O)—NH$_2$, —O—$R^{62}$, —S—$R^{62}$, —N($R^{63}$)—C(O)—$R^{62}$, —N($R^{63}$)—S(O)—$R^{62}$, —N($R^{63}$)—S(O)$_2$—$R^{62}$, —C(O)—N($R^{63}$)—$R^{62}$, —C(O)—O—$R^{62}$, —C(O)—$R^{62}$, —S(O)—N($R^{63}$)—$R^{62}$, —S(O)$_2$—N($R^{63}$)—$R^{62}$, —S(O)—$R^{62}$, —S(O)$_2$—$R^{62}$, lower alkyl, cycloalkyl, heterocycloalkyl, aryl and heteroaryl, wherein lower alkyl is optionally substituted with one or more substituents selected from the group consisting of fluoro, lower alkoxy, fluoro substituted lower alkoxy, lower alkylthio, fluoro substituted lower alkylthio, mono-alkylamino, di-alkylamino, cycloalkyl, heterocycloalkyl, aryl, and heteroaryl, wherein cycloalkyl, heterocycloalkyl, aryl, and heteroaryl as $R^{42}$ or as substituents of lower alkyl are optionally substituted with one or more substituents selected from the group consisting of —OH, —NH$_2$, —CN, —NO$_2$, —C(O)—OH, —S(O)—NH$_2$, —S(O)$_2$—NH$_2$, —C(O)—NH$_2$, —O—$R^{64}$, —S—$R^{64}$, —N($R^{63}$)—$R^{64}$, —N($R^{63}$)—C(O)—$R^{64}$, —N($R^{63}$)—S(O)—$R^{64}$, —N($R^{63}$)—S(O)$_2$—$R^{64}$, —C(O)—$R^{64}$, —S(O)—$R^{64}$, —S(O)$_2$—$R^{64}$, —C(O)—O—$R^{64}$, —C(O)—N($R^{63}$)—$R^{64}$, —S(O)—N($R^{63}$)—$R^{64}$, —S(O)$_2$—N($R^{63}$)—$R^{64}$, halogen, lower alkyl, fluoro substituted lower alkyl, and cycloalkylamino;

$R^{43}$ is independently selected from the group consisting of hydrogen, —OH, —NH$_2$, —CN, —NO$_2$, —C(O)—OH, —S(O)—NH$_2$, —S(O)$_2$—NH$_2$, —C(O)—NH$_2$, —O—$R^{65}$, —S—$R^{65}$, —N($R^{66}$)—$R^{65}$, —N($R^{66}$)—C(O)—$R^{65}$, —N($R^{66}$)—S(O)—$R^{65}$, —N($R^{66}$)—S(O)$_2$—$R^{65}$, —C(O)—N($R^{66}$)—$R^{65}$, —C(O)—O—$R^{65}$, —C(O)—$R^{65}$, —S(O)—N($R^{66}$)—$R^{65}$, —S(O)$_2$—N($R^{66}$)—$R^{65}$, —S(O)—$R^{65}$, —S(O)$_2$—$R^{65}$, halogen, lower alkyl, cycloalkyl, heterocycloalkyl, aryl and heteroaryl, wherein lower alkyl is optionally substituted with one or more substituents selected from the group consisting of fluoro, lower alkoxy, fluoro substituted lower alkoxy, lower alkylthio, fluoro substituted lower alkylthio, mono-alkylamino, di-alkylamino, cycloalkyl, heterocycloalkyl, aryl, and heteroaryl, wherein cycloalkyl, heterocycloalkyl, aryl, and heteroaryl as $R^{43}$ or as substituents of lower alkyl are optionally substituted with one or more substituents selected from the group consisting of —OH, —NH$_2$, —CN, —NO$_2$, —C(O)—OH, —S(O)—NH$_2$, —S(O)$_2$—NH$_2$, —C(O)—NH$_2$, —O—$R^{67}$, —S—$R^{67}$, —N($R^{66}$)—$R^{67}$, —N($R^{66}$)—C(O)—$R^{67}$, —N($R^{66}$)—S(O)—$R^{67}$, —N($R^{66}$)—S(O)$_2$—$R^{67}$, —C(O)—$R^{67}$, —S(O)—$R^{67}$, —S(O)$_2$—$R^{67}$, —C(O)—O—$R^{67}$, —C(O)—N($R^{66}$)—$R^{67}$, —S(O)—N($R^{66}$)—$R^{67}$, —S(O)$_2$—N($R^{66}$)—$R^{67}$, halogen, lower alkyl, fluoro substituted lower alkyl, and cycloalkylamino;

$R^{58}$ is selected from the group consisting of optionally substituted cycloalkyl, optionally substituted heterocycloalkyl, optionally substituted aryl or optionally substituted heteroaryl;

$R^{44}$, $R^{45}$, $R^{49}$ and $R^{50}$ at each occurrence are independently selected from the group consisting of hydrogen, fluoro, lower alkyl, fluoro substituted lower alkyl, lower alkoxy, fluoro substituted lower alkoxy, lower alkylthio, fluoro substituted lower alkylthio, mono-alkylamino, di-alkylamino, and cycloalkylamino; or $R^{44}$ and $R^{45}$, or any two of $R^{49}$ and $R^{50}$ on the same or different carbons, combine to form a 3-7 membered monocyclic cycloalkyl or 5-7 membered monocyclic heterocycloalkyl, and any others of $R^{49}$ and $R^{50}$ are independently selected from the group consisting of hydrogen, fluoro, lower alkyl, fluoro substituted lower alkyl, lower alkoxy, fluoro substituted lower alkoxy, lower alkylthio, fluoro substituted lower alkylthio, mono-alkylamino, di-alkylamino, and cycloalkylamino, wherein the 3-7 membered monocyclic cycloalkyl or 5-7 membered monocyclic heterocycloalkyl is optionally substituted with one or more substituents selected from the group consisting of halogen, —OH, —NH$_2$, lower alkyl, fluoro substituted lower alkyl, lower alkoxy, fluoro substituted lower alkoxy, lower alkylthio, fluoro substituted lower alkylthio, mono-alkylamino, di-alkylamino, and cycloalkylamino;

$R^{52}$, $R^{53}$, $R^{55}$, and $R^{56}$ are independently selected from the group consisting of hydrogen, halogen, lower alkyl, —N($R^{70}$)—$R^{71}$, —O—$R^{70}$, and —S—$R^{72}$, wherein lower alkyl is optionally substituted with one or more substituents selected from the group consisting of fluoro, —OH, —NH$_2$, lower alkoxy, fluoro substituted lower alkoxy, lower alkylthio, fluoro substituted lower alkylthio, mono-alkylamino, fluoro substituted mono-alkylamino, di-alkylamino, fluoro substituted di-alkylamino, and cycloalkylamino;

$R^{57}$ is hydrogen, lower alkyl, or lower alkyl substituted with one or more substituents selected from the group consisting of fluoro, —OH, —NH$_2$, lower alkoxy, fluoro substituted lower alkoxy, lower alkylthio, fluoro substituted lower alkylthio, mono-alkylamino, fluoro substituted mono-alkylamino, di-alkylamino, fluoro substituted di-alkylamino, and cycloalkylamino;

$R^{59}$, $R^{62}$, and $R^{65}$ are independently selected from the group consisting of lower alkyl, cycloalkyl, heterocycloalkyl, aryl and heteroaryl, wherein lower alkyl is optionally substituted with one or more substituents selected from the group consisting of fluoro, lower alkoxy, fluoro substituted lower alkoxy, lower alkylthio, fluoro substituted lower alkylthio, mono-alkylamino, di-alkylamino, cycloalkyl, heterocycloalkyl, aryl, and heteroaryl, and wherein cycloalkyl, heterocycloalkyl, aryl, and heteroaryl as $R^{59}$, $R^{62}$, or $R^{65}$ or as substituents of lower alkyl are optionally substituted with one or more substituents selected from the group consisting of —OH, —NH$_2$, —CN, —NO$_2$, —C(O)—OH, —S(O)—NH$_2$, —S(O)$_2$—NH$_2$, —C(O)—NH$_2$, —O—$R^{69}$, —S—$R^{69}$, —N($R^{68}$)—$R^{69}$, —N($R^{68}$)—C(O)—$R^{69}$, —N($R^{68}$)—S(O)—$R^{69}$, —N($R^{68}$)—S(O)$_2$—$R^{69}$, —C(O)—$R^{69}$, —S(O)—$R^{69}$, —S(O)$_2$—$R^{69}$, —C(O)—O—$R^{69}$, —C(O)—N($R^{68}$)—$R^{69}$, —S(O)—N($R^{68}$)—$R^{69}$, —S(O)$_2$—N($R^{68}$)—$R^{69}$, halogen, lower alkyl, fluoro substituted lower alkyl, and cycloalkylamino;

$R^{46}$, $R^{51}$, $R^{60}$, $R^{63}$, $R^{66}$ and $R^{68}$ at each occurrence are independently hydrogen, lower alkyl, or lower alkyl substituted with one or more substituents selected from the group consisting of fluoro, —OH, —NH$_2$, lower alkoxy, fluoro substituted lower alkoxy, lower alkylthio, fluoro substituted lower alkylthio, mono-alkylamino, fluoro substituted mono-alkylamino, di-alkylamino, fluoro substituted di-alkylamino, and cycloalkylamino;

$R^{61}$, $R^{64}$, $R^{67}$ and $R^{69}$ at each occurrence are independently selected from the group consisting of lower alkyl, heterocycloalkyl and heteroaryl, wherein lower alkyl is optionally substituted with one or more substituents selected from the group consisting of fluoro, lower alkoxy, fluoro substituted lower alkoxy, lower alkylthio, fluoro substituted lower alkylthio, mono-alkylamino, di-alkylamino, and cycloalkylamino, and wherein heterocycloalkyl and heteroaryl are optionally substituted with one or more substituents selected from the group consisting of halogen, —CN, lower alkyl, fluoro substituted lower alkyl, lower alkoxy and fluoro substituted lower alkoxy;

$R^{70}$ and $R^{71}$ at each occurrence are independently hydrogen, lower alkyl or lower alkyl substituted with one or more substituents selected from the group consisting of fluoro, —OH, —NH$_2$, lower alkoxy, fluoro substituted lower alkoxy, lower alkylthio, fluoro substituted lower alkylthio, mono-alkylamino, fluoro substituted mono-alkylamino, di-alkylamino, fluoro substituted di-alkylamino, and cycloalkylamino; and $R^{72}$ at each occurrence is lower alkyl or lower alkyl substituted with one or more substituents selected from the group consisting of fluoro, —OH, —NH$_2$, lower alkoxy, fluoro substituted lower alkoxy, lower alkylthio, fluoro substituted lower alkylthio, mono-alkylamino, fluoro substituted mono-alkylamino, di-alkylamino, fluoro substituted di-alkylamino, and cycloalkylamino.

In some embodiments of compounds of Formula I or Formula Ia, further to any of the above embodiments of Formula I or Formula Ia, $R^{20}$ is selected from the group consisting of lower alkyl, lower alkenyl, and lower alkynyl, wherein lower alkyl, lower alkenyl or lower alkynyl are optionally substituted with one or more substituents $R^{74}$, $R^{21}$ is selected from the group consisting of hydrogen, lower alkyl optionally substituted with one or more substituents $R^{74}$, cycloalkyl, heterocycloalkyl, aryl, heteroaryl, and —O—$R^{73}$, wherein cycloalkyl, heterocycloalkyl, aryl or heteroaryl are optionally substituted with one or more substituents $R^{75}$, and $R^{19}$ and $R^{58}$, respectively, are selected from the group consisting of cycloalkyl, heterocycloalkyl, aryl and heteroaryl, wherein cycloalkyl, heterocycloalkyl, aryl or heteroaryl are optionally substituted with one or more substituents $R^{75}$, wherein:

$R^{73}$ is lower alkyl optionally substituted with one or more substituents $R^{74}$, $R^{74}$ at each occurrence is independently selected from the group consisting of —OH, —NH$_2$, —C(O)—OH, —S(O)—NH$_2$, —S(O)$_2$—NH$_2$, —C(O)—NH$_2$, —O—$R^{76}$, —S—$R^{76}$, —N($R^{77}$)—$R^{76}$, —N($R^{77}$)—C(O)—$R^{76}$, —N($R^{77}$)—S(O)—$R^{76}$, —N($R^{77}$)—S(O)$_2$—$R^{76}$, —C(O)—N($R^{77}$)—$R^{76}$, —C(O)—O—$R^{76}$, —C(O)—$R^{76}$, —S(O)—N($R^{77}$)—$R^{76}$, —S(O)$_2$—N($R^{77}$)—$R^{76}$, —S(O)—$R^{76}$ fluoro, cycloalkyl, heterocycloalkyl, aryl and heteroaryl, wherein cycloalkyl, heterocycloalkyl, aryl and heteroaryl are optionally substituted with one or more substituents $R^{75}$;

$R^{75}$ at each occurrence is independently selected from the group consisting of —OH, —NH$_2$, —NO$_2$, —CN, —C(O)—OH, —S(O)—NH$_2$, —S(O)$_2$—NH$_2$, —C(O)—NH$_2$, —O—$R^{76}$, —S—$R^{76}$, —N($R^{77}$)—$R^{76}$, —N($R^{77}$)—C(O)—$R^{76}$, —N($R^{77}$)—S(O)—$R^{76}$, —N($R^{77}$)—S(O)$_2$—$R^{76}$, —S(O)—$R^{76}$, —S(O)$_2$—$R^{76}$, —C(O)—$R^{76}$, —C(O)—O—$R^{76}$, —C(O)—N($R^{77}$)—$R^{76}$, —S(O)—N($R^{77}$)—$R^{76}$, —S(O)$_2$—N($R^{77}$)—$R^{76}$, halogen, lower alkyl, cycloalkyl, heterocycloalkyl, aryl and heteroaryl, wherein lower alkyl is optionally substituted with one or more substituents selected from the group consisting of fluoro, lower alkoxy, fluoro substituted lower alkoxy, lower alkylthio, fluoro substituted lower alkylthio, mono-alkylamino, di-alkylamino, cycloalkyl, heterocycloalkyl, aryl, and heteroaryl, and wherein cycloalkyl, heterocycloalkyl, aryl, and heteroaryl as $R^{75}$, or as substituents of lower alkyl, are optionally substituted with one or more substituents selected from the group consisting of —OH, —NH$_2$, —NO$_2$, —CN, —C(O)—OH, —S(O)$_2$—NH$_2$, —C(O)—NH$_2$, —O—R$^{78}$, —S—R$^{78}$, —N(R$^{77}$)—R$^{78}$, —N(R$^{77}$)—C(O)—R$^{78}$, —N(R$^{77}$)—S(O)$_2$—R$^{78}$, —S(O)—R$^{78}$, —S(O)$_2$—R$^{78}$, —C(O)—R$^{78}$, —C(O)—O—R$^{78}$, —C(O)—N(R$^{77}$)—R$^{78}$, —S(O)$_2$—N(R$^{77}$)—R$^{78}$, halogen, lower alkyl, fluoro substituted lower alkyl, and cycloalkylamino;

$R^{76}$ at each occurrence is independently selected from the group consisting of lower alkyl, cycloalkyl, heterocycloalkyl, aryl and heteroaryl, wherein lower alkyl is optionally substituted with one or more substituents selected from the group consisting of fluoro, lower alkoxy, fluoro substituted lower alkoxy, lower alkylthio, fluoro substituted lower alkylthio, mono-alkylamino, di-alkylamino, cycloalkyl, heterocycloalkyl, aryl, and heteroaryl, and wherein cycloalkyl, heterocycloalkyl, aryl, and heteroaryl as $R^{76}$ or as substituents of lower alkyl are optionally substituted with one or more substituents selected from the group consisting of —OH, —NH$_2$, —CN, —NO$_2$, —C(O)—OH, —S(O)$_2$—NH$_2$, —C(O)—NH$_2$, —O—R$^{80}$, —S—R$^{80}$, —N(R$^{79}$)—R$^{80}$, —N(R$^{79}$)—C(O)—R$^{80}$, —N(R$^{79}$)—S(O)$_2$—R$^{80}$, —C(O)—R$^{80}$, —S(O)—R$^{80}$, —S(O)$_2$—R$^{80}$, —C(O)—O—R$^{80}$, —C(O)—N(R$^{79}$)—R$^{80}$, —S(O)$_2$—N(R$^{79}$)—R$^{80}$, halogen, lower alkyl, fluoro substituted lower alkyl, and cycloalkylamino;

$R^{77}$ and $R^{79}$ at each occurrence are independently hydrogen, lower alkyl, or lower alkyl substituted with one or more substituents selected from the group consisting of fluoro, —OH, —NH$_2$, lower alkoxy, fluoro substituted lower alkoxy, lower alkylthio, fluoro substituted lower alkylthio, mono-alkylamino, fluoro substituted mono-alkylamino, di-alkylamino, fluoro substituted di-alkylamino, and cycloalkylamino; and $R^{78}$ and $R^{80}$ at each occurrence are independently selected from the group consisting of lower alkyl, heterocycloalkyl and heteroaryl, wherein lower alkyl is optionally substituted with one or more substituents selected from the group consisting of fluoro, lower alkoxy, fluoro substituted lower alkoxy, lower alkylthio, fluoro substituted lower alkylthio, mono-alkylamino, di-alkylamino, and cycloalkylamino, and wherein heterocycloalkyl and heteroaryl are optionally substituted with one or more substituents selected from the group consisting of halogen, —CN, lower alkyl, fluoro substituted lower alkyl, lower alkoxy and fluoro substituted lower alkoxy.

In some embodiments of compounds of Formula I or Formula Ia, further to any of the above embodiments of Formula I or Formula Ia, $R^{20}$ is selected from the group consisting of lower alkyl, lower alkenyl, and lower alkynyl, wherein lower alkyl, lower alkenyl or lower alkynyl are optionally substituted with one or more substituents $R^{74}$, $R^{21}$ is selected from the group consisting of hydrogen, lower alkyl optionally substituted with one or more substituents $R^{74}$, cycloalkyl, heterocycloalkyl, aryl, heteroaryl, and —O—R$^{73}$, wherein cycloalkyl, heterocycloalkyl, aryl or heteroaryl are optionally substituted with one or more substituents $R^{75}$, and $R^{19}$ and $R^{58}$, respectively, are selected from the group consisting of cycloalkyl, heterocycloalkyl, aryl and heteroaryl, wherein cycloalkyl, heterocycloalkyl, aryl or heteroaryl are optionally substituted with one or more substituents $R^{75}$; wherein $R^{73}$ is lower alkyl optionally substituted with one or more substituents $R^{74}$, wherein $R^{74}$ at each occurrence is independently selected from the group consisting of —OH, —NH$_2$, —O—R$^{76}$, —S—R$^{76}$, —N(R$^{77}$)—R$^{76}$, —N(R$^{77}$)—C(O)—R$^{76}$, —N(R$^{77}$)—S(O)—R$^{76}$, —N(R$^{77}$)—S(O)$_2$—R$^{76}$, —C(O)—R$^{76}$, —S(O)—R$^{76}$, —S(O)$_2$—R$^{76}$, fluoro, cycloalkyl, heterocycloalkyl, aryl and heteroaryl, wherein cycloalkyl, heterocycloalkyl, aryl and heteroaryl are optionally substituted with one or more substituents $R^{75}$; $R^{75}$ at each occurrence is independently selected from the group consisting of —OH, —NH$_2$, —NO$_2$, —CN, —O—R$^{76}$, —S—R$^{76}$, —N(R$^{77}$)—R$^{76}$, —N(R$^{77}$)—C(O)—R$^{76}$, —N(R$^{77}$)—S(O)—R$^{76}$, —N(R$^{77}$)—S(O)$_2$—R$^{76}$, —C(O)—R$^{76}$, —S(O)—R$^{76}$, —S(O)$_2$—R$^{76}$, halogen, lower alkyl, cycloalkyl, heterocycloalkyl, aryl and heteroaryl, wherein lower alkyl is optionally substituted with one or more substituents selected from the group consisting of fluoro, lower alkoxy, fluoro substituted lower alkoxy, lower alkylthio, fluoro substituted lower alkylthio, mono-alkylamino, di-alkylamino, cycloalkyl, heterocycloalkyl, aryl, and heteroaryl, and wherein cycloalkyl, heterocycloalkyl, aryl, and heteroaryl as $R^{75}$, or as substituents of lower alkyl, are optionally substituted with one or more substituents selected from the group consisting of —OH, —NH$_2$, —NO$_2$, —CN, —O—R$^{78}$, —S—R$^{78}$, —N(R$^{77}$)—R$^{78}$, —N(R$^{77}$)—C(O)—R$^{78}$, —N(R$^{77}$)—S(O)$_2$—R$^{78}$, —(S)(O)—R$^{78}$, —S(O)$_2$—R$^{78}$, —C(O)—R$^{78}$, halogen, lower alkyl, fluoro substituted lower alkyl, and cycloalkylamino; and wherein $R^{76}$, $R^{77}$, and $R^{78}$ are as defined with respect to some embodiments of Formula I or Formula Ia.

In some embodiments of compounds of Formula Ia, further to any of the above embodiments of Formula Ia, Ar$_1$ is selected from the group consisting of

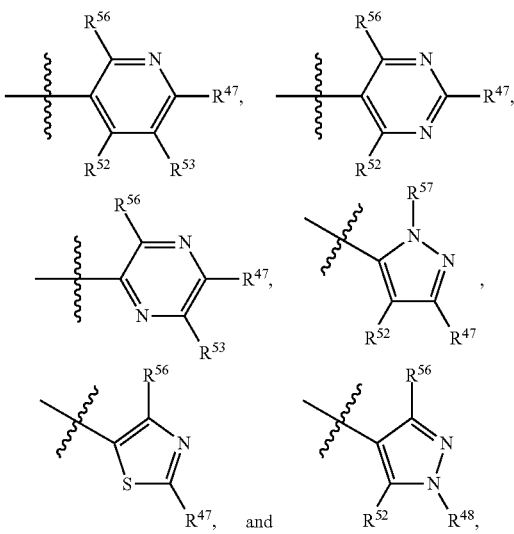

wherein $R^{57}$ is hydrogen, lower alkyl, or fluoro substituted lower alkyl, $R^{52}$, $R^{53}$, and $R^{56}$ are independently hydrogen, halogen, lower alkyl, fluoro substituted lower alkyl, —N(R$^{82}$)—R$^{81}$, —O—R$^{81}$, or —S—R$^{83}$, wherein $R^{81}$ and $R^{82}$ are independently hydrogen, lower alkyl, or fluoro substituted lower alkyl, $R^{83}$ is lower alkyl or fluoro substituted lower alkyl, and $R^{47}$ and $R^{48}$ are as defined with respect to Formula Ia.

In some embodiments of compounds of Formula I or Formula Ia, further to any of the above embodiments of compounds of Formula I or Formula Ia:

$R^4$ and $R^{41}$, respectively, are selected from the group consisting of hydrogen, —CN, —O—$R^{100}$, —S—$R^{100}$, —N($R^{101}$)—$R^{100}$ and lower alkyl, wherein lower alkyl is optionally substituted with one or more substituents selected from the group consisting of fluoro, lower alkoxy, fluoro substituted lower alkoxy, lower alkylthio, fluoro substituted lower alkylthio, mono-alkylamino, di-alkylamino, and cycloalkylamino;

$R^5$ and $R^{42}$, respectively, are selected from the group consisting of hydrogen, —CN, —O—$R^{100}$, —S—$R^{100}$, and lower alkyl, wherein lower alkyl is optionally substituted with one or more substituents selected from the group consisting of fluoro, lower alkoxy, fluoro substituted lower alkoxy, lower alkylthio, fluoro substituted lower alkylthio, mono-alkylamino, di-alkylamino, and cycloalkylamino;

$R^6$ and $R^{43}$, respectively, are hydrogen;

$R^{100}$ is lower alkyl optionally substituted with one or more substituents selected from the group consisting of fluoro, lower alkoxy, fluoro substituted lower alkoxy, lower alkylthio, fluoro substituted lower alkylthio, mono-alkylamino, di-alkylamino, and cycloalkylamino; and $R^{101}$ is hydrogen or lower alkyl optionally substituted with one or more substituents selected from the group consisting of fluoro, lower alkoxy, fluoro substituted lower alkoxy, lower alkylthio, fluoro substituted lower alkylthio, mono-alkylamino, di-alkylamino, and cycloalkylamino.

In a third aspect, compounds of Formula I having the structure according to the following Formula Ib are provided:

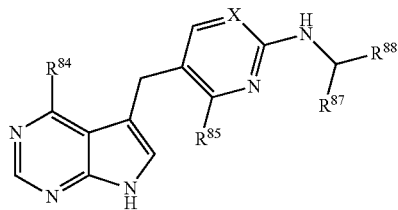

Formula Ib or a salt, a prodrug, a tautomer or a stereoisomer thereof, wherein:

X is N or C($R^{86}$);

$R^{84}$ is hydrogen, lower alkyl, fluoro substituted lower alkyl, lower alkoxy, fluoro substituted lower alkoxy, or cycloalkyl;

$R^{85}$ and $R^{86}$ are independently hydrogen, fluoro, lower alkyl or lower alkoxy;

$R^{87}$ is hydrogen or lower alkyl; and $R^{88}$ is phenyl, pyridinyl or pyrimidinyl, wherein phenyl, pyridinyl or pyrimidinyl are optionally substituted with 1, 2 or 3 substituents independently selected from the group consisting of —CN, fluoro, chloro, bromo, lower alkyl, fluoro substituted lower alkyl, methoxy substituted lower alkyl, lower alkoxy, fluoro substituted lower alkoxy, cycloalkyloxy, alkylsulfonyl, mono-alkylamino, di-alkylamino, or cycloalkylamino.

In one embodiment of compounds of Formula Ib, $R^{84}$ is hydrogen, lower alkyl, lower alkoxy, or cycloalkyl; when X is N, $R^{85}$ is hydrogen; when X is C($R^{86}$), either $R^{85}$ is hydrogen and $R^{86}$ is hydrogen, fluoro, methyl or methoxy, or $R^{86}$ is hydrogen and $R^{85}$ is hydrogen, fluoro or methyl; $R^{87}$ is hydrogen or methyl; and $R^{88}$ is phenyl, pyridinyl or pyrimidinyl, wherein phenyl is optionally substituted with 1 or 2 substituents independently selected from fluoro, chloro, methyl, trifluoromethyl, methoxy and methylsulfonyl, pyridinyl is optionally substituted with 1 or 2 substituents independently selected from the group consisting of —CN, fluoro, chloro, bromo, lower alkyl, fluoro substituted lower alkyl, lower alkoxy, fluoro substituted lower alkoxy, cycloalkyloxy, methylamino, di-methylamino, or cycloalkylamino, and pyrimidine is mono-substituted at the 2-position with lower alkyl, methoxy substituted lower alkyl, mono-alkylamino or di-alkylamino.

In reference to compounds herein, unless clearly indicated to the contrary, specification of a compound or group of compounds includes salts of such compound(s) (including pharmaceutically acceptable salts), formulations of such compound(s) (including pharmaceutically acceptable formulations), conjugates thereof, derivatives thereof, forms thereof, prodrugs thereof, and all stereoisomers thereof. In reference to compositions, kits, methods of use, etc. of compounds of Formula I described herein, it is understood (unless indicated otherwise) that a compound of Formula I includes all sub-embodiments thereof (e.g. including Formula Ia, Formula Ib and all embodiments as described herein).

In one embodiment of compounds of Formula I, the compound is selected from the group consisting of:

(4-Chloro-benzyl)-[5-(7H-pyrrolo[2,3-d]pyrimidin-5-ylmethyl)-pyridin-2-yl]-amine (P-0001), (6-Methoxy-pyridin-3-ylmethyl)-[5-(7H-pyrrolo[2,3-d]pyrimidin-5-ylmethyl)-pyridin-2-yl]-amine (P-0002), (2-Chloro-benzyl)-[5-(7H-pyrrolo[2,3-d]pyrimidin-5-ylmethyl)-pyridin-2-yl]-amine (P-0003),

[5-(7H-Pyrrolo[2,3-d]pyrimidin-5-ylmethyl)-pyridin-2-yl]-(6-trifluoromethyl-pyridin-3-ylmethyl)-amine (P-0004), (2-Chloro-benzyl)-[6-fluoro-5-(7H-pyrrolo[2,3-d]pyrimidin-5-ylmethyl)-pyridin-2-yl]-amine (P-0005), (4-Chloro-benzyl)-[6-fluoro-5-(7H-pyrrolo[2,3-d]pyrimidin-5-ylmethyl)-pyridin-2-yl]-amine (P-0006),

[6-Fluoro-5-(7H-pyrrolo[2,3-d]pyrimidin-5-ylmethyl)-pyridin-2-yl]-(6-trifluoromethyl-pyridin-3-ylmethyl)-amine (P-0007), {6-[(6-Methoxy-pyridin-3-ylmethyl)-amino]-pyridin-3-yl}-(7H-pyrrolo[2,3-d]pyrimidin-5-yl)-methanone (P-0008),

[6-Fluoro-5-(7H-pyrrolo[2,3-d]pyrimidin-5-ylmethyl)-pyridin-2-yl]-(6-methoxy-pyridin-3-ylmethyl)-amine (P-0009), (5-Fluoro-6-methoxy-pyridin-3-ylmethyl)-[6-fluoro-5-(7H-pyrrolo[2,3-d]pyrimidin-5-ylmethyl)-pyridin-2-yl]-amine (P-0010), (5-Fluoro-2-methoxy-pyridin-3-ylmethyl)-[6-fluoro-5-(7H-pyrrolo[2,3-d]pyrimidin-5-ylmethyl)-pyridin-2-yl]-amine (P-0011), (6-Methoxy-pyridin-3-ylmethyl)-[3-methyl-5-(7H-pyrrolo[2,3-d]pyrimidin-5-ylmethyl)-pyridin-2-yl]-amine (P-0012), (6-Methoxy-pyridin-3-ylmethyl)-[5-(4-methoxy-7H-pyrrolo[2,3-d]pyrimidin-5-ylmethyl)-pyridin-2-yl]-amine (P-0013), (2-Chloro-benzyl)-[5-(4-methoxy-7H-pyrrolo[2,3-d]pyrimidin-5-ylmethyl)-pyridin-2-yl]-amine (P-0014), (6-Methoxy-pyridin-3-ylmethyl)-[5-(7H-pyrrolo[2,3-d]pyrimidin-5-ylmethyl)-pyrimidin-2-yl]-amine (P-0015),

[(S)-1-(4-Fluoro-phenyl)-ethyl]-[6-fluoro-5-(7H-pyrrolo[2,3-d]pyrimidin-5-ylmethyl)-pyridin-2-yl]-amine (P-0016),
[3-Fluoro-5-(7H-pyrrolo[2,3-d]pyrimidin-5-ylmethyl)-pyridin-2-yl]-(6-methoxy-pyridin-3-ylmethyl)-amine (P-0017),
[6-Fluoro-5-(7H-pyrrolo[2,3-d]pyrimidin-5-ylmethyl)-pyridin-2-yl]-(4-trifluoromethyl-pyridin-3-ylmethyl)-amine (P-0018),
{6-[(6-Methoxy-pyridin-3-ylmethyl)-amino]-2-methyl-pyridin-3-yl}-(7H-pyrrolo[2,3-d]pyrimidin-5-yl)-methanone (P-0019),
[6-Fluoro-5-(7H-pyrrolo[2,3-d]pyrimidin-5-ylmethyl)-pyridin-2-yl]-(2-methyl-pyridin-4-ylmethyl)-amine (P-0020),
(5-Fluoro-2-methoxy-pyridin-4-ylmethyl)-[6-fluoro-5-(7H-pyrrolo[2,3-d]pyrimidin-5-ylmethyl)-pyridin-2-yl]-amine (P-0021),
(5-Fluoro-2-methoxy-pyridin-3-ylmethyl)-[5-(7H-pyrrolo[2,3-d]pyrimidin-5-ylmethyl)-pyrimidin-2-yl]-amine (P-0022),
[6-Fluoro-5-(7H-pyrrolo[2,3-d]pyrimidin-5-ylmethyl)-pyridin-2-yl]-(2-methoxy-pyridin-4-ylmethyl)-amine (P-0023),
(5-Fluoro-6-methoxy-pyridin-3-ylmethyl)-[5-(7H-pyrrolo[2,3-d]pyrimidin-5-ylmethyl)-pyrimidin-2-yl]-amine (P-0024),
(5-Fluoro-2-methoxy-pyridin-4-ylmethyl)-[5-(7H-pyrrolo[2,3-d]pyrimidin-5-ylmethyl)-pyrimidin-2-yl]-amine (P-0025),
[6-Fluoro-5-(7H-pyrrolo[2,3-d]pyrimidin-5-ylmethyl)-pyridin-2-yl]-(2-methoxy-pyridin-3-ylmethyl)-amine (P-0026),
(5-Chloro-pyridin-2-ylmethyl)-[6-fluoro-5-(7H-pyrrolo[2,3-d]pyrimidin-5-ylmethyl)-pyridin-2-yl]-amine (P-0027),
Pyridin-2-ylmethyl-[5-(7H-pyrrolo[2,3-d]pyrimidin-5-ylmethyl)-pyrimidin-2-yl]-amine (P-0028),
(6-Chloro-pyridin-3-ylmethyl)-[5-(7H-pyrrolo[2,3-d]pyrimidin-5-ylmethyl)-pyrimidin-2-yl]-amine (P-0029),
[5-(7H-Pyrrolo[2,3-d]pyrimidin-5-ylmethyl)-pyrimidin-2-yl]-(6-trifluoromethyl-pyridin-3-ylmethyl)-amine (P-0030),
(6-Morpholin-4-yl-pyridin-2-ylmethyl)-[5-(7H-pyrrolo[2,3-d]pyrimidin-5-ylmethyl)-pyrimidin-2-yl]-amine (P-0031),
(6-Pyrrolidin-1-yl-pyridin-2-ylmethyl)-[5-(7H-pyrrolo[2,3-d]pyrimidin-5-ylmethyl)-pyrimidin-2-yl]-amine (P-0032),
(5-Ethyl-pyridin-2-ylmethyl)-[5-(7H-pyrrolo[2,3-d]pyrimidin-5-ylmethyl)-pyrimidin-2-yl]-amine (P-0033),
(3-Methyl-pyridin-4-ylmethyl)-[5-(7H-pyrrolo[2,3-d]pyrimidin-5-ylmethyl)-pyrimidin-2-yl]-amine (P-0034),
(2-Methyl-pyridin-4-ylmethyl)-[5-(7H-pyrrolo[2,3-d]pyrimidin-5-ylmethyl)-pyrimidin-2-yl]-amine (P-0035),
(2-Morpholin-4-yl-pyridin-4-ylmethyl)-[5-(7H-pyrrolo[2,3-d]pyrimidin-5-ylmethyl)-pyrimidin-2-yl]-amine (P-0036),
[6-Fluoro-5-(7H-pyrrolo[2,3-d]pyrimidin-5-ylmethyl)-pyridin-2-yl]-(3,4,5-trimethoxy-benzyl)-amine (P-0037),
(2,5-Dimethoxy-benzyl)-[6-fluoro-5-(7H-pyrrolo[2,3-d]pyrimidin-5-ylmethyl)-pyridin-2-yl]-amine (P-0038),
[6-Fluoro-5-(7H-pyrrolo[2,3-d]pyrimidin-5-ylmethyl)-pyridin-2-yl]-(6-morpholin-4-yl-pyridin-3-ylmethyl)-amine (P-0039),
[6-Fluoro-5-(7H-pyrrolo[2,3-d]pyrimidin-5-ylmethyl)-pyridin-2-yl]-(5-methoxy-pyridin-3-ylmethyl)-amine (P-0040),
(5-Fluoro-pyridin-2-ylmethyl)-[6-fluoro-5-(7H-pyrrolo[2,3-d]pyrimidin-5-ylmethyl)-pyridin-2-yl]-amine (P-0041),
(5-{[6-Fluoro-5-(7H-pyrrolo[2,3-d]pyrimidin-5-ylmethyl)-pyridin-2-ylamino]-methyl}-pyrimidin-2-yl)-methyl-amine (P-0042),
(2,6-Dimethoxy-pyridin-3-ylmethyl)-[6-fluoro-5-(7H-pyrrolo[2,3-d]pyrimidin-5-ylmethyl)-pyridin-2-yl]-amine (P-0043),
(5-Chloro-pyridin-3-ylmethyl)-[6-fluoro-5-(7H-pyrrolo[2,3-d]pyrimidin-5-ylmethyl)-pyridin-2-yl]-amine (P-0044),
(6-Chloro-pyridin-3-ylmethyl)-[6-fluoro-5-(7H-pyrrolo[2,3-d]pyrimidin-5-ylmethyl)-pyridin-2-yl]-amine (P-0045),
(3-Bromo-pyridin-4-ylmethyl)-[6-fluoro-5-(7H-pyrrolo[2,3-d]pyrimidin-5-ylmethyl)-pyridin-2-yl]-amine (P-0046),
(3-Chloro-pyridin-4-ylmethyl)-[6-fluoro-5-(7H-pyrrolo[2,3-d]pyrimidin-5-ylmethyl)-pyridin-2-yl]-amine (P-0047),
[6-Fluoro-5-(7H-pyrrolo[2,3-d]pyrimidin-5-ylmethyl)-pyridin-2-yl]-(2-methyl-pyrimidin-5-ylmethyl)-amine (P-0048),
(3-Fluoro-pyridin-4-ylmethyl)-[6-fluoro-5-(7H-pyrrolo[2,3-d]pyrimidin-5-ylmethyl)-pyridin-2-yl]-amine (P-0049),
(5-Fluoro-pyridin-3-ylmethyl)-[6-fluoro-5-(7H-pyrrolo[2,3-d]pyrimidin-5-ylmethyl)-pyridin-2-yl]-amine (P-0050),
[6-Fluoro-5-(7H-pyrrolo[2,3-d]pyrimidin-5-ylmethyl)-pyridin-2-yl]-[2-(2,2,2-trifluoro-ethoxy)-pyridin-3-ylmethyl]-amine (P-0051),
(5-Fluoro-2-methanesulfonyl-benzyl)-[6-fluoro-5-(7H-pyrrolo[2,3-d]pyrimidin-5-ylmethyl)-pyridin-2-yl]-amine (P-0052),
(5-Bromo-pyridin-2-ylmethyl)-[6-fluoro-5-(7H-pyrrolo[2,3-d]pyrimidin-5-ylmethyl)-pyridin-2-yl]-amine (P-0053),
(3,5-Bis-trifluoromethyl-benzyl)-[6-fluoro-5-(7H-pyrrolo[2,3-d]pyrimidin-5-ylmethyl)-pyridin-2-yl]-amine (P-0054),
[6-Fluoro-5-(7H-pyrrolo[2,3-d]pyrimidin-5-ylmethyl)-pyridin-2-yl]-(3-methyl-pyridin-4-ylmethyl)-amine (P-0055),
[6-Fluoro-5-(7H-pyrrolo[2,3-d]pyrimidin-5-ylmethyl)-pyridin-2-yl]-(4-methoxy-pyridin-3-ylmethyl)-amine (P-0056),
[6-Fluoro-5-(7H-pyrrolo[2,3-d]pyrimidin-5-ylmethyl)-pyridin-2-yl]-(2-isopropoxy-pyridin-3-ylmethyl)-amine (P-0057),
[6-Fluoro-5-(7H-pyrrolo[2,3-d]pyrimidin-5-ylmethyl)-pyridin-2-yl]-(4-methyl-pyridin-2-ylmethyl)-amine (P-0058),
[6-Fluoro-5-(7H-pyrrolo[2,3-d]pyrimidin-5-ylmethyl)-pyridin-2-yl]-(2-pyrrolidin-1-yl-pyridin-4-ylmethyl)-amine (P-0059),
(4-Chloro-2-methanesulfonyl-benzyl)-[6-fluoro-5-(7H-pyrrolo[2,3-d]pyrimidin-5-ylmethyl)-pyridin-2-yl]-amine (P-0060),
(2-Dimethylamino-benzyl)-[6-fluoro-5-(7H-pyrrolo[2,3-d]pyrimidin-5-ylmethyl)-pyridin-2-yl]-amine (P-0061),
[6-Fluoro-5-(7H-pyrrolo[2,3-d]pyrimidin-5-ylmethyl)-pyridin-2-yl]-(5-methyl-pyridin-2-ylmethyl)-amine (P-0062),
(3,5-Dimethyl-benzyl)-[6-fluoro-5-(7H-pyrrolo[2,3-d]pyrimidin-5-ylmethyl)-pyridin-2-yl]-amine (P-0063),
(3-Fluoro-5-methyl-benzyl)-[6-fluoro-5-(7H-pyrrolo[2,3-d]pyrimidin-5-ylmethyl)-pyridin-2-yl]-amine (P-0064),
(3,5-Dimethoxy-benzyl)-[6-fluoro-5-(7H-pyrrolo[2,3-d]pyrimidin-5-ylmethyl)-pyridin-2-yl]-amine (P-0065),
[6-Fluoro-5-(7H-pyrrolo[2,3-d]pyrimidin-5-ylmethyl)-pyridin-2-yl]-(2-methylamino-pyridin-3-ylmethyl)-amine (P-0066),
(3-Chloro-5-fluoro-benzyl)-[6-fluoro-5-(7H-pyrrolo[2,3-d]pyrimidin-5-ylmethyl)-pyridin-2-yl]-amine (P-0067),
(2-Fluoro-pyridin-3-ylmethyl)-[6-fluoro-5-(7H-pyrrolo[2,3-d]pyrimidin-5-ylmethyl)-pyridin-2-yl]-amine (P-0068),
(2-Ethoxy-pyridin-3-ylmethyl)-[6-fluoro-5-(7H-pyrrolo[2,3-d]pyrimidin-5-ylmethyl)-pyridin-2-yl]-amine (P-0069), (2-Cyclopentyloxy-pyridin-3-ylmethyl)-[6-fluoro-5-(7H-pyrrolo[2,3-d]pyrimidin-5-ylmethyl)-pyridin-2-yl]-amine (P-0070),

[6-Fluoro-5-(7H-pyrrolo[2,3-d]pyrimidin-5-ylmethyl)-pyridin-2-yl]-(2-trifluoromethyl-pyridin-3-ylmethyl)-amine (P-0071), (2-Chloro-5-fluoro-pyridin-4-ylmethyl)-[6-fluoro-5-(7H-pyrrolo[2,3-d]pyrimidin-5-ylmethyl)-pyridin-2-yl]-amine (P-0072), 4-{[6-Fluoro-5-(7H-pyrrolo[2,3-d]pyrimidin-5-ylmethyl)-pyridin-2-ylamino]-methyl}-pyridine-2-carbonitrile (P-0073), (2-Fluoro-pyridin-4-ylmethyl)-[6-fluoro-5-(7H-pyrrolo[2,3-d]pyrimidin-5-ylmethyl)-pyridin-2-yl]-amine (P-0074),

[6-Fluoro-5-(7H-pyrrolo[2,3-d]pyrimidin-5-ylmethyl)-pyridin-2-yl]-(2-trifluoromethyl-pyridin-4-ylmethyl)-amine (P-0075), (2-Chloro-pyridin-4-ylmethyl)-[6-fluoro-5-(7H-pyrrolo[2,3-d]pyrimidin-5-ylmethyl)-pyridin-2-yl]-amine (P-0076), (5-Chloro-2-fluoro-pyridin-3-ylmethyl)-[6-fluoro-5-(7H-pyrrolo[2,3-d]pyrimidin-5-ylmethyl)-pyridin-2-yl]-amine (P-0077), (2-Ethyl-pyrimidin-5-ylmethyl)-[6-fluoro-5-(7H-pyrrolo[2,3-d]pyrimidin-5-ylmethyl)-pyridin-2-yl]-amine (P-0078),

[6-Fluoro-5-(7H-pyrrolo[2,3-d]pyrimidin-5-ylmethyl)-pyridin-2-yl]-(2-isopropyl-pyrimidin-5-ylmethyl)-amine (P-0079),

[6-Fluoro-5-(7H-pyrrolo[2,3-d]pyrimidin-5-ylmethyl)-pyridin-2-yl]-[2-(2-methoxy-ethyl)-pyrimidin-5-ylmethyl]-amine (P-0080), (2-Butyl-pyrimidin-5-ylmethyl)-[6-fluoro-5-(7H-pyrrolo[2,3-d]pyrimidin-5-ylmethyl)-pyridin-2-yl]-amine (P-0081),

[6-Fluoro-5-(7H-pyrrolo[2,3-d]pyrimidin-5-ylmethyl)-pyridin-2-yl]-(3-methoxy-5-trifluoromethyl-benzyl)-amine (P-0082), (3-Fluoro-5-methoxy-benzyl)-[6-fluoro-5-(7H-pyrrolo[2,3-d]pyrimidin-5-ylmethyl)-pyridin-2-yl]-amine (P-0083), (2-Methoxy-pyridin-3-ylmethyl)-[5-(7H-pyrrolo[2,3-d]pyrimidin-5-ylmethyl)-pyrimidin-2-yl]-amine (P-0084), (2-Ethoxy-pyridin-3-ylmethyl)-[5-(7H-pyrrolo[2,3-d]pyrimidin-5-ylmethyl)-pyrimidin-2-yl]-amine (P-0085), (2-Cyclopentyloxy-pyridin-3-ylmethyl)-[5-(7H-pyrrolo[2,3-d]pyrimidin-5-ylmethyl)-pyrimidin-2-yl]-amine (P-0086), (2-Cyclopentyloxy-pyridin-4-ylmethyl)-[5-(7H-pyrrolo[2,3-d]pyrimidin-5-ylmethyl)-pyrimidin-2-yl]-amine (P-0087), (2-Cyclohexyloxy-pyridin-3-ylmethyl)-[6-fluoro-5-(7H-pyrrolo[2,3-d]pyrimidin-5-ylmethyl)-pyridin-2-yl]-amine (P-0088),

[6-Fluoro-5-(7H-pyrrolo[2,3-d]pyrimidin-5-ylmethyl)-pyridin-2-yl]-(5-pyrrolidin-1-yl-pyridin-2-ylmethyl)-amine (P-0089), (2-Chloro-benzyl)-[6-fluoro-5-(4-methoxy-7H-pyrrolo[2,3-d]pyrimidin-5-ylmethyl)-pyridin-2-yl]-amine (P-0090), (5-Fluoro-6-methoxy-pyridin-3-ylmethyl)-[6-fluoro-5-(4-methoxy-7H-pyrrolo[2,3-d]pyrimidin-5-ylmethyl)-pyridin-2-yl]-amine (P-0091), (5-Fluoro-6-methoxy-pyridin-3-ylmethyl)-[5-(4-methoxy-7H-pyrrolo[2,3-d]pyrimidin-5-ylmethyl)-pyrimidin-2-yl]-amine (P-0092), (5-Fluoro-2-methoxy-pyridin-3-ylmethyl)-[5-(4-methoxy-7H-pyrrolo[2,3-d]pyrimidin-5-ylmethyl)-pyrimidin-2-yl]-amine (P-0093), (5-Fluoro-2-methoxy-pyridin-3-ylmethyl)-[6-fluoro-5-(4-methoxy-7H-pyrrolo[2,3-d]pyrimidin-5-ylmethyl)-pyridin-2-yl]-amine (P-0094),

[6-Fluoro-5-(4-methoxy-7H-pyrrolo[2,3-d]pyrimidin-5-ylmethyl)-pyridin-2-yl]-(4-trifluoromethyl-pyridin-3-ylmethyl)-amine (P-0095),

[3-Methoxy-5-(4-methoxy-7H-pyrrolo[2,3-d]pyrimidin-5-ylmethyl)-pyridin-2-yl]-(6-trifluoromethyl-pyridin-3-ylmethyl)-amine (P-0096),

[6-Fluoro-5-(4-methoxy-7H-pyrrolo[2,3-d]pyrimidin-5-ylmethyl)-pyridin-2-yl]-(2-methoxy-pyridin-3-ylmethyl)-amine (P-0097), (5-Fluoro-pyridin-3-ylmethyl)-[5-(4-methoxy-7H-pyrrolo[2,3-d]pyrimidin-5-ylmethyl)-pyrimidin-2-yl]-amine (P-0098), 5-{6-[(5-Fluoro-2-methoxy-pyridin-3-ylmethyl)-amino]-pyridin-3-ylmethyl}-7H-pyrrolo[2,3-d]pyrimidin-4-ol (P-0099),

[5-(4-Methoxy-7H-pyrrolo[2,3-d]pyrimidin-5-ylmethyl)-pyridin-2-yl]-(6-trifluoromethyl-pyridin-3-ylmethyl)-amine (P-0100),

[6-Fluoro-5-(4-methoxy-7H-pyrrolo[2,3-d]pyrimidin-5-ylmethyl)-pyridin-2-yl]-(6-trifluoromethyl-pyridin-3-ylmethyl)-amine (P-0101),

[5-(4-Methoxy-7H-pyrrolo[2,3-d]pyrimidin-5-ylmethyl)-pyrimidin-2-yl]-(6-trifluoromethyl-pyridin-3-ylmethyl)-amine (P-0102),

[3-Fluoro-5-(4-methoxy-7H-pyrrolo[2,3-d]pyrimidin-5-ylmethyl)-pyridin-2-yl]-(6-trifluoromethyl-pyridin-3-ylmethyl)-amine (P-0103),

[5-(4-Cyclopentyl-7H-pyrrolo[2,3-d]pyrimidin-5-ylmethyl)-pyridin-2-yl]-(6-trifluoromethyl-pyridin-3-ylmethyl)-amine (P-0104),

[6-Fluoro-5-(7H-pyrrolo[2,3-d]pyrimidin-5-ylmethyl)-pyridin-2-yl]-(4-methoxy-benzyl)-amine (P-0105), and any salt, prodrug, tautomer, or isomer thereof.

In a fourth aspect, methods are provided for treating a protein kinase mediated disease or condition in an animal subject in need thereof, wherein the method involves administering to the subject an effective amount of any one or more compound(s) of Formula I. The terms "treat," "therapy," and like terms refer to the administration of material, e.g., any one or more compound(s) of Formula I in an amount effective to prevent, alleviate, or ameliorate one or more symptoms of a disease or condition, i.e., indication, and/or to prolong the survival of the subject being treated. The term "protein kinase mediated disease or condition" refers to a disease or condition in which the biological function of a protein kinase affects the development, course, and/or symptoms of the disease or condition, and/or in which modulation of the protein kinase alters the development, course, and/or symptoms of the disease or condition. A protein kinase mediated disease or condition includes a disease or condition for which modulation provides a therapeutic benefit, e.g. wherein treatment with protein kinase inhibitors, including compounds described herein, provides a therapeutic benefit to the subject suffering from or at risk of the disease or condition. In certain embodiments, the method involves administering to the subject an effective amount of a compound of Formula I in combination with one or more other therapies for the disease or condition.

In a fifth aspect, the invention provides methods for treating a Fms protein kinase mediated disease or condition in an animal subject in need thereof, wherein the method involves administering to the subject an effective amount of any one or more compound(s) of Formula I. The terms "fms protein kinase mediated disease or condition," "c-fms mediated disease or condition," and the like refer to a disease or condition in which the biological function of a Fms protein kinase, including any mutations thereof, affects the development, course, and/or symptoms of the disease or condition, and/or in which modulation of the Fms protein kinase alters the development, course, and/or symptoms of the disease or condition. The Fms protein kinase mediated disease or condition includes a disease or condition for which Fms inhibition provides a therapeutic benefit, e.g. wherein treatment with Fms inhibitors, including compounds described herein, provides a therapeutic benefit to the subject suffering from or at risk of the disease or condition. In one embodiment, the method involves administering to the subject an effective amount of a compound of Formula I in combination with one or more other therapies for the disease or condition.

In a sixth aspect, the invention provides methods for treating a Kit protein kinase mediated disease or condition in an animal subject in need thereof, wherein the method involves administering to the subject an effective amount of any one or more compound(s) of Formula I. The terms "kit protein kinase mediated disease or condition," "c-kit mediated disease or condition," and the like refer to a disease or condition in which the biological function of a Kit protein kinase, including any mutations thereof, affects the development, course, and/or symptoms of the disease or condition, and/or in which modulation of the Kit protein kinase alters the development, course, and/or symptoms of the disease or condition. The Kit protein kinase mediated disease or condition includes a disease or condition for which Kit inhibition provides a therapeutic benefit, e.g. wherein treatment with kit inhibitors, including compounds described herein, provides a therapeutic benefit to the subject suffering from or at risk of the disease or condition. In one embodiment, the method involves administering to the subject an effective amount of a compound of Formula I in combination with one or more other therapies for the disease or condition.

In a seventh aspect, a compound of Formula I will have an $IC_{50}$ of less than 500 nm, less than 100 nM, less than 50 nM, less than 20 nM, less than 10 nM, less than 5 nM, or less than 1 nM as determined in a generally accepted kinase activity assay. In some embodiments, a compound of Formula I will have an $IC_{50}$ of less than 500 nm, less than 100 nM, less than 50 nM, less than 20 nM, less than 10 nM, less than 5 nM, or less than 1 nM with respect to at least one kinase selected from the group consisting of Abl, Akt1, Akt2, Akt3, ALK, Alk5, A-Raf, B-Raf, Brk, Btk, Cdk2, CDK4, CDK5, CDK6, CHK1, c-Raf-1, Csk, EGFR, EphA1, EphA2, EphB2, EphB4, Erk2, Fak, FGFR1, FGFR2, FGFR3, FGFR4, Flt1, Flt3, Flt4, Fms, Frk, Fyn, Gsk3α, Gsk3β, HCK, Her2/Erbb2, Her4/Erbb4, IGF1R, IKK beta, Irak4, Itk, Jak1, Jak2, Jak3, Jnk1, Jnk2, Jnk3, Kdr, Kit, Lck, Lyn, MAP2K1, MAP2K2, MAP4K4, MAPKAPK2, Met, Mnk1, MLK1, mTOR, p38, PDGFRA, PDGFRB, PDPK1, PI3Kα, PI3Kβ, PI3Kδ, PI3Kγ, Pim1, Pim2, Pim3, PKC alpha, PKC beta, PKC theta, Plk1, Pyk2, Ret, ROCK1, ROCK2, Ron, Src, Stk6, Syk, TEC, Tie2, TrkA, TrkB, Yes, and Zap70, including any mutations thereof.

In an eighth aspect, a compound of Formula I will have an $IC_{50}$ of less than 500 nm, less than 100 nM, less than 50 nM, less than 20 nM, less than 10 nM, less than 5 nM, or less than 1 nM with respect to at least one kinase selected from the group consisting of Abl, Akt1, Akt2, Akt3, ALK, Alk5, A-Raf, B-Raf, Btk, Cdk2, CDK4, CDK5, CDK6, CHK1, c-Raf-1, Csk, EGFR, EphA1, EphA2, EphB2, EphB4, Erk2, Fak, Fms, Fyn, Gsk3α, Gsk3β, HCK, Her2/Erbb2, Her4/Erbb4, IGF1R, IKK beta, Irak4, Itk, Jak1, Jak2, Jak3, Jnk1, Jnk2, Jnk3, Kit, Lck, Lyn, MAP2K1, MAP2K2, MAP4K4, MAPKAPK2, Met, Mnk1, MLK1, mTOR, p38, PDPK1, PI3Kα, PI3Kβ, PI3Kδ, PI3Kγ, Pim1, Pim2, Pim3, PKC alpha, PKC beta, PKC theta, Plk1, Pyk2, Ron, Src, Stk6, Syk, TEC, Tie2, TrkA, TrkB, Yes, and Zap70, including any mutations thereof.

In a ninth aspect, a compound of Formula I will have an $IC_{50}$ of less than 500 nm, less than 100 nM, less than 50 nM, less than 20 nM, less than 10 nM, less than 5 nM, or less than 1 nM with respect to at least one kinase selected from the group consisting of Abl, A-Raf, B-Raf, Btk, c-Raf-1, EGFR, EphB2, Erk2, Fak, FGFR1, Flt1, Flt3, Flt4, Fms, Irak4, Jnk1, Jnk2, Jnk3, Kdr, Kit, Lck, Lyn, MAP2K1, MAP4K4, MAPKAPK2, Met, mTOR, p38, PDGFRB, PI3Kα, PI3Kβ, PI3Kδ, PI3Kγ, Pim1, PKC theta, Pyk2, Ret, Src, Stk6, TrkA, TrkB, Yes, and Zap70, including any mutations thereof.

In a tenth aspect, a compound of Formula I will have an $IC_{50}$ of less than 500 nm, less than 100 nM, less than 50 nM, less than 20 nM, less than 10 nM, less than 5 nM, or less than 1 nM with respect to at least one kinase selected from the group consisting of Abl, A-Raf, B-Raf, Btk, c-Raf-1, EGFR, EphB2, Erk2, Fak, Fms, Irak4, Jnk1, Jnk2, Jnk3, Kit, Lck, Lyn, MAP2K1, MAP4K4, MAPKAPK2, Met, mTOR, p38, PI3Kα, PI3Kβ, PI3Kδ, PI3Kγ, Pim1, PKC theta, Pyk2, Src, Stk6, TrkA, TrkB, Yes, and Zap70, including any mutations thereof.

In an eleventh aspect, a compound of Formula I will have an $IC_{50}$ of less than 500 nm, less than 100 nM, less than 50 nM, less than 20 nM, less than 10 nM, less than 5 nM, or less than 1 nM with respect to at least one kinase selected from the group consisting of Fms, Kit, MAP4K4, TrkA, and TrkB, including any mutations thereof.

In a twelfth aspect, a compound of Formula I is an inhibitor of a Kit kinase and has an $IC_{50}$ of less than 100 nM, less than 50 nM, less than 20 nM, less than 10 nM, or less than 5 nM as determined in a generally accepted Kit kinase activity assay. In some embodiments, the selectivity of the compound is such that the compound is at least 2-fold, 5-fold, 10-fold, or 100-fold more active on Kit than on Ret, PDGF, or both Ret and PDGF. In some embodiments, the selectivity of the compound is such that the compound is at least 2-fold, 5-fold, 10-fold, or 100-fold more active on Kit than on Fms.

In a thirteenth aspect, a compound of Formula I is an inhibitor of a Fms kinase and has an $IC_{50}$ of less than 100 nM, less than 50 nM, less than 20 nM, less than 10 nM, or less than 5 nM as determined in a generally accepted Fms kinase activity assay. In some embodiments, the selectivity of the compound is such that the compound is at least 2-fold, 5-fold, 10-fold, or 100-fold more active on Fms than on Ret, PDGF, or both Ret and PDGF. In some embodiments, the selectivity of the compound is such that the compound is at least 2-fold, 5-fold, 10-fold, or 100-fold more active on Fms than on Kit.

In a fourteenth aspect, a compound of Formula I has an $IC_{50}$ of less than 100 nM, less than 50 nM, less than 20 nM, less than 10 nM, or less than 5 nM as determined in a generally accepted kinase activity assay for Kit, Fms, or both Kit and Fms kinase activity. In some embodiments, the selectivity of the compound is such that the compound is at least 2-fold, 5-fold, 10-fold, or 100-fold more active on Kit, Fms, or both Kit and Fms than on Ret, PDGF, or both Ret and PDGF.

In a fifteenth aspect, a compound of Formula I has an $IC_{50}$ of less than 100 nM, less than 50 nM, less than 20 nM, less than 10 nM, or less than 5 nM as determined in a generally accepted kinase activity assay for Kit, Fms, or both Kit and Fms kinase activity, and further has an $IC_{50}$ of less than 100 nM, less than 50 nM, less than 20 nM, less than 10 nM, or less than 5 nM as determined in a generally accepted kinase activity assay for at least one of MAP4K4, TrkA, or TrkB kinase activity.

Further to any of the above mentioned aspects and embodiments, a compound of Formula I will also inhibit the effects of a mutation of the kinase, including, but not limited to, a mutation that is related to a disease state, such as a cancer.

Further to any of the above mentioned aspects and embodiments, a compound of Formula I may selectively inhibit one kinase relative to one or more other kinases, where preferably inhibition is selective with respect to any of the other kinases, whether a kinase discussed herein, or other kinases. In some embodiments, the compound may selectively inhibit Fms relative to Kit. Selective inhibition of one kinase relative to another is such that the $IC_{50}$ for the one kinase may be at least about 2-fold, also 5-fold, also 10-fold, also 20-fold, also 50-fold, or at least about 100-fold less than the $IC_{50}$ for any of the other kinases as determined in a generally accepted kinase activity assay.

In a sixteenth aspect, compositions are provided that include a therapeutically effective amount of any one or more compound(s) of Formula I and at least one pharmaceutically acceptable carrier, excipient, and/or diluent, including combinations of any two or more compounds of Formula I. The composition can further include a plurality of different pharmacologically active compounds, which can include a plurality of compounds of Formula I. In certain embodiments, the composition can include any one or more compound(s) of Formula I along with one or more compounds that are therapeutically effective for the same disease indication. In one embodiment, the composition includes any one or more compound(s) of Formula I along with one or more compounds that are therapeutically effective for the same disease indication, wherein the compounds have a synergistic effect on the disease indication. In one embodiment, the composition includes any one or more compound(s) of Formula I effective in treating a cancer and one or more other compounds that are effective in treating the same cancer, further wherein the compounds are synergistically effective in treating the cancer.

In a seventeenth aspect, methods are provided for modulating the activity of a protein kinase selected from the group consisting of Abl, Akt1, Akt2, Akt3, ALK, Alk5, A-Raf, B-Raf, Brk, Btk, Cdk2, CDK4, CDK5, CDK6, CHK1, c-Raf-1, Csk, EGFR, EphA1, EphA2, EphB2, EphB4, Erk2, Fak, FGFR1, FGFR2, FGFR3, FGFR4, Flt1, Flt3, Flt4, Fms, Frk, Fyn, Gsk3α, Gsk3β, HCK, Her2/Erbb2, Her4/Erbb4, IGF1R, IKK beta, Irak4, Itk, Jak1, Jak2, Jak3, Jnk1, Jnk2, Jnk3, Kdr, Kit, Lck, Lyn, MAP2K1, MAP2K2, MAP4K4, MAPKAPK2, Met, Mnk1, MLK1, mTOR, p38, PDGFRA, PDGFRB, PDPK1, PI3Kα, PI3Kβ, PI3Kδ, PI3Kγ, Pim1, Pim2, Pim3, PKC alpha, PKC beta, PKC theta, Plk1, Pyk2, Ret, ROCK1, ROCK2, Ron, Src, Stk6, Syk, TEC, Tie2, TrkA, TrkB, Yes, and Zap70, including any mutations thereof, by contacting the protein kinase with an effective amount of any one or more compound(s) of Formula I.

In an eighteenth aspect, methods are provided for treating a protein kinase mediated disease or condition in an animal subject in need thereof, wherein the method involves administering to the subject an effective amount of a composition including any one or more compound(s) of Formula I.

In a nineteenth aspect, methods are provided for treating a disease or condition mediated by a protein kinase selected from the group consisting of Abl, Akt1, Akt2, Akt3, ALK, Alk5, A-Raf, B-Raf, Brk, Btk, Cdk2, CDK4, CDK5, CDK6, CHK1, c-Raf-1, Csk, EGFR, EphA1, EphA2, EphB2, EphB4, Erk2, Fak, FGFR1, FGFR2, FGFR3, FGFR4, Flt1, Flt3, Flt4, Fms, Frk, Fyn, Gsk3α, Gsk3β, HCK, Her2/Erbb2, Her4/Erbb4, IGF1R, IKK beta, Irak4, Itk, Jak1, Jak2, Jak3, Jnk1, Jnk2, Jnk3, Kdr, Kit, Lck, Lyn, MAP2K1, MAP2K2, MAP4K4, MAPKAPK2, Met, Mnk1, MLK1, mTOR, p38, PDGFRA, PDGFRB, PDPK1, PI3Kα, PI3Kβ, PI3Kδ, PI3Kγ, Pim1, Pim2, Pim3, PKC alpha, PKC beta, PKC theta, Plk1, Pyk2, Ret, ROCK1, ROCK2, Ron, Src, Stk6, Syk, TEC, Tie2, TrkA, TrkB, Yes, and Zap70, including any mutations thereof, in a subject in need thereof by administering to the subject an effective amount of a composition including any one or more compound(s) of Formula I.

In a twentieth aspect, the invention provides methods for treating a disease or condition mediated by a protein kinase selected from the group consisting of Abl, Akt1, Akt2, Akt3, ALK, Alk5, A-Raf, B-Raf, Btk, Cdk2, CDK4, CDK5, CDK6, CHK1, c-Raf-1, Csk, EGFR, EphA1, EphA2, EphB2, EphB4, Erk2, Fak, Fms, Fyn, Gsk3α, Gsk3β, HCK, Her2/Erbb2, Her4/Erbb4, IGF1R, IKK beta, Irak4, Itk, Jak1, Jak2, Jak3, Jnk1, Jnk2, Jnk3, Kit, Lck, Lyn, MAP2K1, MAP2K2, MAP4K4, MAPKAPK2, Met, Mnk1, MLK1, mTOR, p38, PDPK1, PI3Kα, PI3Kβ, PI3Kδ, PI3Kγ, Pim1, Pim2, Pim3, PKC alpha, PKC beta, PKC theta, Plk1, Pyk2, Ron, Src, Stk6, Syk, TEC, Tie2, TrkA, TrkB, Yes, and Zap70, including any mutations thereof, in a subject in need thereof by administering to the subject an effective amount of a composition including any one or more compound(s) of Formula I.

In a twenty-first aspect, the invention provides methods for treating a disease or condition mediated by a protein kinase selected from the group consisting of Abl, A-Raf, B-Raf, Btk, c-Raf-1, EGFR, EphB2, Erk2, Fak, FGFR1, Flt1, Flt3, Flt4, Fms, Irak4, Jnk1, Jnk2, Jnk3, Kdr, Kit, Lck, Lyn, MAP2K1, MAP4K4, MAPKAPK2, Met, mTOR, p38, PDGFRB, PI3Kα, PI3Kβ, PI3Kδ, PI3Kγ, Pim1, PKC theta, Pyk2, Ret, Src, Stk6, TrkA, TrkB, Yes, and Zap70, including any mutations thereof, in a subject in need thereof by administering to the subject an effective amount of a composition including any one or more compound(s) of Formula I.

In a twenty-second aspect, the invention provides methods for treating a disease or condition mediated by a protein kinase selected from the group consisting of Abl, A-Raf, B-Raf, Btk, c-Raf-1, EGFR, EphB2, Erk2, Fak, Fms, Irak4, Jnk1, Jnk2, Jnk3, Kit, Lck, Lyn, MAP2K1, MAP4K4, MAPKAPK2, Met, mTOR, p38, PI3Kα, PI3β, PI3δ, PI3Kγ, Pim1, PKC theta, Pyk2, Src, Stk6, TrkA, TrkB, Yes, and Zap70, including any mutations thereof, in a subject in need thereof by administering to the subject an effective amount of a composition including any one or more compound(s) of Formula I.

In a twenty-third aspect, the invention provides methods for treating a disease or condition mediated by a protein kinase selected from the group consisting of Fms, Kit, MAP4K4, TrkA, and TrkB, including any mutations thereof, in a subject in need thereof by administering to the subject an effective amount of a composition including any one or more compound(s) of Formula I.

In a twenty-fourth aspect, the invention provides methods for treating a disease or condition mediated by Fms or Kit, including any mutations thereof, in a subject in need thereof by administering to the subject an effective amount of a composition including any one or more compound(s) of Formula I. In one embodiment, the invention provides methods for treating a disease or condition mediated by Fms or Kit, including any mutations thereof, in a subject in need thereof by administering to the subject an effective amount of a composition including any one or more compound(s) of Formula I in combination with one or more other suitable therapies for treating the disease.

In a twenty-fifth aspect, the invention provides a method of treating a cancer in a subject in need thereof by administering to the subject an effective amount of a composition including any one or more compound(s) of Formula I, in combination with one or more other therapies or medical procedures effective in treating the cancer. Other therapies or medical procedures include suitable anticancer therapy (e.g. drug therapy, vaccine therapy, gene therapy, photodynamic therapy) or medical procedure (e.g. surgery, radiation treatment, hyperthermia heating, bone marrow or stem cell transplant). In one embodiment, the one or more suitable anticancer therapies or medical procedures is selected from treatment with a chemotherapeutic agent (e.g. chemotherapeutic drug), radiation treatment (e.g. x-ray, γ-ray, or electron, proton, neutron, or α particle beam), hyperthermia heating (e.g. microwave, ultrasound, radiofrequency ablation), Vaccine therapy (e.g. AFP gene hepatocellular carcinoma vaccine, AFP adenoviral vector vaccine, AG-858, allogeneic GM-CSF-secretion breast cancer vaccine, dendritic cell peptide vaccines), gene therapy (e.g. Ad5CMV-p53 vector, adenovector encoding MDA7, adenovirus 5-tumor necrosis factor alpha), photodynamic therapy (e.g. aminolevulinic acid, motexafin lutetium), surgery, or bone marrow and stem cell transplantation.

In a twenty-sixth aspect, the invention provides a method of treating a cancer in a subject in need thereof by administering to the subject an effective amount of a composition including any one or more compound(s) of Formula I, in combination with one or more suitable chemotherapeutic agents. In one embodiment, the one or more suitable chemotherapeutic agents is selected from an alkylating agent, including, but not limited to, adozelesin, altretamine, bendamustine, bizelesin, busulfan, carboplatin, carboquone, carmofur, carmustine, chlorambucil, cisplatin, cyclophosphamide, dacarbazine, estramustine, etoglucid, fotemustine, hepsulfam, ifosfamide, improsulfan, irofulven, lomustine, mannosulfan, mechlorethamine, melphalan, mitobronitol, nedaplatin, nimustine, oxaliplatin, piposulfan, prednimustine, procarbazine, ranimustine, satraplatin, semustine, streptozocin, temozolomide, thiotepa, treosulfan, triaziquone, triethylenemelamine, triplatin tetranitrate, trofosphamide, and uramustine; an antibiotic, including, but not limited to, aclarubicin, amrubicin, bleomycin, dactinomycin, daunorubicin, doxorubicin, elsamitrucin, epirubicin, idarubicin, menogaril, mitomycin, neocarzinostatin, pentostatin, pirarubicin, plicamycin, valrubicin, and zorubicin; an antimetabolite, including, but not limited to, aminopterin, azacitidine, azathioprine, capecitabine, cladribine, clofarabine, cytarabine, decitabine, floxuridine, fludarabine, 5-fluorouracil, gemcitabine, hydroxyurea, mercaptopurine, methotrexate, nelarabine, pemetrexed, azathioprine, raltitrexed, tegafur-uracil, thioguanine, trimethoprim, trimetrexate, and vidarabine; an immunotherapy, including, but not limited to, alemtuzumab, bevacizumab, cetuximab, galiximab, gemtuzumab, panitumumab, pertuzumab, rituximab, tositomomab, trastuzumab, 90Y ibritumomab tiuxetan, ipilimumab, and tremelimumab; a hormone or hormone antagonist, including, but not limited to, anastrozole, androgens, buserelin, diethylstilbestrol, exemestane, flutamide, fulvestrant, goserelin, idoxifene, letrozole, leuprolide, magestrol, raloxifene, tamoxifen, and toremifene; a taxane, including, but not limited to, DJ-927, docetaxel, TPI 287, larotaxel, ortataxel, paclitaxel, DHA-paclitaxel, and tesetaxel; a retinoid, including, but not limited to, alitretinoin, bexarotene, fenretinide, isotretinoin, and tretinoin; an alkaloid, including, but not limited to, demecolcine, homoharringtonine, vinblastine, vincristine, vindesine, vinflunine, and vinorelbine; an antiangiogenic agent, including, but not limited to, AE-941 (GW786034, Neovastat), ABT-510, 2-methoxyestradiol, lenalidomide, and thalidomide; a topoisomerase inhibitor, including, but not limited to, amsacrine, belotecan, edotecarin, etoposide, etoposide phosphate, exatecan, irinotecan (also active metabolite SN-38 (7-ethyl-10-hydroxy-camptothecin)), lucanthone, mitoxantrone, pixantrone, rubitecan, teniposide, topotecan, and 9-aminocamptothecin; a kinase inhibitor, including, but not limited to, axitinib (AG 013736), dasatinib (BMS 354825), erlotinib, gefitinib, flavopiridol, imatinib mesylate, lapatinib, motesanib diphosphate (AMG 706), nilotinib (AMN107), seliciclib, sorafenib, sunitinib malate, AEE-788, BMS-599626, UCN-01 (7-hydroxystaurosporine), and vatalanib; a targeted signal transduction inhibitor including, but not limited to bortezomib, geldanamycin, and rapamycin; a biological response modifier, including, but not limited to, imiquimod, interferon-α, and interleukin-2; and other chemotherapeutics, including, but not limited to 3-AP (3-amino-2-carboxyaldehyde thiosemicarbazone), altrasentan, aminoglutethimide, anagrelide, asparaginase, bryostatin-1, cilengitide, elesclomol, eribulin mesylate (E7389), ixabepilone, lonidamine, masoprocol, mitoguanazone, oblimersen, sulindac, testolactone, tiazofurin, mTOR inhibitors (e.g. temsirolimus, everolimus, deforolimus), PI3K inhibitors (e.g. BEZ235, GDC-0941, XL147, XL765), Cdk4 inhibitors (e.g. PD-332991), Akt inhibitors, Hsp90 inhibitors (e.g. tanespimycin) and farnesyltransferase inhibitors (e.g. tipifarnib). Preferably, the method of treating a cancer involves administering to the subject an effective amount of a composition including any one or more compound(s) of Formula I in combination with a chemotherapeutic agent selected from capecitabine, 5-fluorouracil, carboplatin, dacarbazine, gefitinib, oxaliplatin, paclitaxel, SN-38, temozolomide, vinblastine, bevacizumab, cetuximab, interferon-α, interleukin-2, or erlotinib.

In a twenty-seventh aspect, the invention provides a method of treating or prophylaxis of a disease or condition in a mammal in need thereof, by administering to the mammal a therapeutically effective amount of any one or more compound(s) of Formula I, a prodrug of such compound, a pharmaceutically acceptable salt of such compound or prodrug, or a pharmaceutically acceptable formulation of such compound or prodrug. The compound can be alone or can be part of a composition.

In one embodiment, the invention provides a method of treating or prophylaxis of a disease or condition in a mammal in need thereof, by administering to the mammal a therapeutically effective amount of any one or more compound(s) of Formula I, a prodrug of such compound, a pharmaceutically acceptable salt of such compound or prodrug, or a pharmaceutically acceptable formulation of such compound or prodrug in combination with one or more other suitable therapies for the disease or condition.

In a twenty-eighth aspect, the invention provides kits that include a compound or composition thereof as described herein. In some embodiments, the compound or composition is packaged, e.g., in a vial, bottle, flask, which may be further packaged, e.g., within a box, envelope, or bag; the compound or composition is approved by the U.S. Food and Drug Administration or similar regulatory agency for administration to a mammal, e.g., a human; the compound or composition is approved for administration to a mammal, e.g., a human, for a protein kinase mediated disease or condition; the invention kit includes written instructions for use and/or other indication that the compound or composition is suitable or approved for administration to a mammal, e.g., a human, for a protein kinase-mediated disease or condition; and the compound or composition is packaged in unit dose or single dose form, e.g., single dose pills, capsules, or the like.

In aspects and embodiments involving treatment or prophylaxis of a disease or condition with the compounds of Formula I, the invention provides methods for treating a Kit-mediated disease or condition in an animal subject in need thereof (e.g. a mammal such as a human, other primates, sports animals, animals of commercial interest such as cattle, farm animals such as horses, or pets such as dogs and cats), e.g., a disease or condition characterized by abnormal Kit activity (e.g. kinase activity). In some embodiments, invention methods may involve administering to the subject suffering from or at risk of a c-kit-mediated disease or condition an effective amount of a compound of Formula I. In one embodiment, the Kit mediated disease is selected from the group consisting of malignancies, including, but not limited to, mast cell tumors, small cell lung cancer, non-small cell lung cancer (NSCLC), testicular cancer, pancreatic cancer, breast cancer, merkel cell carcinoma, carcinomas of the female genital tract, sarcomas of neuroectodermal origin, colorectal carcinoma, carcinoma in situ, gastrointestinal stromal tumors (GISTs), tumor angiogenesis, glioblastoma, astrocytoma, neuroblastoma, Schwann cell neoplasia associated with neurofibromatosis, neurofibromatosis not associated with Schwann cell neoplasia, acute myeloid leukemia, acute lymphocytic leukemia, chronic myeloid leukemia, mastocytosis, melanoma, and canine mast cell tumors; cardiovascular disease, including but not limited to atherosclerosis, cardiomyopathy, heart failure, pulmonary hypertension; inflammatory and autoimmune indications, including, but not limited to, allergy, anaphylaxis, asthma, rheumatoid arthritis, allergic rhinitis, multiple sclerosis, inflammatory bowel disease, transplant rejection, hypereosinophilia, urticaria and dermatitis; gastrointestinal indications, including but not limited to gastroesophageal reflux disease (GERD), esophagitis, and gastrointestinal tract ulcers; ophthalmic indications, including but not limited to uveitis and retinitis; and neurologic indications, including but not limited to migraine.

In aspects and embodiments involving treatment or prophylaxis of a disease or condition with the compounds of Formula I, the invention provides methods for treating a Fms-mediated disease or condition in an animal subject in need thereof (e.g. a mammal such as a human, other primates, sports animals, animals of commercial interest such as cattle, farm animals such as horses, or pets such as dogs and cats), e.g., a disease or condition characterized by abnormal Fms activity (e.g. kinase activity). In some embodiments, invention methods may involve administering to the subject suffering from or at risk of a Fms-mediated disease or condition an effective amount of compound of Formula I. In one embodiment, the Fms mediated disease is selected from the group consisting of inflammatory and autoimmune indications, including, but not limited to, rheumatoid arthritis, osteoarthritis, psoriatic arthritis, psoriasis, dermatitis, ankylosing spondylitis, polymyositis, dermatomyositis, systemic sclerosis, juvenile idiopathic arthritis, polymyalgia rheumatica, Sjogren's disease, Langerhan's cell histiocytosis (LCH), Still's disease, inflammatory bowel disease, ulcerative colitis, Crohn's disease, systemic lupus erythematosis (SLE), immune thrombocytopenic purpura (ITP), myelopreparation for autologous transplantation, transplant rejection, chronic obstructive pulmonary disease (COPD), emphysema, Kawasaki's Disease, hemophagocytic syndrome (macrophage activation syndrome), multicentric reticulohistiocytosis, and atherosclerosis; metabolic disorders, including, but not limited to, Type I diabetes, Type II diabetes, insulin resistance, hyperglycemia, obesity, and lipolysis; disorders of bone structure, mineralization and bone formation and resorption, including, but not limited to, osteoporosis, osteodystrophy, increased risk of fracture, Paget's disease, hypercalcemia, infection-mediated osteolysis (e.g. osteomyelitis), and peri-prosthetic or wear-debris-mediated osteolysis; kidney and genitourinary diseases, including, but not limited to, endometriosis, nephritis (e.g. glomerulonephritis, interstitial nephritis, Lupus nephritis), tubular necrosis, diabetes-associated renal complications (e.g. diabetic nephropathy), and renal hypertrophy; disorders of the nervous system, including, but not limited to, demyelinating disorders (e.g. multiple sclerosis, Charcot Marie Tooth syndrome), amyotrophic lateral sclerosis (ALS), myasthenia gravis, chronic demyelinating polyneuropathy, other demyelinating disorders, stroke, Alzheimer's disease and Parkinson's disease; pain, including, but not limited to, chronic pain, acute pain, inflammatory pain, neuropathic pain, bone pain; malignancies, including, but not limited to, multiple myeloma, acute myeloid leukemia (AML), chronic myeloid leukemia (CML), lung cancer, pancreatic cancer, prostate cancer, breast cancer, ovarian cancer, neuroblastoma, sarcoma, osteosarcoma, giant cell tumors, (e.g. giant cell tumor of bone, giant cell tumor of tendon sheath (TGCT)), pigmented villonodular synovitis (PVNS), tumor angiogenesis, melanoma, glioblastoma multiforme, glioma, other tumors of the central nervous system, metastasis of tumors to other tissues, osteolytic bone metastases, and other chronic myeloproliferative diseases such as myelofibrosis; vasculitis, including but not limited to collagen vascular disease, polyarteritis nodosa, Behcet's disease, sarcoidosis, familiar Mediterranean fever, Churg-Strauss vasculitis, temporal arteritis, giant cell arteritis, Takayasu's arteritis; ophthalmic indications, including but not limited to uveitis, scleritis, retinitis, age related macular degeneration, choroidal neovascularization, diabetic retinopathy; inherited disorders, including but not limited to cherubism, neurofibromatosis; infectious disease indications, including but not limited to infections associated with human immunodeficiency virus, hepatitis B virus, hepatitis C virus, human granulocytic anaplasmosis; lysosomal storage disorders, including but not limited to Gaucher's disease, Fabry's disease, Niemann-Pick disease; gastrointestinal indications, including but not limited to liver cirrhosis; pulmonary indications, including but not limited to pulmonary fibrosis, acute lung injury (e.g. ventilator-induced, smoke- or toxin-induced); and surgical indications, including but not limited to (cardiopulmonary) bypass surgery, vascular surgery, and vascular grafts.

In aspects and embodiments involving treatment or prophylaxis of a disease or condition with the compounds of Formula I, the invention provides methods for treating a disease or condition mediated by Fms and Kit in an animal subject in need thereof (e.g. a mammal such as a human, other primates, sports animals, animals of commercial interest such as cattle, farm animals such as horses, or pets such as dogs and cats), e.g., a disease or condition characterized by abnormal Fms activity and Kit activity (e.g. kinase activity). In some embodiments, invention methods may involve administering to the subject suffering from or at risk of a disease or condition mediated by Fms and Kit an effective amount of compound of Formula I. In one embodiment, the condition mediated by Fms and Kit is selected from the group consisting of rheumatoid arthritis, osteoarthritis, psoriatic arthritis, psoriasis, dermatitis, allergy, anaphylaxis, asthma, allergic rhinitis, ankylosing spondylitis, polymyositis, dermatomyositis, systemic sclerosis, juvenile idiopathic arthritis, polymyalgia rheumatica, Sjogren's disease, Langerhan's cell histiocytosis, Still's disease, inflammatory bowel disease, ulcerative colitis, Crohn's disease, systemic lupus erythematosis, immune thrombocytopenic purpura, myelopreparation for autologous transplantation, transplant rejection, chronic obstructive pulmonary disease, emphysema, Kawasaki's Disease, hemophagocytic syndrome, multicentric reticulohistiocytosis, hypereosinophilia, and urticaria type I diabetes, type II diabetes, insulin resistance, hyperglycemia, obesity, and lipolysis, osteoporosis, osteodystrophy, increased risk of fracture, Paget's disease, hypercalcemia, infection-mediated osteolysis, and peri-prosthetic or wear-debris-mediated osteolysis, endometriosis, nephritis, tubular necrosis, diabetes-associated renal complications, and renal hypertrophy, multiple sclerosis, Charcot Marie Tooth syndrome, amyotrophic lateral sclerosis, myasthenia gravis, chronic demyelinating polyneuropathy, other demyelinating disorders, stroke, Alzheimer's disease and Parkinson's disease, acute pain, neuropathic pain, inflammatory pain, chronic pain, migraine, multiple myeloma, acute lymphocytic leukemia, acute myeloid leukemia, chronic myeloid leukemia, mast cell tumors, canine mast cell tumors, lung cancer, testicular cancer, pancreatic cancer, prostate cancer, breast cancer, ovarian cancer, merkel cell carcinoma, carcinomas of the female genital tract, colorectal carcinoma, carcinoma in situ, gastrointestinal stromal tumors, tumor angiogenesis, astrocytoma, neuroblastoma, sarcoma, osteosarcoma, sarcomas of neuroectodermal origin, giant cell tumor of bone, giant cell tumor of tendon sheath, pigmented villonodular synovitis, melanoma, glioblastoma, glioblastoma multiforme, glioma, other tumors of the central nervous system, Schwann cell neoplasia associated with neurofibromatosis, neurofibromatosis not associated with Schwann cell neoplasia, mastocytosis, metastasis of tumors to other tissues, osteolytic bone metastases, and other chronic myeloproliferative diseases such as myelofibrosis, collagen vascular disease, polyarteritis nodosa, Behcet's disease, sarcoidosis, familiar Mediterranean fever, Churg-Strauss vasculitis, temporal arteritis, giant cell arteritis, Takayasu's arteritis, uveitis, scleritis, retinitis, age related macular degeneration, choroidal neovascularization, diabetic retinopathy, cherubism, neurofibromatosis, infections associated with human immunodeficiency virus, hepatitis B virus, hepatitis C virus, human granulocytic anaplasmosis, Gaucher's disease, Fabry's disease, Niemann-Pick disease, liver cirrhosis, gastroesophageal reflux disease, esophagitis, and gastrointestinal tract ulcers, pulmonary fibrosis, acute lung injury, bypass surgery, vascular surgery, and vascular grafts, atherosclerosis, cardiomyopathy, heart failure, and pulmonary hypertension.

In aspects and embodiments involving treatment or prophylaxis of a disease or condition with the compounds of Formula I, invention methods may involve administering an effective amount of compound of Formula Ito a subject in need thereof suffering from or at risk of a disease or condition selected from the group consisting of rheumatoid arthritis, osteoarthritis, osteoporosis, peri-prosthetic osteolysis, systemic sclerosis, demyelinating disorders, multiple sclerosis, Charcot Marie Tooth syndrome, amyotrophic lateral sclerosis, Alzheimer's disease, Parkinson's disease, ulcerative colitis, Crohn's disease, immune thrombocytopenic purpura, myelopreparation for autologous transplantation, transplant rejection, nephritis, nephropathy, type I diabetes, acute pain, inflammatory pain, neuropathic pain, breast cancer, prostate cancer, pancreatic cancer, lung cancer, ovarian cancer, gliomas, glioblastomas, neurofibromatosis, osteolytic bone metastasis, and giant cell tumors.

In a twenty-ninth aspect, compounds of Formula I can be used in the preparation of a medicament for the treatment of a Kit-mediated disease or condition selected from the group consisting of malignancies, including, but not limited to, mast cell tumors, small cell lung cancer, non-small cell lung cancer, testicular cancer, pancreatic cancer, breast cancer, merkel cell carcinoma, carcinomas of the female genital tract, sarcomas of neuroectodermal origin, colorectal carcinoma, carcinoma in situ, gastrointestinal stromal tumors, tumor angiogenesis, glioblastoma, astrocytoma, neuroblastoma, Schwann cell neoplasia associated with neurofibromatosis, neurofibromatosis not associated with Schwann cell neoplasia, acute myeloid leukemia, acute lymphocytic leukemia, chronic myeloid leukemia, mastocytosis, melanoma, and canine mast cell tumors; cardiovascular disease, including but not limited to atherosclerosis, cardiomyopathy, heart failure, pulmonary hypertension; inflammatory and autoimmune indications, including, but not limited to, allergy, anaphylaxis, asthma, rheumatoid arthritis, allergic rhinitis, multiple sclerosis, inflammatory bowel disease, transplant rejection, hypereosinophilia, urticaria and dermatitis; gastrointestinal indications, including but not limited to gastroesophageal reflux disease, esophagitis, and gastrointestinal tract ulcers; ophthalmic indications, including but not limited to uveitis and retinitis; and neurologic indications, including but not limited to migraine.

In a thirtieth aspect, compounds of Formula I can be used in the preparation of a medicament for the treatment of a Fms-mediated disease or condition selected from the group consisting of inflammatory and autoimmune indications, including, but not limited to, rheumatoid arthritis, osteoarthritis, psoriatic arthritis, psoriasis, dermatitis, ankylosing spondylitis, polymyositis, dermatomyositis, systemic sclerosis, juvenile idiopathic arthritis, polymyalgia rheumatica, Sjogren's disease, Langerhan's cell histiocytosis (LCH), Still's disease, inflammatory bowel disease, ulcerative colitis, Crohn's disease, systemic lupus erythematosis (SLE), immune thrombocytopenic purpura (ITP), myelopreparation for autologous transplantation, transplant rejection, chronic obstructive pulmonary disease (COPD), emphysema, Kawasaki's Disease, hemophagocytic syndrome (macrophage activation syndrome), multicentric reticulohistiocytosis, and atherosclerosis; metabolic disorders, including, but not limited to, Type I diabetes, Type II diabetes, insulin resistance, hyperglycemia, obesity, and lipolysis; disorders of bone structure, mineralization and bone formation and resorption, including, but not limited to, osteoporosis, osteodystrophy, increased risk of fracture, Paget's disease, hypercalcemia, infection-mediated osteolysis (e.g. osteomyelitis), and peri-prosthetic or wear-debris-mediated osteolysis; kidney and genitourinary diseases, including, but not limited to, endometriosis, nephritis (e.g. glomerulonephritis, interstitial nephritis, Lupus nephritis), tubular necrosis, diabetes-associated renal complications (e.g. diabetic nephropathy), and renal hypertrophy; disorders of the nervous system, including, but not limited to, demyelinating disorders (e.g. multiple sclerosis, Charcot Marie Tooth syndrome), amyotrophic lateral sclerosis (ALS), myasthenia gravis, chronic demyelinating polyneuropathy, other demyelinating disorders, stroke, Alzheimer's disease and Parkinson's disease; pain, including, but not limited to, chronic pain, acute pain, inflammatory pain, neuropathic pain, bone pain; malignancies, including, but not limited to, multiple myeloma, acute myeloid leukemia (AML), chronic myeloid leukemia (CML), lung cancer, pancreatic cancer, prostate cancer, breast cancer, ovarian cancer, neuroblastoma, sarcoma, osteosarcoma, giant cell tumors, (e.g. giant cell tumor of bone, giant cell tumor of tendon sheath (TGCT)), pigmented villonodular synovitis (PVNS), tumor angiogenesis, melanoma, glioblastoma multiforme, glioma, other tumors of the central nervous system, metastasis of tumors to other tissues, osteolytic bone metastases, and other chronic myeloproliferative diseases such as myelofibrosis; vasculitis, including but not limited to collagen vascular disease, polyarteritis nodosa, Behcet's disease, sarcoidosis, familiar Mediterranean fever, Churg-Strauss vasculitis, temporal arteritis, giant cell arteritis, Takayasu's arteritis; ophthalmic indications, including but not limited to uveitis, scleritis, retinitis, age related macular degeneration, choroidal neovascularization, diabetic retinopathy; inherited disorders, including but not limited to cherubism, neurofibromatosis; infectious disease indications, including but not limited to infections associated with human immunodeficiency virus, hepatitis B virus, hepatitis C virus, human granulocytic anaplasmosis; lysosomal storage disorders, including but not limited to Gaucher's disease, Fabry's disease, Niemann-Pick disease; gastrointestinal indications, including but not limited to liver cirrhosis; pulmonary indications, including but not limited to pulmonary fibrosis, acute lung injury (e.g. ventilator-induced, smoke- or toxin-induced); and surgical indications, including but not limited to (cardiopulmonary) bypass surgery, vascular surgery, and vascular grafts.

In a thirty-first aspect, compounds of Formula I can be used in the preparation of a medicament for the treatment of a Fms-mediated and Kit mediated disease or condition selected from the group consisting of rheumatoid arthritis, osteoarthritis, psoriatic arthritis, psoriasis, dermatitis, allergy, anaphylaxis, asthma, allergic rhinitis, ankylosing spondylitis, polymyositis, dermatomyositis, systemic sclerosis, juvenile idiopathic arthritis, polymyalgia rheumatica, Sjogren's disease, Langerhan's cell histiocytosis, Still's disease, inflammatory bowel disease, ulcerative colitis, Crohn's disease, systemic lupus erythematosis, immune thrombocytopenic purpura, myelopreparation for autologous transplantation, transplant rejection, chronic obstructive pulmonary disease, emphysema, Kawasaki's Disease, hemophagocytic syndrome, multicentric reticulohistiocytosis, hypereosinophilia, and urticaria type I diabetes, type II diabetes, insulin resistance, hyperglycemia, obesity, and lipolysis, osteoporosis, osteodystrophy, increased risk of fracture, Paget's disease, hypercalcemia, infection-mediated osteolysis, and peri-prosthetic or wear-debris-mediated osteolysis, endometriosis, nephritis, tubular necrosis, diabetes-associated renal complications, and renal hypertrophy, multiple sclerosis, Charcot Marie Tooth syndrome, amyotrophic lateral sclerosis, myasthenia gravis, chronic demyelinating polyneuropathy, other demyelinating disorders, stroke, Alzheimer's disease and Parkinson's disease, acute pain, neuropathic pain, inflammatory pain, chronic pain, migraine, multiple myeloma, acute lymphocytic leukemia, acute myeloid leukemia, chronic myeloid leukemia, mast cell tumors, canine mast cell tumors, lung cancer, testicular cancer, pancreatic cancer, prostate cancer, breast cancer, ovarian cancer, merkel cell carcinoma, carcinomas of the female genital tract, colorectal carcinoma, carcinoma in situ, gastrointestinal stromal tumors, tumor angiogenesis, astrocytoma, neuroblastoma, sarcoma, osteosarcoma, sarcomas of neuroectodermal origin, giant cell tumor of bone, giant cell tumor of tendon sheath, pigmented villonodular synovitis, melanoma, glioblastoma, glioblastoma multiforme, glioma, other tumors of the central nervous system, Schwann cell neoplasia associated with neurofibromatosis, neurofibromatosis not associated with Schwann cell neoplasia, mastocytosis, metastasis of tumors to other tissues, osteolytic bone metastases, and other chronic myeloproliferative diseases such as myelofibrosis, collagen vascular disease, polyarteritis nodosa, Behcet's disease, sarcoidosis, familiar Mediterranean fever, Churg-Strauss vasculitis, temporal arteritis, giant cell arteritis, Takayasu's arteritis, uveitis, scleritis, retinitis, age related macular degeneration, choroidal neovascularization, diabetic retinopathy, cherubism, neurofibromatosis, infections associated with human immunodeficiency virus, hepatitis B virus, hepatitis C virus, human granulocytic anaplasmosis, Gaucher's disease, Fabry's disease, Niemann-Pick disease, liver cirrhosis, gastroesophageal reflux disease, esophagitis, and gastrointestinal tract ulcers, pulmonary fibrosis, acute lung injury, bypass surgery, vascular surgery, and vascular grafts, atherosclerosis, cardiomyopathy, heart failure, and pulmonary hypertension.

In a thirty-second aspect, compounds of Formula I can be used in the preparation of a medicament for the treatment of a disease or condition selected from the group consisting of rheumatoid arthritis, osteoarthritis, osteoporosis, peri-prosthetic osteolysis, systemic sclerosis, demyelinating disorders, multiple sclerosis, Charcot Marie Tooth syndrome, amyotrophic lateral sclerosis, Alzheimer's disease, Parkinson's disease, ulcerative colitis, Crohn's disease, immune thrombocytopenic purpura, myelopreparation for autologous transplantation, transplant rejection, nephritis, nephropathy, type I diabetes, acute pain, inflammatory pain, neuropathic pain, breast cancer, prostate cancer, pancreatic cancer, lung cancer, ovarian cancer, gliomas, glioblastomas, neurofibromatosis, osteolytic bone metastases, and giant cell tumors.

The compounds of Formula I with kinase activity $IC_{50}$ less than 10 μM as determined in a standard assay described herein can be used to treat protein kinase mediated diseases and conditions related to the following protein kinases, including any mutations thereof, for example without limitation:

Abl, related to chronic myeloid leukemia (CML), acute lymphoblastic leukemia (ALL) and acute myelogenous leukemia (AML);

Akt1, related to gastric, prostate, colorectal, ovarian, pancreatic and breast cancer, glioblastoma and leukemia, as well as schizophrenia and bipolar disorders, and also use in combination with other chemotherapeutic drugs;

Akt2, related to hyperglycemia due to peripheral insulin resistance and nonsuppressible hepatic glucose production accompanied by inadequate compensatory hyperinsulinemia, also related to pancreatic, ovarian and breast cancer;

Akt3, related to melanoma, prostate and breast cancer;

ALK, related to non-Hodgkin lymphomas such as diffuse large B-cell lymphoma and anaplastic large cell lymphoma;

Alk5, related to pancreatic and biliary cancers, and cutaneous T-cell lymphoma;

A-Raf, related to neurologic diseases such as multi-infarct dementia, head injury, spinal cord injury, Alzheimer's disease (AD), Parkinson's disease; neoplastic diseases including, but not limited to, melanoma, glioma, sarcoma, carcinoma (e.g. colorectal, lung, breast, pancreatic, thyroid, renal, ovarian), lymphoma (e.g. histiocytic lymphoma), neurofibromatosis, myelodysplastic syndrome, leukemia, tumor angiogenesis; pain of neuropathic or inflammatory origin, including acute pain, chronic pain, cancer-related pain and migraine; and diseases associated with muscle regeneration or degeneration, including, but not limited to, vascular restenosis, sarcopenia, muscular dystrophies (including, but not limited to, Duchenne, Becker, Emery-Dreifuss, Limb-Girdle, Facioscapulohumeral, Myotonic, Oculopharyngeal, Distal and Congenital Muscular Dystrophies), motor neuron diseases (including, but not limited to, amyotrophic lateral sclerosis, infantile progressive spinal muscular atrophy, intermediate spinal muscular atrophy, juvenile spinal muscular atrophy, spinal bulbar muscular atrophy, and adult spinal muscular atrophy), inflammatory myopathies (including, but not limited to, dermatomyositis, polymyositis, and inclusion body myositis), diseases of the neuromuscular junction (including, but not limited to, myasthenia gravis, Lambert-Eaton syndrome, and congenital myasthenic syndrome), myopathies due to endocrine abnormalities (including, but not limited to, hyperthyroid myopathy and hypothyroid myopathy) diseases of peripheral nerve (including, but not limited to, Charcot-Marie-Tooth disease, Dejerine-Sottas disease, and Friedreich's ataxia), other myopathies (including, but not limited to, myotonia congenita, paramyotonia congenita, central core disease, nemaline myopathy, myotubular myopathy, and periodic paralysis), and metabolic diseases of muscle (including, but not limited to, phosphorylase deficiency, acid maltase deficiency, phosphofructokinase deficiency, debrancher enzyme deficiency, mitochondrial myopathy, carnitine deficiency, carnitine palmatyl transferase deficiency, phosphoglycerate kinase deficiency, phosphoglycerate mutase deficiency, lactate dehydrogenase deficiency, and myoadenylate deaminase deficiency);

B-Raf or c-Raf-1, related to neurologic diseases, including, but not limited to, as multi-infarct dementia, head injury, spinal cord injury, Alzheimer's disease (AD), Parkinson's disease; neoplastic diseases including, but not limited to, melanoma, glioma, sarcoma, carcinoma (e.g. colorectal, lung, breast, pancreatic, thyroid, renal, ovarian), lymphoma (e.g. histiocytic lymphoma) neurofibromatosis, acute myeloid leukemia, myelodysplastic syndrome, leukemia, tumor angiogenesis, neuroendocrine tumors such as medullary thyroid cancer, carcinoid, small cell lung cancer and pheochromocytoma; pain of neuropathic or inflammatory origin, including, but not limited to, acute pain, chronic pain, cancer-related pain, and migraine; cardiovascular diseases including, but not limited to, heart failure, ischemic stroke, cardiac hypertrophy, thrombosis (e.g. thrombotic microangiopathy syndromes), atherosclerosis, reperfusion injury; inflammation including, but not limited to, psoriasis, arthritis and autoimmune diseases and conditions, osteoarthritis, endometriosis, scarring, vascular restenosis, fibrotic disorders, rheumatoid arthritis, inflammatory bowel disease (IBD); immunodeficiency diseases, including, but not limited to, organ transplant rejection, graft versus host disease; renal or prostatic diseases, including, but not limited to, diabetic nephropathy, polycystic kidney disease, nephrosclerosis, glomerulonephritis, prostate hyperplasia; metabolic disorders, including, but not limited to, obesity; infection, including, but not limited to, *Helicobacter pylori*, Hepatitis and Influenza viruses, fever, and sepsis; pulmonary diseases including, but not limited to, chronic obstructive pulmonary disease (COPD) and acute respiratory distress syndrome (ARDS); genetic developmental diseases, including, but not limited to, Noonan's syndrome, Costello syndrome, (faciocutaneoskeletal syndrome), LEOPARD syndrome, cardio-faciocutaneous syndrome (CFC), and neural crest syndrome abnormalities causing cardiovascular, skeletal, intestinal, skin, hair and endocrine diseases;

Brk, related to breast and colon cancer, and head and neck squamous cell carcinoma;

Btk, related to X-linked agammaglobulinemia, acute lymphocytic leukemia, autoimmune diseases such as multiple sclerosis, systemic lupus erythematosis, rheumatoid arthritis, and Graves' disease, immune suppression in organ transplant, and drug sensitivity of B-lineage cells;

Cdk2, related to prostate, breast, colorectal and ovarian cancer;

Cdk4, related to glioblastoma (e.g. glioblastoma multiforme), anaplastic astrocytoma, and breast cancer;

Cdk5, related to Alzheimer's disease, amyotrophic lateral sclerosis and Lewy body disease;

Cdk6, related to glioblastoma multiforme, non-Hodgkin's lymphoma, splenic marginal zone lymphoma, T-cell lymphoblastic lymphoma (T-LBL) and T-cell acute lymphoblastic leukemia (T-ALL);

CHK1, related to DNA damage repair, sensitizes cells to chemotherapeutic agents;

Csk, related to colon and pancreatic carcinomas and autoimmune pathology such as type 1 diabetes, rheumatoid arthritis and systemic lupus erythematosus;

EGFR, related to breast, colorectal, bladder, prostate and non small cell lung cancer, squamous cell carcinomas of the head and neck cancer, oral cavity, and esophagus, and glioblastoma multiforme;

EphA1, related to head and neck squamous cell carcinoma, hepatoma and lung cancer;

EphA2, related to aberrant short-range contact-mediated axonal guidance, bladder, breast, prostate, colon, skin, cervical, ovarian, pancreatic and lung cancers, and metastatic melanoma;

EphB2, related to angiogenesis disorder (e.g. ocular angiogenesis disease such as retinopathy), and cancer (e.g. glioblastoma, breast and liver cancer);

EphB4, related to colorectal cancer (CRC), head and neck squamous cell carcinoma, and tumours of the prostate, breast, endometrium, and bladder;

Erk2, related to aberrant proliferation, differentiation, transcription regulation and development, and may be useful in treating inflammation, for example inflammation associated with Lyme neuroborreliosis, and in treating cancers, such as gastric cancer;

Fak, related to colon and breast tumors, and is also related to esophageal squamous cell carcinoma, melanoma, anaplastic astrocytoma, glioblastoma, ductal carcinoma in situ, prostate and hepatocellular carcinoma, and tumor metastases, and may also provide synergistic effects when used with other chemotherapeutic drugs;

FGFR1, related to 8p11 myeloproliferative syndrome;

FGFR2, related to Crouzon Syndrome, Jackson-Weiss Syndrome, Apert Syndrome, craniosynostosis, Pfeiffer Syndrome, acrocephalo syndactyly type V, and Beare-Stevenson Cutis Gyrata Syndrome;

FGFR3, related to angiogenesis, wound healing, achondroplasia, Muenke craniosynostosis, Crouzon syndrome, acanthosis nigricans, thanatophoric dysplasia, bladder carcinomas, and multiple myeloma;

FGFR4, related to cancer of the breast, lung, colon, medullary thyroid, pancreas, ovary, prostate, endometrium, and fallopian tube, head and neck squamous cell carcinomas and leiomyosarcoma;

Flt1, related to non-small cell lung carcinoma, prostate carcinoma, and colorectal cancer;

Flt3, related to acute myeloid leukemia, myelodysplastic syndrome, acute lymphoblastic leukemia;

Flt4, related to primary lymphoedema; Fms, related to any and all diseases and indications discussed herein;

Frk, related to acute myeloid leukemia and type 1 diabetes;

Fyn, related to Alzheimer's disease, schizophrenia and prevention of metastases, e.g. in melanoma and squamous cell carcinoma;

GSK3 (Gsk3α and/or Gsk3β), related to CNS disorders such as Alzheimer's disease, Parkinson's disease, amyotrophic lateral sclerosis, diabetes type II, bipolar disorders, stroke, cancer, chronic inflammatory disease, leucopenia, schizophrenia, chronic pain, neuropathic pain, and traumatic head injury;

HCK, related to chronic myelogenous leukemia and acute lymphocytic leukemia;

Her2/Erbb2, related to prostate and breast cancer;

Her4/Erbb4, related to childhood medulloblastoma;

IGF1R, related to prostate cancer, hepatocellular carcinoma;

IKK beta, related to leukemia of T-cells, necrosis, insulin resistance, and malignant neoplasms;

Irak4, related to bacterial infections, immunodeficiency syndrome, Crohn's disease, ulcerative colitis, asthma, chronic bronchitis, cardio hypertrophy, and kidney hypertension;

Itk, related to allergic asthma;

Jak1, related to Hepatitis C virus infection;

Jak2, related to myeloproliferative disorders such as polycythaemia vera, myelofibrosis, essential thrombocythemia, myeloid metaplasia and leukemias, including acute lymphoblastic leukemia, chronic neutrophilic leukemia, juvenile myelomonocytic leukemia, CMML, Philadelphia chromosome-negative CML, megakaryocytic leukemia, and acute erythroid leukemia;

Jak3, related to X-linked severe combined immunodeficiency, myeloproliferative disorders, transplant rejection and autoimmune diseases such as rheumatoid arthritis, inflammatory bowel syndrome, Crohn's disease, systemic lupus erythematosis, ulcerative colitis, psoriasis and multiple sclerosis;

Jnk (Jnk1, Jnk2, Jnk3), related to metabolic diseases including type 1 diabetes, type 2 diabetes, metabolic syndrome, obesity, and hepatic steatosis; cardiovascular diseases such as atherosclerosis, ischemia (e.g. cerebrovascular ischemia, liver ischemia), reperfusion injury, cardiac hypertrophy; renal diseases such as chronic renal failure; neoplastic diseases and associated complications, including chemotherapy-induced hypoxia, prostate tumors, myeloid leukemia and cancers of the liver, bone, skin, brain, pancreas, lung breast, colon, prostate and ovary; transplant rejection; pain of neuropathic or inflammatory origin including acute and chronic pain; inflammatory and autoimmune diseases including age-related macular degeneration, rheumatoid arthritis, inflammatory bowel disease, ulcerative colitis, Crohn's disease, systemic lupus erythematosis, Sjogren's Syndrome, psoriasis, scleroderma, chronic thyroiditis, Grave's disease, myasthenia gravis, and multiple sclerosis, and inflammation in other organs including CNS inflammation, pancreatitis, nephritis, atopic dermatitis, and hepatitis; airway inflammatory diseases such as asthma, allergy, bronchitis, pulmonary fibrosis, chronic obstructive pulmonary disease; neurologic diseases such as stroke, cerebrovascular ischemia, neurodegenerative diseases such as Parkinson's disease, Alzheimer's disease, amyotrophic lateral sclerosis, dementia, senile chorea, head and spinal cord trauma, and Huntington's disease. More particularly, Jnk1 is related to type 1 diabetes, type 2 diabetes, metabolic syndrome, obesity and hepatic steatosis, Jnk2 is related to atherosclerosis, and Jnk3 is related to inflammatory diseases including autoimmune diseases such as rheumatoid arthritis, inflammatory bowel syndrome, Crohn's disease, systemic lupus erythematosis, Sjogren's Syndrome, psoriasis and multiple sclerosis, airway inflammatory diseases such as asthma, allergy, pulmonary fibrosis, and chronic obstructive pulmonary disease, and inflammation in other organs, such as CNS inflammation, pancreatitis, nephritis, and hepatitis; neurologic diseases such as stroke, cerebrovascular ischemia, and neurodegenerative diseases such as Parkinson's disease, Alzheimer's disease, and Huntington's disease; and neoplastic diseases such as prostate tumors and myeloid leukemia;

Kdr, related to anti-angiogenesis for treating solid tumor growth (e.g. ovarian, lung, breast, pancreatic, prostate, colon, gastrointestinal stromal tumor, non small cell lung cancer, and epidermoid cancer), metastasis, psoriasis, rheumatoid arthritis, diabetic retinopathy and age related macular degeneration;

Kit, related to any and all diseases and indications discussed herein;

Lck, related to acute lymphoblastic leukemia, T-cell lymphoma, lymphopenia, renal carcinoma, colon carcinoma, severe combined immunodeficiency, multiple sclerosis, inflammatory bowel and type I diabetes;

Lyn, related to dyslipidemia, dyslipoproteinemia, metabolic syndrome, septicemia, type II diabetes, cancer, obesity, pancreatitis, hypertension, renal disease, inflammation, and impotence;

MAP2K1, related to acute myeloid leukemia, breast, ovarian and liver cancer;

MAP2K2, related to cancer and inflammation;

MAP4K4, related to metabolic indications, including re-sensitizing fat and muscle cells to insulin, ameliorating the pathology in adipocytes, ameliorating the pathology in muscle cells, metabolic syndrome, and type II diabetes; a broad range of oncology indications, including blocking the migration, invasion and metastasis in many different tumor types; and T-cell mediated autoimmune diseases; MAPKAPK2, cancer (e.g. prostate, breast), stroke, menengitis, and inflammatory disorders;

Met, related to kidney, breast, bladder, non-small-cell lung, colorectal, and bladder cancers, and hepatocellular carcinoma;

Mnk1, related to conditions associated with heat shock, nutrient deprivation, oxidative or osmotic stress, and infection of mammalian cells (e.g. with viruses such as adenovirus (Ad) or influenza virus), and autoimmune diseases;

MLK1, related to neurodegenerative diseases such as Alzheimer's disease and Parkinson's disease, and inflammatory disorders;

mTOR, related to neuronal tumors, breast cancer, prostate cancer, acute myelogenous leukemia, lung cancer, pancreatic cancer, colon cancer, renal cancer and myeloma;

p38, related to acute coronary syndrome, stroke, atherosclerosis, and inflammatory autoimmune diseases such as rheumatoid arthritis, inflammatory bowel disease, and Crohn's disease;

PDGFR (PDGFRA, PDGFRB), related to idiopathic hypereosinophilic syndrome, chronic eosinophilic leukemia, glioma, gastrointestinal stromal tumors (GISTs), juvenile myelomonocytic leukemia, metastatic medulloblastoma, atherogenesis, and restenosis. More particularly, PDGFRA related to idiopathic hypereosinophilic syndrome, chronic eosinophilic leukemia, glioma, gastrointestinal stromal tumors (GISTs), juvenile myelomonocytic leukemia, metastatic medulloblastoma, atherogenesis, and restenosis, and PDGFRB related to idiopathic hypereosinophilic syndrome, chronic eosinophilic leukemia, juvenile myelomonocytic leukemia, and metastatic medulloblastoma;

PDPK1, related to cancer and diabetes;

PI3K (including PI3Kα, PI3Kβ, PI3δ and PI3Kγ), related to inflammatory disease, including asthma, chronic obstructive pulmonary disease, bronchitis, emphysema, eosinophilia, lung fibrosis, osteoarthritis, ankylosing spondylitis, sepsis, septic shock, inflammatory myopathies, meningitis, encephalitis, lacrimal parotid gland syndrome, acute respiratory distress syndrome and pancreatitis, graft vs. host disease; allergies, including allergic rhinitis, type I hypersensitivity reactions, atopic dermatitis, contact dermatitis, and eczema; cardiovascular disease, including atherosclerosis, pulmonary hypertension, deep venous thrombosis, stroke, myocardial infarction, myocardial contractility disorders, ischemia, thromoemolism, pulmonary embolism, acute arterial ischemia, peripheral thrombotic occlusions, coronary artery disease and acute coronary syndrome; autoimmune disease, including systemic lupus erythematosus, rheumatoid arthritis, multiple sclerosis, glomerulonephritis, scleroderma, chronic thyroiditis, Graves' disease, autoimmune gastritis, type I diabetes, autoimmune hemolytic anemia, autoimmune neutropenia, thrombocytopenia, atopic dermatitis, myasthenia gravis, inflammatory bowel disease, ulcerative colitis, Crohn's disease, psoriasis, and Sjogren's syndrome; cancers, including ovarian cancer, cervical cancer, breast cancer, colorectal cancer, endometrial cancer, gastric carcinomas, hepatocellular carcinoma, pancreatic cancer, small and non-small cell lung cancer, thyroid carcinoma, lymphomas, multiple myelomas, leukemias (e.g. acute myelogenous leukemia, chronic myelogenous leukemia), neuroblastomas and glioblastomas;

Pim1, related to cancers such as hematopoietic (e.g. acute myeloid and acute lymphoid leukemias) and prostate cancers, and non-Hodgkin's lymphomas;

Pim2, related to lymphomas;

Pim3, related to hepatocellular carcinoma;

PKC alpha, related to pituitary tumors and prefrontal cortical dysfunction such as distractibility, impaired judgment, impulsivity, and thought disorder, also may be used to sensitize chemotherapy in breast, colon, and non small cell lung cancers;

PKC beta, related to diabetic retinopathy;

PKC-theta, related to insulin resistance, T-cell lymphoma;

Plk1, related to cancers (e.g. lymphoma of the thyroid, non-Hodgkin's lymphomas, colorectal cancers, leukemias and melanoma), also useful as sensitizer in chemotherapy;

Pyk2, related to inflammation (e.g. osteoporosis, polycystic kidney disease, rheumatoid arthritis and inflammatory bowel disease), CNS disease (e.g. Parkinson's disease and Alzheimer's disease), stroke and cancers (e.g. gliomas, breast cancer, and pancreatic cancer);

Ret, related to cancer of the thyroid, neuroblastoma, familial medullary thyroid carcinoma (FMTC), multiple endocrine neoplasia type IIA and IIB (MEN2A, MEN2B), and neurodegenerative disorders (e.g. Hirschsprung's disease, Parkinson's disease, Alzheimer's disease, and amyotrophic lateral sclerosis);

ROCK (ROCK-1, ROCK-2), related to cancers (e.g. ovarian cancer, hepatocellular carcinoma, pancreatic cancer), ocular disease (e.g. glaucoma), cardiac hypertrophy, improved renal perfusion, transplant rejection, and acute respiratory distress syndrome;

Ron, related to cancer and inflammation;

Src, related to cancer and osteoporosis;

Stk6, related to gastric, bladder, breast, lung, CNS, ovarian, kidney, colon, prostate, pancreas, and cervical cancers, melanoma, leukemia, and neuroblastoma;

Syk, related to lymphomas (e.g. mantle cell lymphoma);

TEC, related to sepsis, septic shock, inflammation, rheumatoid arthritis, Crohn's disease, irritable bowel disease (IBD), and ulcerative colitis;

Tie2 (TEK), related to cancer, arthritis (e.g. rheumatoid arthritis), and atherosclerosis;

TrkA, related to pain (e.g. chronic pain, neuropathic pain), cancer (e.g. prostate cancer, lung cancer, pancreatic cancer), allergic disorders (e.g. asthma), arthritis, diabetic retinopathy, macular degeneration and psoriasis;

TrkB, related to obesity, hyperphagia, developmental delays, cancer (e.g. prostate cancer, lung cancer, Wilms tumors, neuroblastoma, pancreatic cancer), various neuropathies (e.g. stroke, multiple sclerosis, transverse myelitis, and encephalitis), and diabetes.

Yes, related to various cancers including esophageal squamous cell carcinoma; and Zap70, related to AIDS, systemic lupus erythematosus, myasthenia gravis, atherosclerosis, rejection of transplanted organs or tissues, allograft rejection including acute and chronic allograft rejection, graft versus host disease, rheumathoid arthritis, psoriasis, systemic sclerosis, atopic dermatitis, eczematous dermatitis, alopecia, and inflammation of the nasal mucus membrane, including all forms of rhinitis.

Additional aspects and embodiments will be apparent from the following Detailed Description of the Invention and from the claims.

DETAILED DESCRIPTION OF THE INVENTION

As used herein the following definitions apply unless clearly indicated otherwise:

All atoms designated within a Formula described herein, either within a structure provided, or within the definitions of variables related to the structure, is intended to include any isotope thereof, unless clearly indicated to the contrary. It is understood that for any given atom, the isotopes may be present essentially in ratios according to their natural occurrence, or one or more particular atoms may be enhanced with respect to one or more isotopes using synthetic methods known to one skilled in the art. Thus, hydrogen includes for example $^{1}H$, $^{2}H$, $^{3}H$; carbon includes for example $^{11}C$, $^{12}C$, $^{13}C$, $^{14}C$; oxygen includes for example $^{16}O$, $^{17}O$, $^{18}O$; nitrogen includes for example $^{13}N$, $^{14}N$, $^{15}N$; sulfur includes for example $^{32}S$, $^{33}S$, $^{34}S$, $^{35}S$, $^{36}S$, $^{37}S$, $^{38}S$; fluoro includes for example $^{17}F$, $^{18}F$, $^{19}F$; chloro includes for example $^{35}Cl$, $^{36}Cl$, $^{37}Cl$, $^{38}Cl$, $^{39}Cl$; and the like.

"Halogen" refer to all halogens, that is, chloro (Cl), fluoro (F), bromo (Br), or iodo (I).

"Hydroxyl" or "hydroxy" refer to the group —OH.

"Thiol" refers to the group —SH.

"Lower alkyl" alone or in combination means an alkane-derived radical containing from 1 to 6 carbon atoms (unless specifically defined) that includes a straight chain alkyl or branched alkyl. The straight chain or branched lower alkyl group is chemically feasible and attached at any available point to provide a stable compound. In many embodiments, a lower alkyl is a straight or branched alkyl group containing from 1-6, 1-4, or 1-2, carbon atoms, such as methyl, ethyl, propyl, isopropyl, butyl, t-butyl, and the like. A "substituted lower alkyl" denotes lower alkyl that is independently substituted, unless indicated otherwise, with one or more, preferably 1, 2, 3, 4 or 5, also 1, 2, or 3 substituents, attached at any available atom to provide a stable compound, wherein the substituents are selected from the group consisting of —F, —OH, —NH$_2$, —NO$_2$, —CN, —C(O)—OH, —C(S)—OH, —C(O)—NH$_2$, —C(S)—NH$_2$, —S(O)—NH$_2$, —S(O)$_2$—

NH$_2$, —C(O)—N(H)—OH, —C(S)—N(H)—OH, —N(H)—C(O)—NH$_2$, —N(H)—C(S)—NH$_2$, —N(H)—S(O)$_2$—NH$_2$, —C(NH)—NH$_2$, —O—R$^o$, —S—R$^o$, —O—C(O)—R$^o$, —O—C(S)—R$^o$, —C(O)—R$^o$, —C(S)—R$^o$, —C(O)—O—R$^o$, —C(S)—O—R$^o$, —S(O)—R$^o$, —S(O)$_2$—R$^o$, —C(O)—N(H)—R$^o$, —C(S)—N(H)—R$^o$, —C(O)—N(R$^o$)—R$^o$, —C(S)—N(R$^o$)—R$^o$, —S(O)—N(H)—R$^o$, —S(O)—N(R$^o$)—R$^o$, —S(O)$_2$—N(H)—R$^o$, —S(O)$_2$—N(R$^o$)—R$^o$, —C(O)—N(H)—O—R$^o$, —C(O)—N(R$^o$)—O—R$^o$, —C(S)—N(H)—O—R$^o$, —C(S)—N(R$^o$)—O—R$^o$, —C(O)—N(H)—S(O)$_2$—R$^o$, —C(O)—N(R$^o$)—S(O)$_2$—R$^o$, —C(S)—N(H)—S(O)$_2$—R$^o$, —C(S)—N(R$^o$)—S(O)$_2$—R$^o$, —S(O)$_2$—N(H)—C(O)—R$^o$, —S(O)$_2$—N(R$^o$)—C(O)—R$^o$, —S(O)$_2$—N(H)—C(S)—R$^o$, —S(O)$_2$—N(R$^o$)—C(S)—R$^o$, —C(NH)—N(H)—R$^o$, —C(NH)—N(R$^o$)—R$^o$, —N(H)—C(O)—R$^o$, —N(H)—C(S)—R$^o$, —N(R$^o$)—C(O)—R$^o$, —N(R$^o$)—C(S)—R$^o$, —N(H)—S(O)—R$^o$, —N(R$^o$)—S(O)—R$^o$, —N(H)—S(O)$_2$—R$^o$, —N(R$^o$)—S(O)$_2$—R$^o$, —N(H)—C(O)—N(H)—R$^o$, —N(H)—C(S)—N(H)—R$^o$, —N(R$^o$)—C(O)—NH$_2$, —N(R$^o$)—C(S)—NH$_2$, —N(R$^o$)—C(O)—N(H)—R$^o$, —N(R$^o$)—C(S)—N(H)—R$^o$, —N(H)—C(O)—N(R$^o$)—R$^o$, —N(H)—C(S)—N(R$^o$)—R$^o$, —N(R$^o$)—C(O)—N(R$^o$)—R$^o$, —N(R$^o$)—C(S)—N(R$^o$)—R$^o$, —N(H)—S(O)$_2$—N(H)—R$^o$, —N(R$^o$)—S(O)$_2$—NH$_2$, —N(R$^o$)—S(O)$_2$—N(H)—R$^o$, —N(H)—S(O)$_2$—N(R$^o$)—R$^o$, —N(R$^o$)—S(O)$_2$—N(R$^o$)—R$^o$, —N(H)—R$^o$, —N(R$^o$)—R$^o$, —R$^e$, —R$^f$, and —R$^g$. Furthermore, possible substitutions include subsets of these substitutions, such as are indicated herein, for example, in the description of compounds of Formula I, attached at any available atom to produce a stable compound. For example "fluoro substituted lower alkyl" denotes a lower alkyl group substituted with one or more fluoro atoms, such as perfluoroalkyl, where preferably the lower alkyl is substituted with 1, 2, 3, 4 or 5 fluoro atoms, also 1, 2, or 3 fluoro atoms. It is understood that substitutions are chemically feasible and attached at any available atom to provide a stable compound.

"Lower alkenyl" alone or in combination means a straight or branched hydrocarbon containing 2-6 carbon atoms (unless specifically defined) and at least one, preferably 1-3, more preferably 1-2, most preferably one, carbon to carbon double bond. Carbon to carbon double bonds may be either contained within a straight chain or branched portion. The straight chain or branched lower alkenyl group is chemically feasible and attached at any available point to provide a stable compound. Examples of lower alkenyl groups include ethenyl, propenyl, isopropenyl, butenyl, and the like. A "substituted lower alkenyl" denotes lower alkenyl that is independently substituted, unless indicated otherwise, with one or more, preferably 1, 2, 3, 4 or 5, also 1, 2, or 3 substituents, attached at any available atom to provide a stable compound, wherein the substituents are selected from the group consisting of —F, —OH, —NH$_2$, —NO$_2$, —CN, —C(O)—OH, —C(S)—OH, —C(O)—NH$_2$, —C(S)—NH$_2$, —S(O)—NH$_2$, —S(O)$_2$—NH$_2$, —C(O)—N(H)—OH, —C(S)—N(H)—OH, —N(H)—C(O)—NH$_2$, —N(H)—C(S)—NH$_2$, —N(H)—S(O)$_2$—NH$_2$, —C(NH)—NH$_2$, —O—R$^o$, —S—R$^o$, —O—C(O)—R$^o$, —O—C(S)—R$^o$, —C(O)—R$^o$, —C(S)—R$^o$, —C(O)—O—R$^o$, —C(S)—O—R$^o$, —S(O)—R$^o$, —S(O)$_2$—R$^o$, —C(O)—N(H)—R$^o$, —C(S)—N(H)—R$^o$, —C(O)—N(R$^o$)—R$^o$, —C(S)—N(R$^o$)—R$^o$, —S(O)—N(H)—R$^o$, —S(O)—N(R$^o$)—R$^o$, —S(O)$_2$—N(H)—R$^o$, —S(O)$_2$—N(R$^o$)—R$^o$, —C(O)—N(H)—O—R$^o$, —C(O)—N(R$^o$)—O—R$^o$, —C(S)—N(H)—O—R$^o$, —C(S)—N(R$^o$)—O—R$^o$, —C(O)—N(H)—S(O)$_2$—R$^o$, —C(O)—N(R$^o$)—S(O)$_2$—R$^o$, —C(S)—N(H)—S(O)$_2$—R$^o$, —C(S)—N(R$^o$)—S(O)$_2$—R$^o$, —S(O)$_2$—N(H)—C(O)—R$^o$, —S(O)$_2$—N(R$^o$)—C(O)—R$^o$, —S(O)$_2$—N(H)—C(S)—R$^o$, —S(O)$_2$—N(R$^o$)—C(S)—R$^o$, —C(NH)—N(H)—R$^o$, —C(NH)—N(R$^p$)—R$^c$, —N(H)—C(O)—R$^o$, —N(H)—C(S)—R$^o$, —N(R$^o$)—C(O)—R$^o$, —N(R$^o$)—C(S)—R$^o$, —N(H)—S(O)—R$^o$, —N(R$^o$)—S(O)—R$^o$, —N(H)—S(O)$_2$—R$^o$, —N(R$^o$)—S(O)$_2$—R$^o$, —N(H)—C(O)—N(H)—R$^o$, —N(H)—C(S)—N(H)—R$^o$, —N(R$^o$)—C(O)—NH$_2$, —N(R$^o$)—C(S)—NH$_2$, —N(R$^o$)—C(O)—N(H)—R$^o$, —N(R$^o$)—C(S)—N(H)—R$^o$, N(H)—C(O)—N(R$^o$)—R$^o$, —N(H)—C(S)—N(R$^o$)—R$^o$, —N(R$^o$)—C(O)—N(R$^o$)—R$^o$, —N(R$^o$)—C(S)—N(R$^o$)—R$^o$, —N(H)—S(O)$_2$—N(H)—R$^o$, —N(R$^o$)—S(O)$_2$—NH$_2$, —N(R$^o$)—S(O)$_2$—N(H)—R$^o$, —N(H)—S(O)$_2$—N(R$^o$)—R$^o$, —N(R$^o$)—S(O)$_2$—N(R$^o$)—R$^o$, —N(H)—R$^o$, —N(R$^o$)—R$^o$, —R$^d$, —R$^e$, and —R$^g$. Further, possible substitutions include subsets of these substitutions, such as are indicated herein, for example, in the description of compounds of Formula I, attached at any available atom to provide a stable compound. For example "fluoro substituted lower alkenyl" denotes a lower alkenyl group substituted with one or more fluoro atoms, where preferably the lower alkenyl is substituted with 1, 2, 3, 4 or 5 fluoro atoms, also 1, 2, or 3 fluoro atoms. It is understood that substitutions are chemically feasible and attached at any available atom to provide a stable compound.

"Lower alkynyl" alone or in combination means a straight or branched hydrocarbon containing 2-6 carbon atoms (unless specifically defined) containing at least one, preferably one, carbon to carbon triple bond. The straight chain or branched lower alkynyl group is chemically feasible and attached at any available point to provide a stable compound. Examples of alkynyl groups include ethynyl, propynyl, butynyl, and the like. A "substituted lower alkynyl" denotes lower alkynyl that is independently substituted, unless indicated otherwise, with one or more, preferably 1, 2, 3, 4 or 5, also 1, 2, or 3 substituents, attached at any available atom to provide a stable compound, wherein the substituents are selected from the group consisting of —F, —OH, —NH$_2$, —NO$_2$, —CN, —C(O)—OH, —C(S)—OH, —C(O)—NH$_2$, —C(S)—NH$_2$, —S(O)—NH$_2$, —S(O)$_2$—NH$_2$, —C(O)—N(H)—OH, —C(S)—N(H)—OH, —N(H)—C(O)—NH$_2$, —N(H)—C(S)—NH$_2$, —N(H)—S(O)$_2$—NH$_2$, —C(NH)—NH$_2$, —O—R$^o$, —S—R$^o$, —O—C(O)—R$^o$, —O—C(S)—R$^o$, —C(O)—R$^o$, —C(S)—R$^o$, —C(O)—O—R$^o$, —C(S)—O—R$^o$, —S(O)—R$^o$, —S(O)$_2$—R$^o$, —C(O)—N(H)—R$^o$, —C(S)—N(H)—R$^o$, —C(O)—N(R$^o$)—R$^o$, —C(S)—N(R$^o$)—R$^o$, —S(O)—N(H)—R$^o$, —S(O)—N(R$^o$)—R$^o$, —S(O)$_2$—N(H)—R$^o$, —S(O)$_2$—N(R$^o$)—R$^o$, —C(O)—N(H)—O—R$^o$, —C(O)—N(R$^o$)—O—R$^o$, —C(S)—N(H)—O—R$^o$, —C(S)—N(R$^o$)—O—R$^o$, —C(O)—N(H)—S(O)$_2$—R$^o$, —C(O)—N(R$^o$)—S(O)$_2$—R$^o$, —C(S)—N(H)—S(O)$_2$—R$^o$, —C(S)—N(R$^o$)—S(O)$_2$—R$^o$, —S(O)$_2$—N(H)—C(O)—R$^o$, —S(O)$_2$—N(R$^o$)—C(O)—R$^o$, —S(O)$_2$—N(H)—C(S)—R$^o$, —S(O)$_2$—N(R$^o$)—C(S)—R$^o$, —C(NH)—N(H)—R$^o$, —C(NH)—N(R$^p$)—R$^c$, —N(H)—C(O)—R$^o$, —N(H)—C(S)—R$^o$, —N(R$^o$)—C(O)—R$^o$, —N(R$^o$)—C(S)—R$^o$, —N(H)—S(O)—R$^o$, —N(R$^o$)—S(O)—R$^o$, —N(H)—S(O)$_2$—R$^o$, —N(R$^o$)—S(O)$_2$—R$^o$, —N(H)—C(O)—N(H)—R$^o$, —N(H)—C(S)—N(H)—R$^o$, —N(R$^o$)—C(O)—NH$_2$, —N(R$^o$)—C(S)—NH$_2$, —N(R$^o$)—C(O)—N(H)—R$^o$, N(H)—C(O)—N(R$^o$—R$^o$, —N(H)—C(S)—N(R$^o$)—R$^o$, —N(R$^o$)—C(O)—N(R$^o$)—R$^o$, —N(R$^o$)—C(S)—N(R$^o$)—R$^o$, —N(H)—S(O)$_2$—N(H)—R$^o$, —N(R$^o$)—S(O)$_2$—NH$_2$, —N(R$^o$)—S(O)$_2$—N(H)—R$^o$, —N(H)—S(O)$_2$—N(R$^o$)—R$^o$, —N(R$^o$)—S(O)$_2$—N(R$^o$)—R$^o$, —N(H)—R$^o$, —N(R$^o$)—R$^o$, —R$^d$, —R$^e$, and —R$^g$. Further, possible substitutions include subsets of these substitutions, such as are indicated herein, for example, in the description of compounds of Formula I, attached at any available atom to provide a stable compound. For example "fluoro substituted lower alkynyl" denotes a lower alkynyl group substituted with one or more fluoro atoms, where preferably the lower alkynyl is substituted with 1, 2, 3, 4 or 5 fluoro atoms, also 1, 2, or 3 fluoro atoms. It is understood that substitutions are chemically feasible and attached at any available atom to provide a stable compound.

"Cycloalkyl" refers to saturated or unsaturated, non-aromatic monocyclic, bicyclic or tricyclic carbon ring systems of 3-10, also 3-8, more preferably 3-6, ring members per ring, such as cyclopropyl, cyclopentyl, cyclohexyl, adamantyl, and the like. "Cycloalkylene" is a divalent cycloalkyl. A "substituted cycloalkyl" is a cycloalkyl that is independently substituted, unless indicated otherwise, with one or more, preferably 1, 2, 3, 4 or 5, also 1, 2, or 3 substituents, attached at any available atom to provide a stable compound, wherein the substituents are selected from the group consisting of halogen, —OH, —NH$_2$, —NO$_2$, —CN, —C(O)—OH, —C(S)—OH, —C(O)—NH$_2$, —C(S)—NH$_2$, —S(O)—NH$_2$, —S(O)$_2$—NH$_2$, —C(O)—N(H)—OH, —C(S)—N(H)—OH, —N(H)—C(O)—NH$_2$, —N(H)—C(S)—NH$_2$, —N(H)—S(O)$_2$—NH$_2$, —C(NH)—NH$_2$, —O—R$^o$, —S—R$^o$, —O—C(O)—R$^o$, —O—C(S)—R$^o$, —C(O)—R$^o$, —C(S)—R$^o$, —C(O)—O—R$^o$, —C(S)—O—R$^o$, —S(O)—R$^o$, —S(O)$_2$—R$^o$, —C(O)—N(H)—R$^o$, —C(S)—N(H)—R$^o$, —C(O)—N(R$^o$)—R$^o$, —C(S)—N(R$^o$)—R$^o$, —S(O)—N(H)—R$^o$, —S(O)—N(R$^o$)—R$^o$, —S(O)$_2$—N(H)—R$^o$, —S(O)$_2$—N(R$^o$)—R$^o$, —C(O)—N(H)—O—R$^o$, —C(O)—N(R$^o$)—O—R$^o$, —C(S)—N(H)—O—R$^o$, —C(S)—N(R$^o$)—O—R$^o$, —C(O)—N(H)—S(O)$_2$—R$^o$, —C(O)—N(R$^o$)—S(O)$_2$—R$^o$, —C(S)—N(H)—S(O)$_2$—R$^o$, —C(S)—N(R$^o$)—S(O)$_2$—R$^o$, —S(O)$_2$—N(H)—C(O)—R$^o$, —S(O)$_2$—N(R$^o$)—C(O)—R$^o$, —S(O)$_2$—N(H)—C(S)—R$^o$, —S(O)$_2$—N(R$^o$)—C(S)—R$^o$, —C(NH)—N(H)—R$^o$, —C(NH)—N(R$^p$)—R$^c$, —N(H)—C(O)—R$^o$, —N(H)—C(S)—R$^o$, —N(R$^o$)—C(O)—R$^o$, —N(R$^o$)—C(S)—R$^o$, —N(H)—S(O)—R$^o$, —N(R$^o$)—S(O)—R$^o$, —N(H)—S(O)$_2$—R$^o$, —N(R$^o$)—S(O)$_2$—R$^o$, —N(H)—C(O)—N(H)—R$^o$, —N(H)—C(S)—N(H)—R$^o$, —N(R$^o$)—C(O)—NH$_2$, —N(R$^o$)—C(S)—NH$_2$, —N(R$^o$)—C(O)—N(H)—R$^o$, —N(R$^o$)—C(S)—N(H)—R$^o$, —N(H)—C(O)—N(R$^o$)—R$^o$, —N(H)—C(S)—N(R$^o$)—R$^o$, —N(R$^o$)—C(O)—N(R$^o$)—R$^o$, —N(R$^o$)—C(S)—N(R$^o$)—R$^o$, —N(H)—S(O)$_2$—N(H)—R$^o$, —N(R$^o$)—S(O)$_2$—NH$_2$, —N(R$^o$)—S(O)$_2$—N(H)—R$^o$, —N(H)—S(O)$_2$—N(R$^o$)—R$^o$, —N(R$^o$)—S(O)$_2$—N(R$^o$)—R$^o$, —N(H)—R$^o$, —N(R$^o$)—R$^o$, —R$^d$, —R$^e$, —R$^f$, and —R$^g$. It is understood that substitutions are chemically feasible and attached at any available atom to provide a stable compound.

"Heterocycloalkyl" refers to a saturated or unsaturated non-aromatic cycloalkyl group having from 5 to 10 atoms in which from 1 to 3 carbon atoms in the ring are replaced by heteroatoms of O, S or N, and are optionally fused with benzo or heteroaryl of 5-6 ring members. Heterocycloalkyl is also intended to include oxidized S or N, such as sulfinyl, sulfonyl and N-oxide of a tertiary ring nitrogen. Heterocycloalkyl is also intended to include compounds in which a ring carbon may be oxo substituted, i.e. the ring carbon is a carbonyl group, such as lactones and lactams. The point of attachment of the heterocycloalkyl ring is at a carbon or nitrogen atom such that a stable ring is retained. Examples of heterocycloalkyl groups include, but are not limited to, morpholino, tetrahydrofuranyl, dihydropyridinyl, piperidinyl, pyrrolidinyl, pyrrolidonyl, piperazinyl, dihydrobenzofuryl, and dihydroindolyl. "Heterocycloalkylene" is a divalent heterocycloalkyl. A "substituted heterocycloalkyl" is a heterocycloalkyl that is independently substituted, unless indicated otherwise, with one or more, preferably 1, 2, 3, 4 or 5, also 1, 2, or 3 substituents, attached at any available atom to provide a stable compound, wherein the substituents are selected from the group consisting of halogen, —OH, —NH$_2$, —NO$_2$, —CN, —C(O)—OH, —C(S)—OH, —C(O)—NH$_2$, —C(S)—NH$_2$, —S(O)—NH$_2$, —S(O)$_2$—NH$_2$, —C(O)—N(H)—OH, —C(S)—N(H)—OH, —N(H)—C(O)—NH$_2$, —N(H)—C(S)—NH$_2$, —N(H)—S(O)$_2$—NH$_2$, —C(NH)—NH$_2$, —O—R$^o$, —S—R$^o$, —O—C(O)—R$^o$, —O—C(S)—R$^o$, —C(O)—R$^o$, —C(S)—R$^o$, —C(O)—O—R$^o$, —C(S)—O—R$^o$, —S(O)—R$^o$, —S(O)$_2$—R$^o$, —C(O)—N(H)—R$^o$, —C(S)—N(H)—R$^o$, —C(O)—N(R$^o$)—R$^o$, —C(S)—N(R$^o$)—R$^o$, —S(O)—N(H)—R$^o$, —S(O)—N(R$^o$)—R$^o$, —S(O)$_2$—N(H)—R$^o$, —S(O)$_2$—N(R$^o$)—R$^o$, —C(O)—N(H)—O—R$^o$, —C(O)—N(R$^o$)—O—R$^o$, —C(S)—N(H)—O—R$^o$, —C(S)—N(R$^o$)—O—R$^o$, —C(O)—N(H)—S(O)$_2$—R$^o$, —C(O)—N(R$^o$)—S(O)$_2$—R$^o$, —C(S)—N(H)—S(O)$_2$—R$^o$, —C(S)—N(R$^o$)—S(O)$_2$—R$^o$, —S(O)$_2$—N(H)—C(O)—R$^o$, —S(O)$_2$—N(R$^o$)—C(O)—R$^o$, —S(O)$_2$—N(H)—C(S)—R$^o$, —S(O)$_2$—N(R$^o$)—C(S)—R$^o$, —C(NH)—N(H)—R$^o$, —C(NH)—N(R$^p$)—R$^c$, —N(H)—C(O)—R$^o$, —N(H)—C(S)—R$^o$, —N(R$^o$)—C(O)—R$^o$, —N(R$^o$)—C(S)—R$^o$, —N(H)—S(O)—R$^o$, —N(R$^o$)—S(O)—R$^o$, —N(H)—S(O)$_2$—R$^o$, —N(R$^o$)—S(O)$_2$—R$^o$, —N(H)—C(O)—N(H)—R$^o$, —N(H)—C(S)—N(H)—R$^o$, "Aryl" alone or in combination refers to a monocyclic or bicyclic ring system containing aromatic hydrocarbons such as phenyl or naphthyl, which may be optionally fused with a cycloalkyl of preferably 5-7, more preferably 5-6, ring members. "Arylene" is a divalent aryl. A "substituted aryl" is an aryl that is independently substituted, unless indicated otherwise, with one or more, preferably 1, 2, 3, 4 or 5, also 1, 2, or 3 substituents, attached at any available atom to provide a stable compound, wherein the substituents are selected from the group consisting of halogen, —OH, —NH$_2$, —NO$_2$, —CN, —C(O)—OH, —C(S)—OH, —C(O)—NH$_2$, —C(S)—NH$_2$, —S(O)—NH$_2$, —S(O)$_2$—NH$_2$, —C(O)—N(H)—OH, —C(S)—N(H)—OH, —N(H)—C(O)—NH$_2$, —N(H)—C(S)—NH$_2$, —N(H)—S(O)$_2$—NH$_2$, —C(NH)—NH$_2$, —O—R$^o$, —S—R$^o$, —O—C(O)—R$^o$, —O—C(S)—R$^o$, —C(O)—R$^o$, —C(S)—R$^o$, —C(O)—O—R$^o$, —C(S)—O—R$^o$, —S(O)—R$^o$, —S(O)$_2$—R$^o$, —C(O)—N(H)—R$^o$, —C(S)—N(H)—R$^o$, —C(O)—N(R$^o$)—R$^o$, —C(S)—N(R$^o$)—R$^o$, —S(O)—N(H)—R$^o$, —S(O)—N(R$^o$)—R$^o$, —S(O)$_2$—N(H)—R$^o$, —S(O)$_2$—N(R$^o$)—R$^o$, —C(O)—N(H)—O—R$^o$, —C(O)—N(R$^o$)—O—R$^o$, —C(S)—N(H)—O—R$^o$, —C(S)—N(R$^o$)—O—R$^o$, —C(O)—N(H)—S(O)$_2$—R$^o$, —C(O)—N(R$^o$)—S(O)$_2$—R$^o$, —C(S)—N(H)—S(O)$_2$—R$^o$, —C(S)—N(R$^o$)—S(O)$_2$—R$^o$, —S(O)$_2$—N(H)—C(O)—R$^o$, —S(O)$_2$—N(R$^o$)—C(O)—R$^o$, —S(O)$_2$—N(H)—C(S)—R$^o$, —S(O)$_2$—N(R$^o$)—C(S)—R$^o$, —C(NH)—N(H)—R$^o$, —C(NH)—N(R$^p$)—R$^c$, —N(H)—C(O)—R$^o$, —N(H)—C(S)—R$^o$, —N(R$^o$)—C(O)—R$^o$, —N(R$^o$)—C(S)—R$^o$, —N(H)—S(O)—R$^o$, —N(R$^o$)—S(O)—R$^o$, —N(H)—S(O)$_2$—R$^o$, —N(R$^o$)—S(O)$_2$—R$^o$, —N(H)—C(O)—N(H)—R$^o$, —N(H)—C(S)—N(H)—R$^o$, —N(R$^o$)—C(O)—NH$_2$, —N(R$^o$)—C(S)—NH$_2$, —N(R$^o$)—C(O)—N(H)—R$^o$, —N(R$^o$)—C(S)—N(H)—R$^o$, —N(H)—C(O)—N(R$^o$)—R$^o$, —N(H)—C(S)—N(R$^o$)—R$^o$, —N(R$^o$)—C(O)—N(R$^o$)—R$^o$, —N(R$^o$)—C(S)—N(R$^o$)—R$^o$, —N(H)—S(O)$_2$—N(H)—R$^o$, —N(R$^o$)—S(O)$_2$—NH$_2$, —N(R$^o$)—S(O)$_2$—N(H)—R$^o$, —N(H)—S(O)$_2$—N(R$^o$)—R$^o$, —N(R$^o$)—S(O)$_2$—N(R$^o$)—R$^o$, —N(H)—R$^o$, —N(R$^o$)—R$^o$, —R$^d$, —R$^e$, —R$^f$, and —R$^g$. A "substituted arylene" is a divalent substituted aryl. It is understood that substitutions are chemically feasible and attached at any available atom to provide a stable compound.

"Heteroaryl" alone or in combination refers to a monocyclic aromatic ring structure containing 5 or 6 ring atoms, or a bicyclic aromatic group having 8 to 10 atoms, containing one or more, preferably 1-4, more preferably 1-3, even more preferably 1-2, heteroatoms independently selected from the group consisting of O, S, and N. Heteroaryl is also intended to include oxidized S or N, such as sulfinyl, sulfonyl and N-oxide of a tertiary ring nitrogen. A carbon or nitrogen atom is the point of attachment of the heteroaryl ring structure such that a stable compound is provided. Examples of heteroaryl groups include, but are not limited to, pyridinyl, pyridazinyl, pyrazinyl, quinaoxalyl, indolizinyl, benzo[b]thienyl, quinazolinyl, purinyl, indolyl, quinolinyl, pyrimidinyl, pyrrolyl, pyrazolyl, oxazolyl, thiazolyl, thienyl, isoxazolyl, oxathiadiazolyl, isothiazolyl, tetrazolyl, imidazolyl, triazolyl, furanyl, benzofuryl, and indolyl. "Nitrogen containing heteroaryl" refers to heteroaryl wherein any heteroatoms are N. "Heteroarylene" is a divalent heteroaryl. A "substituted heteroaryl" is a heteroaryl that is independently substituted, unless indicated otherwise, with one or more, preferably 1, 2, 3, 4 or 5, also 1, 2, or 3 substituents, attached at any available atom to provide a stable compound, wherein the substituents are selected from the group consisting of halogen, —OH, —NH$_2$, —NO$_2$, —CN, —C(O)—OH, —C(S)—OH, —C(O)—NH$_2$, —C(S)—NH$_2$, —S(O)—NH$_2$, —S(O)$_2$—NH$_2$, —C(O)—N(H)—OH, —C(S)—N(H)—OH, —N(H)—C(O)—NH$_2$, —N(H)—C(S)—NH$_2$, —N(H)—S(O)$_2$—NH$_2$, —C(NH)—NH$_2$, —O—R$^o$, —S—R$^o$, —O—C(O)—R$^o$, —O—C(S)—R$^o$, —C(O)—R$^o$, —C(S)—R$^o$, —C(O)—O—R$^o$, —C(S)—O—R$^o$, —S(O)—R$^o$, —S(O)$_2$—R$^o$, —C(O)—N(H)—R$^o$, —C(S)—N(H)—R$^o$, —C(O)—N(R$^o$)—R$^o$, —C(S)—N(R$^o$)—R$^o$, —S(O)—N(H)—R$^o$, —S(O)—N(R$^o$)—R$^o$, —S(O)$_2$—N(H)—R$^o$, —S(O)$_2$—N(R$^o$)—R$^o$, —C(O)—N(H)—O—R$^o$, —C(O)—N(R$^o$)—O—R$^o$, —C(S)—N(H)—O—R$^o$, —C(S)—N(R$^o$)—O—R$^o$, —C(O)—N(H)—S(O)$_2$—R$^o$, —C(O)—N(R$^o$)—S(O)$_2$—R$^o$, —C(S)—N(H)—S(O)$_2$—R$^o$, —C(S)—N(R$^o$)—S(O)$_2$—R$^o$, —S(O)$_2$—N(H)—C(O)—R$^o$, —S(O)$_2$—N(R$^o$)—C(O)—R$^o$, —S(O)$_2$—N(H)—C(S)—R$^o$, —S(O)$_2$—N(R$^o$)—C(S)—R$^o$, —C(NH)—N(H)—R$^o$, —C(NH)—N(R$^p$)—R$^c$, —N(H)—C(O)—R$^o$, —N(H)—C(S)—R$^o$, —N(R$^o$)—C(O)—R$^o$, —N(R$^o$)—C(S)—R$^o$, —N(H)—S(O)—R$^o$, —N(R$^o$)—S(O)—R$^o$, —N(H)—S(O)$_2$—R$^o$, —N(R$^o$)—S(O)$_2$—R$^o$, —N(H)—C(O)—N(H)—R$^o$, —N(H)—C(S)—N(H)—R$^o$, —N(R$^o$)—C(O)—NH$_2$, —N(R$^o$)—C(S)—NH$_2$, —N(R$^o$)—C(O)—N(H)—R$^o$, —N(R$^o$)—C(S)—N(H)—R$^o$, —N(H)—C(O)—N(R$^o$)—R$^o$, —N(H)—C(S)—N(R$^o$)—R$^o$, —N(R$^o$)—C(O)—N(R$^o$)—R$^o$, —N(R$^o$)—C(S)—N(R$^o$)—R$^o$, —N(H)—S(O)$_2$—N(H)—R$^o$, —N(R$^o$)—S(O)$_2$—NH$_2$, —N(R$^o$)—S(O)$_2$—N(H)—R$^o$, —N(H)—S(O)$_2$—N(R$^o$)—R$^o$, —N(R$^o$)—S(O)$_2$—N(R$^o$)—R$^o$, —N(H)—R$^o$, —N(R$^o$)—R$^o$, —R$^d$, —R$^e$, —R$^f$, and —R$^g$. "Substituted heteroarylene" is a divalent substituted heteroaryl. It is understood that substitutions are chemically feasible and attached at any available atom to provide a stable compound.

The variables R$^o$, R$^p$, R$^c$, R$^d$, R$^e$, R$^f$ and R$^g$ as used in the description of optional substituents for alkyl, alkenyl, alkynyl, cycloalkyl, heterocycloalkyl, aryl and heteroaryl are defined as follows:

each R$^o$, R$^p$, and R$^e$ are independently selected from the group consisting of R$^d$, R$^e$, R$^f$, and R$^g$, or R$^p$ and R$^c$ combine with the nitrogen to which they are attached to form a 5-7 membered heterocycloalkyl or a 5 or 7 membered nitrogen containing heteroaryl, wherein the 5-7 membered heterocycloalkyl or 5 or 7 membered nitrogen containing heteroaryl are optionally substituted with one or more, preferably 1, 2, 3, 4 or 5, also 1, 2, or 3 substituents selected from the group consisting of halogen, —NO$_2$, —CN, —OH, —NH$_2$, —O—R$^u$, —S—R$^u$, —N(H)—R$^u$, —N(R$^u$)—R$^u$, —R$^x$, and —R$^y$;

each R$^d$ is independently lower alkyl, wherein lower alkyl is optionally substituted with one or more, preferably 1, 2, 3, 4 or 5, also 1, 2 or 3 substituents selected from the group consisting of fluoro, —OH, —NH$_2$, —NO$_2$, —CN, —C(O)—OH, —C(S)—OH, —C(O)—NH$_2$, —C(S)—NH$_2$, —S(O)—NH$_2$, —S(O)$_2$—NH$_2$, —C(O)—N(H)—OH, —C(S)—N(H)—OH, —N(H)—C(O)—NH$_2$, —N(H)—C(S)—NH$_2$, —N(H)—S(O)$_2$—NH$_2$, —C(NH)—NH$_2$, —O—R$^k$, —S—R$^k$, —O—C(O)—R$^k$, —O—C(S)—R$^k$, —C(O)—R$^k$, —C(S)—R$^k$, —C(O)—O—R$^k$, —C(S)—O—R$^k$, —S(O)—R$^k$, —S(O)$_2$—R$^k$, —C(O)—N(H)—R$^k$, —C(S)—N(H)—R$^k$, —C(O)—N(R$^k$)—R$^k$, —C(S)—N(R$^k$)—R$^k$, —S(O)—N(H)—R$^k$, —S(O)—N(R$^k$)—R$^k$, —S(O)$_2$—N(H)—R$^k$, —S(O)$_2$—N(R$^k$)—R$^k$, —C(O)—N(H)—O—R$^k$, —C(O)—N(R$^k$)—O—R$^k$, —C(S)—N(H)—O—R$^k$, —C(S)—N(R$^k$)—O—R$^k$, —C(O)—N(H)—S(O)$_2$—R$^k$, —C(O)—N(R$^k$)—S(O)$_2$—R$^k$, —C(S)—N(H)—S(O)$_2$—R$^k$, —C(S)—N(R$^k$)—S(O)$_2$—R$^k$, —S(O)$_2$—N(H)—C(O)—R$^k$, —S(O)$_2$—N(R$^k$)—C(O)—R$^k$, —S(O)$_2$—N(H)—C(S)—R$^k$, —S(O)$_2$—N(R$^k$)—C(S)—R$^k$, —C(NH)—N(H)—R$^k$, —C(NH)—N(R$^m$)—R$^n$, —N(H)—C(O)—R$^k$, —N(H)—C(S)—R$^k$, —N(R$^k$)—C(O)—R$^k$, —N(R$^k$)—C(S)—R$^k$, —N(H)—S(O)—R$^k$, —N(R$^k$)—S(O)—R$^k$, —N(R$^k$)—S(O)$_2$—R$^k$, —N(H)—C(O)—N(H)—R$^k$, —N(H)—C(S)—N(H)—R$^k$, —N(R$^k$)—C(O)—NH$_2$, —N(R$^k$)—C(S)—NH$_2$, —N(R$^k$)—C(O)—N(H)—R$^k$, —N(R$^k$)—C(S)—N(H)—R$^k$, —N(H)—C(O)—N(R$^k$)—R$^k$, —N(H)—C(S)—N(R$^k$)—R$^k$, —N(R$^k$)—C(O)—N(R$^k$)—R$^k$, —N(R$^k$)—C(S)—N(R$^k$)—R$^k$, —N(H)—S(O)$_2$—N(H)—R$^k$, —N(R$^k$)—S(O)$_2$—NH$_2$, —N(R$^k$)—S(O)$_2$—N(H)—R$^k$, —N(H)—S(O)$_2$—N(R$^k$)—R$^k$, —N(R$^k$)—S(O)$_2$—N(R$^k$)—R$^k$, —N(H)—R$^k$, —N(R$^k$)—R$^k$, —R$^i$, and —R$^j$;

each R$^e$ is independently lower alkenyl, wherein lower alkenyl is optionally substituted with one or more, preferably 1, 2, 3, 4 or 5, also 1, 2 or 3 substituents selected from the group consisting of fluoro, —OH, —NH$_2$, —NO$_2$, —CN, —C(O)—OH, —C(S)—OH, —C(O)—NH$_2$, —C(S)—NH$_2$, —S(O)—NH$_2$, —S(O)$_2$—NH$_2$, —C(O)—N(H)—OH, —C(S)—N(H)—OH, —N(H)—C(O)—NH$_2$, —N(H)—C(S)—NH$_2$, —N(H)—S(O)$_2$—NH$_2$, —C(NH)—NH$_2$, —O—R$^k$, —S—R$^k$, —O—C(O)—R$^k$, —O—C(S)—R$^k$, —C(O)—R$^k$, —C(S)—R$^k$, —C(O)—O—R$^k$, —C(S)—O—R$^k$, —S(O)—R$^k$, —S(O)$_2$—R$^k$, —C(O)—N(H)—R$^k$, —C(S)—N(H)—R$^k$, —C(O)—N(R$^k$)—R$^k$, —C(S)—N(R$^k$)—R$^k$, —S(O)—N(H)—R$^k$, —S(O)—N(R$^k$)—R$^k$, —S(O)$_2$—N(H)—R$^k$, —S(O)$_2$—N(R$^k$)—R$^k$, —C(O)—N(H)—O—R$^k$, —C(O)—N(R$^k$)—O—R$^k$, —C(S)—N(H)—O—R$^k$, —C(S)—N(R$^k$)—O—R$^k$, —C(O)—N(H)—S(O)$_2$—R$^k$, —C(O)—N(R$^k$)—S(O)$_2$—R$^k$, —C(S)—N(H)—S(O)$_2$—R$^k$, —C(S)—N(R$^k$)—S(O)$_2$—R$^k$, —S(O)$_2$—N(H)—C(O)—R$^k$, —S(O)$_2$—N(R$^k$)—C(O)—R$^k$, —S(O)$_2$—

—N(H)—C(S)—R$^k$, —S(O)$_2$—N(R$^k$)—C(S)—R$^k$, —C(NH)—N(H)—R$^k$, —C(NH)—N(R$^m$)—R$^n$, —N(H)—C(O)—R$^k$, —N(H)—C(S)—R$^k$, —N(R$^k$)—C(O)—R$^k$, —N(H)—S(O)—R$^k$, —N(R$^k$)—S(O)—R$^k$, —N(H)—S(O)$_2$—R$^k$, —N(R$^k$)—S(O)$_2$—R$^k$, —N(H)—C(O)—N(H)—R$^k$, —N(H)—C(S)—N(H)—R$^k$, —N(R$^k$)—C(O)—NH$_2$, —N(R$^k$)—C(S)—NH$_2$, —N(R$^k$)—C(O)—N(H)—R$^k$, —N(R$^k$)—C(S)—N(H)—R$^k$, —N(H)—C(O)—N(R$^k$)—R$^k$, —N(H)—C(S)—N(R$^k$)—R$^k$, —N(R$^k$)—C(O)—N(R)—R$^k$, —N(R$^k$)—C(S)—N(R$^k$)—R$^k$, —N(H)—S(O)$_2$—N(H)—R$^k$, —N(R$^k$)—S(O)$_2$—NH$_2$, —N(R$^k$)—S(O)$_2$—N(H)—R$^k$, —N(H)—S(O)$_2$—N(R$^k$)—R$^k$, —N(R$^k$)—S(O)$_2$—N(R$^k$)—R$^k$, —N(H)—R$^k$, —N(R$^k$)—R$^k$, —R$^h$, and —R$^j$;

each R$^f$ is independently lower alkynyl, wherein lower alkynyl is optionally substituted with one or more, preferably 1, 2, 3, 4 or 5, also 1, 2 or 3 substituents selected from the group consisting of fluoro, —OH, —NH$_2$, —NO$_2$, —CN, —C(O)—OH, —C(S)—OH, —C(O)—NH$_2$, —C(S)—NH$_2$, —S(O)—NH$_2$, —S(O)$_2$—NH$_2$, —C(O)—N(H)—OH, —C(S)—N(H)—OH, —N(H)—C(O)—NH$_2$, —N(H)—C(S)—NH$_2$, —N(H)—S(O)$_2$—NH$_2$, —C(NH)—NH$_2$, —O—R$^k$, —S—R$^k$, —O—C(O)—R$^k$, —O—C(S)—R$^k$, —C(O)—R$^k$, —C(S)—R$^k$, —C(O)—O—R$^k$, —C(S)—O—R$^k$, —S(O)—R$^k$, —S(O)$_2$—R$^k$, —C(O)—N(H)—R$^k$, —C(S)—N(H)—R$^k$, —C(O)—N(R$^k$)—R$^k$, —C(S)—N(R$^k$)—R$^k$, —S(O)—N(H)—R$^k$, —S(O)—N(R$^k$)—R$^k$, —S(O)$_2$—N(H)—R$^k$, —S(O)$_2$—N(R$^k$)—R$^k$, —C(O)—N(H)—O—R$^k$, —C(O)—N(R$^k$)—O—R$^k$, —C(S)—N(H)—O—R$^k$, —C(S)—N(R$^k$)—O—R$^k$, —C(O)—N(H)—S(O)$_2$—R$^k$, —C(O)—N(R$^k$)—S(O)$_2$—R$^k$, —C(S)—N(H)—S(O)$_2$—R$^k$, —C(S)—N(R$^k$)—S(O)$_2$—R$^k$, —S(O)$_2$—N(H)—C(O)—R$^k$, —S(O)$_2$—N(R$^k$)—C(O)—R$^k$, —S(O)$_2$—N(H)—C(S)—R$^k$, —S(O)$_2$—N(R$^k$)—C(S)—R$^k$, —C(NH)—N(H)—R$^k$, —C(NH)—N(R$^m$)—R$^n$, —N(H)—C(O)—R$^k$, —N(H)—C(S)—R$^k$, —N(R$^k$)—C(O)—R$^k$, —N(R$^k$)—C(S)—R$^k$, —N(H)—S(O)—R$^k$, —N(R$^k$)—S(O)—R$^k$, —N(H)—S(O)$_2$—R$^k$, —N(R$^k$)—S(O)$_2$—R$^k$, —N(H)—C(O)—N(H)—R$^k$, —N(H)—C(S)—N(H)—R$^k$, —N(R$^k$)—C(O)—NH$_2$, —N(R$^k$)—C(S)—NH$_2$, —N(R$^k$)—C(O)—N(H)—R$^k$, —N(R$^k$)—C(S)—N(H)—R$^k$, —N(H)—C(O)—N(R$^k$)—R$^k$, —N(H)—C(S)—N(R$^k$)—R$^k$, —N(R$^k$)—C(O)—N(R$^k$)—R$^k$, —N(R$^k$)—C(S)—N(R$^k$)—R$^k$, —N(H)—S(O)$_2$—N(H)—R$^k$, —N(R$^k$)—S(O)$_2$—NH$_2$, —N(R$^k$)—S(O)$_2$—N(H)—R$^k$, —N(H)—S(O)$_2$—N(R$^k$)—R$^k$, —N(R$^k$)—S(O)$_2$—N(R$^k$)—R$^k$, —N(H)—R$^k$, —N(R$^k$)—R$^k$, —R$^h$, and —R$^j$;

each R$^g$ is independently selected from the group consisting of cycloalkyl, heterocycloalkyl, aryl, and heteroaryl, wherein cycloalkyl, heterocycloalkyl, aryl, and heteroaryl are optionally substituted with one or more, preferably 1, 2, 3, 4 or 5, also 1 or 2 or 3 substituents selected from the group consisting of halogen, —OH, —NH$_2$, —NO$_2$, —CN, —C(O)—OH, —C(S)—OH, —C(O)—NH$_2$, —C(S)—NH$_2$, —S(O)—NH$_2$, —S(O)$_2$—NH$_2$, —C(O)—N(H)—OH, —C(S)—N(H)—OH, —N(H)—C(O)—NH$_2$, —N(H)—C(S)—NH$_2$, —N(H)—S(O)$_2$—NH$_2$, —C(NH)—NH$_2$, —O—R$^k$, —S—R$^k$, —O—C(O)—R$^k$, —O—C(S)—R$^k$, —C(O)—R$^k$, —C(S)—R$^k$, —C(O)—O—R$^k$, —C(S)—O—R$^k$, —S(O)—R$^k$, —S(O)$_2$—R$^k$, —C(O)—N(H)—R$^k$, —C(S)—N(H)—R$^k$, —C(O)—N(R$^k$)—R$^k$, —C(S)—N(R$^k$)—R$^k$, —S(O)—N(H)—R$^k$, —S(O)—N(R$^k$)—R$^k$, —S(O)$_2$—N(H)—R$^k$, —S(O)$_2$—N(R$^k$)—R$^k$, —C(O)—N(H)—O—R$^k$, —C(O)—N(R$^k$)—O—R$^k$, —C(S)—N(H)—O—R$^k$, —C(S)—N(R$^k$)—O—R$^k$, —C(O)—N(H)—S(O)$_2$—R$^k$, —C(O)—N(R$^k$)—S(O)$_2$—R$^k$, —C(S)—N(H)—S(O)$_2$—R$^k$, —C(S)—N(R$^k$)—S(O)$_2$—R$^k$, —S(O)$_2$—N(H)—C(O)—R$^k$, —S(O)$_2$—N(R$^k$)—C(O)—R$^k$, —S(O)$_2$—N(H)—C(S)—R$^k$, —S(O)$_2$—N(R$^k$)—C(S)—R$^k$, —C(NH)—N(H)—R$^k$, —C(NH)—N(R$^m$)—R$^n$, —N(H)—C(O)—R$^k$, —N(H)—C(S)—R$^k$, —N(R$^k$)—C(O)—R$^k$, —N(R$^k$)—C(S)—R$^k$, —N(H)—S(O)—R$^k$, —N(R$^k$)—S(O)—R$^k$, —N(H)—S(O)$_2$—R$^k$, —N(R$^k$)—S(O)$_2$—R$^k$, —N(H)—C(O)—N(H)—R$^k$, —N(H)—C(S)—N(H)—R$^k$, —N(R$^k$)—C(O)—NH$_2$, —N(R$^k$)—C(S)—NH$_2$, —N(R$^k$)—C(O)—N(H)—R$^k$, —N(R$^k$)—C(S)—N(H)—R$^k$, —N(H)—C(O)—N(R$^k$)—R$^k$, —N(H)—C(S)—N(R$^k$)—R$^k$, —N(R$^k$)—C(O)—N(R$^k$)—R$^k$, —N(R$^k$)—C(S)—N(R$^k$)—R$^k$, —N(H)—S(O)$_2$—N(H)—R$^k$, —N(R$^k$)—S(O)$_2$—NH$_2$, —N(R$^k$)—S(O)$_2$—N(H)—R$^k$, —N(H)—S(O)$_2$—N(R$^k$)—R$^k$, —N(R$^k$)—S(O)$_2$—N(R$^k$)—R$^k$, —N(H)—R$^k$, —N(R$^k$)—R$^k$, —R$^h$, —R$^i$, and —R$^j$;

wherein R$^k$, R$^m$, and R$^n$ at each occurrence are independently selected from the group consisting of R$^h$, R$^i$, and R$^j$, or R$^m$ and R$^n$ combine with the nitrogen to which they are attached form a 5-7 membered heterocycloalkyl or a 5 or 7 membered nitrogen containing heteroaryl, wherein the 5-7 membered heterocycloalkyl or 5 or 7 membered nitrogen containing heteroaryl are optionally substituted with one or more, preferably 1, 2, 3, 4 or 5, also 1, 2, or 3 substituents selected from the group consisting of halogen, —NO$_2$, —CN, —OH, —NH$_2$, —O—R$^u$, —S—R$^u$, —N(H)—R$^u$, —N(R$^u$)—R$^u$, —R$^x$, and —R$^y$;

wherein each R$^h$ is independently lower alkyl optionally substituted with one or more, preferably 1, 2, 3, 4 or 5, also 1, 2, or 3 substituents selected from the group consisting of fluoro, —OH, —NH$_2$, —NO$_2$, —CN, —C(O)—OH, —C(S)—OH, —C(O)—NH$_2$, —C(S)—NH$_2$, —S(O)—NH$_2$, —S(O)$_2$—NH$_2$, —C(O)—N(H)—OH, —C(S)—N(H)—OH, —N(H)—C(O)—NH$_2$, —N(H)—C(S)—NH$_2$, —N(H)—S(O)$_2$—NH$_2$, —C(NH)—NH$_2$, —O—R$^r$, —S—R$^r$, —O—C(O)—R$^r$, —O—C(S)—R$^r$, —C(O)—R$^r$, —C(S)—R$^r$, —C(O)—O—R$^r$, —C(S)—O—R$^r$, —S(O)—R$^r$, —S(O)$_2$—R$^r$, —C(O)—N(H)—R$^r$, —C(S)—N(H)—R$^r$, —C(O)—N(R$^r$)—R$^r$, —C(S)—N(R$^r$)—R$^r$, —S(O)—N(H)—R$^r$, —S(O)—N(R$^r$)—R$^r$, —S(O)$_2$—N(H)—R$^r$, —S(O)$_2$—N(R$^r$)—R$^r$, —C(O)—N(H)—O—R$^r$, —C(O)—N(R$^r$)—O—R$^r$, —C(S)—N(H)—O—R$^r$, —C(S)—N(R$^r$)—O—R$^r$, —C(O)—N(H)—S(O)$_2$—R$^r$, —C(O)—N(R$^r$)—S(O)$_2$—R$^r$, —C(S)—N(H)—S(O)$_2$—R$^r$, —C(S)—N(R$^r$)—S(O)$_2$—R$^r$, —S(O)$_2$—N(H)—C(O)—R$^r$, —S(O)$_2$—N(R$^r$)—C(O)—R$^r$, —S(O)$_2$—N(H)—C(S)—R$^r$, —S(O)$_2$—N(R$^r$)—C(S)—R$^r$, —C(NH)—N(H)—R$^r$, —C(NH)—N(R$^s$)—R$^t$, —N(H)—C(O)—R$^r$, —N(H)—C(S)—R$^r$, —N(R$^r$)—C(O)—R$^r$, —N(R$^r$)—C(S)—R$^r$, —N(H)—S(O)—R$^r$, —N(R$^r$)—S(O)—R$^r$, —N(H)—S(O)$_2$—R$^r$, —N(R$^r$)—S(O)$_2$—R$^r$, —N(H)—C(O)—N(H)—R$^r$, —N(H)—C(S)—N(H)—R$^r$, —N(R$^r$)—C(O)—NH$_2$, —N(R$^r$)—C(S)—NH$_2$, —N(R$^r$)—C(O)—N(H)—R$^r$, —N(R$^r$)—C(S)—N(H)—R$^r$, —N(H)—C(O)—N(R$^r$)—R$^r$, —N(H)—C(S)—N(R$^r$)—R$^r$, —N(R$^r$)—C(O)—N(R$^r$)—R$^r$, —N(R$^r$)—C(S)—N(R$^r$)—R$^r$, —N(H)—S(O)$_2$—N(H)—R$^r$, —N(R$^r$)—S(O)$_2$—NH$_2$, —N(R$^r$)—S(O)$_2$—N(H)—R$^r$, —N(H)—S(O)$_2$—N(R$^r$)—R$^r$, —N(R$^r$)—S(O)$_2$—N(R$^r$)—R$^r$, —N(H)—R$^r$, —N(R$^r$)—R$^r$, —R$^i$, and —R$^j$;

wherein each R$^i$ is independently selected from the group consisting of lower alkenyl and lower alkynyl, wherein lower alkenyl or lower alkynyl are optionally substituted with one or more, preferably 1, 2, 3, 4 or 5, also 1, 2 or 3 substituents selected from the group consisting of fluoro, —OH, —NH$_2$, —NO$_2$, —CN, —C(O)—OH, —C(S)—OH, —C(O)—NH$_2$, —C(S)—NH$_2$, —S(O)—NH₂, —S(O)₂—NH₂, —C(O)—N(H)—OH, —C(S)—N(H)—OH, —N(H)—C(O)—NH₂, —N(H)—C(S)—NH₂, —N(H)—S(O)₂—NH₂, —C(NH)—NH₂, —O—R$^r$, —S—R$^r$, —O—C(O)—R$^r$, —O—C(S)—R$^r$, —C(O)—R$^r$, —C(S)—R$^r$, —C(O)—O—R$^r$, —C(S)—O—R$^r$, —S(O)—R$^r$, —S(O)₂—R$^r$, —C(O)—N(H)—R$^r$, —C(S)—N(H)—R$^r$, —C(O)—N(R$^r$)—R$^r$, —C(S)—N(R$^r$)—R$^r$, —S(O)—N(H)—R$^r$, —S(O)—N(R$^r$)—R$^r$, —S(O)₂—N(H)—R$^r$, —S(O)₂—N(R$^r$)—R$^r$, —C(O)—N(H)—O—R$^r$, —C(O)—N(R$^r$)—O—R$^r$, —C(S)—N(H)—O—R$^r$, —C(S)—N(R$^r$)—O—R$^r$, —C(O)—N(H)—S(O)₂—R$^r$, —C(O)—N(R$^r$)—S(O)₂—R$^r$, —C(S)—N(H)—S(O)₂—R$^r$, —C(S)—N(R$^r$)—S(O)₂—R$^r$, —S(O)₂—N(H)—C(O)—R$^r$, —S(O)₂—N(R$^r$)—C(O)—R$^r$, —S(O)₂—N(H)—C(S)—R$^r$, —S(O)₂—N(R$^r$)—C(S)—R$^r$, —C(NH)—N(H)—R$^r$, —C(NH)—N(R$^r$)—R$^r$, —N(H)—C(O)—R$^r$, —N(H)—C(S)—R$^r$, —N(R$^r$)—C(O)—R$^r$, —N(R$^r$)—C(S)—R$^r$, —N(H)—S(O)—R$^r$, —N(R$^r$)—S(O)—R$^r$, —N(H)—S(O)₂—R$^r$, —N(R$^r$)—S(O)₂—R$^r$, —N(H)—C(O)—N(H)—R$^r$, —N(H)—C(S)—N(H)—R$^r$, —N(R$^r$)—C(O)—NH₂, —N(R$^r$)—C(S)—NH₂, —N(R$^r$)—C(O)—N(H)—R$^r$, —N(R$^r$)—C(S)—N(H)—R$^r$, —N(H)—C(O)—N(R$^r$)—R$^r$, —N(H)—C(S)—N(R$^r$)—R$^r$, —N(R$^r$)—C(O)—N(R$^r$)—R$^r$, —N(R$^r$)—C(S)—N(R$^r$)—R$^r$, —N(H)—S(O)₂—N(H)—R$^r$, —N(R$^r$)—S(O)₂—NH₂, —N(R$^r$)—S(O)₂—N(H)—R$^r$, —N(H)—S(O)₂—N(R$^r$)—R$^r$, —N(R$^r$)—S(O)₂—N(R$^r$)—R$^r$, —N(H)—R$^r$, —N(R$^r$)—R$^r$, and —R$^j$;

wherein each R$^j$ is independently selected from the group consisting of cycloalkyl, heterocycloalkyl, aryl, and heteroaryl, wherein cycloalkyl, heterocycloalkyl, aryl, and heteroaryl are optionally substituted with one or more, preferably 1, 2, 3, 4 or 5, also 1, 2 or 3 substituents selected from the group consisting of halogen, —OH, —NH₂, —NO₂, —CN, —C(O)—OH, —C(S)—OH, —C(O)—NH₂, —C(S)—NH₂, —S(O)—NH₂, —S(O)₂—NH₂, —C(O)—N(H)—OH, —C(S)—N(H)—OH, —N(H)—C(O)—NH₂, —N(H)—C(S)—NH₂, —N(H)—S(O)₂—NH₂, —C(NH)—NH₂, —O—R$^r$, —S—R$^r$, —O—C(O)—R$^r$, —O—C(S)—R$^r$, —C(O)—R$^r$, —C(S)—R$^r$, —C(O)—O—R$^r$, —C(S)—O—R$^r$, —S(O)—R$^r$, —S(O)₂—R$^r$, —C(O)—N(H)—R$^r$, —C(S)—N(H)—R$^r$, —C(O)—N(R$^r$)—R$^r$, —C(S)—N(R$^r$)—R$^r$, —S(O)—N(H)—R$^r$, —S(O)—N(R$^r$)—R$^r$, —S(O)₂—N(H)—R$^r$, —S(O)₂—N(R$^r$)—R$^r$, —C(O)—N(H)—O—R$^r$, —C(O)—N(R$^r$)—O—R$^r$, —C(S)—N(H)—O—R$^r$, —C(S)—N(R$^r$)—O—R$^r$, —C(O)—N(H)—S(O)₂—R$^r$, —C(O)—N(R$^r$)—S(O)₂—R$^r$, —C(S)—N(H)—S(O)₂—R$^r$, —C(S)—N(R$^r$)—S(O)₂—R$^r$, —S(O)₂—N(H)—C(O)—R$^r$, —S(O)₂—N(R$^r$)—C(O)—R$^r$, —S(O)₂—N(H)—C(S)—R$^r$, —S(O)₂—N(R$^r$)—C(S)—R$^r$, —C(NH)—N(H)—R$^r$, —C(NH)—N(R$^r$)—R$^t$, —N(H)—C(O)—R$^r$, —N(H)—C(S)—R$^r$, —N(R$^r$)—C(O)—R$^r$, —N(R$^r$)—C(S)—R$^r$, —N(H)—S(O)—R$^r$, —N(R$^r$)—S(O)—R$^r$, —N(H)—S(O)₂—R$^r$, —N(Rr)—S(O)₂—R$^r$, —N(H)—C(O)—N(H)—R$^r$, —N(H)—C(S)—N(H)—R$^r$, —N(R$^r$)—C(O)—NH₂, —N(R$^r$)—C(S)—NH₂, —N(R$^r$)—C(O)—N(H)—R$^r$, —N(R$^r$)—C(S)—N(H)—R$^r$, —N(H)—C(O)—N(R$^r$)—R$^r$, —N(H)—C(S)—N(R$^r$)—R$^r$, —N(R$^r$)—C(O)—N(R$^r$)—R$^r$, —N(R$^r$)—C(S)—N(R$^r$)—R$^r$, —N(H)—S(O)₂—N(H)—R$^r$, —N(R$^r$)—S(O)₂—NH₂, —N(R$^r$)—S(O)₂—N(H)—R$^r$, —N(H)—S(O)₂—N(R$^r$)—R$^r$, —N(R$^r$)—S(O)₂—N(R$^r$)—R$^r$, —N(H)—R$^r$, —N(R$^r$)—R$^r$, cycloalkylamino, and —R$^x$;

wherein each R$^r$, R$^s$, and R$^t$ at each occurrence are independently selected from the group consisting of lower alkyl, C$_{3-6}$ alkenyl, C$_{3-6}$ alkynyl, cycloalkyl, heterocycloalkyl, aryl and heteroaryl, wherein lower alkyl is optionally substituted with one or more, preferably 1, 2, 3, 4 or 5, also 1, 2, or 3 substituents selected from the group consisting of —R$^y$, fluoro, —OH, —NH₂, lower alkoxy, fluoro substituted lower alkoxy, lower alkylthio, fluoro substituted lower alkylthio, monoalkylamino, di-alkylamino, and cycloalkylamino, and wherein C$_{3-6}$ alkenyl or C$_{3-6}$ alkynyl are optionally substituted with one or more, preferably 1, 2, 3, 4 or 5, also 1, 2, or 3 substituents selected from the group consisting of —R$^y$, fluoro, lower alkyl, fluoro substituted lower alkyl, lower alkoxy, fluoro substituted lower alkoxy, lower alkylthio, fluoro substituted lower alkylthio, mono-alkylamino, di-alkylamino, and cycloalkylamino, and wherein cycloalkyl, heterocycloalkyl, aryl, and heteroaryl are optionally substituted with one or more, preferably 1, 2, 3, 4 or 5, also 1, 2, or 3 substituents selected from the group consisting of halogen, —OH, —NH₂, —NO₂, —CN, lower alkyl, fluoro substituted lower alkyl, lower alkoxy, fluoro substituted lower alkoxy, lower alkylthio, fluoro substituted lower alkylthio, mono-alkylamino, di-alkylamino, and cycloalkylamino, or R$^s$ and R$^t$ combine with the nitrogen to which they are attached form a 5-7 membered heterocycloalkyl or a 5 or 7 membered nitrogen containing heteroaryl, wherein the 5-7 membered heterocycloalkyl or 5 or 7 membered nitrogen containing heteroaryl are optionally substituted with one or more, preferably 1, 2, 3, 4 or 5, also 1, 2, or 3 substituents selected from the group consisting of halogen, —NO₂, —CN, —OH, —NH₂, O—R$^u$, —S—R$^u$, —N(H)—R$^u$, —N(R$^u$)—R$^u$, —R$^x$, and —R$^y$;

wherein each R$^u$ is independently selected from the group consisting of lower alkyl, C$_{3-6}$ alkenyl, C$_{3-6}$ alkynyl, cycloalkyl, heterocycloalkyl, aryl, and heteroaryl, wherein lower alkyl is optionally substituted with one or more, preferably 1, 2, 3, 4 or 5, also 1, 2, or 3 substituents selected from the group consisting of —R$^y$, fluoro, —OH, —NH₂, lower alkoxy, fluoro substituted lower alkoxy, lower alkylthio, fluoro substituted lower alkylthio, mono-alkylamino, di-alkylamino, and cycloalkylamino, and wherein C$_{3-6}$ alkenyl or C$_{3-6}$ alkynyl are optionally substituted with one or more, preferably 1, 2, 3, 4 or 5, also 1, 2, or 3 substituents selected from the group consisting of —R$^y$, fluoro, —OH, —NH₂, lower alkyl, fluoro substituted lower alkyl, lower alkoxy, fluoro substituted lower alkoxy, lower alkylthio, fluoro substituted lower alkylthio, mono-alkylamino, di-alkylamino, and cycloalkylamino, and wherein cycloalkyl, heterocycloalkyl, aryl, and heteroaryl are optionally substituted with one or more, preferably 1, 2, 3, 4 or 5, also 1, 2, or 3 substituents selected from the group consisting of halogen, —OH, —NH₂, —NO₂, —CN, lower alkyl, fluoro substituted lower alkyl, lower alkoxy, fluoro substituted lower alkoxy, lower alkylthio, fluoro substituted lower alkylthio, mono-alkylamino, di-alkylamino, and cycloalkylamino;

wherein each R$^x$ is selected from the group consisting of lower alkyl, lower alkenyl and lower alkynyl, wherein lower alkyl is optionally substituted with one or more, preferably 1, 2, 3, 4 or 5, also 1, 2, or 3 substituents selected from the group consisting of —R$^y$, fluoro, —OH, —NH$_2$, lower alkoxy, fluoro substituted lower alkoxy, lower alkylthio, fluoro substituted lower alkylthio, mono-alkylamino, di-alkylamino, and cycloalkylamino, and wherein lower alkenyl or lower alkynyl are optionally substituted with one or more, preferably 1, 2, 3, 4 or 5, also 1, 2, or 3 substituents selected from the group consisting of —R$^y$, fluoro, —OH, —NH$_2$, lower alkyl, fluoro substituted lower alkyl, lower alkoxy, fluoro substituted lower alkoxy, lower alkylthio, fluoro substituted lower alkylthio, mono-alkylamino, di-alkylamino, and cycloalkylamino;

wherein each R$^y$ is selected from the group consisting of cycloalkyl, heterocycloalkyl, aryl, and heteroaryl, wherein cycloalkyl, heterocycloalkyl, aryl, and heteroaryl are optionally substituted with one or more, preferably 1, 2, 3, 4 or 5, also 1, 2, or 3 substituents selected from the group consisting of halogen, —OH, —NH$_2$, —NO$_2$, —CN, lower alkyl, fluoro substituted lower alkyl, lower alkoxy, fluoro substituted lower alkoxy, lower alkylthio, fluoro substituted lower alkylthio, mono-alkylamino, di-alkylamino, and cycloalkylamino.

In some embodiments, all occurrences of optionally substituted lower alkyl, optionally substituted lower alkenyl, or optionally substituted lower alkynyl are optionally substituted with one or more, also 1, 2 or 3 groups or substituents selected from the group consisting of fluoro, —NO$_2$, —CN, —O—R$^{1a}$, —S—R$^{1a}$, —N(R$^{1a}$)—R$^{1a}$, —O—C(O)—R$^{1a}$, —O—C(S)—R$^{1a}$, —C(O)—R$^{1a}$, —C(S)—R$^{1a}$, —C(O)—O—R$^{1a}$, —C(S)—O—R$^{1a}$, —C(O)—N(R$^{1a}$)—R$^{1a}$, —C(S)—N(R$^{1a}$)—R$^{1a}$, —S(O)$_2$—N(R$^{1a}$)—R$^{1a}$, —C(O)—N(R$^{1a}$)—O—R$^{1a}$, —C(S)—N(R$^{1a}$)—O—R$^{1a}$, —C(O)—N(R$^{1a}$)—S(O)$_2$—R$^{1a}$, —C(S)—N(R$^{1a}$)—S(O)$_2$—R$^{1a}$, —S(O)$_2$—N(R$^{1a}$)—C(O)—R$^{1a}$, —S(O)$_2$—N(R$^{1a}$)—C(S)—R$^{1a}$, —C(NH)—N(R$^{1a}$)—R$^{1a}$, —N(R$^{1a}$)—C(O)—R$^{1a}$, —N(R$^{1a}$)—S(S)—R$^{1a}$, —N(R$^{1a}$)—S(O)$_2$—R$^{1a}$, —N(R$^{1a}$)—C(O)—N(R$^{1a}$)—R$^{1a}$, —N(R$^{1a}$)—C(S)—N(R$^{1a}$)—R$^{1a}$, —N(R$^{1a}$)—S(O)$_2$—N(R$^{1a}$)—S(O)$_2$—N(R$^{1a}$)—R$^{1a}$, —S(O)—R$^{1a}$, —S(O)$_2$—R$^{1a}$, cycloalkyl, heterocycloalkyl, aryl and heteroaryl, wherein cycloalkyl, heterocycloalkyl, aryl and heteroaryl are optionally substituted with one or more, also 1, 2 or 3 groups or substituents selected from the group consisting of halogen, —NO$_2$, —CN, —O—R$^{1a}$, —S—R$^{1a}$, —N(R$^{1a}$)—O—C(O)—R$^{1a}$, —O—C(S)—R$^{1a}$, —C(O)—R$^{1a}$, —C(S)—R$^{1a}$, —C(O)—O—R$^{1a}$, —C(S)—O—R$^{1a}$, —C(O)—N(R$^{1a}$)—R$^{1a}$, —C(S)—N(R$^{1a}$)—R$^{1a}$, —S(O)$_2$—N(R$^{1a}$)—R$^{1a}$, —C(O)—N(R$^{1a}$)—O—R$^{1a}$, —C(S)—N(R$^{1a}$)—O—R$^{1a}$, —C(O)—N(R$^{1a}$)—S(O)$_2$—R$^{1a}$, —C(S)—N(R$^{1a}$)—S(O)$_2$—R$^{1a}$, —S(O)$_2$—N(R$^{1a}$)—C(O)—R$^{1a}$, —S(O)$_2$—N(R$^{1a}$)—C(S)—R$^{1a}$, —C(NH)—N(R$^{1a}$)—R$^{1a}$, —N(R$^{1a}$)—C(O)—R$^{1a}$, —N(R$^{1a}$)—C(S)R$^{1a}$, —N(R$^{1a}$)—S(O)$_2$—R$^{1a}$, —N(R$^{1a}$)—C(O)—N(R$^{1a}$)—R$^{1a}$, —N(R$^{1a}$)—C(S)—N(R$^{1a}$)—R$^{1a}$, —N(R$^{1a}$)—S(O)$_2$—N(R$^{1a}$)—R$^{1a}$, —S(O)R$^{1a}$, —S(O)$_2$—R$^{1a}$, R$^{1b}$, and lower alkyl optionally substituted with one or more, also 1, 2 or 3 groups or substituents selected from the group consisting of fluoro, —OH, —NH$_2$, lower alkoxy, fluoro substituted lower alkoxy, lower alkylthio, fluoro substituted lower alkylthio, mono-alkylamino, di-alkylamino, and —R$^{1b}$, and all occurrences of optionally substituted cycloalkyl, optionally substituted heterocycloalkyl, optionally substituted 5-7 membered heterocycloalkyl, optionally substituted aryl, optionally substituted arylene, optionally substituted heteroaryl, optionally substituted heteroarylene, or optionally substituted 5 or 7 membered nitrogen containing heteroaryl are optionally substituted with one or more, also 1, 2, or 3 groups or substituents selected from the group consisting of halogen, —NO$_2$, —CN, —O—R$^{1a}$, —S—R$^{1a}$, —N(R$^{1a}$)—R$^{1a}$, —O—C(O)—R$^{1a}$, —O—C(S)—R$^{1a}$, —C(O)—R$^{1a}$, —C(S)—R$^{1a}$, —C(O)—O—R$^{1a}$, —C(S)—O—R$^{1a}$, —C(O)—N(R$^{1a}$)—R$^{1a}$, —C(S)—N(R$^{1a}$)—R$^{1a}$, —S(O)$_2$—N(R$^{1a}$)—R$^{1a}$, —C(O)—N(R$^{1a}$)—O—R$^{1a}$, —C(S)—N(R$^{1a}$)—O—R$^{1a}$, —C(O)—N(R$^{1a}$)—S(O)$_2$—R$^{1a}$, —C(S)—N(R$^{1a}$), —S(O)$_2$—R$^{1a}$, —S(O)$_2$—N(R$^{1a}$)—C(O)—R$^{1a}$, —S(O)$_2$—N(R$^{1a}$)—C(S)—R$^{1a}$, —C(NH)—N(R$^{1a}$)—R$^{1a}$, —N(R$^{1a}$)—C(O)—R$^{1a}$, —N(R$^{1a}$)—C(S)—R$^{1a}$, —N(R$^{1a}$)—S(O)$_2$—R$^{1a}$, —N(R$^{1a}$)—C(O)—N(R$^{1a}$)—R$^{1a}$, —N(R$^{1a}$)—C(S)—N(R$^{1a}$)—R$^{1a}$, —N(R$^{1a}$)—S(O)$_2$—N(R$^{1a}$)—R$^{1a}$, —S(O)$_2$—R$^{1a}$, —R$^{1b}$, and lower alkyl optionally substituted with one or more, also 1, 2 or 3 groups or substituents selected from the group consisting of fluoro, —OH, —NH$_2$, lower alkoxy, fluoro substituted lower alkoxy, lower alkylthio, fluoro substituted lower alkylthio, mono-alkylamino, di-alkylamino, and —R$^{1b}$, wherein R$^{1a}$ is selected from the group consisting of hydrogen, —R$^{1b}$, and lower alkyl optionally substituted with one or more, also 1, 2 or 3 groups or substituents selected from the group consisting of fluoro, —OH, —NH$_2$, lower alkoxy, fluoro substituted lower alkoxy, lower alkylthio, fluoro substituted lower alkylthio, mono-alkylamino, di-alkylamino, and —R$^{1b}$, and wherein —R$^{1b}$ is selected from the group consisting of cycloalkyl, heterocycloalkyl, aryl and heteroaryl, wherein cycloalkyl, heterocycloalkyl, aryl and heteroaryl are optionally substituted with one or more, also 1, 2 or 3 groups or substituents selected from the group consisting of halogen, —CN, —OH, —NH$_2$, lower alkoxy, fluoro substituted lower alkoxy, lower alkylthio, fluoro substituted lower alkylthio, mono-alkylamino, di-alkylamino, and cycloalkylamino.

In some embodiments, all occurrences of optionally substituted lower alkyl, optionally substituted lower alkenyl, or optionally substituted lower alkynyl are optionally substituted with one or more, also 1, 2 or 3 groups or substituents selected from the group consisting of fluoro, —CN, —O—R$^{1a}$, —S—R$^{1a}$, —N(R$^{1a}$)—R$^{1a}$, —C(O)—R$^{1a}$, —C(S)—R$^{1a}$, —C(O)—O—R$^{1a}$, —C(O)—N(R$^{1a}$)—R$^{1a}$, —C(S)—N(R$^{1a}$)—R$^{1a}$, —S(O)$_2$—N(R$^{1a}$)—R$^{1a}$, —N(R$^{1a}$)—C(O)—R$^{1a}$, —N(R$^{1a}$)—C(S)—R$^{1a}$, —N(R$^{1a}$)—S(O)$_2$—R$^{1a}$, —S(O)—R$^{1a}$, —S(O)$_2$—R$^{1a}$, cycloalkyl, heterocycloalkyl, aryl and heteroaryl, wherein cycloalkyl, heterocycloalkyl, aryl and heteroaryl are optionally substituted with one or more, also 1, 2 or 3 groups or substituents selected from the group consisting of halogen, —CN, —O—R$^{1a}$—S—R$^{1a}$, —N(R$^{1a}$)—R$^{1a}$, —C(O)—R$^{1a}$, —C(S)—R$^{1a}$, —C(O)—O—R$^{1a}$, —C(O)—N(R$^{1a}$)—R$^{1a}$, —C(S)—N(R$^{1a}$)—R$^{1a}$, —S(O)$_2$—N(R$^{1a}$)—R$^{1a}$, —N(R$^{1a}$)—C(O)—R$^{1a}$, —N(R$^{1a}$)—C(S)—R$^{1a}$, —N(R$^{1a}$)—S(O)$_2$—R$^{1a}$, —S(O)—R$^{1a}$, —S(O)$_2$—R$^{1a}$, —R$^{1b}$, and lower alkyl optionally substituted with one or more, also 1, 2 or 3 groups or substituents selected from the group consisting of fluoro, —OH, —NH$_2$, lower alkoxy, fluoro substituted lower alkoxy, lower alkylthio, fluoro substituted lower alkylthio, mono-alkylamino, di-alkylamino, and —R$^{1b}$, and all occurrences of optionally substituted cycloalkyl, optionally substituted heterocycloalkyl, optionally substituted 5-7 membered heterocycloalkyl, optionally substituted aryl, optionally substituted arylene, optionally substituted heteroaryl, optionally substituted heteroarylene, or optionally substituted 5 or 7 membered nitrogen containing heteroaryl are optionally substituted with one or more, also 1, 2, or 3 groups or substituents selected from the group consisting of halogen, —CN, —O—R$^{1a}$, —S—R$^{1a}$, —N($R^{1a}$)—$R^{1a}$, —C(O)—$R^{1a}$, —C(S)—$R^{1a}$, —C(O)—O—$R^{1a}$, —C(O)—N($R^{1a}$)—$R^{1a}$, —C(S)—N($R^{1a}$)—$R^{1a}$, —S(O)$_2$—N($R^{1a}$)—$R^{1a}$, —N($R^{1a}$)—C(O)—$R^{1a}$, —N($R^{1a}$)—C(S)—$R^{1a}$, —N($R^{1a}$)—S(O)$_2$—$R^{1a}$, —S(O)—$R^{1a}$, —S(O)$_2$—$R^{1a}$, —$R^{1b}$, and lower alkyl optionally substituted with one or more, also 1, 2 or 3 groups or substituents selected from the group consisting of fluoro, —OH, —NH$_2$, lower alkoxy, fluoro substituted lower alkoxy, lower alkylthio, fluoro substituted lower alkylthio, mono-alkylamino, di-alkylamino, and —$R^{1b}$, wherein $R^{1a}$ is selected from the group consisting of hydrogen, —$R^{1b}$, and lower alkyl optionally substituted with one or more, also 1, 2 or 3 groups or substituents selected from the group consisting of fluoro, —OH, —NH$_2$, lower alkoxy, fluoro substituted lower alkoxy, lower alkylthio, fluoro substituted lower alkylthio, mono-alkylamino, di-alkylamino, and —$R^{1b}$, and wherein —$R^{1b}$ is selected from the group consisting of cycloalkyl, heterocycloalkyl, aryl and heteroaryl, wherein cycloalkyl, heterocycloalkyl, aryl and heteroaryl are optionally substituted with one or more, also 1, 2 or 3 groups or substituents selected from the group consisting of halogen, —CN, —OH, —NH$_2$, lower alkoxy, fluoro substituted lower alkoxy, lower alkylthio, fluoro substituted lower alkylthio, mono-alkylamino, di-alkylamino, and cycloalkylamino.

"Lower alkoxy" denotes the group —OR$^z$, where R$^z$ is lower alkyl. "Substituted lower alkoxy" denotes lower alkoxy in which R$^z$ is lower alkyl substituted with one or more substituents as indicated herein, for example, in the description of compounds of Formula I, including descriptions of substituted cycloalkyl, heterocycloalkyl, aryl and heteroaryl, attached at any available atom to provide a stable compound. Preferably, substitution of lower alkoxy is with 1, 2, 3, 4, or 5 substituents, also 1, 2, or 3 substituents. For example "fluoro substituted lower alkoxy" denotes lower alkoxy in which the lower alkyl is substituted with one or more fluoro atoms, where preferably the lower alkoxy is substituted with 1, 2, 3, 4 or 5 fluoro atoms, also 1, 2, or 3 fluoro atoms. It is understood that substitutions on alkoxy are chemically feasible and attached at any available atom to provide a stable compound.

"Lower alkylthio" denotes the group —SR$^{aa}$, where R$^{aa}$ is lower alkyl. "Substituted lower alkylthio" denotes lower alkylthio in which R$^{aa}$ is lower alkyl substituted with one or more substituents as indicated herein, for example, in the description of compounds of Formula I, including descriptions of substituted cycloalkyl, heterocycloalkyl, aryl and heteroaryl, attached at any available atom to provide a stable compound. Preferably, substitution of lower alkylthio is with 1, 2, 3, 4, or 5 substituents, also 1, 2, or 3 substituents. For example "fluoro substituted lower alkylthio" denotes lower alkylthio in which the lower alkyl is substituted with one or more fluoro atoms, where preferably the lower alkylthio is substituted with 1, 2, 3, 4 or 5 fluoro atoms, also 1, 2, or 3 fluoro atoms. It is understood that substitutions on alkylthio are chemically feasible and attached at any available atom to provide a stable compound.

"Amino" or "amine" denotes the group —NH$_2$. "Mono-alkylamino" denotes the group —NHR$^{bb}$ where R$^{bb}$ is lower alkyl. "Di-alkylamino" denotes the group —NR$^{bb}$R$^{cc}$, where R$^{bb}$ and R$^{cc}$ are independently lower alkyl. "Cycloalkylamino" denotes the group —NR$^{dd}$R$^{ee}$, where R$^{dd}$ and R$^{ee}$ combine with the nitrogen to form a 5-7 membered heterocycloalkyl, where the heterocycloalkyl may contain an additional heteroatom within the ring, such as O, N, or S, and may also be further substituted with lower alkyl. Examples of 5-7 membered heterocycloalkyl include, but are not limited to, piperidine, piperazine, 4-methylpiperazine, morpholine, and thiomorpholine. It is understood that when mono-alkylamino, di-alkylamino, or cycloalkylamino are substituents on other moieties, these are chemically feasible and attached at any available atom to provide a stable compound.

"Cycloalkyloxy" denotes the group —OR$^{ff}$, where R$^{ff}$ is cycloalkyl.

"Alkylsulfonyl" denotes the group —S(O)$_2$R$^{gg}$, where R$^{gg}$ is lower alkyl.

As used herein, the term "solid form" refers to a solid preparation (i.e. a preparation that is neither gas nor liquid) of a pharmaceutically active compound that is suitable for administration to an intended animal subject for therapeutic purposes. The solid form includes any complex, such as a salt, co-crystal or an amorphous complex, as well as any polymorph of the compound. The solid form may be substantially crystalline, semi-crystalline or substantially amorphous. The solid form may be administered directly or used in the preparation of a suitable composition having improved pharmaceutical properties. For example, the solid form may be used in a formulation comprising at least one pharmaceutically acceptable carrier or excipient.

As used herein, the term "substantially crystalline" material embraces material which has greater than about 90% crystallinity; and "crystalline" material embraces material which has greater than about 98% crystallinity.

As used herein, the term "substantially amorphous" material embraces material which has no more than about 10% crystallinity; and "amorphous" material embraces material which has no more than about 2% crystallinity.

As used herein, the term "semi-crystalline" material embraces material which is greater than 10% crystallinity, but no greater than 90% crystallinity; preferably "semi-crystalline" material embraces material which is greater than 20% crystallinity, but no greater than 80% crystallinity. In one aspect of the present invention, a mixture of solid forms of a compound may be prepared, for example, a mixture of amorphous and crystalline solid forms, e.g. to provide a "semi-crystalline" solid form. Such a "semi-crystalline" solid form may be prepared by methods known in the art, for example by mixing an amorphous solid form with a crystalline solid form in the desired ratio. In some instances, a compound mixed with acid or base forms an amorphous complex; a semi-crystalline solid can be prepared employing an amount of compound component in excess of the stoichiometry of the compound and acid or base in the amorphous complex, thereby resulting in an amount of the amorphous complex that is based on the stoichiometry thereof, with excess compound in a crystalline form. The amount of excess compound used in the preparation of the complex can be adjusted to provide the desired ratio of amorphous complex to crystalline compound in the resulting mixture of solid forms. For example, where the amorphous complex of acid or base and compound has a 1:1 stoichiometry, preparing said complex with a 2:1 mole ratio of compound to acid or base will result in a solid form of 50% amorphous complex and 50% crystalline compound. Such a mixture of solid forms may be beneficial as a drug product, for example, by providing an amorphous component having improved biopharmaceutical properties along with the crystalline component. The amorphous component would be more readily bioavailable while the crystalline component would have a delayed bioavailablity. Such a mixture may provide both rapid and extended exposure to the active compound.

As used herein, the term "complex" refers to a combination of a pharmaceutically active compound and an additional molecular species that forms or produces a new chemical species in a solid form. In some instances, the complex may be a salt, i.e. where the additional molecular species provides an acid/base counter ion to an acid/base group of the compound resulting in an acid:base interaction that forms a typical salt. While such salt forms are typically substantially crystalline, they can also be partially crystalline, substantially amorphous, or amorphous forms. In some instances, the additional molecular species, in combination with the pharmaceutically active compound, forms a non-salt co-crystal, i.e. the compound and molecular species do not interact by way of a typical acid:base interaction, but still form a substantially crystalline structure. Co-crystals may also be formed from a salt of the compound and an additional molecular species. In some instances, the complex is a substantially amorphous complex, which may contain salt-like acid:base interactions that do not form typical salt crystals, but instead form a substantially amorphous solid, i.e. a solid whose X-ray powder diffraction pattern exhibits no sharp peaks (e.g. exhibits an amorphous halo).

As used herein, the term "stoichiometry" refers to the molar ratio of two or more reactants that combine to form a complex, for example, the molar ratio of acid or base to compound that form an amorphous complex. For example, a 1:1 mixture of acid or base with compound (I.e. 1 mole acid or base per mole of compound) resulting in an amorphous solid form has a 1:1 stoichiometry.

As used herein, the term "composition" refers to a pharmaceutical preparation suitable for administration to an intended animal subject for therapeutic purposes that contains at least one pharmaceutically active compound, including any solid form thereof. The composition may include at least one pharmaceutically acceptable component to provide an improved formulation of the compound, such as a suitable carrier or excipient.

The term "pharmaceutically acceptable" indicates that the indicated material does not have properties that would cause a reasonably prudent medical practitioner to avoid administration of the material to a patient, taking into consideration the disease or conditions to be treated and the respective route of administration. For example, it is commonly required that such a material be essentially sterile, e.g., for injectables.

In the present context, the term "therapeutically effective" or "effective amount" indicates that the materials or amount of material is effective to prevent, alleviate, or ameliorate one or more symptoms of a disease or medical condition, and/or to prolong the survival of the subject being treated.

In the present context, the terms "synergistically effective" or "synergistic effect" indicate that two or more compounds that are therapeutically effective, when used in combination, provide improved therapeutic effects greater than the additive effect that would be expected based on the effect of each compound used by itself.

In the context of compounds binding to a target, the terms "greater affinity" and "selective" indicates that the compound binds more tightly than a reference compound, or than the same compound in a reference condition, i.e., with a lower dissociation constant. In some embodiments, the greater affinity is at least 2, 3, 4, 5, 8, 10, 50, 100, 200, 400, 500, 1000, or 10.000-fold greater affinity.

As used herein in connection with compounds of the invention, the term "synthesizing" and like terms means chemical synthesis from one or more precursor materials.

By "assaying" is meant the creation of experimental conditions and the gathering of data regarding a particular result of the experimental conditions. For example, enzymes can be assayed based on their ability to act upon a detectable substrate. A compound or ligand can be assayed based on its ability to bind to a particular target molecule or molecules.

As used herein, the term "modulating" or "modulate" refers to an effect of altering a biological activity, especially a biological activity associated with a particular biomolecule such as a protein kinase. For example, an agonist or antagonist of a particular biomolecule modulates the activity of that biomolecule, e.g., an enzyme, by either increasing (e.g. agonist, activator), or decreasing (e.g. antagonist, inhibitor) the activity of the biomolecule, such as an enzyme. Such activity is typically indicated in terms of an inhibitory concentration ($IC_{50}$) or excitation concentration ($EC_{50}$) of the compound for an inhibitor or activator, respectively, with respect to, for example, an enzyme.

In the context of the use, testing, or screening of compounds that are or may be modulators, the term "contacting" means that the compound(s) are caused to be in sufficient proximity to a particular molecule, complex, cell, tissue, organism, or other specified material that potential binding interactions and/or chemical reaction between the compound and other specified material can occur.

"Pain" or a "pain condition" can be acute and/or chronic pain, including, without limitation, arachnoiditis; arthritis (e.g. osteoarthritis, rheumatoid arthritis, ankylosing spondylitis, gout); back pain (e.g. sciatica, ruptured disc, spondylolisthesis, radiculopathy); burn pain; cancer pain; dysmenorrhea; headaches (e.g. migraine, cluster headaches, tension headaches); head and facial pain (e.g. cranial neuralgia, trigeminal neuralgia); hyperalgesia; hyperpathia; inflammatory pain (e.g. pain associated with irritable bowel syndrome, inflammatory bowel disease, ulcerative colitis, Crohn's disease, cystitis, pain from bacterial, fungal or viral infection); keloid or scar tissue formation; labor or delivery pain; muscle pain (e.g. as a result of polymyositis, dermatomyositis, inclusion body myositis, repetitive stress injury (e.g. writer's cramp, carpal tunnel syndrome, tendonitis, tenosynovitis)); myofascial pain syndromes (e.g. fibromyalgia); neuropathic pain (e.g. diabetic neuropathy, causalgia, entrapment neuropathy, brachial plexus avulsion, occipital neuralgia, gout, reflex sympathetic dystrophy syndrome, phantom limb or post-amputation pain, postherpetic neuralgia, central pain syndrome, or nerve pain resulting from trauma (e.g. nerve injury), disease (e.g. diabetes, multiple sclerosis, Guillan-Barre Syndrome, myasthenia gravis, neurodegenerative diseases such as Parkinson's disease, Alzheimer's disease, amyotrophic lateral sclerosis, or cancer treatment); pain associated with skin disorders (e.g. shingles, herpes simplex, skin tumors, cysts, neurofibromatosis); sports injuries (e.g. cuts, sprains, strains, bruises, dislocations, fractures, spinal chord, head); spinal stenosis; surgical pain; tactile allodynia; temporomandibular disorders; vascular disease or injury (e.g. vasculitis, coronary artery disease, reperfusion injury (e.g. following ischemia, stroke, or myocardial infarcts)); other specific organ or tissue pain (e.g. ocular pain, corneal pain, bone pain, heart pain, visceral pain (e.g. kidney, gall bladder, gastrointestinal), joint pain, dental pain, pelvic hypersensitivity, pelvic pain, renal colic, urinary incontinence); other disease associated pain (e.g. sickle cell anemia, AIDS, herpes zoster, psoriasis, endometriosis, asthma, chronic obstructive pulmonary disease (COPD), silicosis, pulmonary sarcoidosis, esophagitis, heart burn, gastroesophageal reflux disorder, stomach and duodenal ulcers, functional dyspepsia, bone resorption disease, osteoporosis, cerebral malaria, bacterial meningitis); or pain due to graft v. host rejection or allograft rejections.

The present invention concerns compounds of Formula I, and all sub-generic formulae, that are modulators of protein kinases, for example without limitation, the compounds are modulators of at least one of the kinases selected from the group consisting of Abl, Akt1, Akt2, Akt3, ALK, Alk5, B-Raf, Brk, Btk, Cdk2, CDK4, CDK5, CDK6, CHK1, c-Raf-1, Csk, EGFR, EphA1, EphA2, EphB2, EphB4, Erk2, Fak, FGFR1, FGFR2, FGFR3, FGFR4, Flt1, Flt3, Flt4, Fms, Frk, Fyn, Gsk3α, Gsk3β, HCK, Her2/Erbb2, Her4/Erbb4, IGF1R, IKK beta, Irak4, Itk, Jak1, Jak2, Jak3, Jnk1, Jnk2, Jnk3, Kdr, Kit, Lck, Lyn, MAP2K1, MAP2K2, MAP4K4, MAPKAPK2, Met, Mnk1, MLK1, mTOR, p38, PDGFRA, PDGFRB, PDPK1, PI3Kα, PI3Kβ, PI3Kδ, PI3Kγ, Pim1, Pim2, Pim3, PKC alpha, PKC beta, PKC theta, Plk1, Pyk2, Ret, ROCK1, ROCK2, Ron, Src, Stk6, Syk, TEC, Tie2, TrkA, TrkB, Yes, and Zap70, and the use of such compounds in the treatment of diseases or conditions.

Kinase Targets and Indications of the Invention

Protein kinases play key roles in propagating biochemical signals in diverse biological pathways. More than 500 kinases have been described, and specific kinases have been implicated in a wide range of diseases or conditions (i.e., indications), including for example without limitation, cancer, cardiovascular disease, inflammatory disease, neurological disease, and other diseases. As such, kinases represent important control points for small molecule therapeutic intervention. Specific target protein kinases contemplated by the present invention are described in the art, including, without limitation, protein kinases as described in U.S. patent application Ser. No. 11/473,347 (see also, PCT publication WO2007002433), the disclosure of which is hereby incorporated by reference with respect to such kinase targets, as well as the following:

Fms:

Target kinase Fms (i.e., feline McDonough sarcoma) is a member of the family of genes originally isolated from the Susan McDonough strain of feline sarcoma viruses. Fms is a transmembrane tyrosine kinase of 108.0 kDa coded by chromosome 5q33.2-q33.3 (symbol: CSF1R). The structure of the transmembrane receptor Fms comprises two Ig-like domains, a IgC2-like domain, two additional Ig-like domains, a TM domain, and the TK domain.

Fms is the receptor for the macrophage colony-stimulating factor (M-CSF), and is crucial for the growth and differentiation of the monocyte-macrophage lineage. Upon binding of M-CSF to the extracellular domain of Fms, the receptor dimerizes and trans-autophosphorylates cytoplasmic tyrosine residues.

M-CSF, first described by Robinson and co-workers (Blood. 1969, 33:396-9), is a cytokine that controls the production, differentiation, and function of macrophages. M-CSF stimulates differentiation of progenitor cells to mature monocytes, and prolongs the survival of monocytes. Furthermore, M-CSF enhances cytotoxicity, superoxide production, phagocytosis, chemotaxis, and secondary cytokine production of additional factors in monocytes and macrophages. Examples of such additional factors include granulocyte colony stimulating factor (G-CSF), interleukin-6 (IL-6), and interleukin-8 (IL-8). M-CSF stimulates hematopoiesis, promotes differentiation and proliferation of osteoclast progenitor cells, and has profound effects on lipid metabolism. Furthermore, M-CSF is important in pregnancy. Physiologically, large amounts of M-CSF are produced in the placenta, and M-CSF is believed to play an essential role in trophoblast differentiation (Motoyoshi, Int J Hematol. 1998, 67:109-22). The elevated serum M-CSF levels of early pregnancy may participate in the immunologic mechanisms responsible for the maintenance of the pregnancy (Flanagan & Lader, Curr Opin Hematol. 1998, 5:181-5).

Aberrant expression and/or activation of Fms has been implicated in acute myeloid leukemia, AML (Ridge et al, Proc. Nat. Acad. Sci., 1990, 87:1377-1380). Mutations at codon 301 are believed to lead to neoplastic transformation by ligand independence and constitutive tyrosine kinase activity of the receptor. The tyrosine residue at codon 969 has been shown to be involved in a negative regulatory activity, which is disrupted by amino acid substitutions. Accordingly, Fms mutations are most prevalent (20%) in chronic myelomonocytic leukemia and AML type M4 (23%), both of which are characterized by monocytic differentiation.

A condition related to AML is chronic myeloid leukemia (CML). During the myeloid blast crisis (BC) of CML, non-random additional chromosome abnormalities occur in over 80% of patients. However, these cytogenetic changes have been reported to precede the clinical signs of CML-BC by several months to years suggesting that other biological events may participate in the multistep process of acute transformation of CML. The autocrine production of growth factors has been shown to occur in several hematological malignancies and particularly in AML. Specchia et al [Br J Haematol. 1992 March; 80(3):310-6] have demonstrated that IL-1 beta gene is expressed in almost all cases of CML in myeloid blast crisis, and that a high proportion of cases showed constitutive expression of the M-CSF gene. Many of the same patients in the Specchia et al study demonstrated simultaneous co-expression of Fms. After exposure of leukemic cells to phorbol myristate acetate (PMA), release of M-CSF protein was documented in three of five patients studied; however, no significant interleukin-3 (IL-3), granulocyte-macrophage colony-stimulating factor (GM-CSF) or granulocyte colony-stimulating factor (G-CSF), was detected in these patients. This demonstrates that different patterns of growth factors secretion exist in AML and CML, and that distinct molecular events are likely involved in the control of leukemic proliferation.

The observation that production of M-CSF, the major macrophage growth factor, is increased in tissues during inflammation (Le Meur et al, J. Leukocyte Biology. 2002; 72:530-537) provides a role for Fms in certain diseases. For example, COPD is characterized by airflow limitation that is not fully reversible. The airflow limitation is usually progressive and associated with an abnormal inflammatory response of the lungs to noxious particles or gases. The chronic inflammation of COPD is observed through the airways, parenchyma, and pulmonary vasculature. The inflammatory cell population consists of neutrophils, macrophages, and T lymphocytes, along with eosinophils in some patients. Macrophages are postulated to play an orchestrating role in COPD inflammation by releasing mediators such as TNF-α, IL-8 and LTB4, which are capable of damaging lung structures and/or sustaining neutrophilic inflammation.

Further, M-CSF/fins signaling is critical to osteoclast formation and survival of osteoclast precursors. For example, estrogen loss in menopause results in increased M-CSF and thus increased osteoclast number and bone resorption which leads to increased risk of fracture and osteoporosis. Accordingly, blockage of this signal is a target for the inhibition of bone resorption (Teitelbaum, Science. 2000; 289:1504; Rohan, Science. 2000; 289:1508).

Atherosclerosis, an inflammatory disease of the vessel walls, is associated with significant morbidity and mortality. A effect for Fms inhibition in the treatment and prevention of atherosclerosis depends on several observations (Libby, Nature. 2002; 420:868-874). First, monocytes resident in the arterial intima increase expression of scavenger receptors and internalize modified lipoproteins. The resulting lipid-laden macrophages develop into foam cells characteristic of the atherosclerotic lesion. Macrophages in atheroma secrete cytokines and growth factors involved in lesion progression. Additionally, macrophages replicate within the intima. Through Fms, M-CSF activates the transition from monocyte to lipid-laden macrophage and augments expression of scavenger receptor A. Indeed, atherosclerotic plaques over-express M-CSF which is critical for atherosclerotic progression. Mice deficient in M-CSF have been found to experience less severe atherosclerosis than mice with normal M-CSF (Rajavashisth, et. al., J. Clin. Invest. 1998; 101:2702-2710; Qiao, et. al., Am. J. Path. 1997; 150:1687-1699). Accordingly, inhibitors of Fms disrupt M-CSF signaling, compromising monocyte to macrophage foam cell progression, macrophage survival and replication, and cytokine signaling that participates in lesion progression.

The role of M-CSF and Fms in emphysema appears to involve the regulation of elastin metabolism through control of matrix metalloproteins. M-CSF has a role in the modulation of the accumulation and function of alveolar macrophages (AMs) in vivo (Shibata et al, Blood 2001, 98: pp. 2845-2852). Osteopetrotic (Op/Op) mice have no detectable M-CSF and show variable tissue-specific reductions in macrophage numbers. Accordingly, it was hypothesized that AMs would be decreased in number and have altered function in Op/Op mice because of the absence of M-CSF. Shibata et al found that lung macrophages identified in lung sections were decreased in number in 20-day-old Op/Op mice but not Op/Op mice older than 4 months compared with findings in age-matched littermate controls. The numbers of AMs recovered by bronchoalveolar lavage (BAL) were also reduced in young but not adult Op/Op mice compared with controls. Importantly, AMs of Op/Op mice spontaneously release higher levels of matrix metalloproteinases (MMPs) than AMs of controls. Consistent with an increased release of MMP, Op/Op mice have abnormal elastin deposition and spontaneously develop emphysema in the absence of molecular or cellular evidence of lung inflammation. Accordingly, the modulation of metalloelastase activity in macrophages by M-CSF may control the degradation of elastin fibers in lungs or blood vessels.

Metastatic cancer cells cause bone destruction, with associated fracture, pain, deformation, and hypercalcaemia, due to production of osteoclasticogenic factors including M-CSF by tumor cells (Clohisy et al, Clin. Orthop. 2000, 373: 104-14). Binding of M-CSF to the Fms product stimulates formation of osteoclasts and osteolytic activity (Kodama et al, J. Exp. Med. 1991, 173: 269-72; Feng et al, Endocrinology 2002, 143: 4868-74). Accordingly, inhibition of osteoclast activity at the level of Fms offers a compelling target for amelioration of bone metastasis.

Nephritis is inflammation of the kidneys. It may be caused for example by a bacterial infection of the kidneys or exposure to a toxin. However, nephritis more commonly develops from an abnormal immune reaction, which can occur, for example, when an antibody attacks either the kidney itself or an antigen attached to kidney cells, or when an antigen-antibody complex formed elsewhere in the body attaches to cells in the kidney. Some types of nephritis involve infiltration of kidney tissues by white blood cells and deposits of antibodies. In other types of nephritis, inflammation may consist of tissue swelling or scarring without white blood cells or antibodies. Furthermore, nephritis can occur anywhere in the kidneys. With respect to the glomeruli, progressive damage to glomeruli causes urine production to fall and metabolic waste products to build up in the blood. When damage to glomeruli is severe, inflammatory cells and injured glomerular cells accumulate, compressing the capillaries within the glomerulus and interfering with filtration. Scarring may develop, impairing kidney function and reducing urine production. In some cases, microthrombi may form in the small blood vessels, further decreasing kidney function. Less commonly, nephritis involves the tubulointerstitial tissues; such inflammation is called tubulointerstitial nephritis. When inflammation damages the tubules and the tubulointerstitial tissues, the kidneys may become unable to concentrate urine, eliminate (excrete) metabolic waste products from the body, or balance the excretion of sodium and other electrolytes, such as potassium. When the tubules and tubulointerstitial tissues are damaged, kidney failure often develops. Accordingly, inhibition of Fms offers a target for therapeutic intervention in nephritis due to the modulation of the inflammatory response comprising the etiology of the disease.

Lupus nephritis, i.e., renal involvement in systemic lupus erythematosus (SLE), is a common disease manifestation with a poor prognosis. At least three potentially overlapping, immuno-pathogenic mechanisms for lupus nephritis are supported by experimental data. First, circulating immune complexes consisting chiefly of DNA and anti-DNA are deposited in the kidney. Resulting complement activation and chemotaxis of neutrophils leads to a local inflammatory process. Second, in situ formation of antigen and antibody complexes may similarly lead to complement activation and leucocyte mediated injury. Third, antibodies against specific cellular targets may produce renal injury. An additional mechanism is observed in SLE patients with the antiphospholipid antibody syndrome. Glomerular thrombosis can result from the hypercoagulability that accompanies antibodies directed against negatively charged phospholipid-protein complexes (e.g. biologic false positive VDRL, anticardiolipin antibodies, and lupus anticoagulant). Mesangial lupus nephritis is accompanied by normal diagnostic findings or with a mild degree of proteinuria but typically absence of hypertension or abnormal urinary sediment. Focal and diffuse proliferative lupus glomerulonephritis are often associated with the worst prognosis for renal survival and can be accompanied by nephrotic syndrome, significant hypertension and abnormal urine sediment. Membranous lupus nephritis often presents with proteinuria, moderate to high grade, but usually normal urinary sediment in the absence of hypertension. Mesangial lupus nephropathy is generally associated with an excellent prognosis, whereas proliferative lupus nephropathy, especially diffuse variant, is often characterized by hypertension, red cell casts and significant deterioration of renal function. Nephrotic syndrome in the absence of hypertension, active urinary sediment or significant hypocomplementemia suggest the membranous variant of lupus nephropathy. Membranous nephropathy generally is associated with a good prognosis and relative preservation of renal function. However, in the presence of persistent nephrotic range proteinuria, membranous lupus nephropathy can, in fact, lead to loss of renal function and end stage renal disease (ESRD). Accordingly, inhibition of Fms offers a target for therapeutic intervention in lupus due to the modulation of the inflammatory response comprising the etiology of the disease.

Macrophage accumulation is a prominent feature in many forms of glomerulonephritis. Local proliferation of macrophages within the kidney has been described in human and experimental glomerulonephritis and may have an important role in augmenting the inflammatory response. Isbel et al (Nephrol Dial Transplant 2001, 16: 1638-1647) examined the relationship between local macrophage proliferation and renal expression of M-CSF. Glomerular and tubulointerstitial M-CSF expression was found to be up-regulated in human glomerulonephritis, being most prominent in proliferative forms of disease. Because this correlates with local macrophage proliferation, it suggests that increased renal M-CSF production plays an important role in regulating local macrophage proliferation in human glomerulonephritis. In a model of renal inflammation (UUO—unilateral ureteric obstruction) anti-Fms antibody treatment reduced macrophage accumulation (Le Meur et. al., J Leukocyte Biology, 2002, 72: 530-537). Accordingly, inhibition of Fms offers a target for therapeutic intervention in glomerulonephritis.

Insulin resistance and obesity are hallmark of type II diabetes and there is a strong correlation exists between insulin resistance and abdominal visceral fact accumulation (Bjorntrop, Diabetes Metab. Res. Rev., 1999, 15: 427-441). Current evidence indicates that macrophages accumulating in adipose tissue release TNF-α and other factors that cause adipocyte changes (hypertrophy, lipolysis, reduced insulin sensitivity) and also promote insulin resistance in surrounding tissues. Therefore, macrophage accumulation in type 2 diabetes is important for disease progression. Accordingly, inhibition of Fms has potential in preventing the development of insulin resistance and hyperglycemia.

Similarly, the observation that production of M-CSF, the major macrophage growth factor, is increased in tissues during inflammation points out a role for Fms in diseases, such as for example inflammatory diseases. More particularly, because elevated levels of M-CSF are found in the disease state, modulation of the activity of Fms can ameliorate disease associated with increased levels of M-CSF.

Fms inhibitors may be useful in treating inflammatory and autoimmune indications, including, but not limited to, rheumatoid arthritis, osteoarthritis, psoriatic arthritis, psoriasis, dermatitis, ankylosing spondylitis, polymyositis, dermatomyositis, systemic sclerosis, juvenile idiopathic arthritis, polymyalgia rheumatica, Sjogren's disease, Langerhan's cell histiocytosis (LCH), Still's disease, inflammatory bowel syndrome, ulcerative colitis, Crohn's disease, systemic lupus erythematosis (SLE), transplant rejection, chronic obstructive pulmonary disease (COPD), emphysema, Kawasaki's Disease, hemophagocytic syndrome (macrophage activation syndrome), multicentric reticulohistiocytosis, and atherosclerosis; metabolic disorders, including, but not limited to, Type I diabetes, Type II diabetes, insulin resistance, hyperglycemia, obesity, and lipolysis; disorders of bone structure, mineralization and bone formation and resorption, including, but not limited to, osteoporosis, osteodystrophy, increased risk of fracture, Paget's disease, hypercalcemia, infection-mediated osteolysis (e.g. osteomyelitis), and peri-prosthetic or wear-debris-mediated osteolysis; kidney and genitourinary diseases, including, but not limited to, endometriosis, nephritis (e.g. glomerulonephritis, interstitial nephritis, Lupus nephritis), tubular necrosis, diabetes-associated renal complications (e.g. diabetic nephropathy), and renal hypertrophy; disorders of the central nervous system, including, but not limited to, multiple sclerosis, amyotrophic lateral sclerosis (ALS), myasthenia gravis, chronic demyelinating polyneuropathy, other demyelinating disorders, stroke, Alzheimer's disease and Parkinson's disease; inflammatory and chronic pain, including, but not limited to, bone pain; malignancies, including, but not limited to, multiple myeloma, acute myeloid leukemia (AML), chronic myeloid leukemia (CML), lung cancer, pancreatic cancer, prostate cancer, breast cancer, ovarian cancer, neuroblastoma, sarcoma, osteosarcoma, giant cell tumor of bone, giant cell tumor of tendon sheath (TGCT), pigmented villonodular synovitis (PVNS), tumor angiogenesis, melanoma, glioblastoma multiforme, glioma, other tumors of the central nervous system, metastasis of tumors to other tissues, and other chronic myeloproliferative diseases such as myelofibrosis; vasculitis, including but not limited to collagen vascular disease, polyarteritis nodosa, Behcet's disease, sarcoidosis, familiar Mediterranean fever, Churg-Strauss vasculitis, temporal arteritis, giant cell arteritis, Takayasu's arteritis; ophthalmic indications, including but not limited to uveitis, scleritis, retinitis, age related macular degeneration, choroidal neovascularization, diabetic retinopathy; inherited disorders, including but not limited to cherubism, neurofibromatosis; infectious disease indications, including but not limited to infections associated with human immunodeficiency virus, hepatitis B virus, hepatitis C virus, human granulocytic anaplasmosis; lysosomal storage disorders, including but not limited to Gaucher's disease, Fabry's disease, Niemann-Pick disease; gastrointestinal indications, including but not limited to liver cirrhosis; pulmonary indications, including but not limited to pulmonary fibrosis, acute lung injury (e.g. ventilator-induced, smoke- or toxin-induced); and surgical indications, including but not limited to (cardiopulmonary) bypass surgery, vascular surgery, and vascular grafts.

Kit:

Target kinase Kit (i.e., feline Hardy-Zuckerman 4 sarcoma viral oncogene) is a 109.9 kDa transmembrane tyrosine kinase encoded by chromosome 4q12 (symbol: KIT). Receptor protein tyrosine kinases (RPTKs) regulate key signal transduction cascades that control cellular growth and proliferation. The Stem Cell Factor (SCF) receptor Kit is a type III transmembrane RPTK that includes five extracellular immunoglobulin (IG) domains, a single transmembrane domain, and a split cytoplasmic kinase domain separated by a kinase insert segment. Kit plays an important role in the development of melanocytes, mast, germ, and hematopoietic cells.

Stem Cell Factor (SCF) is a protein encoded by the 51 locus, and has also been called kit ligand (KL) and mast cell growth factor (MGF), based on the biological properties used to identify it (reviewed in Tsujimura, Pathol Int 1996, 46:933-938; Loveland, et al., J. Endocrinol 1997, 153:337-344; Vliagoftis, et al., Clin Immunol 1997, 100:435-440; Broudy, Blood 1997, 90:1345-1364; Pignon, Hermatol Cell Ther 1997, 39:114-116; and Lyman, et al., Blood 1998, 91:1101-1134.). Herein the abbreviation SCF refers to the ligand for Kit.

SCF is synthesized as a transmembrane protein with a molecular weight of 220 or 248 Dalton, depending on alternative splicing of the mRNA to encode exon 6. The larger protein can be proteolytically cleaved to form a soluble, glycosylated protein which noncovalently dimerizes. Both the soluble and membrane-bound forms of SCF can bind to and activate Kit. For example, in the skin, SCF is predominantly expressed by fibroblasts, keratinocytes, and endothelial cells, which modulate the activity of melanocytes and mast cells expressing Kit. In bone, marrow stromal cells express SCF and regulate hematopoiesis of Kit expressing stem cells. In the gastrointestinal tract, intestinal epithelial cells express SCF and affect the interstitial cells of Cajal and intraepithelial lymphocytes. In the testis, sertoli cells and granulosa cells express SCF which regulates spermatogenesis by interaction with Kit on germ cells.

According to OMIM, signaling from Kit is essential for primordial germ cell growth both in vivo and in vitro. Many downstream effectors of the KIT signaling pathway have been identified in other cell types, but how these molecules control primordial germ cell survival and proliferation are unknown. Determination of the KIT effectors acting in primordial germ cells has been hampered by the lack of effective methods to manipulate easily gene expression in these cells. De Miguel et al. (2002) overcame this problem by testing the efficacy of retroviral-mediated gene transfer for manipulating gene expression in mammalian germ cells. They found that primordial germ cells can successfully be infected with a variety of types of retroviruses. They used this method to demonstrate an important role of the AKT1 in regulating primordial germ cell growth (OMIM MIM Number: 164920: Apr. 17, 2006).

Aberrant expression and/or activation of Kit has been implicated in a variety of pathologic states. For example, evidence for a contribution of Kit to neoplastic pathology includes its association with leukemias and mast cell tumors, small cell lung cancer, testicular cancer, and some cancers of the gastrointestinal tract and central nervous system. In addition, Kit has been implicated in playing a role in carcinogenesis of the female genital tract sarcomas of neuroectodermal origin, and Schwann cell neoplasia associated with neurofibromatosis. It was found that mast cells are involved in modifying the tumor microenvironment and enhancing tumor growth (Yang et al., J Clin Invest. 2003, 112:1851-1861; Viskochil, J Clin Invest. 2003, 112:1791-1793).

Kit inhibitors may be useful in treating malignancies, including, but not limited to, mast cell tumors, small cell lung cancer, non-small cell lung cancer (NSCLC), testicular cancer, pancreatic cancer, breast cancer, merkel cell carcinoma, carcinomas of the female genital tract, sarcomas of neuroectodermal origin, colorectal carcinoma, carcinoma in situ, gastrointestinal stromal tumors (GISTs), tumor angiogenesis, glioblastoma, astrocytoma, neuroblastoma, Schwann cell neoplasia associated with neurofibromatosis, neurofibromatosis not associated with Schwann cell neoplasia, acute myelocytic leukemia, acute lymphocytic leukemia, chronic myelogenous leukemia, mastocytosis, melanoma, and canine mast cell tumors; cardiovascular disease, including but not limited to atherosclerosis, cardiomyopathy, heart failure, pulmonary hypertension; inflammatory and autoimmune indications, including, but not limited to, allergy, anaphylaxis, asthma, rheumatoid arthritis, allergic rhinitis, multiple sclerosis, inflammatory bowel syndrome, transplant rejection, hypereosinophilia, urticaria and dermatitis; gastrointestinal indications, including but not limited to gastroesophageal reflux disease (GERD), esophagitis, and gastrointestinal tract ulcers; ophthalmic indications, including but not limited to uveitis and retinitis; and neurologic indications, including but not limited to migraine.

MAP4K4:

Target kinase MAP4K4 (i.e., Mitogen-activated protein kinase kinase kinase 4, aka Hematopoietic progenitor kinase/Germinal center kinase-like Kinase) is a 130 kDa serine/threonine kinase encoded by chromosome 2q11.2-q12 (symbol: MAP4K4) and is also known as HGK. It is a member of the human STE20/mitogen-activated protein kinase kinase kinase kinase (MAP4K) family of serine/threonine kinases and is the human ortholog of mouse NIK (Nck-interacting kinase). The N-terminus of the mature HGK protein has a catalytic kinase domain that shares 47% and 48% amino acid sequence identity to the catalytic domain of Hematopoietic progenitor kinase 1 (HPK1) and Germinal center kinase (GCK), respectively. Yao et al. (J. Biol. Chem. 274: 2118-2125, 1999) identified 2 HGK isoforms, one of which has no proline-rich domains, and another, longer variant that contains such domains and appears to be expressed in brain only. Northern blot analysis revealed expression of 3 HGK transcripts of approximately 4.6, 6.5, and 8.5 kb in heart, brain, skeletal muscle, pancreas, placenta, liver, lung, and kidney. By Western blot analysis with a polyclonal antibody, Yao et al. (J. Biol. Chem. 274: 2118-2125, 1999) found that the 130-kD protein is expressed in multiple cell lines.

Expression of HGK in transfected cell lines resulted in strong JNK activation and, in turn, c-jun transcriptional activity (Yao et al. J. Biol. Chem. 274: 2118-2125, 1999). HGK-induced JNK activation was inhibited by dominant-negative MAP2K4, MAP2K7, and TAK1 mutants. TNF-alpha also stimulated HGK kinase activity. HGK was identified as a putative effect of Rap2 to activate JNK (Machida et al. J. Biol. Chem. 279: 15711-15714, 2004). This link establishes HGK as a potential target for a range of metabolic indications, since the JNK pathway clearly antagonizes insulin signaling. An HGK inhibitor could re-sensitize fat and muscle cells to insulin.

HGK is found to be broadly expressed in human tumor cells and can modulate cellular transformation, invasion, and adhesion (Wright et al. Mol. Cell. Biol. 23: 2068-2082, 2003). Wright et al showed HGK to be highly expressed in most tumor cell lines relative to normal tissue. An active role for this kinase in transformation was suggested by an inhibition of H-Ras (V12)-induced focus formation by expression of inactive, dominant-negative mutants of HGK in both fibroblast and epithelial cell lines. Expression of an inactive mutant of HGK also inhibited the anchorage-independent growth of cells yet had no effect on proliferation in monolayer culture. Expression of HGK mutants modulated integrin receptor expression and had a striking effect on hepatocyte growth factor-stimulated epithelial cell invasion. Together, these results suggest an important role for HGK in cell transformation and invasiveness. More recently, a small interfering RNA screen for modulators of tumor cell motility identifies MAP4K4 as a promigratory kinase (Collins et al. Proc. Natl. Acad. Sci. USA, 103: 3775-3780, 2006). Collins et al. showed that the knockdown of the HGK transcript inhibited the migration of multiple carcinoma cell lines, indicating a broad role in cell motility, and potently suppressed the invasion of SKOV-3 cells in vitro. The effect of HGK on cellular migration was found to be mediated through JNK kinase, independent of AP1 activation and downstream transcription. Accordingly, small molecule inhibition of c-Jun N-terminal kinase suppressed SKOV-3 cell migration, underscoring the potential therapeutic utility of mitogen-activated protein kinase pathway inhibition in cancer progression (Collins et al. Proc. Natl. Acad. Sci. USA, 103: 3775-3780, 2006). These studies strongly support HGK as a target in a broad range of oncology indications. In particular, an HGK inhibitor could have utility in blocking the migration, invasion and metastasis in many different tumor types.

Activation of T-cells by antigens initiates a complex series of signal-transduction events that are critical for immune responses. Mack et al. (Immunol Lett. 96, 129-145, 2005) developed a genetic screen to survey the functional roles of kinases in antigen mediated T-cell activation and identified 19 protein kinases that were previously implicated in T-cell signaling processes and 12 kinases that were not previously linked to T-cell activation, including HGK. siRNA studies showed a role for HGK in antigen mediated T-cell responses in Jurkat and primary T-cells. In addition, by analyzing multiple promoter elements using reporter assays, Mack et al. have shown that MAP4K4 is implicated in the activation of the TNF-alpha promoter. Therefore, inhibition of HGK could have broad therapeutic utility for T-cell-mediated autoimmune diseases.

Insulin-regulated glucose transporter GLUT4 is a key modulator of whole body glucose homeostasis, and its selective loss in adipose tissue or skeletal muscle causes insulin resistance and diabetes. Using an RNA interference-based screen, Tang et al. (Proc Natl Acad Sci USA. 103:2087-2092, 2006) found 4 negative regulators of insulin-responsive glucose transport in mouse adipocytes: Pctk1, Pftk1, Ikbka (CHUK), and HGK. HGK suppressed expression of adipogenic transcription factors, C/EBPA, C/EBPB, and PPARG, and it suppressed surface expression of GLUT4 (SLC2A4), resulting in attenuated membrane hexose transport activity. RNA interference-mediated depletion of HGK early in differentiation enhanced adipogenesis and triglyceride deposition; in fully differentiated adipocytes, loss of HGK upregulated GLUT4 expression. Conversely, conditions that inhibited adipogenesis, such as TNF-alpha treatment or PPARG depletion, markedly upregulated HGK. Tang et al. (Proc Natl Acad Sci USA. 103:2087-2092, 2006) concluded that MAP4K4-dependent signaling inhibited PPARG-responsive gene expression, adipogenesis, and insulin-stimulated glucose transport. Furthermore, TNF-alpha signaling to down-regulate GLUT4 is impaired in the absence of HGK, indicating that HGK expression is required for optimal TNF-alpha action. This study further supports HGK as a target in metabolic disease, and suggests a role for HGK inhibition in ameliorating the pathology in adipocytes.

In a separate study (Bouzakri and Zierath J. Biol. Chem. 282:7783-7789, 2007), using small interfering RNA (siRNA) to suppress the expression of HGK protein 85% in primary human skeletal muscle cells, TNF-alpha-induced insulin resistance on glucose uptake was completely prevented. HGK silencing inhibited TNF-alpha-induced negative signaling inputs by preventing excessive JNK and ERK-1/2 phosphorylation, as well as IRS-1 serine phosphorylation. These results highlight the HGK/JNK/ERK/IRS module in the negative regulation of insulin signaling to glucose transport in response to TNF-alpha. Depletion of HGK also prevented TNF-alpha-induced insulin resistance on AKT and the AKT substrate 160 (AS160), providing evidence that appropriate insulin signaling inputs for glucose metabolism were rescued. The authors suggested that strategies to inhibit HGK may be efficacious in the prevention of TNF-alpha-induced inhibitory signals that cause skeletal muscle insulin resistance on glucose metabolism in humans. Moreover, in myotubes from insulin-resistant type II diabetic patients, siRNA against HGK restored insulin action on glucose uptake to levels observed in healthy subjects. This study further supports HGK as a target in metabolic diseases such as type II diabetes, and suggests a role for HGK inhibition in ameliorating the pathology in muscle cells.

HGK inhibitors may be useful in treating metabolic indications, including re-sensitizing fat and muscle cells to insulin, ameliorating the pathology in adipocytes, ameliorating the pathology in muscle cells, metabolic syndrome and type II diabetes; a broad range of oncology indications, including blocking the migration, invasion and metastasis in many different tumor types; and T-cell mediated autoimmune diseases.

TrkA:

Target kinase TrkA (i.e., neurotrophic tyrosine kinase, receptor, type 1) is a 140 kDa tyrosine kinase encoded by chromosome 1q21-q22 (symbol: NTRK1). TrkA inhibitors may be useful in treating pain (e.g. chronic pain, neuropathic pain), cancer (e.g. prostate cancer, lung cancer, myeloid leukemia, pancreatic cancer), allergic disorders (e.g. asthma), arthritis, diabetic retinopathy, macular degeneration and psoriasis.

TrkA is a plasma member receptor composed of an extracellular domain (responsible for high affinity binding to nerve growth factor, NGF), a transmembrane segment and an intracellular protein tyrosine kinase domain (responsible to transmit the NGF signal to initiate and coordinate neuronal responses). NGF binding induces TrkA clustering on the membrane and activates the kinase. The kinase initiates a cascade of protein phosphorylation events through multiple pathways including SHC/Ras/MAPK, PI3K and PLCg1. A TrkA kinase inhibitor would not prevent NGF/TrkA binding, but could prevent down-stream signal transduction.

Nerve Growth Factor (NGF) is produced by a number of tissues and inflammatory cells during tissue injury and host immune response. It initiates and maintains hypersensitivity to incoming stimulus (hyperalgesia) and the perception of non-noxious stimuli (allodynia). Through its high-affinity receptor TrkA, NGF increases the excitation state of sensory neurons leading to the central nervous system (peripheral sensitization), and increases transmitter release from the dorsal spinal cord (central sensitization). In clinical trials, a single NGF subcutaneous injection generated local hyperalgesia persisting up to 7 weeks. At doses above 0.1 microgram/kg, NGF caused muscle pain that varied from mild to moderate, primarily in the bulbar and truncal musculature. Intravenous NGF produced earlier and more pronounced systemic effects (Petty et al, 1994, Ann Neurol. 36: 244-6). Conversely, TrkA kinase inhibitors could be used to treat diseases of enhanced states of nociception.

In Complete Freund's Adjuvant (CFA)-induced hind-paw inflammation, spinal nerve ligation and streptozoticin-induced neuropathic pain models, a single intraperitoneal injection of anti-NGF reversed established tactile allodynia from day 3 to day 7 following treatment. In the mouse CCI model, anti-NGF reversed tactile allodynia when administered 2 weeks after surgery. Repeated administration of this antibody to CCI mice for 3 weeks produced a sustained reversal of tactile allodynia (Wild et al, 2007, J. Pharmacol. Exp. Ther. 322:282-287).

Prostate tumors that have metastasized to bone frequently induce bone pain which can be difficult to fully control as it seems to be driven simultaneously by inflammatory, neuropathic, and tumorigenic mechanisms. Anti-NGF produced a significant reduction in both early and late stage bone cancer pain-related behaviors. This therapy did not influence tumor-induced bone remodeling, osteoblast proliferation, osteoclastogenesis, tumor growth, or markers of sensory or sympathetic innervation in the skin or bone. All nerve fibers that innervate the bone express TrkA and p'75, and these are the receptors through which NGF sensitizes and/or activates nociceptors (Halvorson et al, 2005, Cancer Res. 65:9426-35).

In patients with mild asthma due to exposure to cat allergen, NGF expression was strongly induced in epithelial cells, fibroblasts, blood vessels, and a few infiltrating cells. TrkA mRNA and protein levels in bronchial biopsies were increased significantly after allergen exposure in infiltrating mast cells before the onset of symptoms (Kassel et al, 2001, Clin Exp Allergy 31:1432-40).

The late phase reaction in asthma following allergen provocation is dominated by an influx of activated eosinophils into the bronchial lumen, which correlates with the release of eosinophilic products into the airways to increase disease severity. The viability and activation of eosinophils from patients with mild asthma were significantly enhanced after NGF stimulation. Addition of neutralizing anti-NGF antibodies ex vivo abrogated the effects (Nassentein et al, 2003, J Exp Med 198:455-467). TrkA kinase inhibitors could decrease this paracrine loop between the respiratory tract and infiltrating mast cells as well as endobronchial eosinophils, and thus be useful for the treatment of asthma and other allergic disorders.

TrkB:

Target kinase TrkB (i.e., neurotrophic tyrosine kinase, receptor, type 2) is a 145 kDa tyrosine kinase encoded by chromosome 9q22.1 (symbol: NTRK2). TrkB inhibitors may be useful in treating various cancers and their metastases (e.g. prostate cancer, lung cancer, Wilms tumors, neuroblastoma, and pancreatic cancer), and various neuropathies (e.g. stroke, multiple sclerosis, transverse myelitis, and encephalitis).

In clinical trials with recombinant BDNF, paresthesia was developed at the site of subcutaneous injection (Coulie et al, 2000, Gastroenterology 119:41-50). Intrathecal infusion of BDNF in humans also induced paresthesia and warmth as side effects (Ochs et al, 2000, Amyotroph Lateral Scler Other Motor Neuron Disord. 1:201-6). Chronic paresthesia is often a symptom of an underlying neurological disease or traumatic nerve damage. Paresthesia can be caused by disorders affecting the central nervous system, such as stroke and transient ischemic attacks (mini-strokes), multiple sclerosis, transverse myelitis, and encephalitis. Since BDNF binds to TrkB specifically with high affinity these neuropath effects are mediated through TrkB signaling. Thus Trkb kinase inhibitors could be used to treat certain patients with neuropathy.

BDNF is known to act at the synapses between primary sensory and spinal dorsal horn neurons to affect pain transmission during inflammation. The primary afferent is the only source of BDNF in the spinal cord, and it is up-regulated in the dorsal root ganglion (DRG) by peripheral NGF a few days after inflammation, and is transported and released into the superficial dorsal horn in an activity-dependent manner. TrkB expression in the dorsal horn also increases for a few days after inflammation. These findings suggest that BDNF may act during the restricted period in the early phase of inflammation. Through TrkB, BDNF activates two distinct channels: (1) transient receptor potential canonicals (TRPC3), which produces a slow response by opening of a non-selective cation channel; and (2) Na+ channel, which mediates a rapid depolarization in the hippocampus. These channels have been strongly associated with inflammatory pain. Anti-BDNF significantly increased the withdrawal threshold in CFA-treated rats, a model of inflammatory pain. Since the swelling at the site of CFA injection was not affected by antiserum, the residual component might be due to peripheral sensitization (Matayoshi et al, 2005, J. Physiol. 569:685-95).

In patients with neuroblastomas, co-expression of TrkB and BDNF, co-expression of TrkB with N-Myc amplification, and expression of truncated TrkB are found to be associated with poorer clinical outcome (Nakagawara et al, 1994, Mol Cell Biol. 14:759-767). Co-expression of TrkB with its ligand BDNF could generate a positive feedback loop through autocrine and paracrine loops. Also TrkB truncations found in these tumors generate activated forms of the intracellular protein tyrosine kinase. The constitutively active TrkB signals through multiple pathways to promote cancer initiation, progression and metastasis. These truncated TrkB kinases were also found in hepatocellular carcinoma (Yang et al, 2005, Cancer. Res 65:219-225). Thus TrkB inhibitors could be used to treat a sub-population of cancer patients with an activated TrkB pathway.

In patients with pancreatic cancer, TrkB expression is correlated with perineural invasion, positive retroperitoneal margin, and shorter latency to development of liver metastasis (Sclabas et al, 2005, Clin. Cancer. Res V11:440-449). Mechanistically, TrkB activates the PI3K pathway to suppress anoikis (apoptosis resulting from loss of cell-matrix interactions) which is one of the physiological barriers to metastasis. TrkB kinase inhibition could break down resistance to anoikis of metastasizing tumors (Douma et al, 2004, Nature 430: 1034-9). Therefore, TrkB inhibitors could have utility in a broad range of tumor types.

PI3 Kinase Family:

Phosphoinositide 3-kinases (PI3K) are a family of enzymes that phosphorylate phosphotidylinositol. One of the key signaling pathways in all eukaryotic cells involves this second messenger phosphatidylinositol 3,4,5-triphosphate (PIP3). PIP3 is generated from phosphatidylinositol 4,5-diphosphate (PIP2) by ATP dependent phosphorylation at the 3-position of the inositol ring. This reaction is catalyzed by the PI3-kinase family of lipid kinases. The PI3K family includes three main classes with varied substrate specificity. Class I, in addition to phosphorylating PI, also phosphorylates PI(4)P and PI(4,5)P2. Class II phosphorylates PI and PI(4)P. Class III phosphorylates only PI. Class I PI3K is a heterodimeric molecule composed of a catalytic subunit and a regulatory subunit, wherein for type IA PI3K, one of five regulatory subunits, p85α, p55α, p50α, p85β or p55γ is attached to a p110α, p110β, or p110δ catalytic subunit, and p101 regulatory subunits and p110γ catalytic subunits comprise type IB PI3K. These sub classes are typically referred to as PI3Kα, PI3Kβ, PI3Kδ and PI3Kγ based on the corresponding catalytic subunit. The p110α and p110β are constitutively expressed in all cell types, while p110δ is expressed mainly in leukocytes and some epithelial cells, and p110γ expression is limited to leukocytes. Dysregulation of the Type 1 PI3-kinases is a frequent event in a variety of human diseases. For example, PI3 kinase-α is frequently mutated in breast, colorectal, and many other cancers. Furthermore, knockout of the γ-isoform, which is primarily expressed in hematopoietic cells, results in mice that are resistant to a variety of inflammatory insults.

PI3 kinases are targets for tumor therapy, as the pathway is regulated by RAS, and is constitutively activated in a variety of human tumors. For example, somatic mutations that activate PI3Kγ have been identified, most frequently in the helical domain (E545K and E542K) and kinase domain (H1047R) of p110α (e.g. Engelman et al., Nature medicine 2008, 14(12): 1351-1355). Thus, inhibitors of PI3K may be used in the treatment of a variety of cancers, including, but not limited to, ovarian cancer, cervical cancer, breast cancer, colorectal cancer, endometrial cancer, gastric carcinomas, hepatocellular carcinoma, pancreatic cancer, small and non-small cell lung cancer, thyroid carcinoma, lymphomas, multiple myelomas, leukemias (e.g. acute myelogenous leukemia, chronic myelogenous leukemia), neuroblastomas and glioblastomas.

PI3 kinase inhibitors are useful in treating a variety of other diseases, including, but not limited to inflammatory disease, including, but not limited to, asthma, chronic obstructive pulmonary disease, bronchitis, emphysema, eosinophilia, lung fibrosis, osteoarthritis, ankylosing spondylitis, sepsis, septic shock, inflammatory myopathies, meningitis, encephalitis, lacrimal parotid gland syndrome, acute respiratory distress syndrome and pancreatitis, graft vs. host disease; allergies, including, but not limited to, allergic rhinitis, type I hypersensitivity reactions, atopic dermatitis, contact dermatitis, and eczema; cardiovascular disease, including, but not limited to, atherosclerosis, pulmonary hypertension, deep venous thrombosis, stroke, myocardial infarction, myocardial contractility disorders, ischemia, thromoemolism, pulmonary embolism, acute arterial ischemia, peripheral thrombotic occlusions, coronary artery disease and acute coronary syndrome; autoimmune disease, including, but not limited to, systemic lupus erythematosus, rheumatoid arthritis, multiple sclerosis, glomerulonephritis, scleroderma, chronic thyroiditis, Graves' disease, autoimmune gastritis, type I diabetes, autoimmune hemolytic anemia, autoimmune neutropenia, thrombocytopenia, atopic dermatitis, myasthenia gravis, inflammatory bowel disease, ulcerative colitis, Crohn's disease, psoriasis, and Sjogren's syndrome.

mTOR:

The mammalian target of rapamycin (mTOR) is a serine/threonine protein kinase involved in the regulation of cell growth and proliferation, including the regulation of response of tumor cells to nutrients and growth factors Inhibitors of mTOR are effective in treating a variety of tumors, including, but not limited to, neuronal tumors, breast cancer, prostate cancer, acute myelogenous leukemia, lung cancer, pancreatic cancer, colon cancer, renal cancer and myeloma.

Kinase Activity Assays

A number of different assays for kinase activity can be utilized for assaying for active modulators and/or determining specificity of a modulator for a particular kinase or group or kinases. In addition to the assay mentioned in the Examples below, one of ordinary skill in the art will know of other assays that can be utilized and can modify an assay for a particular application. For example, numerous papers concerning kinases describe assays that can be used.

Additional alternative assays can employ binding determinations. For example, this sort of assay can be formatted either in a fluorescence resonance energy transfer (FRET) format, or using an AlphaScreen (amplified luminescent proximity homogeneous assay) format by varying the donor and acceptor reagents that are attached to streptavidin or the phosphor-specific antibody.

Organic Synthetic Techniques

A wide array of organic synthetic techniques exist in the art to facilitate the construction of potential modulators. Many of these organic synthetic methods are described in detail in standard reference sources utilized by those skilled in the art. One example of such a reference is March, 1994, *Advanced Organic Chemistry; Reactions, Mechanisms and Structure*, New York, McGraw Hill. Thus, the techniques useful to synthesize a potential modulator of kinase function are readily available to those skilled in the art of organic chemical synthesis.

Alternative Compound Forms or Derivatives

Compounds contemplated herein are described with reference to both generic formulae and specific compounds. In addition, invention compounds may exist in a number of different forms or derivatives, all within the scope of the present invention. Alternative forms or derivatives, include, for example, (a) prodrugs, and active metabolites (b) tautomers, isomers (including stereoisomers and regioisomers), and racemic mixtures (c) pharmaceutically acceptable salts and (d) solid forms, including different crystal forms, polymorphic or amorphous solids, including hydrates and solvates thereof, and other forms.

(a) Prodrugs and Metabolites

In addition to the present formulae and compounds described herein, the invention also includes prodrugs (generally pharmaceutically acceptable prodrugs), active metabolic derivatives (active metabolites), and their pharmaceutically acceptable salts.

Prodrugs are compounds or pharmaceutically acceptable salts thereof which, when metabolized under physiological conditions or when converted by solvolysis, yield the desired active compound. Prodrugs include, without limitation, esters, amides, carbamates, carbonates, ureides, solvates, or hydrates of the active compound. Typically, the prodrug is inactive, or less active than the active compound, but may provide one or more advantageous handling, administration, and/or metabolic properties. For example, some prodrugs are esters of the active compound; during metabolysis, the ester group is cleaved to yield the active drug. Esters include, for example, esters of a carboxylic acid group, or S-acyl or O-acyl derivatives of thiol, alcohol, or phenol groups. In this context, a common example is an alkyl ester of a carboxylic acid. Prodrugs may also include variants wherein an —NH group of the compound has undergone acylation, such as the 7-position of the pyrrolo[2,3-d]pyrimidine ring of compounds of the present invention (e.g. compounds of Formula I), where cleavage of the acyl group provides the free —NH group of the active drug. Some prodrugs are activated enzymatically to yield the active compound, or a compound may undergo further chemical reaction to yield the active compound. Prodrugs may proceed from prodrug form to active form in a single step or may have one or more intermediate forms which may themselves have activity or may be inactive.

As described in *The Practice of Medicinal Chemistry*, Ch. 31-32 (Ed. Wermuth, Academic Press, San Diego, Calif., 2001), prodrugs can be conceptually divided into two non-exclusive categories, bioprecursor prodrugs and carrier prodrugs. Generally, bioprecursor prodrugs are compounds that are inactive or have low activity compared to the corresponding active drug compound, that contain one or more protective groups and are converted to an active form by metabolism or solvolysis. Both the active drug form and any released metabolic products should have acceptably low toxicity. Typically, the formation of active drug compound involves a metabolic process or reaction that is one of the following types:

Oxidative Reactions:

Oxidative reactions are exemplified without limitation by reactions such as oxidation of alcohol, carbonyl, and acid functionalities, hydroxylation of aliphatic carbons, hydroxylation of alicyclic carbon atoms, oxidation of aromatic carbon atoms, oxidation of carbon-carbon double bonds, oxidation of nitrogen-containing functional groups, oxidation of silicon, phosphorus, arsenic, and sulfur, oxidative N-dealkylation, oxidative O- and S-dealkylation, oxidative deamination, as well as other oxidative reactions.

Reductive Reactions:

Reductive reactions are exemplified without limitation by reactions such as reduction of carbonyl functionalitites, reduction of alcohol functionalities and carbon-carbon double bonds, reduction of nitrogen-containing functional groups, and other reduction reactions.

Reactions without Change in the Oxidation State:

Reactions without change in the state of oxidation are exemplified without limitation to reactions such as hydrolysis of esters and ethers, hydrolytic cleavage of carbon-nitrogen single bonds, hydrolytic cleavage of non-aromatic heterocycles, hydration and dehydration at multiple bonds, new atomic linkages resulting from dehydration reactions, hydrolytic dehalogenation, removal of hydrogen halide molecule, and other such reactions.

Carrier prodrugs are drug compounds that contain a transport moiety, e.g., that improves uptake and/or localized delivery to a site(s) of action. Desirably for such a carrier prodrug, the linkage between the drug moiety and the transport moiety is a covalent bond, the prodrug is inactive or less active than the drug compound, the prodrug and any release transport moiety are acceptably non-toxic. For prodrugs where the transport moiety is intended to enhance uptake, typically the release of the transport moiety should be rapid. In other cases, it is desirable to utilize a moiety that provides slow release, e.g., certain polymers or other moieties, such as cyclodextrins. (See, e.g., Cheng et al., U.S. Patent Publ. No. 20040077595, application Ser. No. 10/656,838, incorporated herein by reference.) Such carrier prodrugs are often advantageous for orally administered drugs. In some instances, the transport moiety provides targeted delivery of the drug, for example the drug may be conjugated to an antibody or antibody fragment. Carrier prodrugs can, for example, be used to improve one or more of the following properties: increased lipophilicity, increased duration of pharmacological effects, increased site-specificity, decreased toxicity and adverse reactions, and/or improvement in drug formulation (e.g., stability, water solubility, suppression of an undesirable organoleptic or physiochemical property). For example, lipophilicity can be increased by esterification of hydroxyl groups with lipophilic carboxylic acids, or of carboxylic acid groups with alcohols, e.g., aliphatic alcohols. Wermuth, supra.

Metabolites, e.g., active metabolites, overlap with prodrugs as described above, e.g., bioprecursor prodrugs. Thus, such metabolites are pharmacologically active compounds or compounds that further metabolize to pharmacologically active compounds that are derivatives resulting from metabolic processes in the body of a subject. Of these, active metabolites are such pharmacologically active derivative compounds. For prodrugs, the prodrug compound is generally inactive or of lower activity than the metabolic product. For active metabolites, the parent compound may be either an active compound or may be an inactive prodrug. For example, in some compounds, one or more alkoxy groups can be metabolized to hydroxyl groups while retaining pharmacologic activity and/or carboxyl groups can be esterified, e.g., glucuronidation. In some cases, there can be more than one metabolite, where an intermediate metabolite(s) is further metabolized to provide an active metabolite. For example, in some cases a derivative compound resulting from metabolic glucuronidation may be inactive or of low activity, and can be further metabolized to provide an active metabolite.

Metabolites of a compound may be identified using routine techniques known in the art, and their activities determined using tests such as those described herein. See, e.g., Bertolini et al., 1997, *J. Med. Chem.*, 40:2011-2016; Shan et al., 1997, *J Pharm Sci* 86(7):756-757; Bagshawe, 1995, *Drug Dev. Res.*, 34:220-230; Wermuth, supra.

(b) Tautomers, Stereoisomers, and Regioisomers

It is understood that some compounds may exhibit tautomerism. In such cases, the formulae provided herein expressly depict only one of the possible tautomeric forms. It is therefore to be understood that the formulae provided herein are intended to represent any tautomeric form of the depicted compounds and are not to be limited merely to the specific tautomeric form depicted by the drawings of the formulae.

Likewise, some of the compounds according to the present invention may exist as stereoisomers, i.e. having the same atomic connectivity of covalently bonded atoms yet differing in the spatial orientation of the atoms. For example, compounds may be optical stereoisomers, which contain one or more chiral centers, and therefore, may exist in two or more stereoisomeric forms (e.g. enantiomers or diastereomers). Thus, such compounds may be present as single stereoisomers (i.e., essentially free of other stereoisomers), racemates, and/or mixtures of enantiomers and/or diastereomers. As another example, stereoisomers include geometric isomers, such as cis- or trans-orientation of substituents on adjacent carbons of a double bond. All such single stereoisomers, racemates and mixtures thereof are intended to be within the scope of the present invention. Unless specified to the contrary, all such steroisomeric forms are included within the formulae provided herein.

In some embodiments, a chiral compound of the present invention is in a form that contains at least 80% of a single isomer (60% enantiomeric excess ("e.e.") or diastereomeric excess ("d.e.")), or at least 85% (70% e.e. or d.e.), 90% (80% e.e. or d.e.), 95% (90% e.e. or d.e.), 97.5% (95% e.e. or d.e.), or 99% (98% e.e. or d.e.). As generally understood by those skilled in the art, an optically pure compound having one chiral center is one that consists essentially of one of the two possible enantiomers (i.e., is enantiomerically pure), and an optically pure compound having more than one chiral center is one that is both diastereomerically pure and enantiomerically pure. In some embodiments, the compound is present in optically pure form, such optically pure form being prepared and/or isolated by methods known in the art (e.g. by recrystallization techniques, chiral synthetic techniques (including synthesis from optically pure starting materials), and chromatographic separation using a chiral column.

(c) Pharmaceutically Acceptable Salts

Unless specified to the contrary, specification of a compound herein includes pharmaceutically acceptable salts of such compound. Thus, compounds of Formula I can be in the form of pharmaceutically acceptable salts, or can be formulated as pharmaceutically acceptable salts. Contemplated pharmaceutically acceptable salt forms include, without limitation, mono, bis, tris, tetrakis, and so on. Pharmaceutically acceptable salts are non-toxic in the amounts and concentrations at which they are administered. The preparation of such salts can facilitate the pharmacological use by altering the physical characteristics of a compound without preventing it from exerting its physiological effect. Useful alterations in physical properties include lowering the melting point to facilitate transmucosal administration and increasing the solubility to facilitate administering higher concentrations of the drug. A compound of the invention may possess a sufficiently acidic, a sufficiently basic, or both functional groups, and accordingly can react with any of a number of inorganic or organic bases, and inorganic and organic acids, to form a pharmaceutically acceptable salt.

Pharmaceutically acceptable salts include acid addition salts such as those containing chloride, bromide, iodide, hydrochloride, acetate, phenylacetate, acrylate, ascorbate, aspartate, benzoate, 2-phenoxybenzoate, 2-acetoxybenzoate, dinitrobenzoate, hydroxybenzoate, methoxybenzoate, methylbenzoate, bicarbonate, butyne-1,4 dioate, hexyne-1,6-dioate, caproate, caprylate, chlorobenzoate, cinnamate, citrate, decanoate, formate, fumarate, glycolate, gluconate, glucarate, glucuronate, glucose-6-phosphate, glutamate, heptanoate, hexanoate, isethionate, isobutyrate, gamma-hydroxybutyrate, phenylbutyrate, lactate, malate, maleate, hydroxymaleate, methylmaleate, malonate, mandelate, nicotinate, nitrate, isonicotinate, octanoate, oleate, oxalate, pamoate, phosphate, monohydrogenphosphate, dihydrogenphosphate, orthophosphate, metaphosphate, pyrophosphate, 2-phosphoglycerate, 3-phosphoglycerate, phthalate, propionate, phenylpropionate, propiolate, pyruvate, quinate, salicylate, 4-aminosalicylate, sebacate, stearate, suberate, succinate, sulfate, pyrosulfate, bisulfate, sulfite, bisulfite, sulfamate, sulfonate, benzenesulfonate (i.e. besylate), ethanesulfonate (i.e. esylate), ethane-1,2-disulfonate, 2-hydroxyethanesulfonate (i.e. isethionate), methanesulfonate (i.e. mesylate), naphthalene-1-sulfonate, naphthalene-2-sulfonate (i.e. napsylate), propanesulfonate, p-toluenesulfonate (i.e. tosylate), xylenesulfonates, cyclohexylsulfamate, tartrate, and trifluoroacetate. These pharmaceutically acceptable acid addition salts can be prepared using the appropriate corresponding acid.

When acidic functional groups, such as carboxylic acid or phenol are present, pharmaceutically acceptable salts also include basic addition salts such as those containing benzathine, chloroprocaine, choline, ethanolamine, diethanolamine, triethanolamine, t-butylamine, dicyclohexylamine, ethylenediamine, N,N'-dibenzylethylenediamine, meglumine, hydroxyethylpyrrolidine, piperidine, morpholine, piperazine, procaine, aluminum, calcium, copper, iron, lithium, magnesium, manganese, potassium, sodium, zinc, ammonium, and mono-, di-, or tri-alkylamines (e.g. diethylamine), or salts derived from amino acids such as L-histidine, L-glycine, L-lysine, and L-arginine. For example, see *Remington's Pharmaceutical Sciences,* 19$^{th}$ ed., Mack Publishing Co., Easton, Pa., Vol. 2, p. 1457, 1995. These pharmaceutically acceptable base addition salts can be prepared using the appropriate corresponding base.

Pharmaceutically acceptable salts can be prepared by standard techniques. For example, the free-base form of a compound can be dissolved in a suitable solvent, such as an aqueous or aqueous-alcohol solution containing the appropriate acid and then isolated by evaporating the solution. In another example, a salt can be prepared by reacting the free base and acid in an organic solvent. If the particular compound is an acid, the desired pharmaceutically acceptable salt may be prepared by any suitable method, for example, treatment of the free acid with an appropriate inorganic or organic base.

(d) Other Compound Forms

In the case of agents that are solids, it is understood by those skilled in the art that the compounds and salts may exist in different crystal or polymorphic forms, or may be formulated as co-crystals, or may be in an amorphous form, or may be any combination thereof (e.g. partially crystalline, partially amorphous, or mixtures of polymorphs) all of which are intended to be within the scope of the present invention and specified formulae. Whereas salts are formed by acid/base addition, i.e. a free base or free acid of the compound of interest forms an acid/base reaction with a corresponding addition base or addition acid, respectively, resulting in an ionic charge interaction, co-crystals are a new chemical species that is formed between neutral compounds, resulting in the compound and an additional molecular species in the same crystal structure.

In some instances, compounds of the invention are complexed with an acid or a base, including base addition salts such as ammonium, diethylamine, ethanolamine, ethylenediamine, diethanolamine, t-butylamine, piperazine, meglumine; acid addition salts, such as acetate, acetylsalicylate, besylate, camsylate, citrate, formate, fumarate, glutarate, hydrochlorate, maleate, mesylate, nitrate, oxalate, phosphate, succinate, sulfate, tartrate, thiocyanate and tosylate; and amino acids such as alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine or valine. In combining the compound of the invention with the acid or base, an amorphous complex is preferably formed rather than a crystalline material such as a typical salt or co-crystal. In some instances, the amorphous form of the complex is facilitated by additional processing, such as by spray-drying, mechanochemical methods such as roller compaction, or microwave irradiation of the parent compound mixed with the acid or base. Such amorphous complexes provide several advantages. For example, lowering of the melting temperature relative to the free base facilitiates additional processing, such as hot melt extrusion, to further improve the biopharmaceutical properties of the compound. Also, the amorphous complex is readily friable, which provides improved compression for loading of the solid into capsule or tablet form.

Additionally, the formulae are intended to cover hydrated or solvated as well as unhydrated or unsolvated forms of the identified structures. For example, the indicated compounds include both hydrated and non-hydrated forms. Other examples of solvates include the structures in combination with a suitable solvent, such as isopropanol, ethanol, methanol, DMSO, ethyl acetate, acetic acid, or ethanolamine Formulations and Administration The methods and compounds will typically be used in therapy for human subjects. However, they may also be used to treat similar or identical indications in other animal subjects. Compounds of Formula I can be administered by different routes, including injection (i.e. parenteral, including intravenous, intraperitoneal, subcutaneous, and intramuscular), oral, transdermal, transmucosal, rectal, or inhalant. Such dosage forms should allow the compound to reach target cells. Other factors are well known in the art, and include considerations such as toxicity and dosage forms that retard the compound or composition from exerting its effects. Techniques and formulations generally may be found in Remington: *The Science and Practice of Pharmacy,* 21$^{st}$ edition, Lippincott, Williams and Wilkins, Philadelphia, Pa., 2005 (hereby incorporated by reference herein).

In some embodiments, compositions will comprise pharmaceutically acceptable carriers or excipients, such as fillers, binders, disintegrants, glidants, lubricants, complexing agents, solubilizers, and surfactants, which may be chosen to facilitate administration of the compound by a particular route. Examples of carriers include calcium carbonate, calcium phosphate, various sugars such as lactose, glucose, or sucrose, types of starch, cellulose derivatives, gelatin, lipids, liposomes, nanoparticles, and the like. Carriers also include physiologically compatible liquids as solvents or for suspensions, including, for example, sterile solutions of water for injection (WFI), saline solution, dextrose solution, Hank's solution, Ringer's solution, vegetable oils, mineral oils, animal oils, polyethylene glycols, liquid paraffin, and the like. Excipients may also include, for example, colloidal silicon dioxide, silica gel, talc, magnesium silicate, calcium silicate, sodium aluminosilicate, magnesium trisilicate, powdered cellulose, macrocrystalline cellulose, carboxymethyl cellulose, cross-linked sodium carboxymethylcellulose, sodium benzoate, calcium carbonate, magnesium carbonate, stearic acid, aluminum stearate, calcium stearate, magnesium stearate, zinc stearate, sodium stearyl fumarate, syloid, stearowet C, magnesium oxide, starch, sodium starch glycolate, glyceryl monostearate, glyceryl dibehenate, glyceryl palmitostearate, hydrogenated vegetable oil, hydrogenated cotton seed oil, castor seed oil mineral oil, polyethylene glycol (e.g. PEG 4000-8000), polyoxyethylene glycol, poloxamers, povidone, crospovidone, croscarmellose sodium, alginic acid, casein, methacrylic acid divinylbenzene copolymer, sodium docusate, cyclodextrins (e.g. 2-hydroxypropyl-.delta.-cyclodextrin), polysorbates (e.g. polysorbate 80), cetrimide, TPGS (d-alpha-tocopheryl polyethylene glycol 1000 succinate), magnesium lauryl sulfate, sodium lauryl sulfate, polyethylene glycol ethers, di-fatty acid ester of polyethylene glycols, or a polyoxyalkylene sorbitan fatty acid ester (e.g., polyoxyethylene sorbitan ester Tween®), polyoxyethylene sorbitan fatty acid esters, sorbitan fatty acid ester, e.g. a sorbitan fatty acid ester from a fatty acid such as oleic, stearic or palmitic acid, mannitol, xylitol, sorbitol, maltose, lactose, lactose monohydrate or lactose spray dried, sucrose, fructose, calcium phosphate, dibasic calcium phosphate, tribasic calcium phosphate, calcium sulfate, dextrates, dextran, dextrin, dextrose, cellulose acetate, maltodextrin, simethicone, polydextrosem, chitosan, gelatin, HPMC (hydroxypropyl methyl celluloses), HPC (hydroxypropyl cellulose), hydroxyethyl cellulose, hypromellose, and the like.

In some embodiments, oral administration may be used. Pharmaceutical preparations for oral use can be formulated into conventional oral dosage forms such as capsules, tablets, and liquid preparations such as syrups, elixirs, and concentrated drops. Compounds of Formula I may be combined with solid excipients, optionally grinding a resulting mixture, and processing the mixture of granules, after adding suitable auxiliaries, if desired, to obtain, for example, tablets, coated tablets, hard capsules, soft capsules, solutions (e.g. aqueous, alcoholic, or oily solutions) and the like. Suitable excipients are, in particular, fillers such as sugars, including lactose, glucose, sucrose, mannitol, or sorbitol; cellulose preparations, for example, corn starch, wheat starch, rice starch, potato starch, gelatin, gum tragacanth, methyl cellulose, hydroxypropylmethyl-cellulose, sodium carboxymethylcellulose (CMC), and/or polyvinylpyrrolidone (PVP: povidone); oily excipients, including vegetable and animal oils, such as sunflower oil, olive oil, or codliver oil. The oral dosage formulations may also contain disintegrating agents, such as the cross-linked polyvinylpyrrolidone, agar, or alginic acid, or a salt thereof such as sodium alginate; a lubricant, such as talc or magnesium stearate; a plasticizer, such as glycerol or sorbitol; a sweetening such as sucrose, fructose, lactose, or aspartame; a natural or artificial flavoring agent, such as peppermint, oil of wintergreen, or cherry flavoring; or dye-stuffs or pigments, which may be used for identification or characterization of different doses or combinations. Also provided are dragee cores with suitable coatings. For this purpose, concentrated sugar solutions may be used, which may optionally contain, for example, gum arabic, talc, polyvinylpyrrolidone, carbopol gel, polyethylene glycol, and/or titanium dioxide, lacquer solutions, and suitable organic solvents or solvent mixtures.

Pharmaceutical preparations that can be used orally include push-fit capsules made of gelatin ("gelcaps"), as well as soft, sealed capsules made of gelatin, and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols.

In some embodiments, injection (parenteral administration) may be used, e.g., intramuscular, intravenous, intraperitoneal, and/or subcutaneous. Compounds of Formula I for injection may be formulated in sterile liquid solutions, preferably in physiologically compatible buffers or solutions, such as saline solution, Hank's solution, or Ringer's solution. Dispersions may also be prepared in non-aqueous solutions, such as glycerol, propylene glycol, ethanol, liquid polyethylene glycols, triacetin, and vegetable oils. Solutions may also contain a preservative, such as methylparaben, propylparaben, chlorobutanol, phenol, sorbic acid, thimerosal, and the like. In addition, the compounds may be formulated in solid form, including, for example, lyophilized forms, and redissolved or suspended prior to use.

In some embodiments, transmucosal, topical or transdermal administration may be used. In such formulations of compounds of Formula I, penetrants appropriate to the barrier to be permeated are used. Such penetrants are generally known in the art, and include, for example, for transmucosal administration, bile salts and fusidic acid derivatives. In addition, detergents may be used to facilitate permeation. Transmucosal administration, for example, may be through nasal sprays or suppositories (rectal or vaginal). Compositions of compounds of Formula I for topical administration may be formulated as oils, creams, lotions, ointments, and the like by choice of appropriate carriers known in the art. Suitable carriers include vegetable or mineral oils, white petrolatum (white soft paraffin), branched chain fats or oils, animal fats and high molecular weight alcohol (greater than $C_{12}$). In some embodiments, carriers are selected such that the active ingredient is soluble. Emulsifiers, stabilizers, humectants and antioxidants may also be included as well as agents imparting color or fragrance, if desired. Creams for topical application are preferably formulated from a mixture of mineral oil, self-emulsifying beeswax and water in which mixture the active ingredient, dissolved in a small amount of solvent (e.g., an oil), is admixed. Additionally, administration by transdermal means may comprise a transdermal patch or dressing such as a bandage impregnated with an active ingredient and optionally one or more carriers or diluents known in the art. To be administered in the form of a transdermal delivery system, the dosage administration will be continuous rather than intermittent throughout the dosage regimen.

In some embodiments, compounds are administered as inhalants. Compounds of Formula I may be formulated as dry powder or a suitable solution, suspension, or aerosol. Powders and solutions may be formulated with suitable additives known in the art. For example, powders may include a suitable powder base such as lactose or starch, and solutions may comprise propylene glycol, sterile water, ethanol, sodium chloride and other additives, such as acid, alkali and buffer salts. Such solutions or suspensions may be administered by inhaling via spray, pump, atomizer, or nebulizer, and the like. The compounds of Formula I may also be used in combination with other inhaled therapies, for example corticosteroids such as fluticasone proprionate, beclomethasone dipropionate, triamcinolone acetonide, budesonide, and mometasone furoate; beta agonists such as albuterol, salmeterol, and formoterol; anticholinergic agents such as ipratroprium bromide or tiotropium; vasodilators such as treprostinal and iloprost; enzymes such as DNAase; therapeutic proteins; immunoglobulin antibodies; an oligonucleotide, such as single or double stranded DNA or RNA, siRNA; antibiotics such as tobramycin; muscarinic receptor antagonists; leukotriene antagonists; cytokine antagonists; protease inhibitors; cromolyn sodium; nedocril sodium; and sodium cromoglycate.

The amounts of various compounds to be administered can be determined by standard procedures taking into account factors such as the compound activity (in vitro, e.g. the compound $IC_{50}$ vs. target, or in vivo activity in animal efficacy models), pharmacokinetic results in animal models (e.g. biological half-life or bioavailability), the age, size, and weight of the subject, and the disorder associated with the subject. The importance of these and other factors are well known to those of ordinary skill in the art. Generally, a dose will be in the range of about 0.01 to 50 mg/kg, also about 0.1 to 20 mg/kg of the subject being treated. Multiple doses may be used.

The compounds of Formula I may also be used in combination with other therapies for treating the same disease. Such combination use includes administration of the compounds and one or more other therapeutics at different times, or co-administration of the compound and one or more other therapies. In some embodiments, dosage may be modified for one or more of the compounds of the invention or other therapeutics used in combination, e.g., reduction in the amount dosed relative to a compound or therapy used alone, by methods well known to those of ordinary skill in the art.

It is understood that use in combination includes use with other therapies, drugs, medical procedures etc., where the other therapy or procedure may be administered at different times (e.g. within a short time, such as within hours (e.g. 1, 2, 3, 4-24 hours), or within a longer time (e.g. 1-2 days, 2-4 days, 4-7 days, 1-4 weeks)) than a compound of Formula I, or at the same time as a compound of Formula I. Use in combination also includes use with a therapy or medical procedure that is administered once or infrequently, such as surgery, along with a compound of Formula I administered within a short time or longer time before or after the other therapy or procedure. In some embodiments, the present invention provides for delivery of a compound of Formula I and one or more other drug therapeutics delivered by a different route of administration or by the same route of administration. The use in combination for any route of administration includes delivery of a compound of Formula I and one or more other drug therapeutics delivered by the same route of administration together in any formulation, including formulations where the two compounds are chemically linked in such a way that they maintain their therapeutic activity when administered. In one aspect, the other drug therapy may be co-administered with a compound of Formula I. Use in combination by co-administration includes administration of co-formulations or formulations of chemically joined compounds, or administration of two or more compounds in separate formulations within a short time of each other (e.g. within an hour, 2 hours, 3 hours, up to 24 hours), administered by the same or different routes. Co-administration of separate formulations includes co-administration by delivery via one device, for example the same inhalant device, the same syringe, etc., or administration from separate devices within a short time of each other. Co-formulations of a compound of Formula I and one or more additional drug therapies delivered by the same route includes preparation of the materials together such that they can be administered by one device, including the separate compounds combined in one formulation, or compounds that are modified such that they are chemically joined, yet still maintain their biological activity. Such chemically joined compounds may have a linkage that is substantially maintained in vivo, or the linkage may break down in vivo, separating the two active components.

EXAMPLES

Examples related to the present invention are described below. In most cases, alternative techniques can be used. The examples are intended to be illustrative and are not limiting or restrictive to the scope of the invention. In some examples, the mass spectrometry result indicated for a compound may have more than one value due to the isotope distribution of an atom in the molecule, such as a compound having a bromo or chloro substituent.

Unless specifically indicated otherwise, the Formula enumeration and R group enumeration used in the following examples is not related to such enumeration in other sections of this application. The reagents and solvents used in these examples can be readily substituted with appropriate alternatives as are known in the art and isolation of products is readily achieved by methods known in the art, including, but not limited to, extraction, crystallization, and chromatographic methods.

Ring numbering for the 7H-pyrrolo[2,3-d]pyrimidine in the following Examples is as follows:

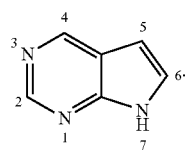

Example 1

Preparation of 7H-pyrrolo[2,3-d]pyrimidine Intermediates 7H-pyrrolo[2,3-d]pyrimidine compounds known in the art may be used in the preparation of starting materials for use in the synthesis of compounds described herein. For example, 2-halo or 4-halo 7H-pyrrolo[2,3-d]pyrimidine can be used to provide starting materials with suitable substitutions at the 2- or 4-position of the 7H-pyrrolo[2,3-d]pyrimidine, e.g. according to the following Schemes I-IX.

Scheme I

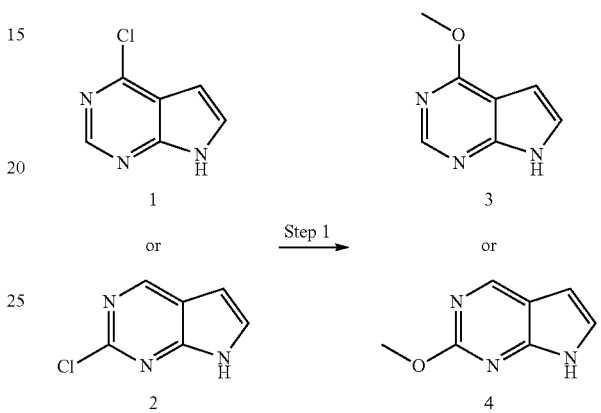

4-methoxy-7H-pyrrolo[2,3-d]pyrimidine (3) or 2-methoxy-7H-pyrrolo[2,3-d]pyrimidine (4) is prepared by reacting 4-chloro-7H-pyrrolo[2,3-d]pyrimidine (1) or 2-chloro-7H-pyrrolo[2,3-d]pyrimidine (2), respectively, with sodium hydroxide in methanol as described by Girgis, N. et. al., J. Heterocyclic. Chem. 1989, 26:317-325.

Scheme II

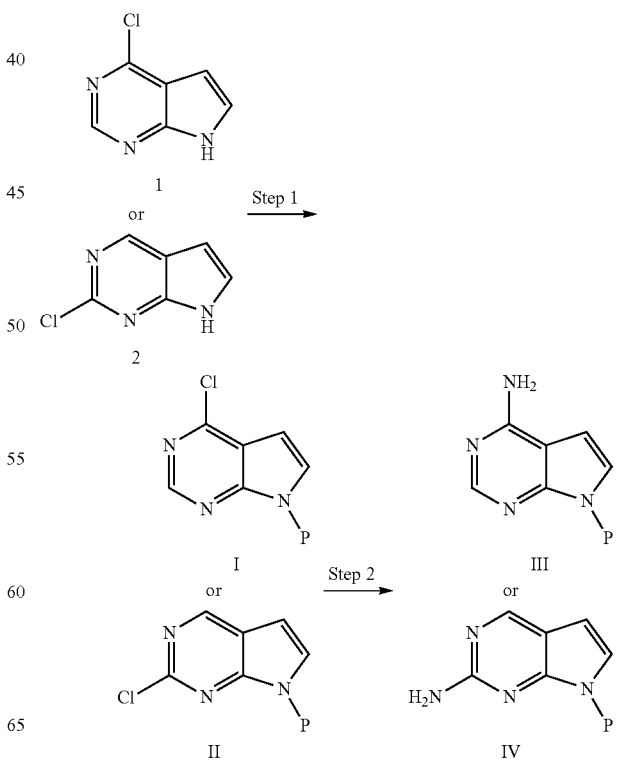

Step 1—Preparation of Compounds of Formula I or II

Compounds of Formula I or II, where P is a suitable protecting group, are prepared by reacting 4-chloro-7H-pyrrolo[2,3-d]pyrimidine (1) or 2-chloro-7H-pyrrolo[2,3-d]pyrimidine (2), respectively, with an appropriate reagent to introduce a suitable protecting group (P—X, e.g. triisopropylsilylchloride) and a base (e.g. sodium hydride) in a solvent (e.g. tetrahydrofuran) typically at room temperature for 8-12 hours. The desired compound is isolated by conventional means (e.g. extraction).

Step 2—Preparation of Compounds of Formula III or IV

Compounds of Formula III or IV are prepared by reacting compounds of Formula I or II, respectively, with ammonium hydroxide in a suitable solvent or with ammonia in methanol. The desired compound is isolated by conventional means (e.g. extraction). Alternatively, 4-chloro-7H-pyrrolo[2,3-d]pyrimidine (1) or 2-chloro-7H-pyrrolo[2,3-d]pyrimidine (2) can be reacted directly by this method to provide the corresponding compounds without the protecting group.

Scheme III

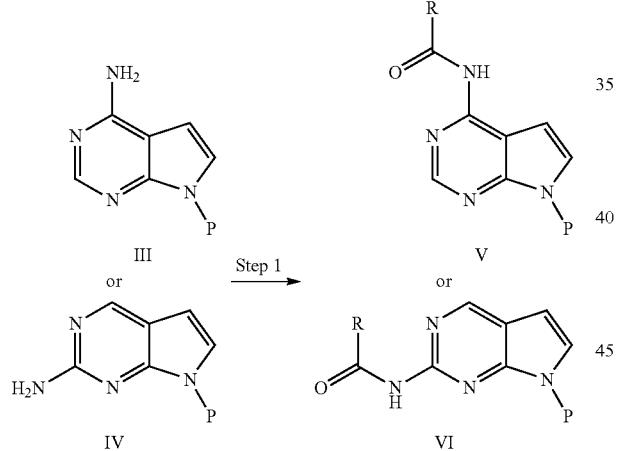

Compounds of Formula V or VI, where R is optionally substituted lower alkyl, optionally substituted lower alkenyl, optionally substituted lower alkynyl, optionally substituted cycloalkyl, optionally substituted heterocycloalkyl, optionally substituted aryl, or optionally substituted heteroaryl, and P is a suitable protecting group, are prepared from a compound of Formula III or IV, respectively, by reaction with an activated carboxylic acid of the formula R—C(O)X where X is a leaving group such as chloro (e.g. benzoyl chloride) in the presence of a base (e.g. N,N-diisopropylethylamine (DIEA)) in a non-reactive solvent (e.g. dichloromethane). After stirring for several hours, isolation by conventional means (e.g. extraction and silica gel chromatography) provides compounds of Formula V or VI.

Scheme IV

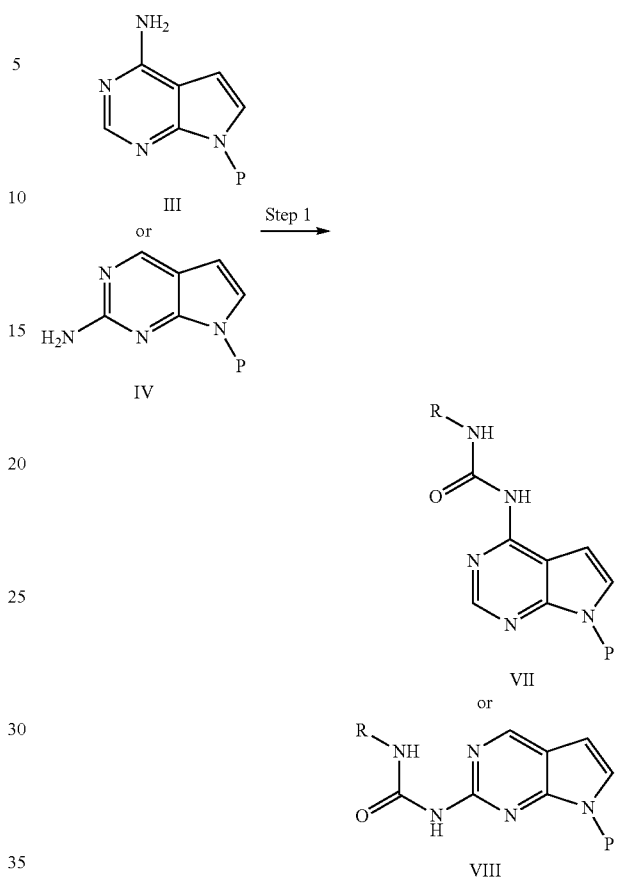

Compounds of Formula VII or VIII, where R is optionally substituted lower alkyl, optionally substituted lower alkenyl, optionally substituted lower alkynyl, optionally substituted cycloalkyl, optionally substituted heterocycloalkyl, optionally substituted aryl, or optionally substituted heteroaryl, and P is a suitable protecting group, are prepared from a compound of Formula III or IV, respectively, by reaction with an isocyanate of the formula R—NCO (e.g. propylisocyanate) in the presence of a base (e.g. DIEA) in a non-reactive solvent (e.g. dichloromethane). After stirring for several hours, isolation by conventional means (e.g. extraction and silica gel chromatography) provides compounds of compounds of Formula VII or VIII.

Scheme V

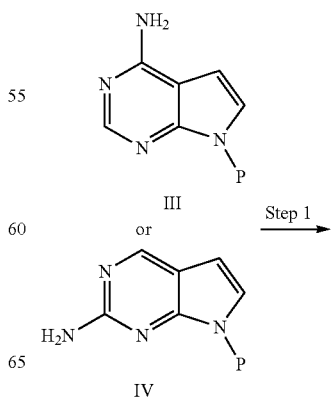

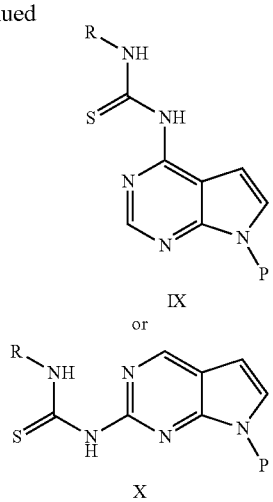

IX or

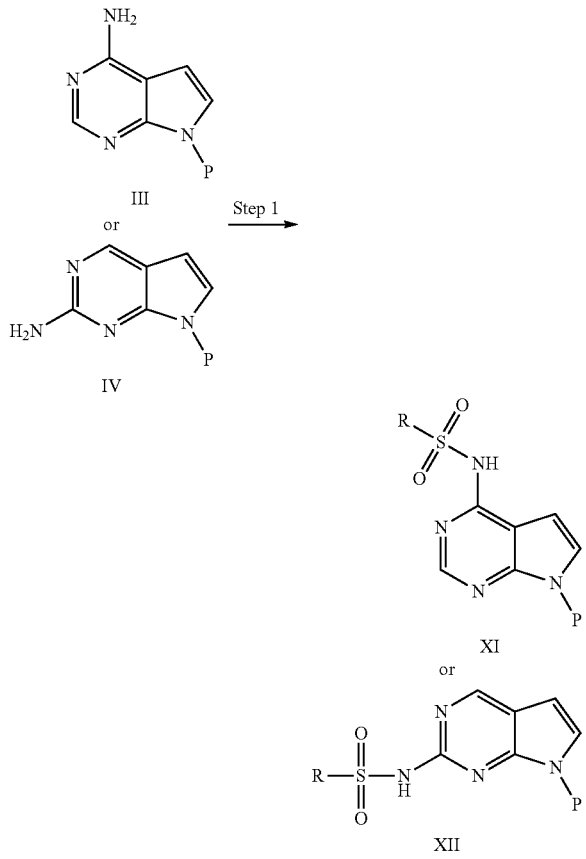

Compounds of Formula IX or X, where R is optionally substituted lower alkyl, optionally substituted lower alkenyl, optionally substituted lower alkynyl, optionally substituted cycloalkyl, optionally substituted heterocycloalkyl, optionally substituted aryl, or optionally substituted heteroaryl, and P is a suitable protecting group, are prepared from a compound of Formula III or IV, respectively, by reaction with an isothiocyanate of the formula R—NCS (e.g. propylisothiocyanate) in the presence of a base (e.g. DIEA) in a non-reactive solvent (e.g. dichloromethane). After stirring for several hours, isolation by conventional means (e.g. extraction and silica gel chromatography) provides compounds of Formula IX or X.

Compounds of Formula XI or XII, where R is optionally substituted lower alkyl, optionally substituted lower alkenyl, optionally substituted lower alkynyl, optionally substituted cycloalkyl, optionally substituted heterocycloalkyl, optionally substituted aryl, or optionally substituted heteroaryl, and P is a suitable protecting group, are prepared from a compound of Formula III or IV, respectively, by reaction with a sulfonyl chloride of the formula R—S(O)$_2$Cl (e.g. propylsulfonyl chloride) in the presence of a base (e.g. DIEA, pyridine) in a non-reactive solvent (e.g. dichloromethane). After stirring for several hours, isolation by conventional means (e.g. extraction and silica gel chromatography) provides compounds of Formula XI or XII.

Scheme VII

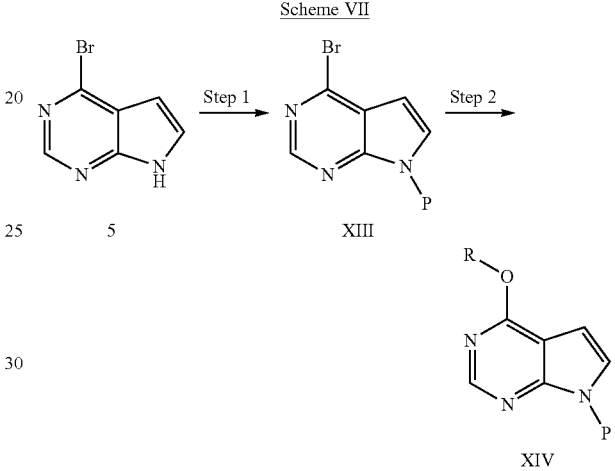

Step 1—Preparation of Compounds of Formula XIII

Compounds of Formula XIII, where P is a suitable protecting group, are prepared by reacting 4-bromo-7H-pyrrolo[2,3-d]pyrimidine (5) with an appropriate reagent to introduce a suitable protecting group (P—X, e.g. triisopropylsilylchloride) and a base (e.g. sodium hydride) in a solvent (e.g. tetrahydrofuran) typically at room temperature for 8-12 hours. The desired compound is isolated by conventional means (e.g. extraction).

Step 2—Preparation of Compounds of Formula XIV

Compounds of Formula XIV, where R is optionally substituted lower alkyl, optionally substituted lower alkenyl, optionally substituted lower alkynyl, optionally substituted cycloalkyl, optionally substituted heterocycloalkyl, optionally substituted aryl, or optionally substituted heteroaryl, and P is a suitable protecting group, are prepared by a compound of Formula XIII with an alcohol of Formula R—OH in the presence of a base (e.g. sodium hydride) and a copper catalyst (e.g. copper bromide) in a non-reactive solvent (e.g. dimethylformamide) with heating (e.g. 120° C.) for several hours. Isolation by conventional means (e.g. extraction and silica gel chromatography), provides compounds of Formula XIV. Alternatively, 4-bromo-7H-pyrrolo[2,3-d]pyrimidine (5) can be reacted directly by this method to provide the corresponding compounds without the protecting group.

Scheme VIII

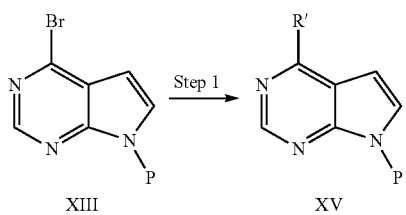

Compounds of Formula XV where R' is optionally substituted lower alkyl and P is a suitable protecting group are prepared by dissolving a compound of Formula XIII in an appropriate solvent (e.g. toluene) followed by the addition of a palladium catalyst (e.g. [1,1'-Bis(diphenylphosphino)ferrocene]dichloropalladium(II), complex with dichloromethane (1:1)). After several minutes, a Grignard reagent of the Formula R'—MgBr is added and the reaction heated (e.g. 90° C.) for one to several hours. After filtration through Celite, isolation by conventional means (e.g. extraction and silica gel chromatography) provides compounds of Formula XV.

Scheme IX

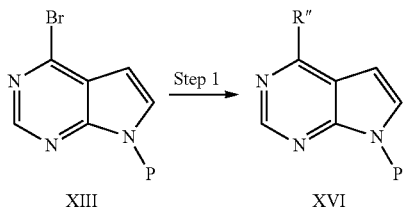

Compounds of Formula XVI where R" is optionally substituted aryl or optionally substituted heteroaryl and P is a suitable protecting group are prepared by reacting a compound of Formula XIII with a boronic acid of the Formula R"—B(OH)$_2$ or boronic ester of the Formula R"—B(OR)$_2$ under Suzuki coupling conditions (Muyaura and Suzuki, Chem. Rev. 1995, 95:2457), such as in the presence of a palladium catalyst (e.g. Tetrakis(triphenylphosphine)palladium(0)) and a base (e.g. aqueous potassium carbonate) in an appropriate solvent (e.g. tetrahydrofuran, acetonitrile) with heating thermally (e.g. 80° C.) for one to several hours or heating with a microwave instrument (e.g. 120° C. for 10 minutes). Isolation by conventional means (e.g. extraction and silica gel chromatography) provides compounds of Formula XVI. Alternatively, 4-bromo-7H-pyrrolo[2,3-d]pyrimidine (5) can be reacted by this method to provide the corresponding compounds without the protecting group.

7H-pyrrolo[2,3-d]pyrimidine compounds can be further derivatized at the 5-position, which are used in the synthesis of compounds described herein. The compounds described in Schemes I-IX, or similar compounds known in the art, may be used with or without the protecting group P, which can be readily removed by methods well known in the art. The following Scheme X provides an exemplary method for preparation of useful 5-carbaldehyde derivatives.

Scheme X

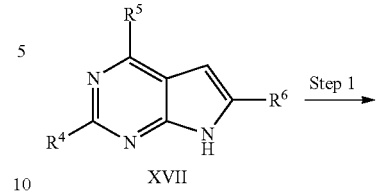

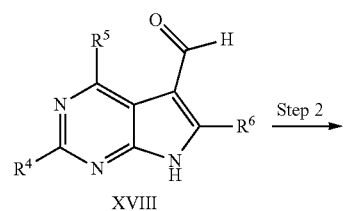

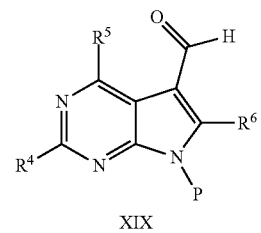

Step 1—Preparation of Compounds of Formula XVIII

Compounds of Formula XVIII are prepared by reacting a compound of Formula XVII (R$^4$, R$^5$ and R$^6$ are as defined with respect to Formula I) with hexamethyltetramine and acetic acid in water with heating to reflux for two hours. After cooling, the desired compound precipitates and may be collected by filtration.

Step 2—Preparation of Compounds of Formula XIX

Compounds of Formula XIX, where P is a suitable protecting group, are prepared by reacting a compound of Formula XVIII with an appropriate reagent to introduce a suitable protecting group (P—X, e.g. triisopropylsilylchloride) and a base (e.g. sodium hydride) in a solvent (e.g. tetrahydrofuran) typically at room temperature for 8-12 hours. The desired compound is isolated by conventional means (e.g. extraction).

Example 2

Preparation of 7H-Pyrrolo[2,3-d]pyrimidine Compounds 7H-pyrrolo[2,3-d]pyrimidine compounds known in the art, or prepared as described in Schemes I-X, may be used to prepare compounds described herein as described in the following Schemes XI-XXII.

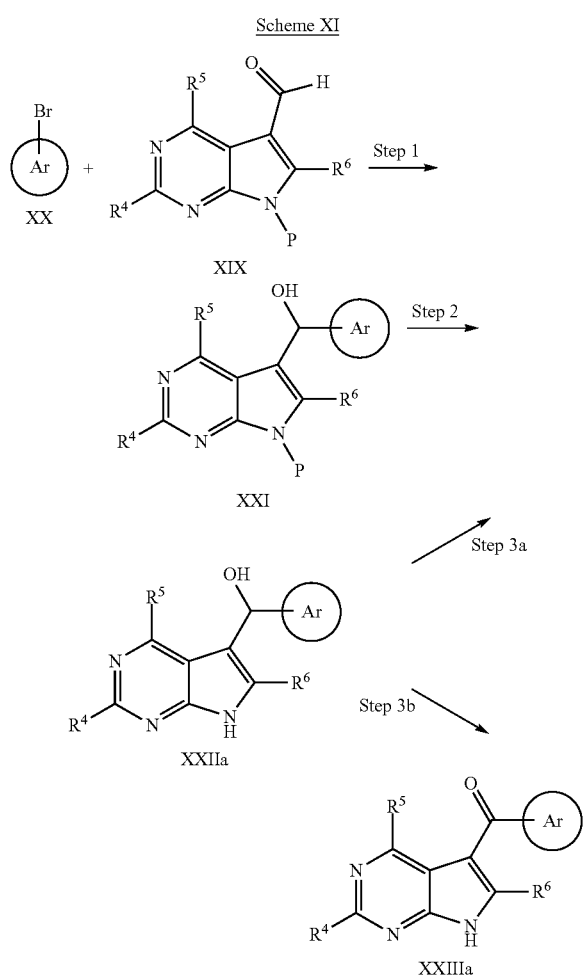

Step 1—Preparation of Compounds of Formula XXI

Compounds of Formula XXI are prepared by reacting a compound of Formula XX (Ar is as defined with respect to Formula I, P is a suitable protecting group) in a solvent (e.g. tetrahydrofuran) under an inert atmosphere, with an appropriate organolithium reagent (e.g. butyllithium) or magnesium and stirring the reaction for several hours at −78° C. A compound of Formula XIX ($R^4$, $R^5$ and $R^6$ are as defined with respect to Formula I) in a solvent (e.g. tetrahydrofuran) is then added to the reaction mixture. The reaction is typically allowed to warm to room temperature and stirred for 30 minutes. The desired compound is isolated by conventional means (e.g. extraction). Compounds of Formula XX are known in the art, for example, as described in US Patent Publication Number US20070032519, or US Patent Publication Number US20090076046, the disclosures of which are hereby incorporated by reference with respect to organic synthesis of compounds.

Step 2—Preparation of Compounds of Formula XXIIa

Compounds of Formula XXIIa are prepared by reacting a compound of Formula XXI with an appropriate reagent to remove the protecting group, P, (e.g. tetra-n-butyl ammonium fluoride) in an appropriate solvent (e.g. tetrahydrofuran). The desired compound is isolated by standard procedures (e.g. extraction and silica gel chromatography).

Step 3a—Preparation of Compounds of Formula XXIIIa

To a compound of Formula XXIIa in an appropriate solvent (e.g. tetrahydrofuran) is added an oxidizing agent (e.g. Dess-Martin periodane, TEMPO, DDQ). Typically, the reaction is allowed to stir at room temperature for 20 minutes. Isolation by conventional means (e.g. extraction and silica gel column chromatography) provides compounds of Formula XXIIIa.

Step 3b—Preparation of Compounds of Formula XXIIIb

To a compound of Formula XXIIa in an appropriate solvent (e.g. acetonitrile) is added a reducing agent (e.g. trifluoroacetic acid and triethylsilane). Typically, the reaction is allowed to stir at room temperature overnight. Isolation by conventional means (e.g. extraction and silica gel column chromatography) provides compounds of Formula XXIIIb.

Compounds of Formula XXI that can be carried through Steps 2 and 3 of Scheme XI may also be prepared following the protocol of the following Scheme XIa.

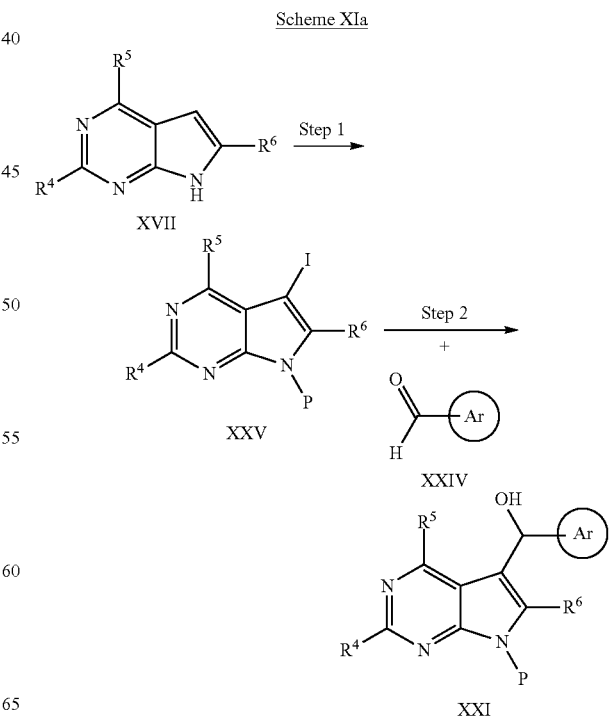

Step 1—Preparation of Compounds of Formula XXV

Compounds of Formula XXV are prepared by reacting a compound of Formula XVII ($R^4$, $R^5$ and $R^6$ are as defined with respect to Formula I) with iodine monochloride in a suitable solvent (e.g. dichloromethane, pyridine) at room temperature for 16-24 hours. The resulting compounds may be isolated by conventional means and reacted with an appropriate reagent to introduce a suitable protecting group (P—X, e.g. triisopropylsilylchloride) and a base (e.g. sodium hydride) in a solvent (e.g. tetrahydrofuran) typically at room temperature for 8-12 hours. Isolation by conventional means (e.g. extraction and silica gel column chromatography) provides compounds of Formula XXV.

Step 2—Preparation of Compounds of Formula XXI

Compounds of Formula XXI are prepared by reacting a compound of Formula XXV with a compound of Formula XXIV (Ar is as defined with respect to Formula I). Compounds of Formula XXV are dissolved in a solvent (e.g. tetrahydrofuran) under an inert atmosphere, and cooled to −20° C. and a solution of an appropriate Grignard reagent (e.g. isopropylmagnesium chloride) in tetrahydrofuran is added and the reaction is stirred, coming to 0° C. The reaction is cooled to −20° C. and a compound of Formula XXIV in tetrahydrofuran is added to the reaction mixture. The reaction is stirred, coming to 0° C. Isolation by conventional means (e.g. extraction and silica gel chromatography) provides compound of Formula XXI. Compounds of Formula XXIV are known in the art, for example, as described in US Patent Publication Number US20070032519, or US Patent Publication Number US20090076046, the disclosures of which are hereby incorporated by reference with respect to organic synthesis of compounds.

mula XXIV (Ar is as defined with respect to Formula I) is added an appropriate solvent (e.g. methanol) followed by an appropriate base (e.g. potassium hydroxide, sodium methoxide). The reaction is typically allowed to stir at room temperature overnight. Isolation by conventional means (e.g. extraction, washing and filtering) provides a mixture of compounds of Formula XXIIa and XXIIb which may be separated by silica gel chromatography if desired.

Step 2a—Preparation of Compounds of Formula XXIIIa

To a compound of Formula XXIIa in an appropriate solvent (e.g. tetrahydrofuran) is added an oxidizing agent (e.g. Dess-Martin periodane, TEMPO, DDQ). Typically, the reaction is allowed to stir at room temperature for 20 minutes. Isolation by conventional means (e.g. extraction and silica gel column chromatography) provides compounds of Formula XXIIIa.

Step 2b—Preparation of Compounds of Formula XXIIIb

To a compound of Formula XXIIa and/or XXIIb in an appropriate solvent (e.g. acetonitrile) is added a reducing agent (e.g. trifluoroacetic acid and triethylsilane). Typically, the reaction is allowed to stir at room temperature overnight. Isolation by conventional means (e.g. extraction and silica gel column chromatography) provides compounds of Formula XXIIIb

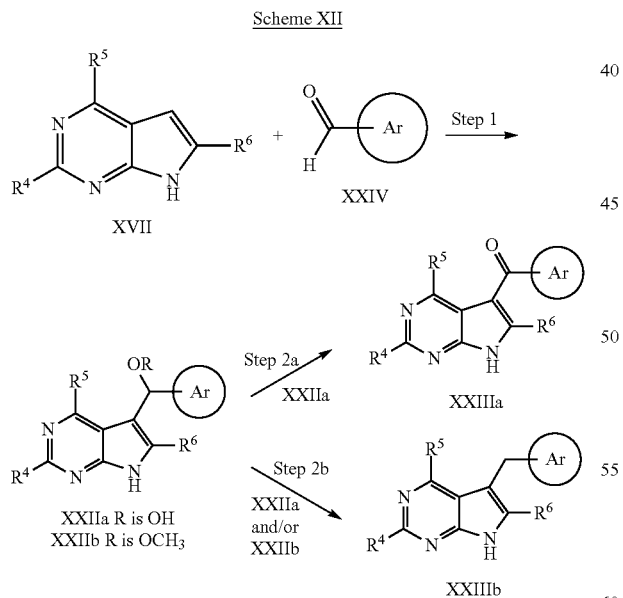

Scheme XII

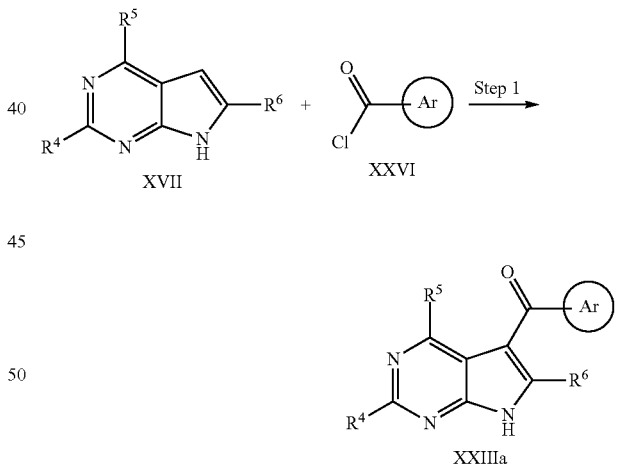

Scheme XIII

Step 1—Preparation of Compounds of Formula XXIIa and XXIIb

To a compound of Formula XVII ($R^4$, $R^5$ and $R^6$ are as defined with respect to Formula I) and a compound of For- Compounds of Formula XXIIIa are prepared by reacting a compound of Formula XVII ($R^4$, $R^5$ and $R^6$ are as defined with respect to Formula I) with a compound of Formula XXVI (Ar is as defined with respect to Formula I) in the presence of a Lewis acid (e.g. aluminum trichloride) in an inert solvent (e.g. dichloromethane) under an inert atmosphere (e.g. argon) at room temperature or with heating up to reflux for 1-18 hours. The desired compound is isolated, for example, by extraction and silica gel column chromatography.

Scheme XIV

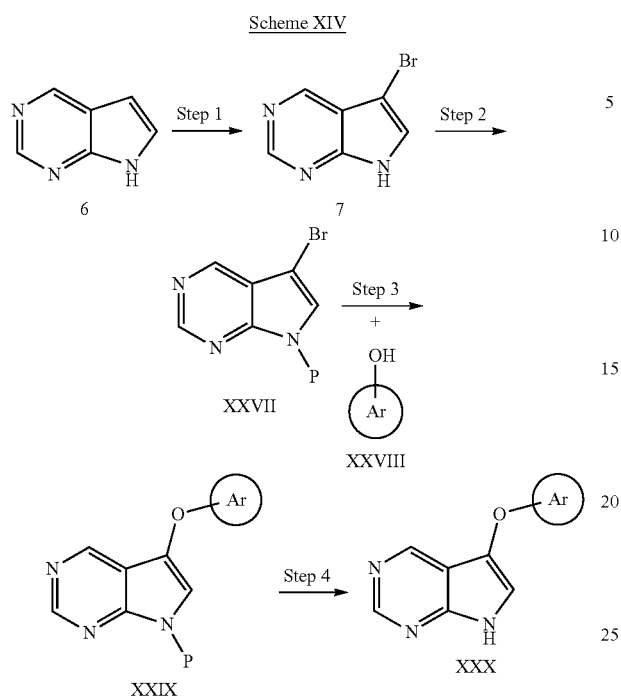

Step 1—Preparation of 5-bromo-7H-pyrrolo[2,3-d]pyrimidine (7)

5-Bromo-7H-pyrrolo[2,3-d]pyrimidine (7) is prepared by dissolving 7H-pyrrolo[2,3-d]pyrimidine (6) in chloroform and slowly adding $Br_2$ in carbon tetrachloride at 0° C. After stirring for 1-2 hours, the reaction may be quenched in aqueous hydrochloric acid. Isolation by conventional means (e.g. extraction and silica gel chromatography) provides compound 7.

Step 2—Preparation of Compounds of Formula XXVII

Compounds of Formula XXVII, where P is a suitable protecting group, are prepared by reacting 5-bromo-7H-pyrrolo[2,3-d]pyrimidine (7) with an appropriate reagent to introduce a suitable protecting group (P—X, e.g. triisopropylsilylchloride) and a base (e.g. sodium hydride) in a solvent (e.g. tetrahydrofuran) typically at room temperature for 8-12 hours. The desired compound is isolated by conventional means (e.g. extraction).

Step 3—Preparation of Compounds of Formula XXIX

Compounds of Formula XXIX are prepared by reacting a compound of Formula XXVII with compound of Formula XXVIII (Ar is as defined with respect to Formula I) in the presence of a base (e.g. sodium hydride) and a copper catalyst (e.g. copper bromide) in a non-reactive solvent (e.g. dimethylformamide) with heating (e.g. 120° C.) for several hours. Isolation by conventional means (e.g. extraction and silica gel chromatography) provides compounds of Formula XXIX.

Step 4—Preparation of Compounds of Formula XXX

Compounds of Formula XXX are prepared by reacting a compound of Formula XXIX with an appropriate reagent to remove the protecting group, P, (e.g. tetra-n-butyl ammonium fluoride) in an appropriate solvent (e.g. tetrahydrofuran). The desired compound is isolated by standard procedures (e.g. extraction and silica gel chromatography).

Scheme XV

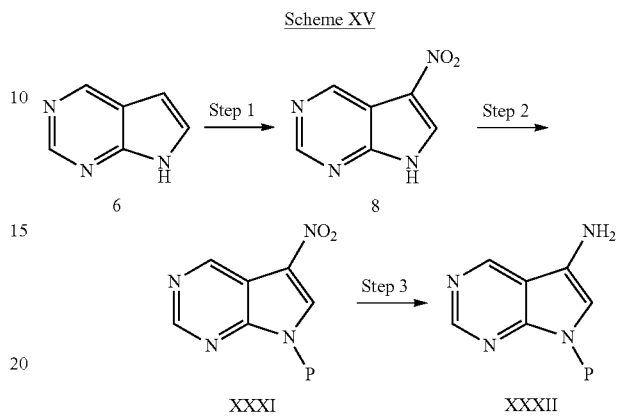

Step 1—Preparation of 5-nitro-7H-pyrrolo[2,3-d]pyrimidine (8)

5-Nitro-7H-pyrrolo[2,3-d]pyrimidine (8) is prepared by adding 7H-pyrrolo[2,3-d]pyrimidine (6) to fuming nitric acid while cooling (e.g. 0° C.). After stirring for one to several hours, water is carefully added and the mixture neutralized with saturated sodium bicarbonate. The solids are collected by filtration and dried to provide 5-nitro-7H-pyrrolo[2,3-d]pyrimidine 8.

Step 2—Preparation of Compounds of Formula XXXI

Compounds of Formula XXXI, where P is a suitable protecting group, are prepared by reacting 5-nitro-7H-pyrrolo[2,3-d]pyrimidine (8) with an appropriate reagent to introduce a suitable protecting group (P—X, e.g. triisopropylsilylchloride) and a base (e.g. sodium hydride) in a solvent (e.g. tetrahydrofuran) typically at room temperature for 8-12 hours. The desired compound is isolated by conventional means (e.g. extraction and silica gel chromatography).

Step 3—Preparation of Compounds of Formula XXXII

Compounds of Formula XXXII are prepared from compounds of Formula XXXI by reduction of the nitro group (e.g. hydrogen gas and palladium on carbon in methanol). The mixture is filtered and concentrated to provide compounds of Formula XXXII.

Scheme XVI

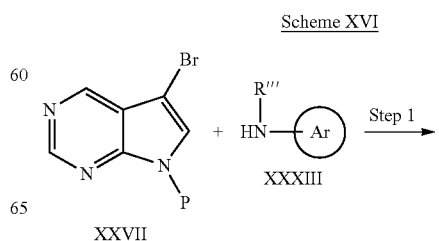

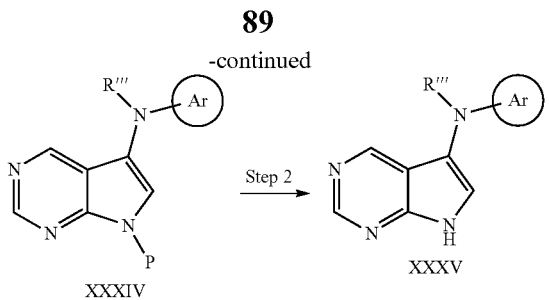

Step 1—Preparation of Compounds of Formula XXXIV

Compounds of Formula XXXIV are prepared by reacting a compound of Formula XXVII (P is a suitable protecting group) with neat compound of Formula XXXIII (Ar is as defined with respect to Formula I, R''' is e.g. hydrogen, lower alkyl) with heating for several hours (e.g. 150° C.). Alternatively, a compound of Formula XXVII may be reacted with compound of Formula XXXIII using palladium catalyzed Buchwald-Hartwig conditions (i.e. a palladium catalyst (e.g. Tris(dibenzylideneacetone)dipalladium(0)), a ligand (e.g. tri-t-butylphosphine), and a base (e.g. sodium t-butoxide) in a non-reactive solvent (e.g. toluene) with heating (e.g. 80° C.) for several hours). Isolation by conventional means (e.g. extraction and silica gel chromatography) provides compound of Formula XXXIV.

Step 2—Preparation of Compounds of Formula XXXV

Compounds of Formula XXXV are prepared by reacting a compound of Formula XXXIV with an appropriate reagent to remove the protecting group, P, (e.g. tetra-n-butyl ammonium fluoride) in an appropriate solvent (e.g. tetrahydrofuran). The desired compound is isolated by standard procedures (e.g. extraction and silica gel chromatography).

Scheme XVII

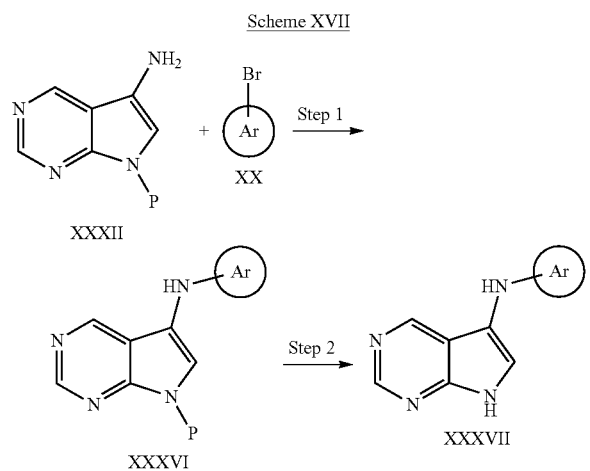

respect to Formula I) with heating for several hours (e.g. 100° C.). Alternatively, compounds of Formula XXXII are reacted with compounds of Formula XX using palladium catalyzed Buchwald-Hartwig conditions (i.e. a palladium catalyst (e.g. Tris(dibenzylideneacetone)dipalladium(0)), a ligand (e.g. tri-t-butylphosphine), and a base (e.g. sodium t-butoxide) in a non-reactive solvent (e.g. toluene) with heating (e.g. 80° C.) for several hours). Isolation by conventional means (e.g. extraction and silica gel chromatography) provides compounds of Formula XXXVI.

Step 2—Preparation of Compounds of Formula XXXVII

Compounds of Formula XXXVII are prepared by reacting a compound of Formula XXXVI with an appropriate reagent to remove the protecting group, P, (e.g. tetra-n-butyl ammonium fluoride) in an appropriate solvent (e.g. tetrahydrofuran). The desired compound is isolated by standard procedures (e.g. extraction and silica gel chromatography).

Scheme XVIII

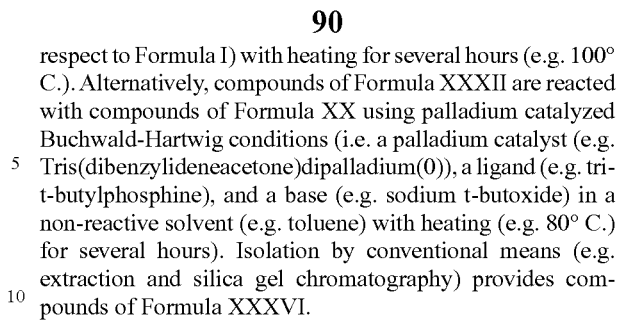

Compounds of Formula XXXIX are prepared by dissolving 7H-pyrrolo[2,3-d]pyrimidine (6) in an appropriate solvent (e.g. dimethylformamide) with a base (e.g. sodium hydride), followed by the addition of a symmetrical aryl disulfide of Formula XXXVIII (Ar is as defined with respect to Formula I). After stirring at room temperature for several hours, the reaction is quenched with water, followed by isolation by conventional means (e.g. extraction and silica gel chromatography) to provide compounds of Formula XXXIX.

Scheme XIX

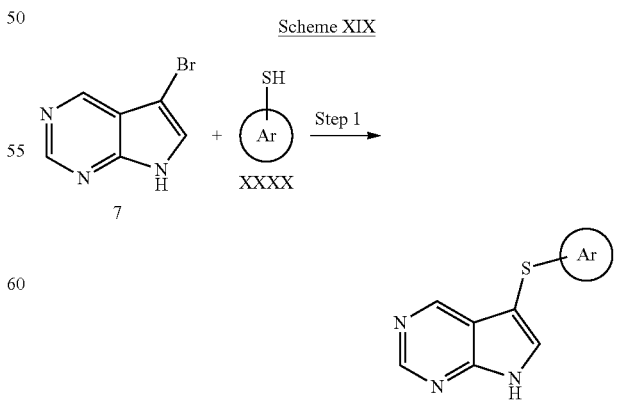

Compounds of Formula XXXIX are prepared by reacting 5-bromo-7H-pyrrolo[2,3-d]pyrimidine (7) with compounds of Formula XXXX (Ar is as defined with respect to Formula I) in the presence of a base (e.g. sodium hydride) in an appropriate solvent (e.g. dimethylformamide) with heating for several hours (e.g. 100° C.). Isolation by conventional means (e.g. extraction and silica gel chromatography) provides compounds of Formula XXXIX.

Scheme XX

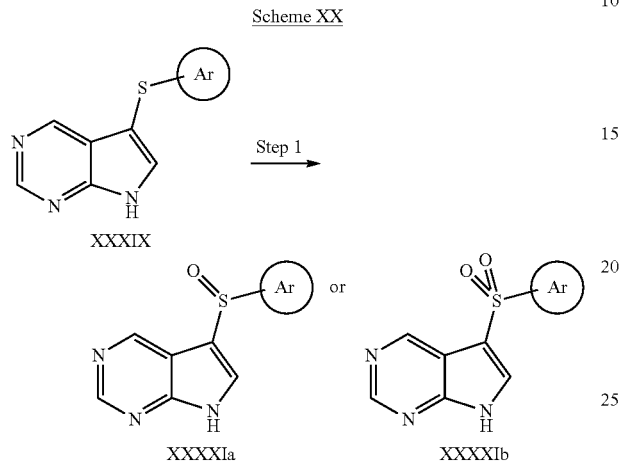

Compounds of Formula XXXXIa or XXXXIb (Ar is as defined with respect to Formula I) are prepared by reacting a compound of Formula XXXIX with an oxidizing agent (e.g. meta-chloro-peroxybenzoic acid, hydrogen peroxide) in an appropriate aprotic solvent (e.g. dichloromethane). Compounds of Formula XXXXIa are prepared using 1 equivalent of oxidizing agent, while compounds of Formula XXXXIb are prepared using 2 equivalents of oxidizing agent. Isolation by conventional means (e.g. extraction and silica gel chromatography) provides compound of Formula XXXXIa or XXXXIb.

Scheme XXI

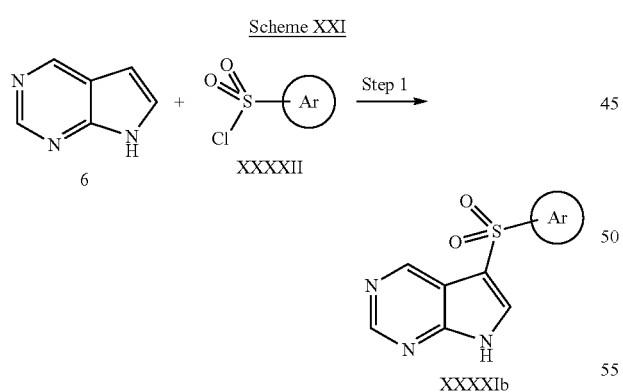

Compounds of Formula XXXXIb (Ar is as defined with respect to Formula I) are prepared by reacting 7H-pyrrolo[2,3-d]pyrimidine (6) with a sulfonyl chloride of Formula XXXXII dissolved in trifluoroacetic acid, in the presence of a catalyst (e.g. indium trichloride) and trifluorosulfonic acid with heating (e.g. 70° C.) for a few hours. Neutralization with sodium hydroxide and isolation by conventional means (e.g. extraction and silica gel chromatography) provides compound of Formula XXXXIb (Garzya et al., Tetrahedron Lett. 2004, 45:1499-1501).

Scheme XXII

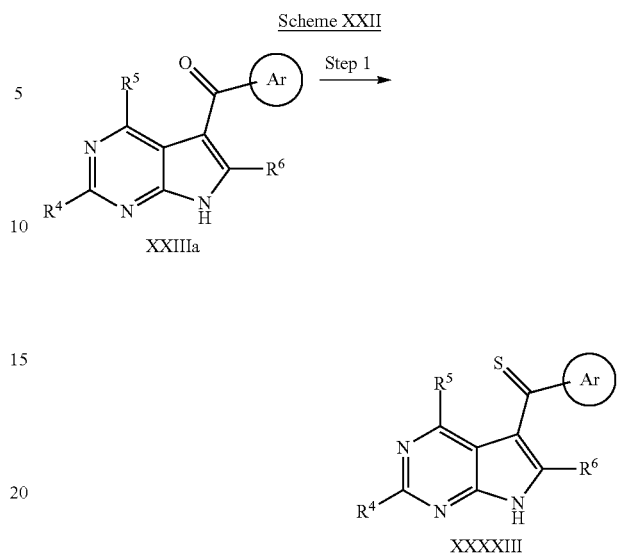

Compounds of Formula XXXXIII (Ar, R⁴, R⁵, and R⁶ are as defined with respect to Formula I) are prepared by reacting a compound of Formula XXIIIa with Lawesson's reagent, (1,3,2,4-dithiadiphosphetane-2,3-disulfide), in an appropriate solvent (e.g. tetrahydrofuran) with heating for several hours. Isolation by conventional means (e.g. extraction and silica gel chromatography) provides compound of Formula XXXXIII.

Additional methods are known in the art, including methods as described in US Patent Publication Number US20070032519, U.S. patent application Ser. No. 11/986,667, and U.S. Pat. No. 7,271,262, the disclosures of which are hereby incorporated by reference with respect to organic synthesis of compounds.

Example 3

Synthesis of Aldehyde Reagents

Aldehyde reagents that are used in coupling to the 5-position of 7H-pyrrolo[2,3-d]pyrimidine compounds are prepared according to the following protocols.

(4-Chloro-benzyl)-(5-formyl-pyridin-2-yl)-carbamic acid tert-butyl ester 13 was prepared in three steps from 5-bromo-pyridin-2-ylamine 9 and 4-chloro-benzaldehyde 10 as shown in Scheme 1.

Scheme 1

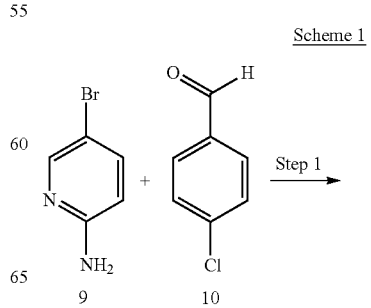

-continued

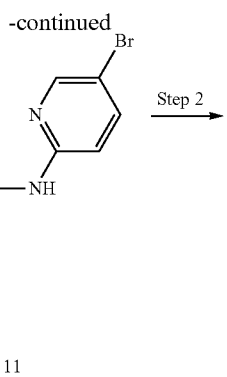

11

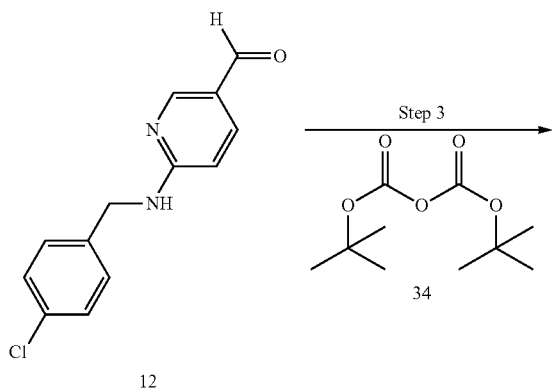

12     34

13

Step 1—Preparation of (5-bromo-pyridin-2-yl)-(4-chloro-benzyl)-amine (11)

5-Bromo-pyridin-2-ylamine (9, 4.0 g, 23 mmol) was dissolved in 100 mL of acetonitrile and 4-chloro-benzaldehyde (10, 3.2 g, 23 mmol) was added. Triethylsilane (11.0 mL, 69 mmol) was added followed by trifluoroacetic acid (5.0 mL, 65 mmol). The reaction was heated to reflux and stirred overnight. The solvent was removed under vacuum and the residue was poured into a solution of 1M potassium carbonate. This was extracted with ethyl acetate and the organic portion was isolated and washed with brine, dried over anhydrous sodium sulfate, filtered and the filtrate concentrated under vacuum. The resulting solid was washed with ether to give the desired compound. The remaining material was purified with silica gel chromatography eluting with a gradient of 0-25% ethyl acetate in hexane. Appropriate fractions were combined and the solvents removed under vacuum to provide additional compound (11, 6.36 g, 92%).

Step 2—Preparation of 6-(4-chloro-benzylamino)-pyridine-3-carbaldehyde (12)

(5-Bromo-pyridin-2-yl)-(4-chloro-benzyl)-amine (11, 3.81 g, 13 mmol) was dissolved in 150 mL of tetrahydrofuran at −78° C. under an atmosphere of nitrogen and tert-butyllithium (7.6 mL, 1.7 M in hexane) was added dropwise. After 30 minutes additional tert-butyllithium (16 mL, 1.7 M in hexane) was added dropwise and the reaction was stirred for 1.5 hours at −78° C. N,N-Dimethylformamide (2.4 mL, 31 mmol) was added and the mixture was stirred for 1.5 hours at −78° C., then allowed to warm up to room temperature for 1 hour. The reaction was poured into aqueous ammonium chloride and extracted with ethyl acetate. The organic portion was dried over anhydrous sodium sulfate and concentrated. The desired compound was crystallized from a mixture of ether in ethyl acetate. The remaining material was purified with silica gel chromatography eluting with ethyl acetate and hexane to provide additional compound (12, 2.7 g, 85%).

Step 3—Preparation of (4-chloro-benzyl)-(5-formyl-pyridin-2-yl)-carbamic acid tert-butyl ester (13)

6-(4-Chloro-benzylamino)-pyridine-3-carbaldehyde (12, 1.36 g, 5.5 mmol) was dissolved in 34 mL of tetrahydrofuran and di-tert-butyldicarbonate (34, 1.44 g, 6.6 mmol) was added, followed by 4-dimethylaminopyridine (0.07 g) and N,N-diisopropylethylamine (2.0 mL, 11 mmol). The reaction was stirred at room temperature overnight. The reaction was concentrated and the resulting material was purified by silica gel column chromatography eluting with a gradient of 5-45% ethyl acetate in hexane. Appropriate fractions were combined and the solvents removed under vacuum to give the desired compound (13, 1.6 g, 84%).

Additional aldehydes were prepared similarly to the protocol of scheme 1, as shown in the following table, where Step 1, Step 2 and Step 3 reactants are provided in columns 1, 2, and 3, respectively, with the resulting Boc protected aldehyde provided in column 4 Reaction conditions were similar to those described for scheme 1, and may have varied slightly for each step, for example, any of solvents, reaction times, temperatures, or work up conditions. In some cases, for step 2, the first addition of t-butyllithium is replaced with n-butyllithium in pentane (indicated with n-BuLi in the table), or by isopropylmagnesium chloride in tetrahydrofuran (indicated with i-PrMgCl in the table). In some cases for step 3, N,N-diisopropylethylamine is replaced with triethylamine (indicated with TEA in table) and in once instance, dichloromethane is used as solvent (indicated as CH$_2$Cl$_2$ in table).

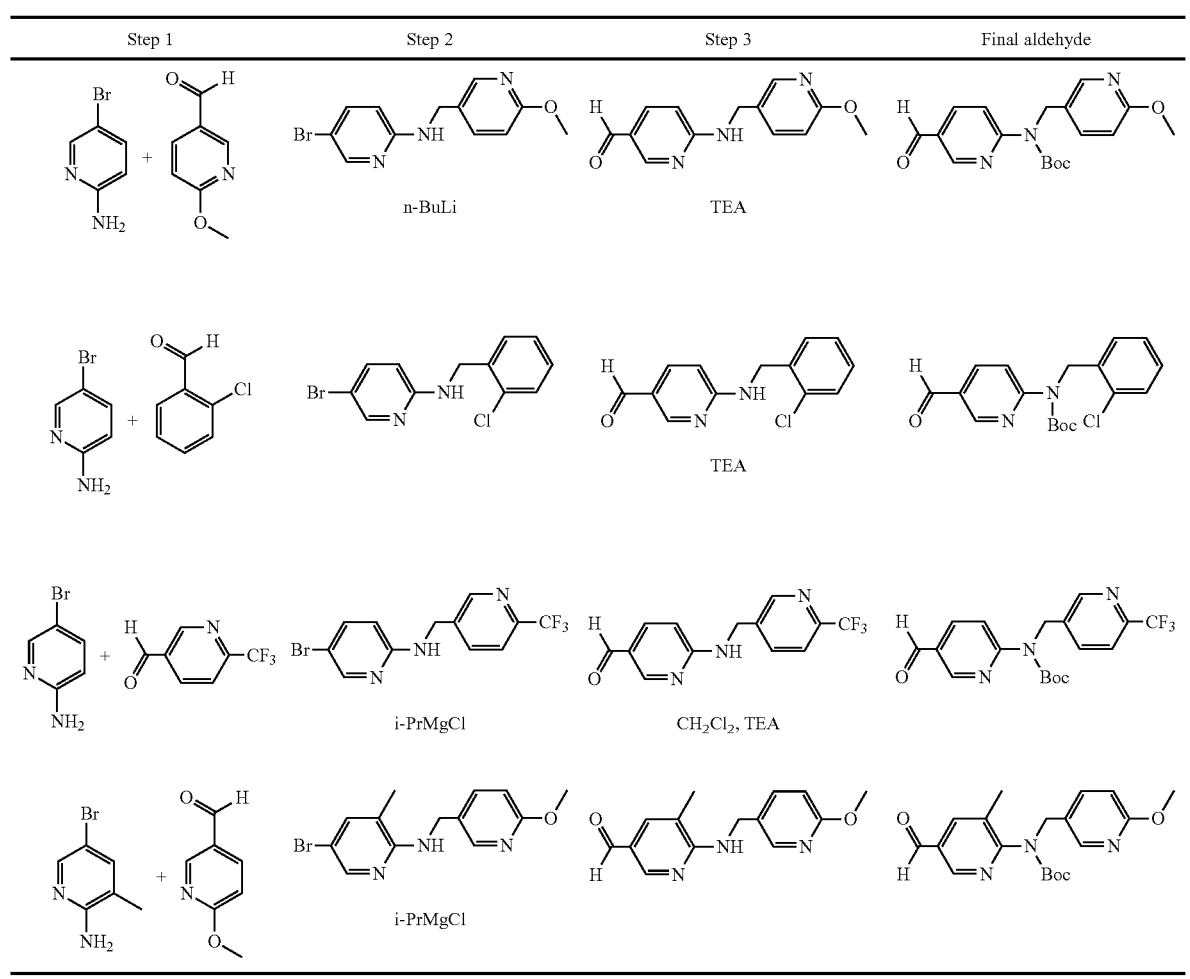
(2-Chloro-benzyl)-(6-fluoro-5-formyl-pyridin-2-yl)-carbamic acid tert-butyl ester 19 was prepared in four steps from 6-fluoro-pyridin-2-ylamine 14 and 2-chloro-benzaldehyde 15 as shown in Scheme 2.
Scheme 2
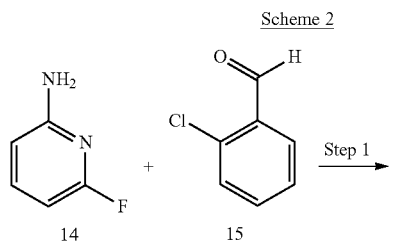
-continued
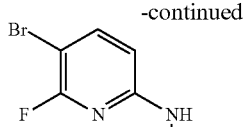
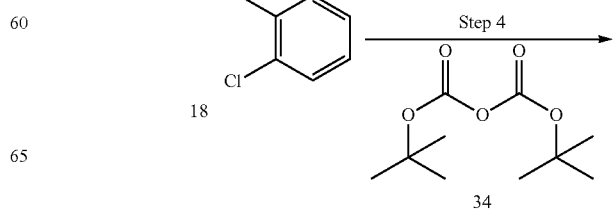

-continued

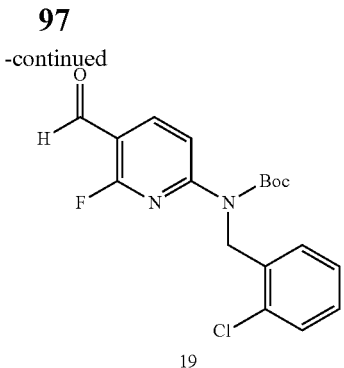

19

Step 1—Preparation of (2-chloro-benzyl)-(6-fluoro-pyridin-2-yl)-amine (16)

To 6-fluoro-pyridin-2-ylamine (14, 2.47 g, 22.0 mmol) in 60.0 mL of acetonitrile, 2-chloro-benzaldehyde (15, 3.09 g, 22.0 mmol), triethylsilane (14.0 mL, 87.6 mmol) and trifluoroacetic acid (7.00 mL, 90.9 mmol) were added. The reaction was stirred at 80° C. for 4 hours, then solvents removed under vacuum, and the residue was combined with aqueous potassium carbonate and extracted with ethyl acetate. The organic layer was washed with brine, dried over sodium sulfate, filtered and the filtrate concentrated under vacuum to provide the desired compound, which was used in the next step without further purification. MS (ESI) [M+H$^+$]$^+$=272.1.

Step 2—Preparation of (5-bromo-6-fluoro-pyridin-2-yl)-(2-chloro-benzyl)-amine (17)

To (2-chloro-benzyl)-(6-fluoro-pyridin-2-yl)-amine (16, 4.70 g, 19.8 mmol) in 100.0 mL of acetonitrile, N-bromosuccinimide (3.53 g, 19.8 mmol) in 20.0 mL of acetonitrile was added slowly at room temperature. The reaction was stirred at room temperature for 4 hours, then poured into aqueous potassium carbonate and extracted with ethyl acetate. The organic layer was dried over sodium sulfate, filtered and the filtrate concentrated under vacuum. The resulting material was washed with ethyl acetate in hexane to provide the desired compound (17, 5.0 g).

Step 3—Preparation of 6-(2-chloro-benzylamino)-2-fluoro-pyridine-3-carbaldehyde (18)

To (5-bromo-6-fluoro-pyridin-2-yl)-(2-chloro-benzyl)-amine (17, 1.85 g, 5.86 mmol) in 25.0 mL of tetrahydrofuran under an atmosphere of nitrogen at −78° C., isopropylmagnesium chloride (3.00 mL, 2.00 M in tetrahydrofuran, 6.00 mmol) was added over 10 minutes. After 50 minutes, tert-butyllithium (7.80 mL, 1.70 M in hexane, 13.3 mmol) was added over 5 minutes. After 20 minutes, N,N-dimethylformamide (1.09 mL, 14.0 mmol) was added and the reaction mixture stirred at −78° C. for 20 minutes, then brought to room temperature over 30 minutes. The reaction mixture was poured into water and extracted with ethyl acetate. The organic layer was washed with brine, dried over sodium sulfate, filtered and the filtrate concentrated under vacuum. The resulting material was purified by silica gel column chromatography, eluting with 35% ethyl acetate in hexane. The appropriate fractions were combined and the solvents removed under vacuum to provide the desired compound (18, 1.45 g). MS (ESI) [M+H$^+$]$^+$=265.4.

Step 4—Preparation of (2-chloro-benzyl)-(6-fluoro-5-formyl-pyridin-2-yl)-carbamic acid tert-butyl ester (19)

To 6-(2-chloro-benzylamino)-2-fluoro-pyridine-3-carbaldehyde (18, 1.45 g, 5.48 mmol) in 31.4 mL of tetrahydrofuran, di-tert-butyldicarbonate (34, 1.79 g, 8.22 mmol) and 4-dimethylaminopyridine (78.6 mg, 0.643 mmol) were added. The reaction was stirred at room temperature for 3 hours, then concentrated under vacuum. The resulting material was purified by silica gel column chromatography, eluting with 15-35% ethyl acetate in hexane. Appropriate fractions were combined and the solvents removed under vacuum to provide the desired compound as a colorless oil (19, 1.60 g).

(4-Chloro-benzyl)-(6-fluoro-5-formyl-pyridin-2-yl)-carbamic acid tert-butyl ester was prepared similarly to the protocol of scheme 2, with the first step modified by reacting 2,6-difluoro-pyridine 20 and 4-chloro-benzylamine 21 according the following step 1a.

Scheme 2 Step 1a

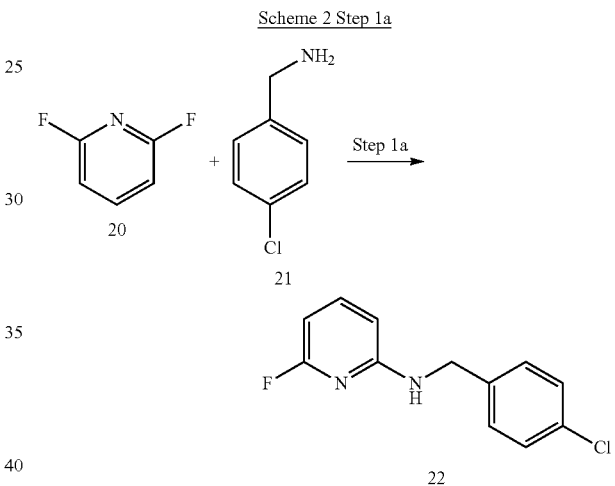

Step 1—Preparation of (4-chloro-benzyl)-(6-fluoro-pyridin-2-yl)-amine (22)

To 2,6-difluoro-pyridine (20, 3.80 g, 33.0 mmol) in 20.0 mL of N-methylpyrrolidone, 4-chloro-benzylamine (21, 5.6 mL, 46.0 mmol) and N,N-diisopropylethylamine (10.0 mL, 57.4 mmol) were added. The reaction was stirred at 90° C. overnight, then poured into water and extracted with ethyl acetate. The organic layer was dried over sodium sulfate, filtered and the filtrate concentrated under vacuum. The resulting material was purified by silica gel column chromatography, eluting with 25% ethyl acetate in hexane. Appropriate fractions were combined and the solvents removed under vacuum, and the resulting material was washed with ethyl acetate/hexane to provide the desired compound as a white solid (22, 5.30 g).

Additional aldehydes were prepared similarly to the protocol of scheme 2, as shown in the following table, where Step 1, Step 2, Step 3 and Step 4 reactants are provided in columns 1, 2, 3, and 4, respectively, with the resulting Boc protected aldehyde provided in column 5 Step 1a, when used, is also indicated in column 1 Reaction conditions were similar to those described for scheme 2, and may have varied slightly for each step, for example, any of solvents, reaction times, temperatures, or work up conditions. In some cases, for step 3, the addition of isopropylmagnesium chloride is replaced with n-butyllithium in hexane (indicated with n-BuLi in the table). In one instance for step 4, triethylamine is included in the reaction (indicated as TEA in table) and dichloromethane is used as solvent (indicated as $CH_2Cl_2$ in table). In one instance for step 1a, no N,N-diisopropylethylamine is used (indicated as no di-iPrEA in table).

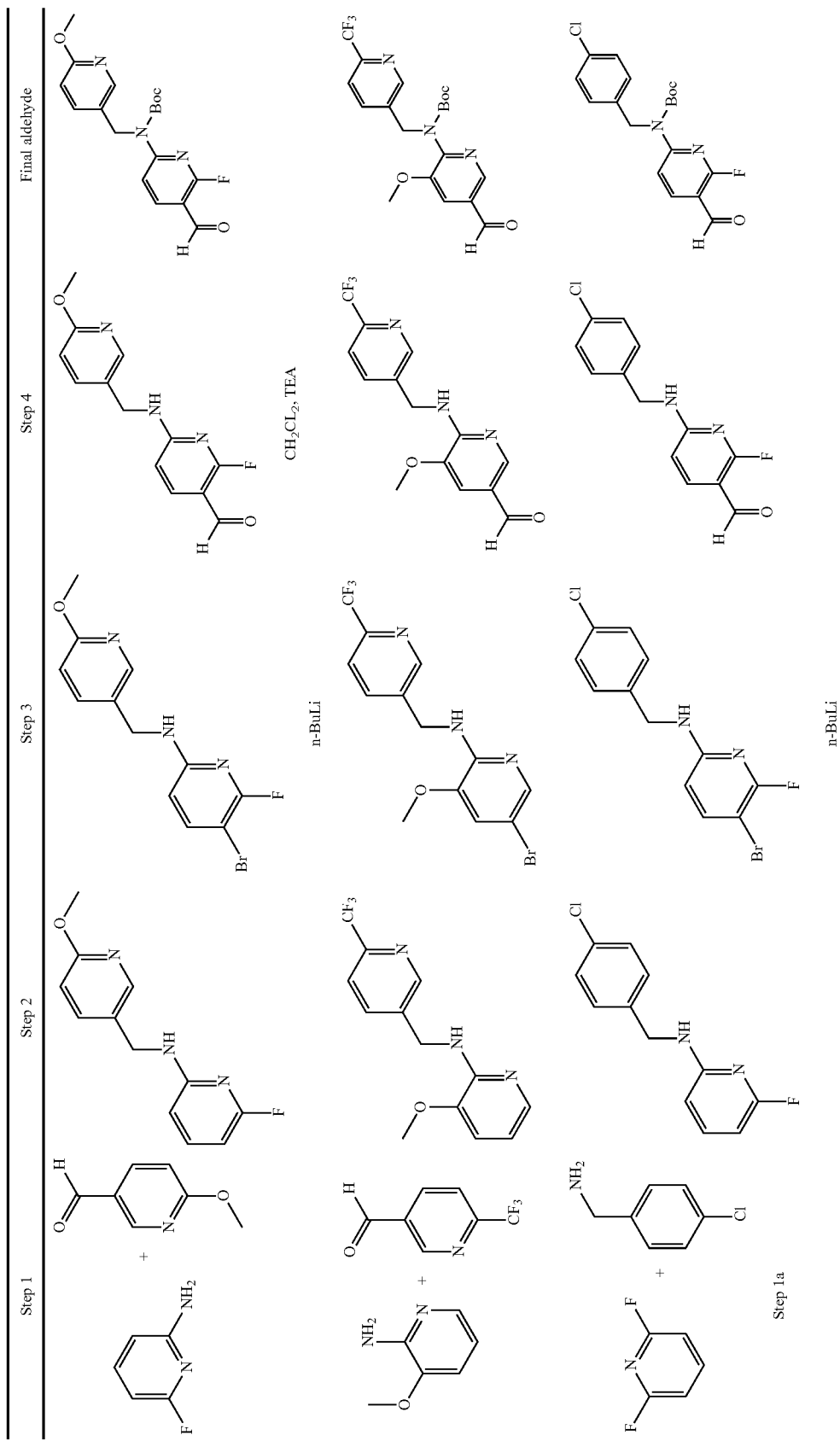

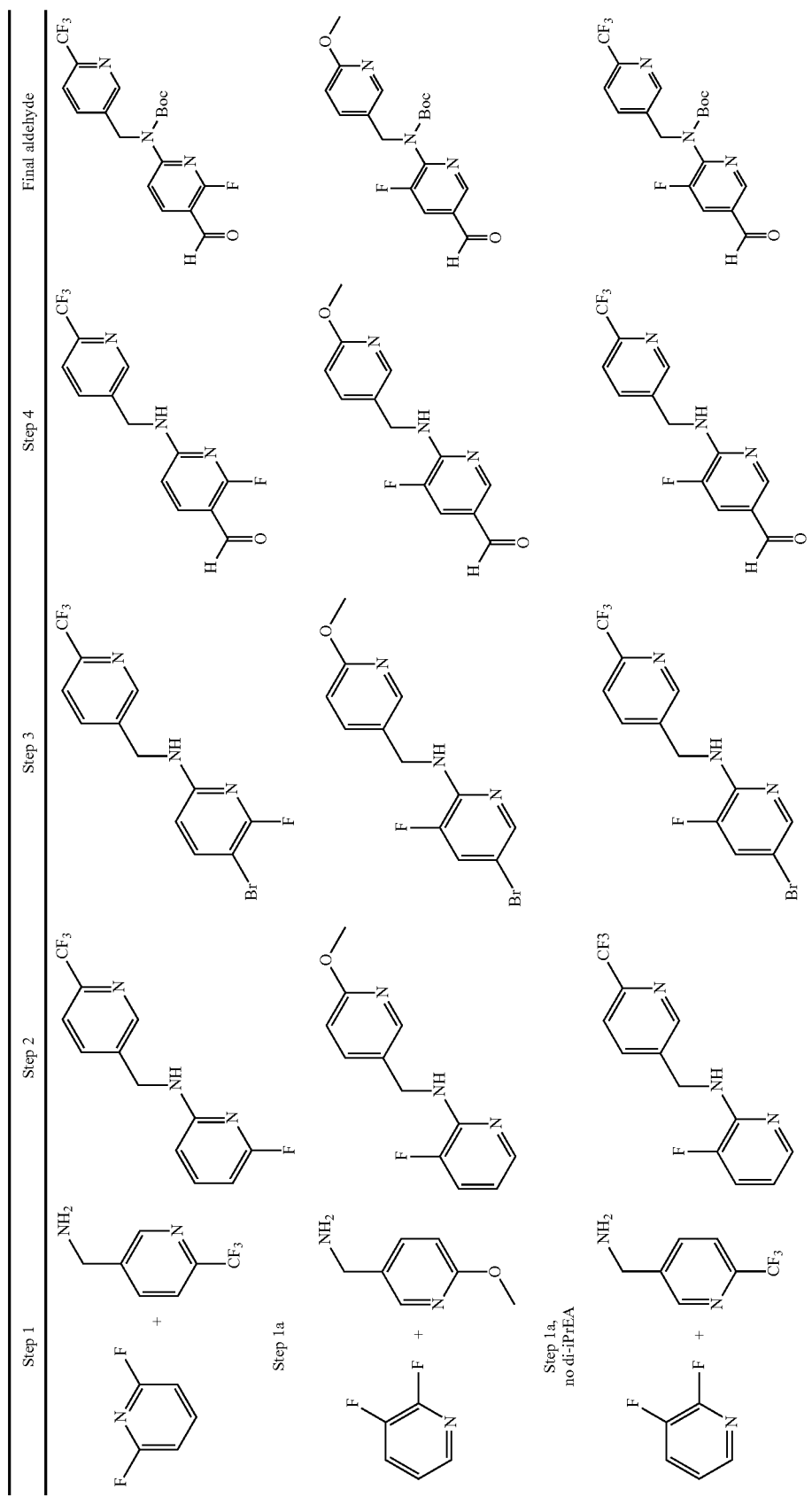

(6-Fluoro-5-formyl-pyridin-2-yl)-(5-fluoro-6-methoxy-pyridin-3-ylmethyl)-carbamic acid tert-butyl ester 27 was prepared in four steps from 6-fluoro-pyridin-2-ylamine 14 and 5-fluoro-6-methoxy-pyridine-3-carbaldehyde 23 as shown in Scheme 3.

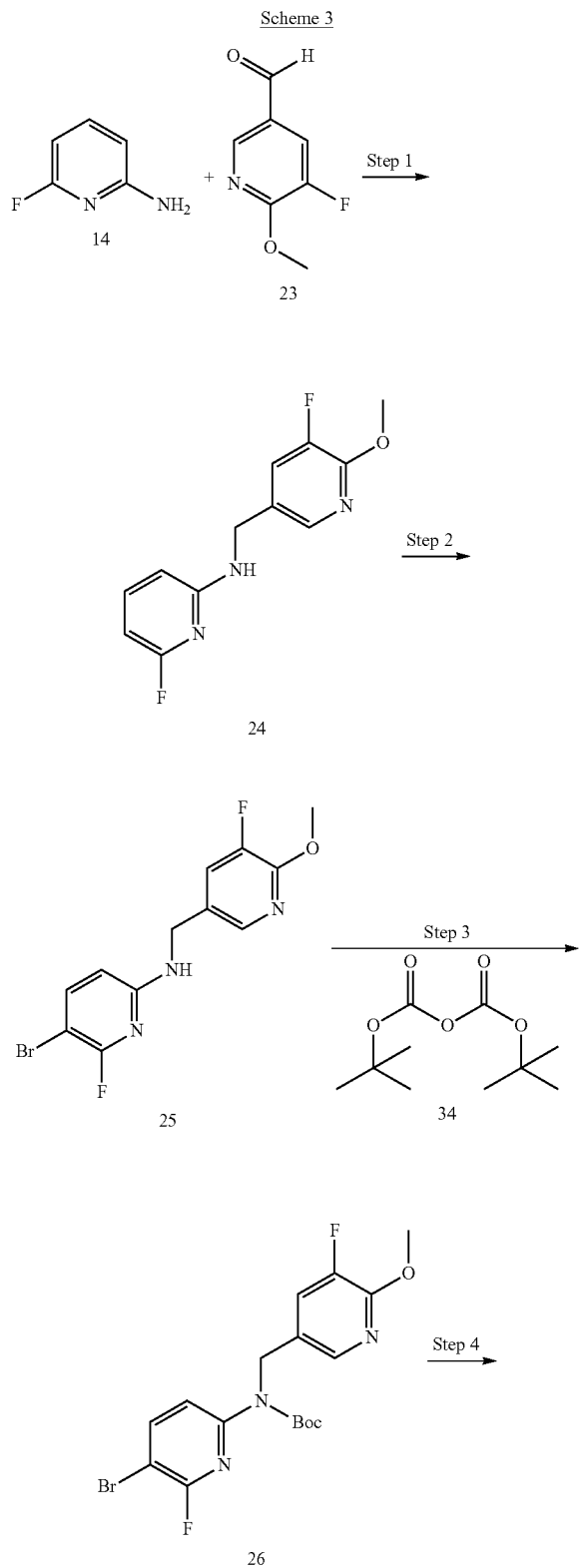

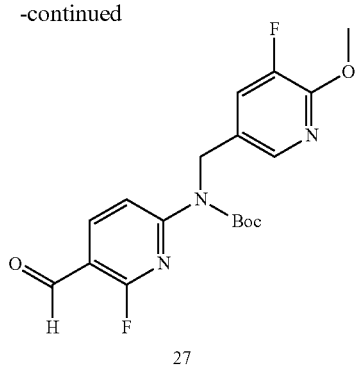

Step 1—Preparation of (5-fluoro-6-methoxy-pyridin-3-ylmethyl)-(6-fluoro-pyridin-2-yl)-amine (24)

To 6-fluoro-pyridin-2-ylamine (14, 1.50 g, 13.4 mmol) in 52.9 mL of acetonitrile, 5-fluoro-6-methoxy-pyridine-3-carbaldehyde (23, 2.00 g, 12.9 mmol), triethylsilane (10.6 mL, 66.3 mmol), and trifluoroacetic acid (5.3 mL, 69.0 mmol) were added. The reaction was stirred at 80° C. overnight, then concentrated under vacuum, combined with water and extracted with ethyl acetate. The organic layer was dried over sodium sulfate, filtered and the filtrate concentrated under vacuum. The resulting material was purified by silica gel column chromatography, eluting with 15-100% ethyl acetate in hexane. Appropriate fractions were combined and concentrated under vacuum to provide the desired compound as white solid (24, 3.21 g).

Step 2—Preparation of (5-bromo-6-fluoro-pyridin-2-yl)-(5-fluoro-6-methoxy-pyridin-3-ylmethyl)-amine (25)

To (5-fluoro-6-methoxy-pyridin-3-ylmethyl)-(6-fluoro-pyridin-2-yl)-amine (24, 3.21 g, 12.8 mmol) in 100 mL of acetonitrile, N-bromosuccinimide (2.30 g, 12.9 mmol) in 30 mL of acetonitrile was added slowly at room temperature. The reaction was stirred at room temperature for 4 hours, then poured into aqueous potassium carbonate and extracted with ethyl acetate. The organic layer was dried over sodium sulfate, filtered and the filtrate concentrated under vacuum. The resulting material was purified by silica gel column chromatography, eluting with 20% ethyl acetate in hexane. Appropriate fractions were combined and concentrated under vacuum to provide the desired compound (25, 3.60 g).

Step 3—Preparation of (5-bromo-6-fluoro-pyridin-2-yl)-(5-fluoro-6-methoxy-pyridin-3-ylmethyl)-carbamic acid tert-butyl ester (26)

To (5-bromo-6-fluoro-pyridin-2-yl)-(5-fluoro-6-methoxy-pyridin-3-ylmethyl)-amine (25, 2.70 g, 8.18 mmol) in 58.7 mL of tetrahydrofuran, di-tert-butyldicarbonate (34, 2.2 g, 9.9 mmol) and 4-dimethylaminopyridine (0.29 g, 2.4 mmol) were added. The reaction was stirred at room temperature for 90 minutes, then concentrated under vacuum. The resulting material was purified by silica gel column chromatography, eluting with 20-100% ethyl acetate in hexane. Appropriate fractions were combined and concentrated under vacuum to provide the desired compound as a colorless oil (26, 3.0 g).

Step 4—Preparation of (6-fluoro-5-formyl-pyridin-2-yl)-(5-fluoro-6-methoxy-pyridin-3-ylmethyl)-carbamic acid tert-butyl ester (27)

To (5-bromo-6-fluoro-pyridin-2-yl)-(5-fluoro-6-methoxy-pyridin-3-ylmethyl)-carbamic acid tert-butyl ester (26, 2.90 g, 6.74 mmol) in 25.0 mL of tetrahydrofuran at −35° C. under an atmosphere of nitrogen, isopropylmagnesium chloride (3.54 mL, 2.00 M in tetrahydrofuran, 7.08 mmol) was added and the reaction was allowed to come to 0° C. over an hour. The reaction was cooled to −45° C. and N,N-dimethylformamide (1.0 mL, 13.0 mmol) was added. The reaction was allowed to warm to room temperature over 2 hours, then poured into aqueous ammonium chloride and extracted with ethyl acetate. The organic layer was dried over sodium sulfate, filtered and the filtrate concentrated under vacuum. The resulting material was purified by silica gel column chromatography, eluting with 20% ethyl acetate in hexane. Appropriate fractions were combined and concentrated under vacuum to provide the desired compound (27, 1.80 g).

(6-Fluoro-5-formyl-pyridin-2-yl)-[(S)-1-(4-fluoro-phenyl)-ethyl]-carbamic acid tert-butyl ester 79

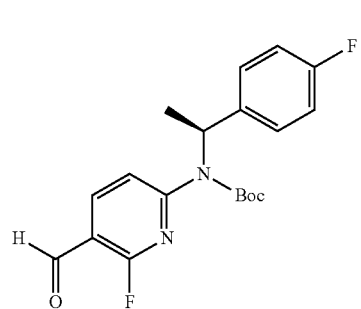

79 was prepared from 2,6-difluoro-pyridine 20 and (S)-1-(4-fluoro-phenyl)-ethylamine similarly to the protocol of step 1a of scheme 2, then steps 2-4 of scheme 3. Step 3 also included N,N-diisopropylethylamine, as well as a subsequent addition of di-tert-butyldicarbonate and N,N-diisopropylethylamine.

(5-Formyl-6-methyl-pyridin-2-yl)-(6-methoxy-pyridin-3-ylmethyl)-carbamic acid tert-butyl ester

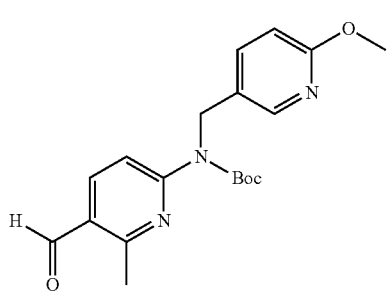

74 was prepared by reacting (5-iodo-6-methyl-pyridin-2-yl)-(6-methoxy-pyridin-3-ylmethyl)-amine 30 similarly to the protocol of Scheme 3, steps 3 and 4, where step 3 included N,N-diisopropylethylamine. (5-Iodo-6-methyl-pyridin-2-yl)-(6-methoxy-pyridin-3-ylmethyl)-amine 30 was prepared in one step from 5-iodo-6-methyl-pyridin-2-ylamine 28 and 6-methoxy-pyridine-3-carbaldehyde 29 as shown in Scheme 4.

Scheme 4

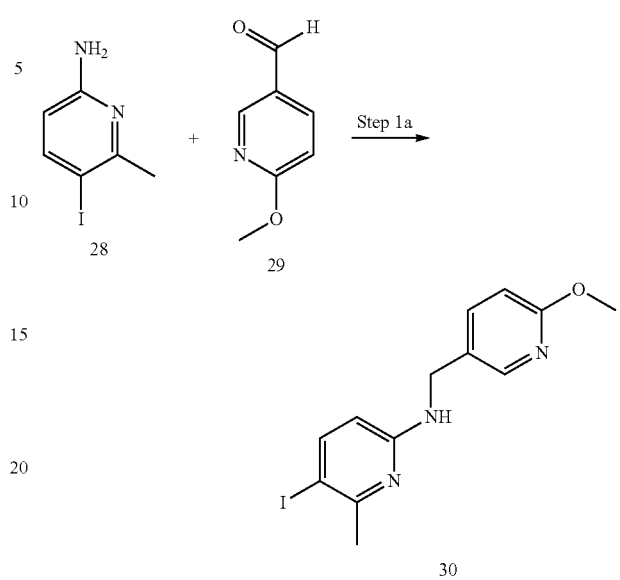

Step 1—Preparation of (5-iodo-6-methyl-pyridin-2-yl)-(6-methoxy-pyridin-3-ylmethyl)-amine (30)

5-Iodo-6-methyl-pyridin-2-ylamine (28, 1.7 g, 7.3 mmol) and 6-methoxy-pyridine-3-carbaldehyde (29, 1.1 g, 8.0 mmol) were combined in a round bottom flask with trifluoroacetic acid (2.80 mL, 36.3 mmol), triethylsilane (5.80 mL, 36.3 mmol) and 50 mL of acetonitrile. The reaction was stirred at room temperature overnight, then heated to reflux for 6 hours. The reaction was concentrated under vacuum, combined with aqueous potassium carbonate and extracted with ethyl acetate. The organic layer was dried over sodium sulfate, filtered and the filtrate concentrated under vacuum. The resulting material was purified by silica gel flash column chromatography, eluting with 10-100% ethyl acetate in hexane. Appropriate fractions were combined and concentrated under vacuum to provide the desired compound (30, 1.80 g). MS (ESI)[M+H$^+$]$^+$=356.80.

(5-Formyl-pyrimidin-2-yl)-(6-trifluoromethyl-pyridin-3-ylmethyl)-carbamic acid tert-butyl ester

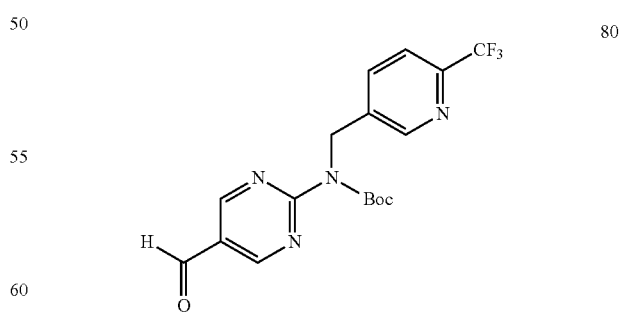

80 was prepared similarly to the protocol of scheme 4 and steps 3 and 4 of scheme 3, replacing 5-iodo-6-methyl-pyridin-2-ylamine 28 with 5-iodo-pyrimidin-2-ylamine and 6-methoxy-pyridine-3-carbaldehyde 29 with 6-trifluoromethyl-pyridine-3-carbaldehyde in scheme 4.

Additional aldehydes were prepared similarly to the protocol of scheme 3, as shown in the following table, where Step 1, Step 2, Step 3 and Step 4 reactants are provided in columns 1, 2, 3, and 4, respectively, with the resulting Boc protected aldehyde provided in column 5 Reaction conditions were similar to those described for scheme 3, and may have varied slightly for each step, for example, any of solvents, reaction times, temperatures, or work up conditions. In some cases, for step 3, N,N-diisopropylethylamine was included in the reaction (indicated with di-iPrEA in the table).

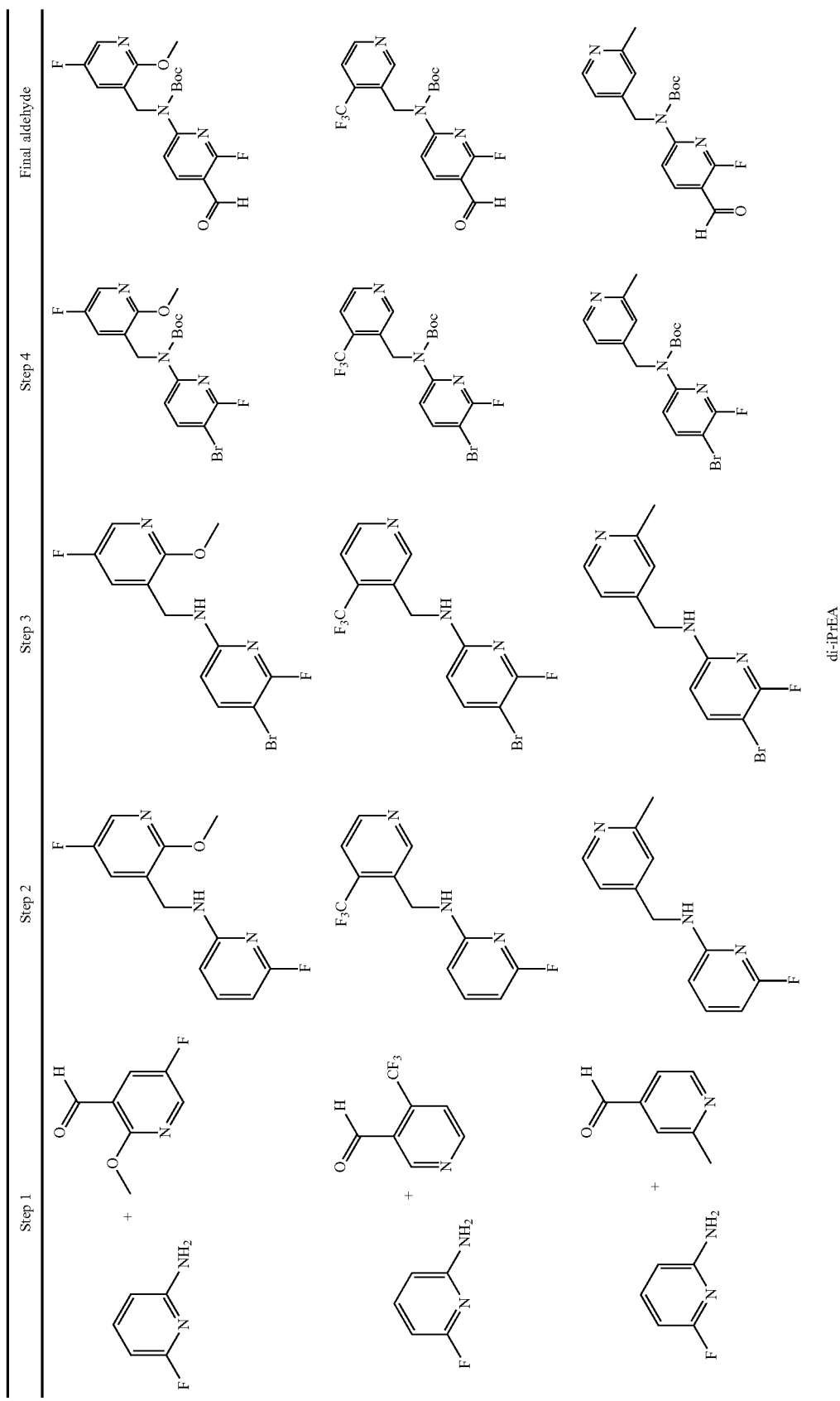

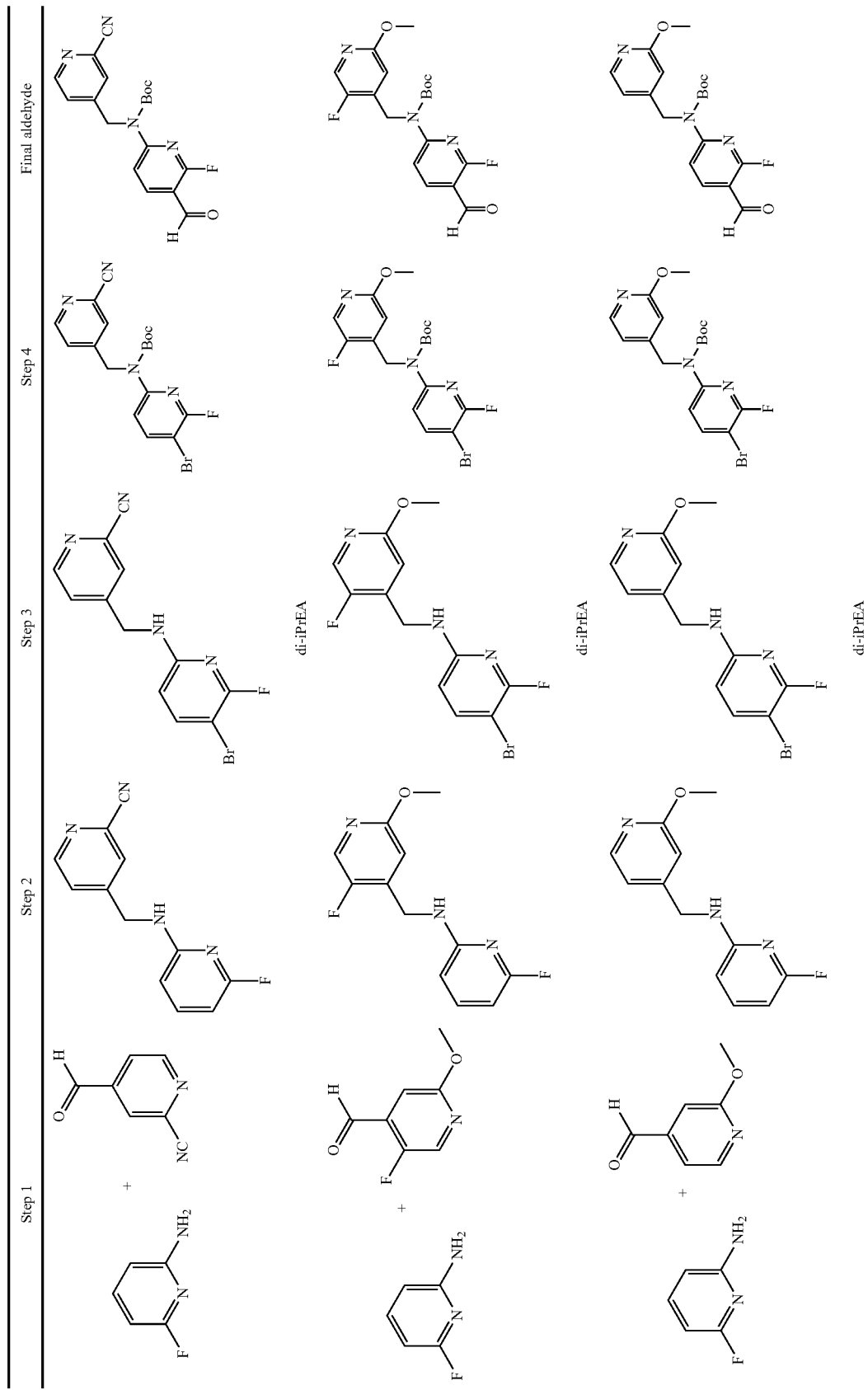

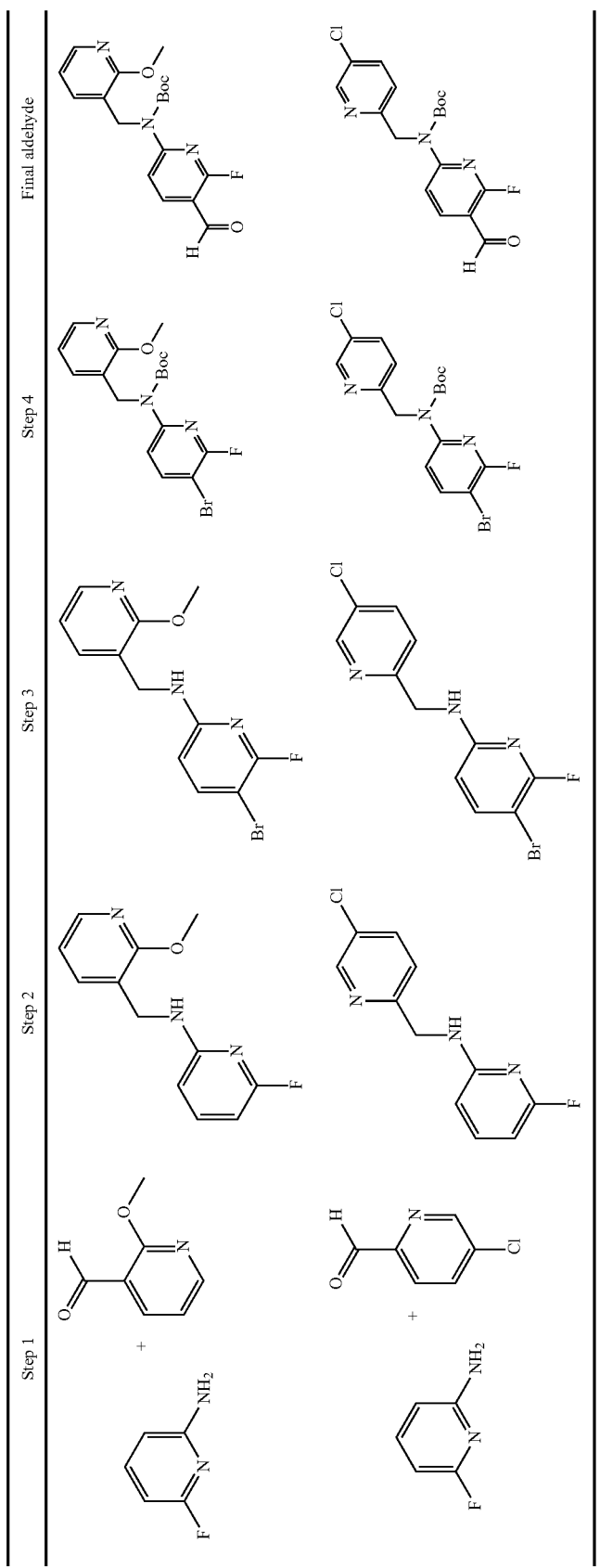

(5-Formyl-pyrimidin-2-yl)-(6-methoxy-pyridin-3-ylmethyl)-carbamic acid tert-butyl ester 33 was prepared in two steps from 2-amino-pyrimidine-5-carbaldehyde 31 and 6-methoxy-pyridine-3-carbaldehyde 29 as shown in Scheme 5.

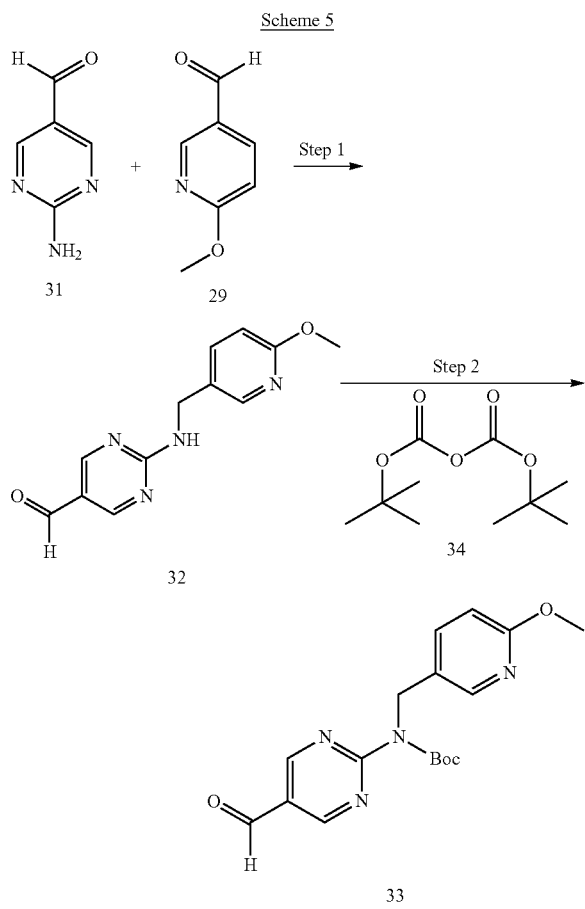

Scheme 5

Step 1—Preparation of 2-[(6-methoxy-pyridin-3-ylmethyl)-amino]-pyrimidine-5-carbaldehyde (32)

In a round bottom flask, 2-amino-pyrimidine-5-carbaldehyde (31, 0.750 g, 6.09 mmol), 6-methoxy-pyridine-3-carbaldehyde (29, 1.67 g, 12.2 mmol), trifluoroacetic acid (2.5 mL, 32.0 mmol), and triethylsilane (5.00 mL, 31.3 mmol) were combined with 10 mL of acetonitrile. The reaction was stirred at room temperature overnight, then concentrated under vacuum and combined with aqueous potassium carbonate and extracted with ethyl acetate. The organic layer was dried over sodium sulfate, filtered and the filtrate concentrated under vacuum. The resulting material was purified by silica gel flash column chromatography, eluting with 15-100% ethyl acetate in hexane. Appropriate fractions were combined and concentrated under vacuum to provide the desired compound.

Step 2—Preparation of (5-formyl-pyrimidin-2-yl)-(6-methoxy-pyridin-3-ylmethyl)-carbamic acid tert-butyl ester (33)

To 2-[(6-methoxy-pyridin-3-ylmethyl)-amino]-pyrimidine-5-carbaldehyde (32, 0.462 g, 1.89 mmol) in 15 mL of tetrahydrofuran, N,N-diisopropylethylamine (0.72 mL, 4.2 mmol), 4-dimethylaminopyridine (0.02 g, 0.2 mmol) and di-tert-butyldicarbonate (34, 0.45 g, 2.1 mmol) were added. The reaction was stirred at room temperature overnight, then poured into water and extracted with ethyl acetate. The organic layer was concentrated under vacuum and the resulting material was purified by silica gel column chromatography, eluting with 20-100% ethyl acetate in hexane. Appropriate fractions were combined and concentrated under vacuum to provide the desired compound. $^1$H NMR was consistent with the compound structure.

Additional aldehydes were prepared similarly to the protocol of scheme 5, as shown in the following table, where Step 1 and Step 2 reactants are provided in columns 1 and 2, respectively, with the resulting Boc protected aldehyde provided in column 3 Reaction conditions were similar to those described for scheme 5, and may have varied slightly for each step, for example, any of solvents, reaction times, temperatures, and work up conditions. In some cases, for step 2, N,N-diisopropylethylamine was not included in the reaction (indicated with no di-iPrEA in the table).

| Step 1 | Step 2 | Final aldehyde |
|---|---|---|
|  |  no di-iPrEA |  |

-continued

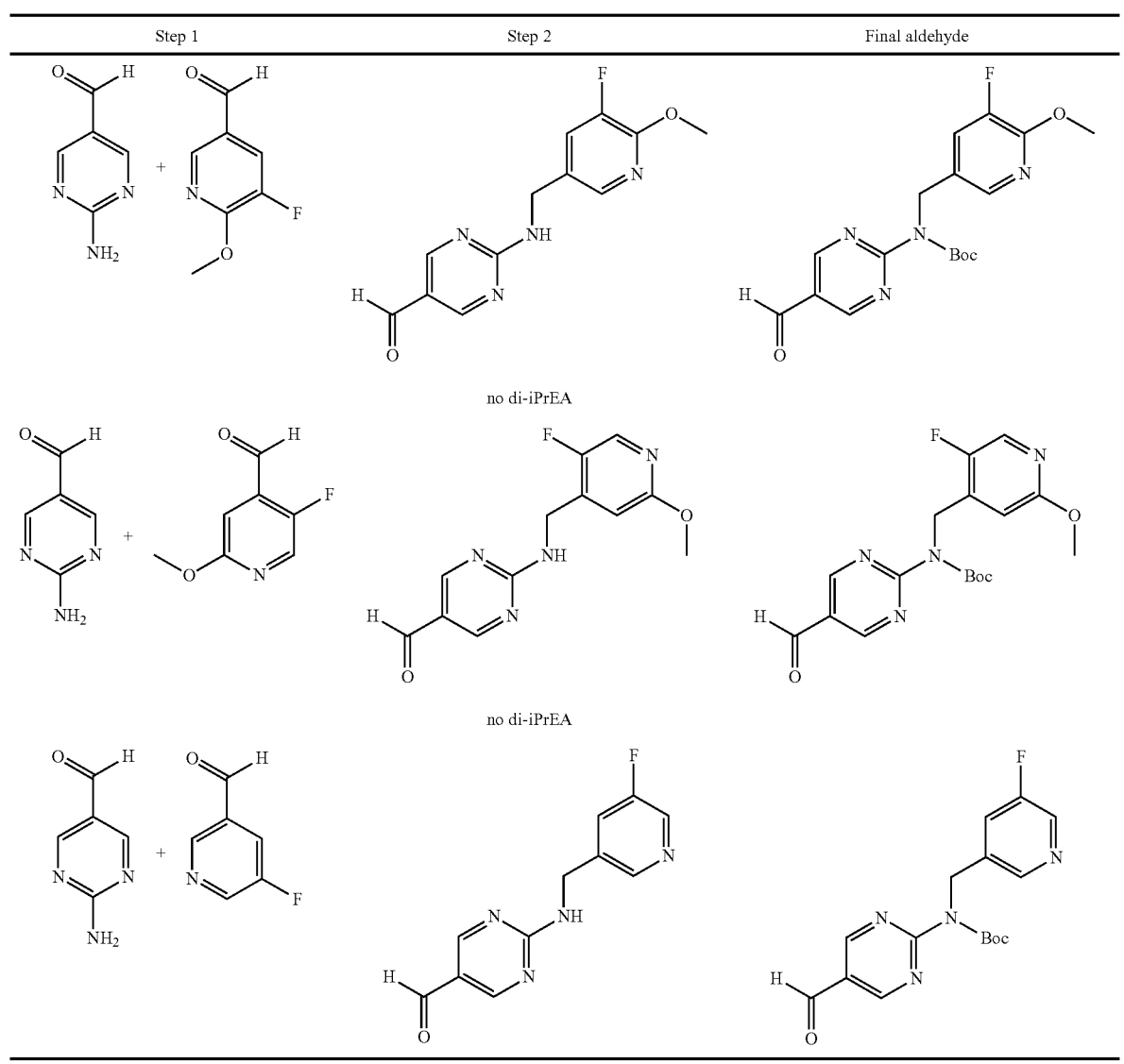

Example 4

Synthesis of 7H-pyrrolo[2,3-d]pyrimidine Reagents 7H-pyrrolo[2,3-d]pyrimidine reagents that are used in coupling to aldehyde compounds such as those described in Example 3 are prepared according to the following protocols.

5-Iodo-4-methoxy-7-triisopropylsilanyl-7H-pyrrolo[2,3-d]pyrimidine 37 is prepared in three steps from 4-chloro-7H-pyrrolo[2,3-d]pyrimidine 1 as shown in scheme 6.

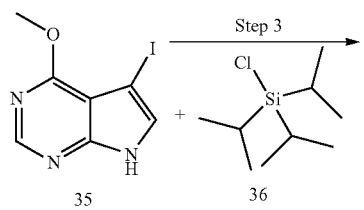

Scheme 6

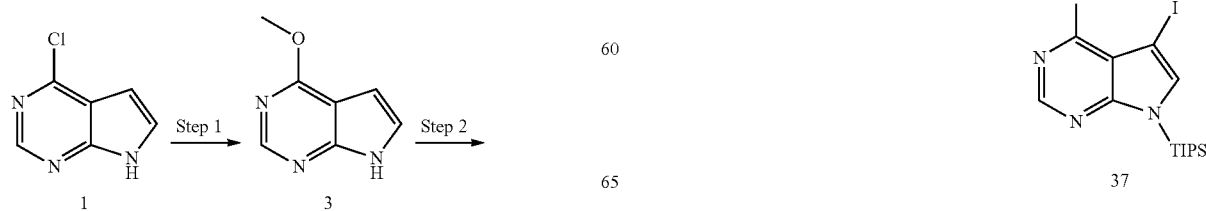

Step 1—Preparation of 4-methoxy-7H-pyrrolo[2,3-d]pyrimidine (3)

To 4-chloro-7H-pyrrolo[2,3-d]pyrimidine (1, 3.5 g, 23.0 mmol) in 70 mL of methanol, potassium hydroxide (2.3 g, 41.0 mmol) was added and the reaction stirred at 60° C. overnight, then poured into water and extracted with ethyl acetate. The organic layer was separated and dried over sodium sulfate, filtered and the filtrate concentrated under vacuum to provide the desired compound (3, 3.20 g).

Step 2—Preparation of 5-iodo-4-methoxy-7H-pyrrolo[2,3-d]pyrimidine (35)

To 4-methoxy-7H-pyrrolo[2,3-d]pyrimidine (3, 3.20 g, 21.4 mmol) in 280 mL of dichloromethane, N-iodosuccinimide (5.3 g, 24.0 mmol) suspended in dichloromethane was added. The reaction was stirred at room temperature for 2 hours, then poured into water and extracted with ethyl acetate. The organic layer was dried over sodium sulfate, filtered and the filtrate concentrated under vacuum. The resulting material was washed with ethyl acetate and hexane to provide the desired compound (35, 4.80 g).

Step 3—Preparation of 5-iodo-4-methoxy-7-triisopropylsilanyl-7H-pyrrolo[2,3-d]pyrimidine (37)

5-Iodo-4-methoxy-7H-pyrrolo[2,3-d]pyrimidine (35, 3.4 g, 12.0 mmol) and 20 mL of N,N-dimethylformamide were combined in a round bottom flask and sodium hydride (350 mg, 8.8 mmol) was added at room temperature. After 20 minutes, chloro-triisopropyl-silane (36, 1.9 mL, 8.8 mmol) was added. The reaction was stirred for 2 hours, then poured into water and extracted 3× with ethyl acetate. The organic layers were combined and washed with brine, then dried over sodium sulfate, filtered and the filtrate concentrated under vacuum. The resulting material was purified by silica gel flash column chromatography eluting with 0-25% ethyl acetate in hexane. Appropriate fractions were combined and solvents removed under vacuum to provide the desired compound (37, 1.3 g).

5-Iodo-7-triisopropylsilanyl-7H-pyrrolo[2,3-d]pyrimidine 38

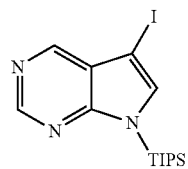

38 may be purchased (e.g. Adesis, Inc. New Castle, Del.) or be prepared similarly to the protocol of scheme 6, step 3, replacing 5-iodo-4-methoxy-7H-pyrrolo[2,3-d]pyrimidine 35 with 5-iodo-7H-pyrrolo[2,3-d]pyrimidine.

7-Benzenesulfonyl-5-iodo-7H-pyrrolo[2,3-d]pyrimidine 41 was prepared in one step from 5-iodo-7H-pyrrolo[2,3-d]pyrimidine 39 as shown in Scheme 7.

Scheme 7

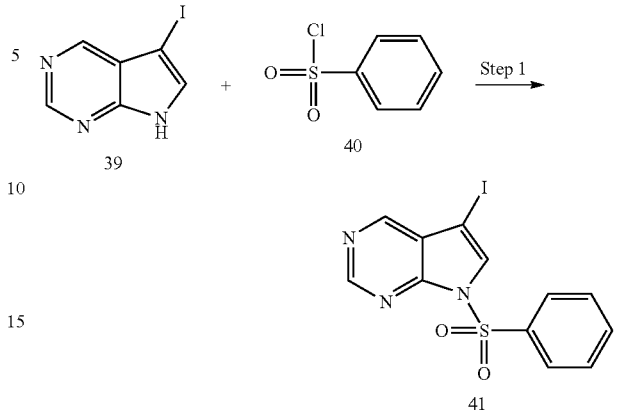

Step 1—Preparation of 7-benzenesulfonyl-5-iodo-7H-pyrrolo[2,3-d]pyrimidine (41)

5-Iodo-7H-pyrrolo[2,3-d]pyrimidine (39, 0.569 g, 2.32 mmol) was added to 10.0 mL of N,N-dimethylformamide in a round bottom flask. Sodium hydride (0.102 g, 2.55 mmol) was added and the reaction stirred at room temperature for 10 minutes, then benzenesulfonyl chloride (40, 326 µL, 2.55 mmol) was added. The reaction was stirred at room temperature overnight, then poured into aqueous saturated sodium bicarbonate and extracted with ethyl acetate. The organic layer was dried over sodium sulfate, filtered and the filtrate adsorbed onto silica. The desired compound was isolated by silica gel column chromatography, eluting with 0.5-6% methanol in dichloromethane. Appropriate fractions were combined and concentrated under vacuum. Toluene was added to the residue, then concentrated under vacuum and the resulting solid was washed with hexane and collected by fitration to provide the desired compound (41, 439 mg). $^1$H NMR consistent with the compound structure.

7-Benzenesulfonyl-5-iodo-4-methoxy-7H-pyrrolo[2,3-d]pyrimidine 42

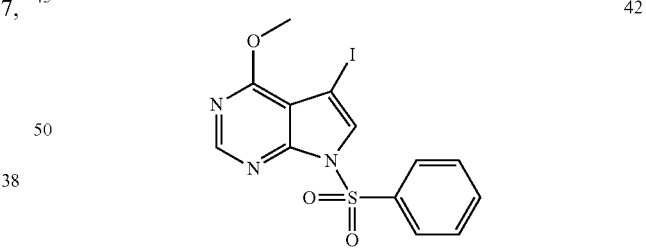

42 was prepared similarly to the protocol of Scheme 7, replacing 5-Iodo-7H-pyrrolo[2,3-d]pyrimidine 39 with 5-Iodo-4-methoxy-7H-pyrrolo[2,3-d]pyrimidine 35. MS (ESI) [M+H$^+$]$^+$=416.0.

Example 5

Synthesis of (4-chloro-benzyl)-[5-(7H-pyrrolo[2,3-d]pyrimidin-5-ylmethyl)-pyridin-2-yl]amine P-0001

(4-Chloro-benzyl)[5-(7H-pyrrolo[2,3-d]pyrimidin-5-ylmethyl)-pyridin-2-yl]-amine P-0001 was prepared in two steps from (4-chloro-benzyl)-(5-formyl-pyridin-2-yl)-carbamic acid tert-butyl ester 13 and 5-Iodo-7-triisopropylsilanyl-7H-pyrrolo[2,3-d]pyrimidine 38 as shown in Scheme 8.

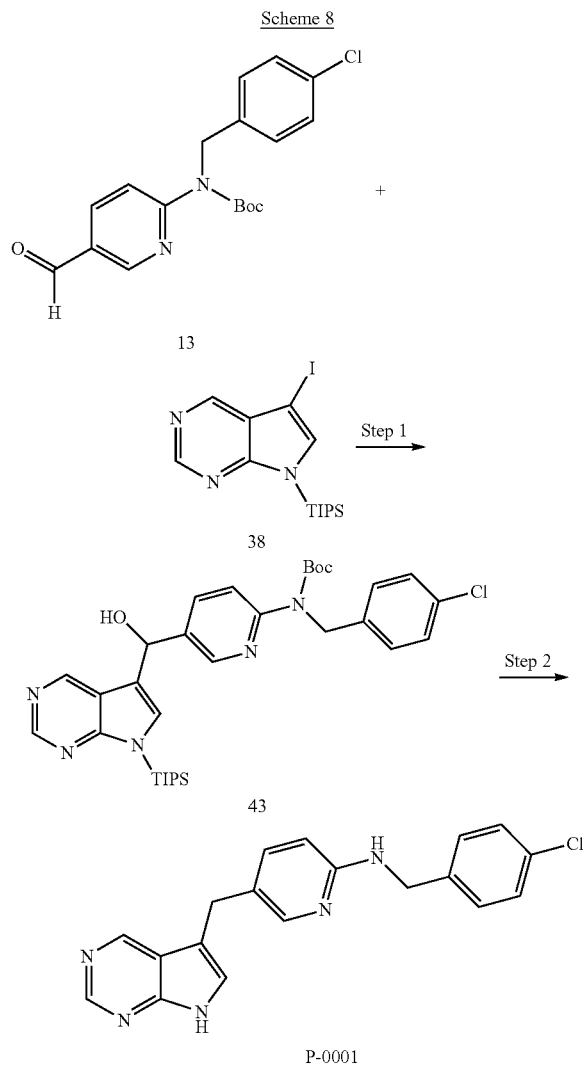

Step 1—Preparation of (4-chloro-benzyl)-{5-[hydroxy-(7-triisopropylsilanyl-7H-pyrrolo[2,3-d]pyrimidin-5-yl)-methyl]-pyridin-2-yl}-carbamic acid tert-butyl ester (43)

5-Iodo-7-triisopropylsilanyl-7H-pyrrolo[2,3-d]pyrimidine (38, 0.160 g, 0.4 mmol) was dissolved in 0.7 mL of tetrahydrofuran under an atmosphere of nitrogen. The reaction was cooled to –20° C. and isopropylmagnesium chloride (0.24 mL, 2.0 M in tetrahydrofuran, 0.48 mmol) was added and the reaction was stirred and allowed to come to 0° C. The reaction was cooled to –20° C. and (4-chloro-benzyl)-(5-formyl-pyridin-2-yl)-carbamic acid tert-butyl ester (13, 0.110 g, 0.32 mmol) in 2.0 mL of tetrahydrofuran was added to the reaction mixture. The reaction was stirred, allowing to come to 0° C., then poured into aqueous saturated sodium bicarbonate and extracted with ethyl acetate. The organic layer was washed with brine, dried over anhydrous sodium sulfate, filtered and the filtrate concentrated under vacuum.

The resulting material was purified by silica gel column chromatography eluting with a gradient of 10-80% ethyl acetate in hexanes. Appropriate fractions were combined and concentrated under vacuum to provide the desired compound (43, 0.103 g, 52%). MS (ESI) [M+H$^+$]$^+$=622.94.

Steps 2—Preparation of (4-chloro-benzyl)-[5-(7H-pyrrolo[2,3-d]pyrimidin-5-ylmethyl)-pyridin-2-yl]-amine (P-0001)

(4-Chloro-benzyl)-5-[hydroxy-(7-triisopropylsilanyl-7H-pyrrolo[2,3-d]pyrimidin-5-yl)-methyl]-pyridin-2-yl-carbamic acid tert-butyl ester (43, 0.1 g, 0.16 mmol) was dissolved in 5 mL of acetonitrile and triethylsilane (0.25 mL, 1.6 mmol) was added followed by trifluoroacetic acid (0.12 mL, 1.6 mmol). The reaction was stirred overnight at 80° C., then cooled and concentrated under vacuum. Ethyl acetate was added and the mixture was washed with 1 M potassium carbonate and brine. The organic portion was dried over anhydrous sodium sulfate, filtered and the filtrate concentrated under vacuum. The resulting material was purified by silica gel column chromatography eluting with a gradient of 0-20% methanol in dichloromethane. Appropriate fractions were combined and concentrated under vacuum to provide the desired compound, which was further washed with a mixture of ethyl acetate in hexane (P-0001, 0.025 g, 44%). MS (ESI) [M+H$^+$]$^+$=349.9.

Additional compounds were prepared similarly to the protocol of Scheme 8, substituting (4-chloro-benzyl)-(5-formyl-pyridin-2-yl)-carbamic acid tert-butyl ester 13 with a suitable Boc protected aldehyde and in some instances, substituting 5-iodo-7-triisopropylsilanyl-7H-pyrrolo[2,3-d]pyrimidine 38 with 5-iodo-4-methoxy-7-triisopropylsilanyl-7H-pyrrolo[2,3-d]pyrimidine 37 in step 1. The following compounds were prepared similarly to the protocol of Scheme 8:

(6-Methoxy-pyridin-3-ylmethyl)-[5-(7H-pyrrolo[2,3-d]pyrimidin-5-ylmethyl)-pyridin-2-yl]-amine (P-0002),
(2-Chloro-benzyl)-[5-(7H-pyrrolo[2,3-d]pyrimidin-5-ylmethyl)-pyridin-2-yl]-amine (P-0003),
[5-(7H-Pyrrolo[2,3-d]pyrimidin-5-ylmethyl)-pyridin-2-yl]-(6-trifluoromethyl-pyridin-3-ylmethyl)-amine (P-0004),
(2-Chloro-benzyl)-[6-fluoro-5-(7H-pyrrolo[2,3-d]pyrimidin-5-ylmethyl)-pyridin-2-yl]-amine (P-0005),
(4-Chloro-benzyl)-[6-fluoro-5-(7H-pyrrolo[2,3-d]pyrimidin-5-ylmethyl)-pyridin-2-yl]-amine (P-0006),
[6-Fluoro-5-(7H-pyrrolo[2,3-d]pyrimidin-5-ylmethyl)-pyridin-2-yl]-(6-trifluoromethyl-pyridin-3-ylmethyl)-amine (P-0007),
[6-Fluoro-5-(7H-pyrrolo[2,3-d]pyrimidin-5-ylmethyl)-pyridin-2-yl]-(6-methoxy-pyridin-3-ylmethyl)-amine (P-0009),
(5-Fluoro-6-methoxy-pyridin-3-ylmethyl)-[6-fluoro-5-(7H-pyrrolo[2,3-d]pyrimidin-5-ylmethyl)-pyridin-2-yl]-amine (P-0010),
(5-Fluoro-2-methoxy-pyridin-3-ylmethyl)-[6-fluoro-5-(7H-pyrrolo[2,3-d]pyrimidin-5-ylmethyl)-pyridin-2-yl]-amine (P-0011),
(6-Methoxy-pyridin-3-ylmethyl)-[3-methyl-5-(7H-pyrrolo[2,3-d]pyrimidin-5-ylmethyl)-pyridin-2-yl]-amine (P-0012),
(6-Methoxy-pyridin-3-ylmethyl)-[5-(4-methoxy-7H-pyrrolo[2,3-d]pyrimidin-5-ylmethyl)-pyridin-2-yl]-amine (P-0013),
(2-Chloro-benzyl)-[5-(4-methoxy-7H-pyrrolo[2,3-d]pyrimidin-5-ylmethyl)-pyridin-2-yl]-amine (P-0014),
(6-Methoxy-pyridin-3-ylmethyl)-[5-(7H-pyrrolo[2,3-d]pyrimidin-5-ylmethyl)-pyrimidin-2-yl]-amine (P-0015),

[(S)-1-(4-Fluoro-phenyl)-ethyl]-[6-fluoro-5-(7H-pyrrolo[2,3-d]pyrimidin-5-ylmethyl)-pyridin-2-yl]-amine (P-0016),
[3-Fluoro-5-(7H-pyrrolo[2,3-d]pyrimidin-5-ylmethyl)-pyridin-2-yl]-(6-methoxy-pyridin-3-ylmethyl)-amine (P-0017),
[6-Fluoro-5-(7H-pyrrolo[2,3-d]pyrimidin-5-ylmethyl)-pyridin-2-yl]-(4-trifluoromethyl-pyridin-3-ylmethyl)-amine (P-0018),
[6-Fluoro-5-(7H-pyrrolo[2,3-d]pyrimidin-5-ylmethyl)-pyridin-2-yl]-(2-methyl-pyridin-4-ylmethyl)-amine (P-0020),
(5-Fluoro-2-methoxy-pyridin-4-ylmethyl)-[6-fluoro-5-(7H-pyrrolo[2,3-d]pyrimidin-5-ylmethyl)-pyridin-2-yl]-amine (P-0021),
(5-Fluoro-2-methoxy-pyridin-3-ylmethyl)-[5-(7H-pyrrolo[2,3-d]pyrimidin-5-ylmethyl)-pyrimidin-2-yl]-amine (P-0022),
[6-Fluoro-5-(7H-pyrrolo[2,3-d]pyrimidin-5-ylmethyl)-pyridin-2-yl]-(2-methoxy-pyridin-4-ylmethyl)-amine (P-0023),
(5-Fluoro-6-methoxy-pyridin-3-ylmethyl)-[5-(7H-pyrrolo[2,3-d]pyrimidin-5-ylmethyl)-pyrimidin-2-yl]-amine (P-0024),
(5-Fluoro-2-methoxy-pyridin-4-ylmethyl)-[5-(7H-pyrrolo[2,3-d]pyrimidin-5-ylmethyl)-pyrimidin-2-yl]-amine (P-0025),
[6-Fluoro-5-(7H-pyrrolo[2,3-d]pyrimidin-5-ylmethyl)-pyridin-2-yl]-(2-methoxy-pyridin-3-ylmethyl)-amine (P-0026),
(5-Chloro-pyridin-2-ylmethyl)-[6-fluoro-5-(7H-pyrrolo[2,3-d]pyrimidin-5-ylmethyl)-pyridin-2-yl]-amine (P-0027), and
(5-Fluoro-pyridin-3-ylmethyl)-[5-(4-methoxy-7H-pyrrolo[2,3-d]pyrimidin-5-ylmethyl)-pyrimidin-2-yl]-amine (P-0098).

The following table indicates the 7H-pyrrolo[2,3-d]pyrimidine compound (column 2), and aldehyde compound (column 3) used in step 1 to afford the desired compound (column 4). The compound number is provided in column 1, and the observed mass is in column 5. The reaction and work up conditions may have varied for each step, for example, any of solvents, reaction times, temperatures, or work up conditions. For example, in some instances, for step 1, the reaction was washed initially with ammonium chloride solution instead of sodium bicarbonate; in some instances, for step 2, the solvent was 1,2-dichloroethane or dichloromethane instead of acetonitrile, and/or the chromatography work up used ethyl acetate/hexane system instead of methanol/dichloromethane.

| Compound number | 7H-pyrrolo[2,3-d] pyrimidine comp. | Aldehyde structure | Compound structure | MS (ESI) [M + H⁺]⁺ |
|---|---|---|---|---|
| P-0002 | | | 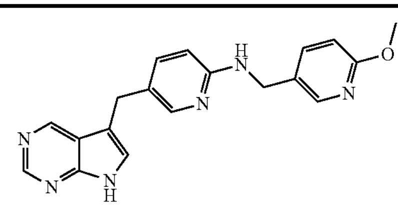 | 374.1 |
| P-0003 | | | 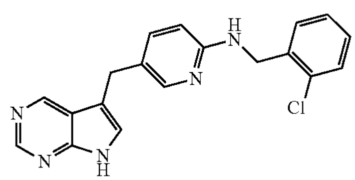 [SMILES: Clc1ccccc1CNc1ccc(Cc2c[nH]c3ncncc23)cn1] | 349.9 |
| P-0004 | | | 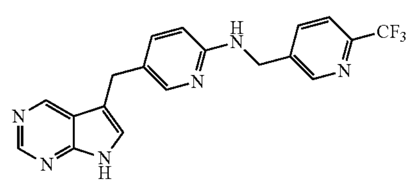 [SMILES: FC(F)(F)c1ccc(CNc2ccc(Cc3c[nH]c4ncncc34)cn2)cn1] | 384.9 |
| P-0005 | | | 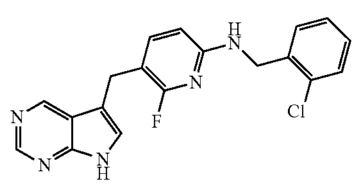 [SMILES: Fc1nc(NCc2ccccc2Cl)ccc1Cc1c[nH]c2ncncc12] | 368.1 |

-continued

| Compound number | 7H-pyrrolo[2,3-d] pyrimidine comp. | Aldehyde structure | Compound structure | MS (ESI) [M + H⁺]⁺ |
|---|---|---|---|---|
| P-0006 | | | 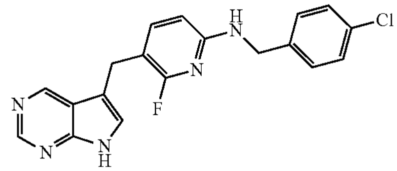 [SMILES: Fc1nc(NCc2ccc(Cl)cc2)ccc1Cc1c[nH]c2ncncc12] | 367.8 |
| P-0007 | | | 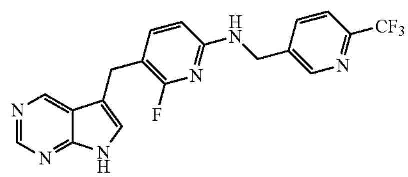 [SMILES: Fc1nc(NCc2ccc(C(F)(F)F)nc2)ccc1Cc1c[nH]c2ncncc12] | 402.9 |
| P-0009 | | | 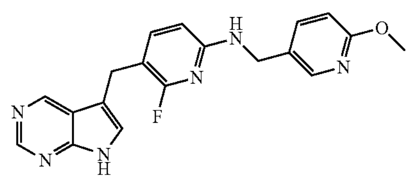 [SMILES: COc1ccc(CNc2ccc(Cc3c[nH]c4ncncc34)c(F)n2)cn1] | 364.9 |
| P-0010 | | | 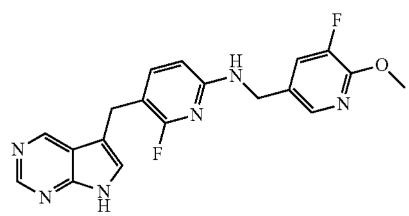 [SMILES: COc1ncc(CNc2ccc(Cc3c[nH]c4ncncc34)c(F)n2)cc1F] | 382.9 |
| P-0011 | | | 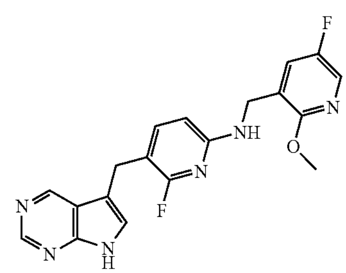 [SMILES: COc1ncc(F)cc1CNc1ccc(Cc2c[nH]c3ncncc23)c(F)n1] | 382.9 |
| P-0012 | | | 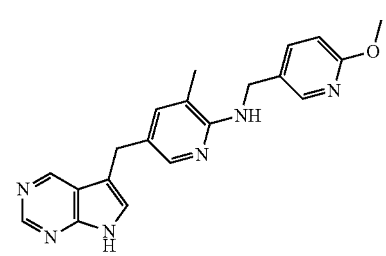 [SMILES: COc1ccc(CNc2ncc(Cc3c[nH]c4ncncc34)cc2C)cn1] | 361.0 |

-continued

| Compound number | 7H-pyrrolo[2,3-d] pyrimidine comp. | Aldehyde structure | Compound structure | MS (ESI) [M + H+]+ |
|---|---|---|---|---|
| P-0013 | | | 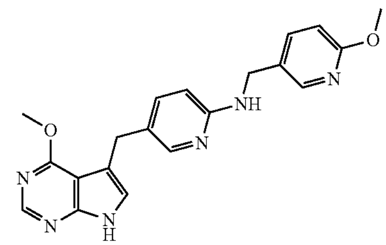 [SMILES: COc1ccc(CNc2ccc(Cc3c[nH]c4ncnc(OC)c34)cn2)cn1] | 376.9 |
| P-0014 | | | 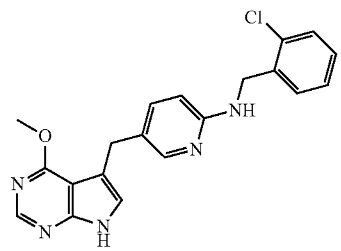 [SMILES: COc1ncnc2[nH]cc(Cc3ccc(NCc4ccccc4Cl)nc3)c12] | 380.05 |
| P-0015 | | | 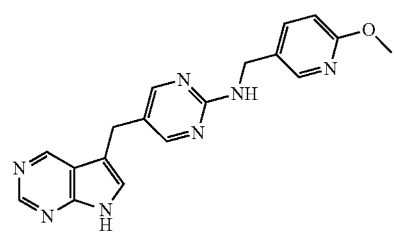 [SMILES: COc1ccc(CNc2ncc(Cc3c[nH]c4ncncc34)cn2)cn1] | 348.05 |
| P-0016 | | | 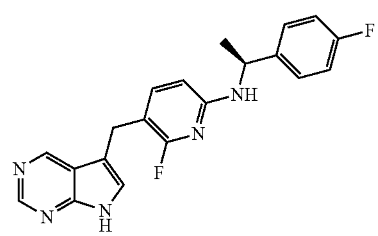 [SMILES: C[C@H](Nc1ccc(Cc2c[nH]c3ncncc23)c(F)n1)c1ccc(F)cc1] | 366.0 |
| P-0017 | | | 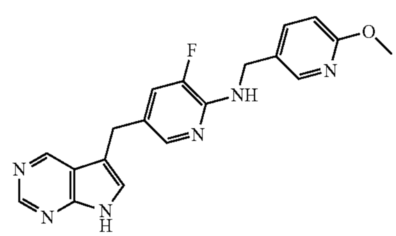 [SMILES: COc1ccc(CNc2ncc(Cc3c[nH]c4ncncc34)cc2F)cn1] | 365.0 |
| P-0018 | | | 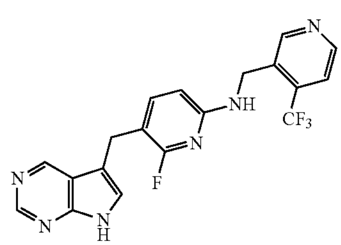 [SMILES: Fc1nc(NCc2cnccc2C(F)(F)F)ccc1Cc1c[nH]c2ncncc12] | 402.9 |

-continued

| Compound number | 7H-pyrrolo[2,3-d] pyrimidine comp. | Aldehyde structure | Compound structure | MS (ESI) [M + H+]+ |
|---|---|---|---|---|
| P-0020 | | | 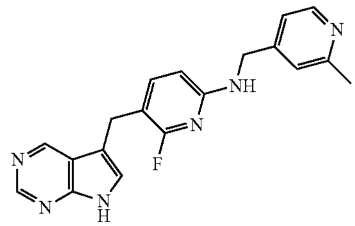 [SMILES: Cc1cc(CNc2ccc(Cc3c[nH]c4ncncc34)c(F)n2)ccn1] | 348.9 |
| P-0021 | | | 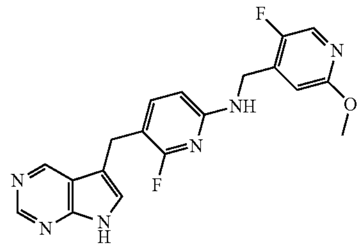 [SMILES: COc1cc(CNc2ccc(Cc3c[nH]c4ncncc34)c(F)n2)c(F)cn1] | 382.9 |
| P-0022 | | | 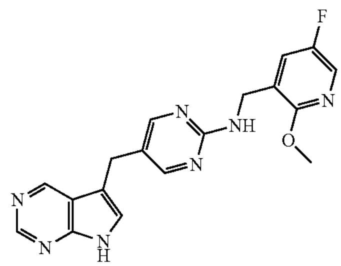 [SMILES: COc1ncc(F)cc1CNc1ncc(Cc2c[nH]c3ncncc23)cn1] | 366.5 |
| P-0023 | | | 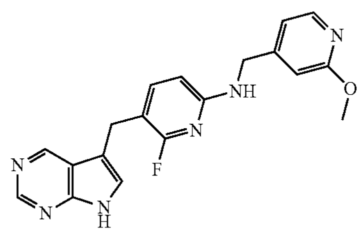 [SMILES: COc1cc(CNc2ccc(Cc3c[nH]c4ncncc34)c(F)n2)ccn1] | 364.9 |
| P-0024 | | | 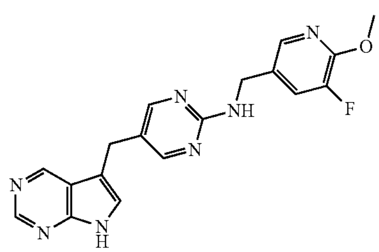 [SMILES: COc1ncc(CNc2ncc(Cc3c[nH]c4ncncc34)cn2)cc1F] | 366.1 |
| P-0025 | | | 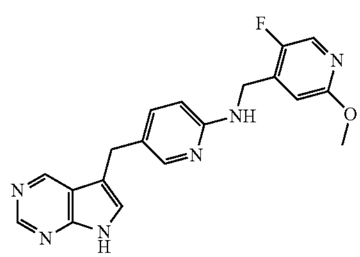 [SMILES: COc1cc(CNc2ccc(Cc3c[nH]c4ncncc34)cn2)c(F)cn1] | 365.9 |

| Compound number | 7H-pyrrolo[2,3-d] pyrimidine comp. | Aldehyde structure | Compound structure | MS (ESI) [M + H⁺]⁺ |
|---|---|---|---|---|
| P-0026 | | | 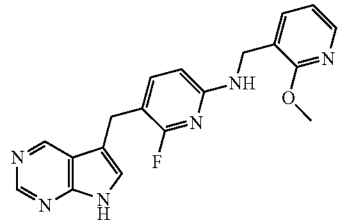 [SMILES: COc1ncccc1CNc1ccc(Cc2c[nH]c3ncncc23)c(F)n1] | 365.15 |
| P-0027 | | | 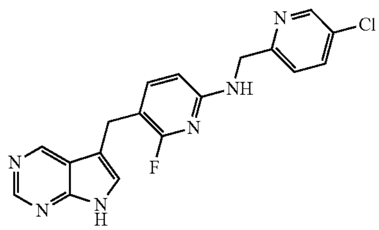 [SMILES: Fc1nc(NCc2ccc(Cl)cn2)ccc1Cc1c[nH]c2ncncc12] | 368.95 |
| P-0098 | | | 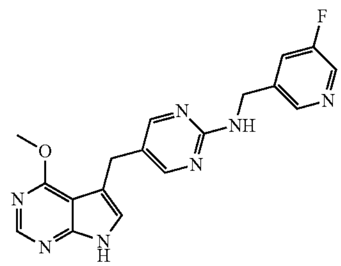 [SMILES: COc1ncnc2[nH]cc(Cc3cnc(NCc4cncc(F)c4)nc3)c12] | 366.0 |

Example 6

Synthesis of (2-chloro-benzyl)-[6-fluoro-5-(4-methoxy-7H-pyrrolo[2,3-d]pyrimidin-5-ylmethyl)-pyridin-2-yl]-amine P-0090

(2-Chloro-benzyl)-[6-fluoro-5-(4-methoxy-7H-pyrrolo[2,3-d]pyrimidin-5-ylmethyl)-pyridin-2-yl]-amine P-0090 was prepared in three steps from 7-benzenesulfonyl-5-iodo-4-methoxy-7H-pyrrolo[2,3-d]pyrimidine 42 and (2-chlorobenzyl)-(6-fluoro-5-formyl-pyridin-2-yl)-carbamic acid tert-butyl ester 19 as shown in Scheme 9.

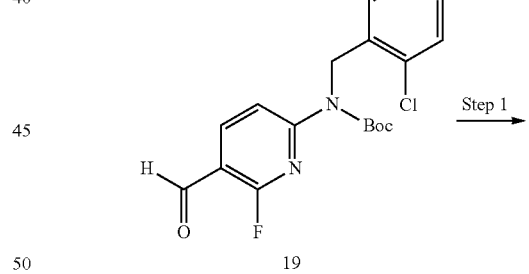

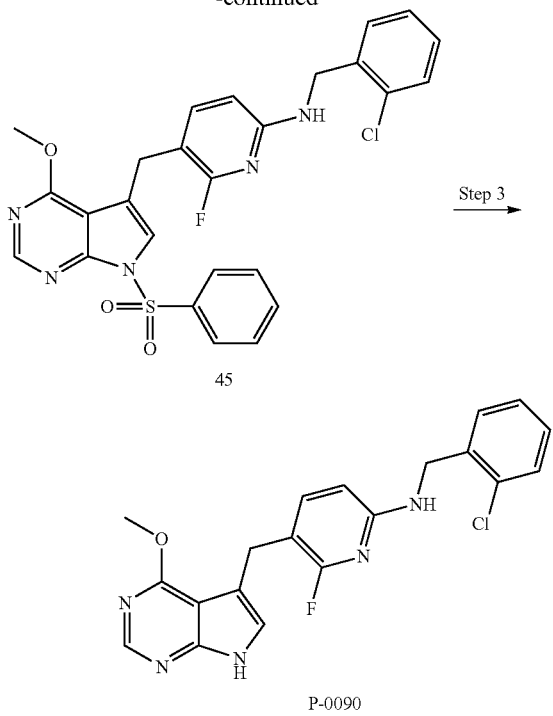

Step 1—Preparation of {5-[(7-Benzenesulfonyl-4-methoxy-7H-pyrrolo[2,3-d]pyrimidin-5-yl)-hydroxy-methyl]-6-fluoro-pyridin-2-yl}-(2-chloro-benzyl)-carbamic acid tert-butyl ester (44)

To a solution of 7-benzenesulfonyl-5-iodo-4-methoxy-7H-pyrrolo[2,3-d]pyrimidine (42, 0.408 g, 0.983 mmol) in 4.0 mL of tetrahydrofuran at −50° C. under an atmosphere of nitrogen, isopropylmagnesium chloride (0.500 mL, 2.00 M in tetrahydrofuran, 1.00 mmol) was added slowly. The reaction was allowed to warm to 5° C. over 70 minutes, cooled to −45° C. and (2-chloro-benzyl)-(6-fluoro-5-formyl-pyridin-2-yl)-carbamic acid tert-butyl ester (19, 0.240 g, 0.658 mmol) in 2.0 mL of tetrahydrofuran was added. The reaction was allowed to warm to room temperature over an hour, then poured into water and extracted with ethyl acetate. The organic layer was dried over sodium sulfate, filtered and the filtrate concentrated under vacuum. The resulting material was purified by silica gel chromatography eluting with 20-100% ethyl acetate in hexane. Appropriate fractions were combined and concentrated under vacuum to provide the desired compound (44, 0.400 g).

Steps 2—Preparation of [5-(7-benzenesulfonyl-4-methoxy-7H-pyrrolo[2,3-d]pyrimidin-5-ylmethyl)-6-fluoro-pyridin-2-yl]-(2-chloro-benzyl)-amine (45)

To {5-[(7-Benzenesulfonyl-4-methoxy-7H-pyrrolo[2,3-d]pyrimidin-5-yl)-hydroxy-methyl]-6-fluoro-pyridin-2-yl}-(2-chloro-benzyl)-carbamic acid tert-butyl ester (44, 0.400 g, 0.612 mmol) in 15.0 mL of 1,2-dichloroethane, triethylsilane (2.0 mL, 12 mmol) and trifluoroacetic acid (1.0 mL, 13 mmol) were added. The reaction was heated at 80° C. for 3 hours, then poured into water and extracted with ethyl acetate. The organic layer was dried over sodium sulfate, filtered and the filtrate concentrated under vacuum. The resulting material was purified by silica gel chromatography eluting with 20-100% ethyl acetate in hexane. Appropriate fractions were combined and concentrated under vacuum to provide the desired compound (45, 0.30 g).

Steps 3—Preparation of (2-chloro-benzyl)-[6-fluoro-5-(4-methoxy-7H-pyrrolo[2,3-d]pyrimidin-5-ylmethyl)-pyridin-2-yl]amine (P-0090)

To [5-(7-benzenesulfonyl-4-methoxy-7H-pyrrolo[2,3-d]pyrimidin-5-ylmethyl)-6-fluoro-pyridin-2-yl]-(2-chloro-benzyl)-amine (45, 0.30 g, 0.558 mmol) in 15 mL of methanol, potassium hydroxide (0.50 g, 8.9 mmol) was added. The reaction was stirred at 45° C. for 2 hours, then poured into water and extracted with ethyl acetate. The organic layer was dried over sodium sulfate, filtered and the filtrate concentrated under vacuum. The resulting material was washed with ethyl acetate to provide the desired compound (P-0090, 0.176 g). MS (ESI) [M+H$^+$]$^+$=397.9.

Additional compounds were prepared similarly to the protocol of Scheme 9, substituting (2-chloro-benzyl)-(6-fluoro-5-formyl-pyridin-2-yl)-carbamic acid tert-butyl ester 19 with a suitable Boc protected aldehyde in step 1. The following compounds were prepared similarly to the protocol of Scheme 9:
(5-Fluoro-6-methoxy-pyridin-3-ylmethyl)-[6-fluoro-5-(4-methoxy-7H-pyrrolo[2,3-d]pyrimidin-5-ylmethyl)-pyridin-2-yl]-amine (P-0091),
(5-Fluoro-6-methoxy-pyridin-3-ylmethyl)-[5-(4-methoxy-7H-pyrrolo[2,3-d]pyrimidin-5-ylmethyl)-pyrimidin-2-yl]-amine (P-0092),
(5-Fluoro-2-methoxy-pyridin-3-ylmethyl)-[5-(4-methoxy-7H-pyrrolo[2,3-d]pyrimidin-5-ylmethyl)-pyrimidin-2-yl]-amine (P-0093),
(5-Fluoro-2-methoxy-pyridin-3-ylmethyl)-[6-fluoro-5-(4-methoxy-7H-pyrrolo[2,3-d]pyrimidin-5-ylmethyl)-pyridin-2-yl]-amine (P-0094),
[6-Fluoro-5-(4-methoxy-7H-pyrrolo[2,3-d]pyrimidin-5-ylmethyl)-pyridin-2-yl]-(4-trifluoromethyl-pyridin-3-ylmethyl)-amine (P-0095),
[3-Methoxy-5-(4-methoxy-7H-pyrrolo[2,3-d]pyrimidin-5-ylmethyl)-pyridin-2-yl]-(6-trifluoromethyl-pyridin-3-ylmethyl)-amine (P-0096),
[6-Fluoro-5-(4-methoxy-7H-pyrrolo[2,3-d]pyrimidin-5-ylmethyl)-pyridin-2-yl]-(2-methoxy-pyridin-3-ylmethyl)-amine (P-0097),
[5-(4-Methoxy-7H-pyrrolo[2,3-d]pyrimidin-5-ylmethyl)-pyridin-2-yl]-(6-trifluoromethyl-pyridin-3-ylmethyl)-amine (P-0100),
[6-Fluoro-5-(4-methoxy-7H-pyrrolo[2,3-d]pyrimidin-5-ylmethyl)-pyridin-2-yl]-(6-trifluoromethyl-pyridin-3-ylmethyl)-amine (P-0101),
[5-(4-Methoxy-7H-pyrrolo[2,3-d]pyrimidin-5-ylmethyl)-pyrimidin-2-yl]-(6-trifluoromethyl-pyridin-3-ylmethyl)-amine (P-0102), and
[3-Fluoro-5-(4-methoxy-7H-pyrrolo[2,3-d]pyrimidin-5-ylmethyl)-pyridin-2-yl]-(6-trifluoromethyl-pyridin-3-ylmethyl)-amine (P-0103).
The following table indicates the 7H-pyrrolo[2,3-d]pyrimidine compound 42 (column 2), and aldehyde compound (column 3) used in step 1 to afford the desired compound (column 4). The compound number is provided in column 1, and the observed mass is in column 5 The reaction and work up conditions may have varied for each step, for example, any of solvents, reaction times, temperatures, or work up conditions. For example, in some instances, for step 1, the reaction was washed initially with ammonium chloride solution instead of water; in some instances, for step 2, the solvent was acetonitrile instead of 1,2-dichloroethane, and/or the reaction was initially washed with potassium carbonate solution instead of water; in some instances, for step 3, chromatography work up used methanol/dichloromethane system instead of ethyl acetate/hexane system.

| Compound number | 7H-pyrrolo[2,3-d] pyrimidine comp. | Aldehyde structure | Compound structure | MS (ESI) [M + H$^+$]$^+$ |
|---|---|---|---|---|
| P-0091 | | | 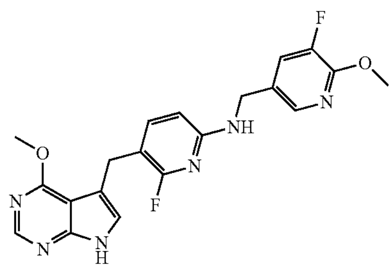 [SMILES: COc1ncc(CNc2ccc(Cc3c[nH]c4ncnc(OC)c34)c(F)n2)cc1F] | 413.3 |
| P-0092 | | | 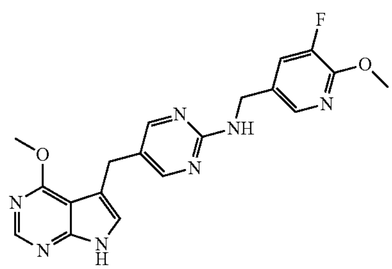 [SMILES: COc1ncc(CNc2ncc(Cc3c[nH]c4ncnc(OC)c34)cn2)cc1F] | 396.0 |
| P-0093 | | | 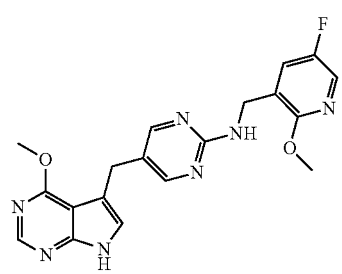 [SMILES: COc1ncc(F)cc1CNc1ncc(Cc2c[nH]c3ncnc(OC)c23)cn1] | 396.1 |
| P-0094 | | | 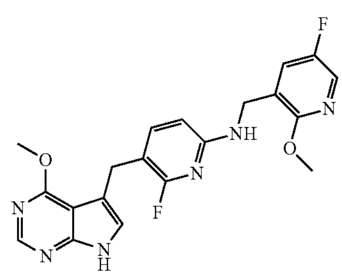 [SMILES: COc1ncc(F)cc1CNc1ccc(Cc2c[nH]c3ncnc(OC)c23)c(F)n1] | 413.3 |
| P-0095 | | | 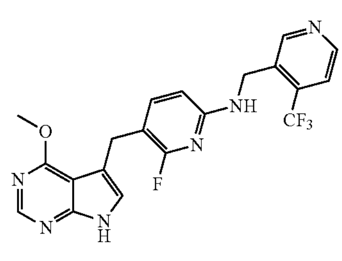 [SMILES: COc1ncnc2[nH]cc(Cc3ccc(NCc4cnccc4C(F)(F)F)nc3F)c12] | 433.0 |

-continued

| Compound number | 7H-pyrrolo[2,3-d] pyrimidine comp. | Aldehyde structure | Compound structure | MS (ESI) [M + H+]+ |
|---|---|---|---|---|
| P-0096 | | | 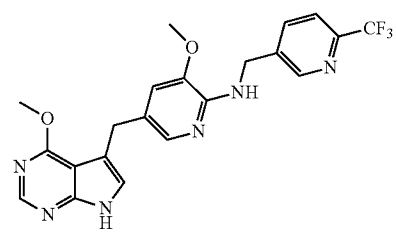 [SMILES: COc1cc(Cc2c[nH]c3ncnc(OC)c23)cnc1NCc1ccc(C(F)(F)F)nc1] | 445.0 |
| P-0097 | | | 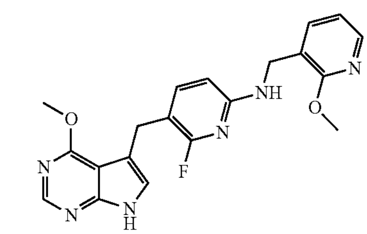 [SMILES: COc1ncccc1CNc1ccc(Cc2c[nH]c3ncnc(OC)c23)c(F)n1] | 394.9 |
| P-0100 | | | 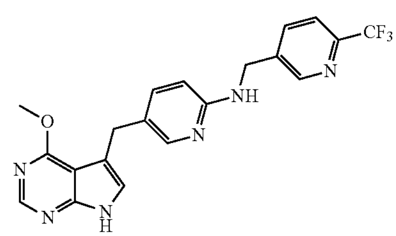 [SMILES: COc1ncnc2[nH]cc(Cc3ccc(NCc4ccc(C(F)(F)F)nc4)nc3)c12] | 415.0 |
| P-0101 | | | 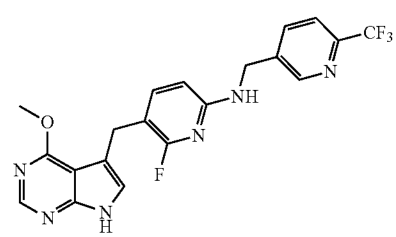 [SMILES: COc1ncnc2[nH]cc(Cc3ccc(NCc4ccc(C(F)(F)F)nc4)nc3F)c12] | 433.0 |
| P-0102 | | | 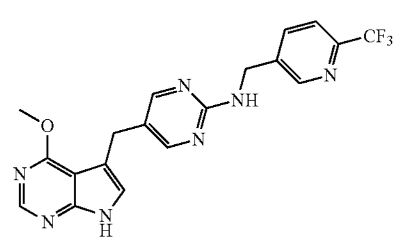 [SMILES: COc1ncnc2[nH]cc(Cc3cnc(NCc4ccc(C(F)(F)F)nc4)nc3)c12] | 416.0 |
| P-0103 | | | 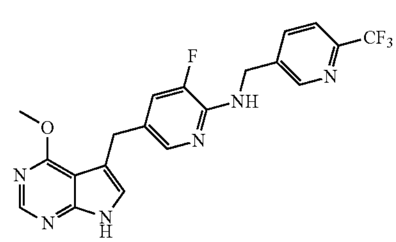 [SMILES: COc1ncnc2[nH]cc(Cc3cnc(NCc4ccc(C(F)(F)F)nc4)c(F)c3)c12] | 433.0 |

Example 7

Synthesis of [5-(4-cyclopentyl-7H-pyrrolo[2,3-d]pyrimidin-5-ylmethyl)-pyridin-2-yl]-(6-trifluoromethyl-pyridin-3-ylmethyl)-amine P-0104

[5-(4-Cyclopentyl-7H-pyrrolo[2,3-d]pyrimidin-5-ylmethyl)-pyridin-2-yl]-(6-trifluoromethyl-pyridin-3-ylmethyl)-amine P-0104 was prepared in six steps from 4-chloro-7H-pyrrolo[2,3-d]pyrimidine 1 and cyclopentylzinc bromide 47 as shown in Scheme 10.

Scheme 10

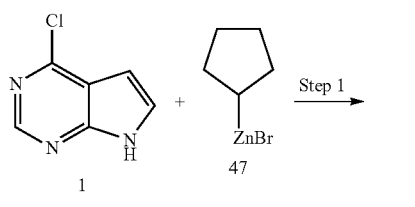

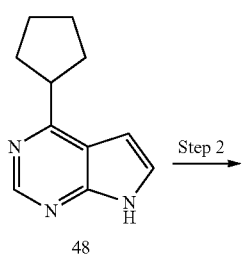

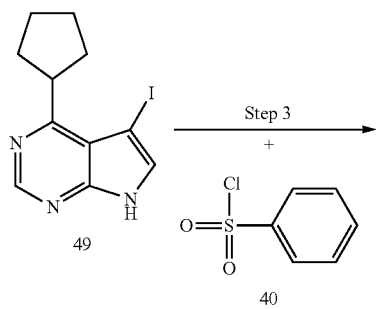

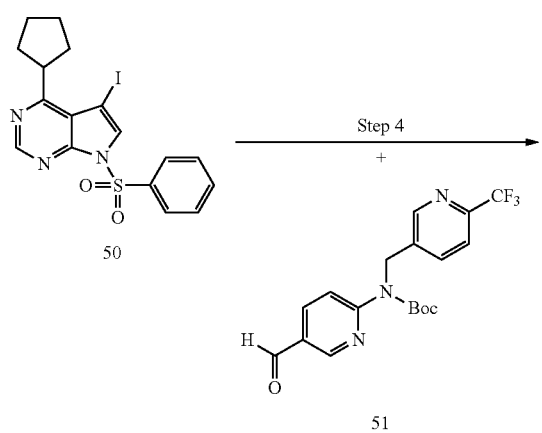

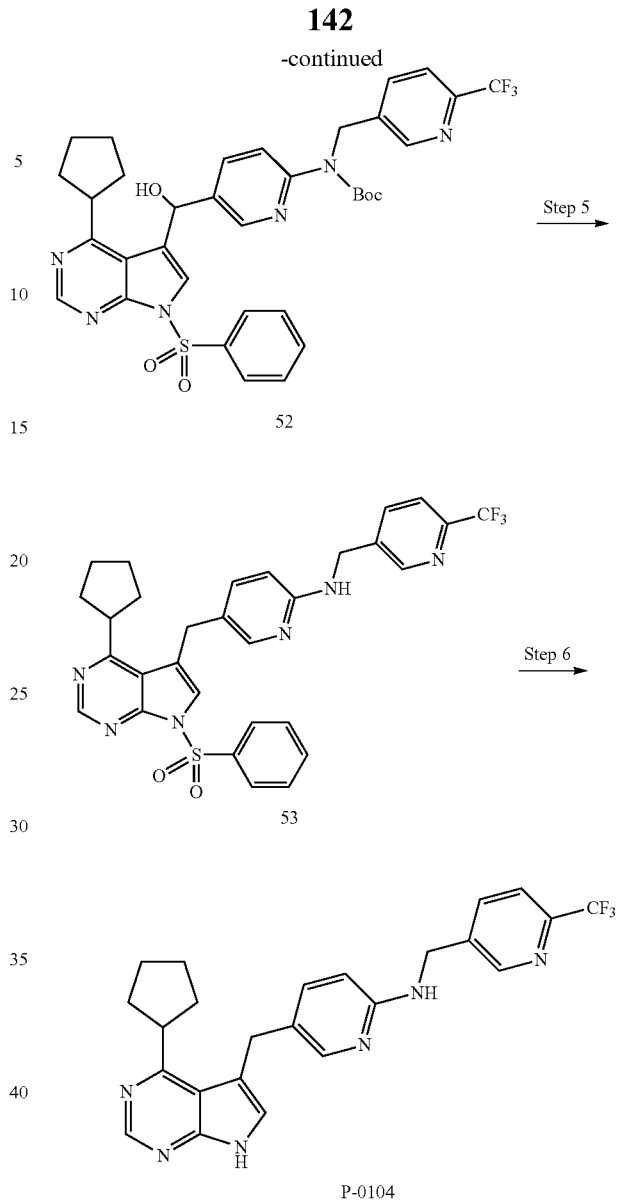

Step 1—Preparation of 4-cyclopentyl-7H-pyrrolo[2,3-d]pyrimidine (48)

4-chloro-7H-pyrrolo[2,3-d]pyrimidine (1, 0.503 g, 3.28 mmol), cyclopentylzinc bromide (47, 29.5 mL, 0.500 M in tetrahydrofuran, 14.7 mmol), [1,3-bis(diphenylphosphino)propane]nickel(II) chloride (0.178 g, 0.328 mmol) and 9.3 mL of 1,4-dioxane were combined. The reaction mixture was heated at 110° C. overnight. Methanol was added and the reaction was concentrated under vacuum. Ethyl acetate and water were added to the residue, filtered through a bed of celite, and the celite washed with ethyl acetate. The filtrate layers were separated and the aqueous layer was extracted with ethyl acetate. The organic layers were combined, washed with brine, dried over sodium sulfate, filtered and the filtrate concentrated under vacuum. The resulting material was purified by silica gel column chromatography, eluting with ethyl acetate and hexane. Appropriate fractions were combined and the solvents removed under vacuum to provide the desired compound (48, 0.101 g). MS (ESI) $[M+H^+]^+=188.0$.

Steps 2—Preparation of 4-cyclopentyl-5-iodo-7H-pyrrolo[2,3-d]pyrimidine (49)

4-Cyclopentyl-7H-pyrrolo[2,3-d]pyrimidine (48, 0.099 g, 0.53 mmol) was dissolved in 3.4 mL of dichloromethane under an atmosphere of nitrogen and N-iodosuccinimide (0.131 g, 0.582 mmol) was added. The mixture was stirred overnight, then quenched with aqueous sodium thiosulfate. The aqueous layer was separated and washed with ethyl acetate. The organic layers were combined and washed with water, brine, dried over sodium sulfate and filtered. The filtrate was concentrated under vacuum to provide the desired compound (49, 0.616 g), used in the next step without further purification. MS (ESI) $[M+H^+]^+=313.9$.

Steps 3—Preparation of 7-benzenesulfonyl-4-cyclopentyl-5-iodo-7H-pyrrolo[2,3-d]pyrimidine (50)

To 4-cyclopentyl-5-iodo-7H-pyrrolo[2,3-d]pyrimidine (49, 0.161 g, 0.514 mmol) in tetrahydrofuran, sodium hydride (0.0308 g, 0.771 mmol) was added under an atmosphere of nitrogen. Benzenesulfonyl chloride (40, 0.0984 mL, 0.771 mmol) in 1 mL of tetrahydrofuran was added dropwise at room temperature under nitrogen. The reaction was stirred overnight at room temperature. The aqueous layer was separated and washed with ethyl acetate. The organic layers were combined and washed with 1 M aqueous sodium bicarbonate, water, then brine, dried over sodium sulfate, filtered and the filtrate concentrated under vacuum. The resulting material was purified by silica gel column chromatography, eluting with ethyl acetate and hexane. Appropriate fractions were combined and the solvents removed under vacuum to provide the desired compound (50, 0.121 g). MS (ESI) $[M+H^+]^+=454.3$.

Steps 4—Preparation of {5-[(7-benzenesulfonyl-4-cyclopentyl-7H-pyrrolo[2,3-d]pyrimidin-5-yl)-hydroxy-methyl]-pyridin-2-yl}-(6-trifluoromethyl-pyridin-3-ylmethyl)-carbamic acid tert-butyl ester (52)

To 7-benzenesulfonyl-4-cyclopentyl-5-iodo-7H-pyrrolo[2,3-d]pyrimidine (50, 0.119 g, 0.262 mmol) in 1.8 mL of tetrahydrofuran at −20° C. under nitrogen, isopropylmagnesium chloride (0.144 mL, 2.0 M in tetrahydrofuran, 0.289 mmol) was added and the reaction stirred and allowed to warm to 0° C. over 1 hour. The reaction was cooled to −15° C. and (5-formyl-pyridin-2-yl)-(6-trifluoromethyl-pyridin-3-ylmethyl)-carbamic acid tert-butyl ester (51, 0.120 g, 0.315 mmol) in 0.53 mL of tetrahydrofuran was added. The reaction was poured into 0.1 N aqueous hydrochloric acid and extracted with ethyl acetate. The organic layer was washed with brine, dried over sodium sulfate, filtered and the filtrate concentrated under vacuum. The resulting material was purified by silica gel column chromatography, eluting with ethyl acetate and hexane. Appropriate fractions were combined and the solvents removed under vacuum to provide the desired compound (52, 0.014 g). MS (ESI) $[M+H^+]^+=709.6$.

Steps 5—Preparation of [5-(7-benzenesulfonyl-4-cyclopentyl-7H-pyrrolo[2,3-d]pyrimidin-5-ylmethyl)-pyridin-2-yl]-(6-trifluoromethyl-pyridin-3-ylmethyl)-amine (53)

{5-[(7-Benzenesulfonyl-4-cyclopentyl-7H-pyrrolo[2,3-d]pyrimidin-5-yl)-hydroxy-methyl]-pyridin-2-yl}-(6-trifluoromethyl-pyridin-3-ylmethyl)-carbamic acid tert-butyl ester (52, 0.014 g, 0.020 mmol), trifluoroacetic acid (0.028 mL, 0.37 mmol), triethylsilane (0.071 mL, 0.45 mmol), and 0.21 mL of acetonitrile were combined in a round bottom flask. The reaction mixture was heated at reflux for 3 hours, then poured into water and extracted with ethyl acetate. The organic layer was washed with brine, dried over sodium sulfate, filtered and the filtrate concentrated under vacuum. The resulting material was purified by silica gel column chromatography, eluting with 25% methanol in dichloromethane. Appropriate fractions were combined and the solvents removed under vacuum to provide the desired compound.

Steps 6—Preparation of [5-(4-cyclopentyl-7H-pyrrolo[2,3-d]pyrimidin-5-ylmethyl)-pyridin-2-yl]-(6-trifluoromethyl-pyridin-3-ylmethyl)-amine (P-0104)

To [5-(7-benzenesulfonyl-4-cyclopentyl-7H-pyrrolo[2,3-d]pyrimidin-5-ylmethyl)-pyridin-2-yl]-(6-trifluoromethyl-pyridin-3-ylmethyl)-amine (53, 0.010 g, 0.017 mmol) in 0.597 mL of tetrahydrofuran under nitrogen, tetra-n-butylammonium fluoride (0.0557 mL, 1.00 M in tetrahydrofuran, 0.0557 mmol) was added. The reaction was stirred for 3 hours, then quenched with water. The aqueous layer was separated and extracted with ethyl acetate. The organic layers were combined and washed with brine, dried over magnesium sulfate, filtered and the filtrate concentrated under vacuum. The resulting material was purified by silica gel column chromatography, eluting with 25% methanol in dichloromethane. Appropriate fractions were combined and solvents removed under vacuum to provide the desired compound (P-0104, 0.002 g). MS (ESI) $[M+H^+]^+=453.1$.

Example 8

Synthesis of pyridin-2-ylmethyl-[5-(7H-pyrrolo[2,3-d]pyrimidin-5-ylmethyl)-pyrimidin-2-yl]-amine P-0028

Pyridin-2-ylmethyl-[5-(7H-pyrrolo[2,3-d]pyrimidin-5-ylmethyl)-pyrimidin-2-yl]-amine P-0028 was prepared in five steps from 5-Iodo-7-triisopropylsilanyl-7H-pyrrolo[2,3-d]pyrimidine 38 as shown in Scheme 11.

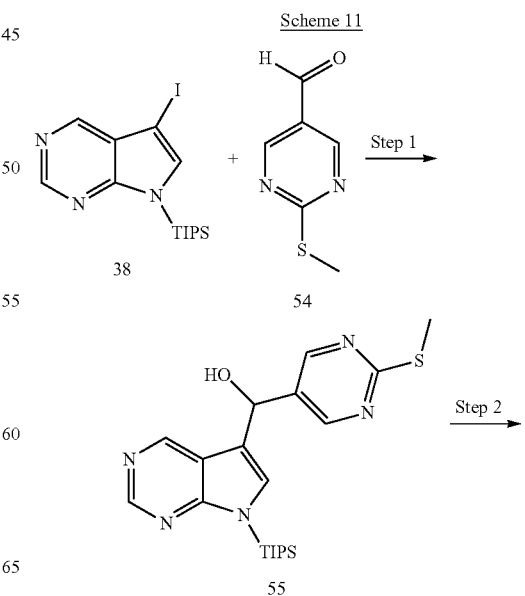

Scheme 11

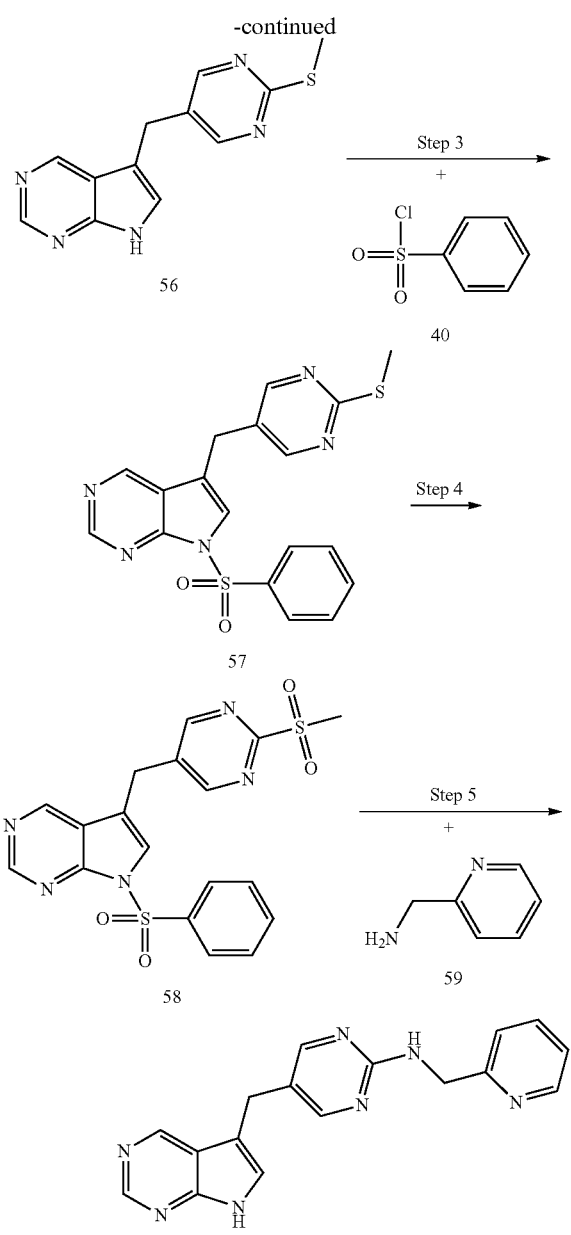

Step 1—Preparation of (2-methylsulfanyl-pyrimidin-5-yl)-(7-triisopropylsilanyl-7H-pyrrolo[2,3-d]pyrimidin-5-yl)-methanol (55)

To a solution of 5-Iodo-7-triisopropylsilanyl-7H-pyrrolo[2,3-d]pyrimidine (38, 4.00 g, 9.97 mmol) in 5.00 mL of tetrahydrofuran at −20° C. under nitrogen, isopropylmagnesium chloride (5.80 mL, 2.0 M in tetrahydrofuran, 11.6 mmol) was added slowly. The reaction was allowed to warm to 0° C. over 70 minutes, then cooled to −20° C., followed by addition of 2-methylsulfanyl-pyrimidine-5-carbaldehyde (54, 1.12 g, 7.26 mmol) in 15.0 mL of tetrahydrofuran. The reaction was allowed to warm to room temperature over 1 hour, then poured into aqueous ammonium chloride and extracted with ethyl acetate. The organic layer was dried over anhydrous sodium sulfate, filtered and the filtrate was concentrated under vacuum. The resulting material was purified by silica gel column chromatography eluting with 20-100% ethyl acetate in hexane. Appropriate fractions were combined and the solvents removed under vacuum to provide the desired compound (55, 2.75 g).

Steps 2—Preparation of 5-(2-methylsulfanyl-pyrimidin-5-ylmethyl)-7H-pyrrolo[2,3-d]pyrimidine (56)

To a solution of (2-methylsulfanyl-pyrimidin-5-yl)-(7-triisopropylsilanyl-7H-pyrrolo[2,3-d]pyrimidin-5-yl)-methanol (55, 2.75 g, 6.40 mmol) in 50.0 mL of 1,2-dichloroethane, triethylsilane (8.00 mL, 50.1 mmol) and trifluoroacetic acid (4.00 mL, 51.9 mmol) were added. The reaction was heated at 80° C. overnight, then concentrated under vacuum, combined with water and extracted with ethyl acetate. The organic layer was dried over sodium sulfate, filtered, and the filtrate was concentrated under vacuum. The resulting material was purified by silica gel column chromatography eluting with 2-15% methanol in dichloromethane. Appropriate fractions were combined and the solvents removed under vacuum to provide the desired compound (56, 1.20 g). MS (ESI) [M+H$^+$]$^+$=258.2.

Steps 3—Preparation of 7-benzenesulfonyl-5-(2-methylsulfanyl-pyrimidin-5-ylmethyl)-7H-pyrrolo[2,3-d]pyrimidine (57)

To 5-(2-methylsulfanyl-pyrimidin-5-ylmethyl)-7H-pyrrolo[2,3-d]pyrimidine (56, 1.20 g, 4.66 mmol) in 55.0 mL of N,N-dimethylformamide, sodium hydride (0.280 g, 7.00 mmol) was added. The reaction mixture was stirred at room temperature for 20 minutes, followed by addition of benzenesulfonyl chloride (40, 0.714 mL, 5.60 mmol). The reaction was stirred at room temperature for 3 hours, then poured into water and extracted with ethyl acetate. The organic layer was dried over sodium sulfate, filtered, and the filtrate was concentrated under vacuum. The resulting material was purified by silica gel column chromatography eluting with 20% ethyl acetate in hexane. Appropriate fractions were combined and the solvents removed under vacuum to provide the desired compound (57, 1.00 g).

Steps 4—Preparation of 7-benzenesulfonyl-5-(2-methanesulfonyl-pyrimidin-5-ylmethyl)-7H-pyrrolo[2,3-d]pyrimidine (58)

To 7-benzenesulfonyl-5-(2-methylsulfanyl-pyrimidin-5-ylmethyl)-7H-pyrrolo[2,3-d]pyrimidine (57, 1.00 g, 2.52 mmol) in 50.0 mL of dichloromethane, meta-chloroperoxybenzoic acid (max. 77%, 1.16 g, 5.18 mmol) was added at 0° C. The reaction was stirred at 0° C. for 60 minutes, then poured into water and extracted with ethyl acetate. The organic layer was dried over sodium sulfate, filtered, and the filtrate was concentrated under vacuum. The resulting material was purified by silica gel column chromatography eluting with 20% ethyl acetate in hexane. Appropriate fractions were combined and the solvents removed under vacuum to provide the desired compound (58, 0.90 g).

Steps 5—Preparation of pyridin-2-ylmethyl-[5-(7H-pyrrolo[2,3-d]pyrimidin-5-ylmethyl)-pyrimidin-2-yl]-amine (P-0028)

In a microwave vial, 7-benzenesulfonyl-5-(2-methanesulfonyl-pyrimidin-5-ylmethyl)-7H-pyrrolo[2,3-d]pyrimidine (58, 12 mg, 0.028 mmol) was mixed with 600 µL of N-methylpyrrolidone and C-pyridin-2-yl-methylamine (59, 19.5 mg, 0.18 mmol). The reaction was irradiated at 160° C. for 40 minutes in microwave, then potassium hydroxide (500 µL, 4.00 M in water) was added and the reaction irradiated at 90° C. for 10 minutes in microwave. The reaction was neutralized with the addition of 120 µL of acetic acid, solvents were removed under vacuum, and the resulting material was dissolved in 400 µL at of dimethylsulfoxide for purification by HPLC. Samples were purified on Phenomenex C18 column (50 mm×10 mm ID) with mobile phase A of 0.1% trifluoroacetic acid in water, mobile phase B of 0.1% trifluoroacetic acid in acetonitrile, 20-100% B over 16 minutes at a flow rate of 6 mL/min. Appropriate fractions were collected and solvents removed under vacuum to provide the desired compound. MS (ESI) [M+H$^+$]$^+$=317.9.

Additional compounds were prepared in following the protocol of Scheme 11, step 5, substituting C-pyridin-2-yl-methylamine 59 with a suitable amine. The following compounds were made using this procedure:

(6-Chloro-pyridin-3-ylmethyl)-[5-(7H-pyrrolo[2,3-d]pyrimidin-5-ylmethyl)-pyrimidin-2-yl]-amine (P-0029),

[5-(7H-Pyrrolo[2,3-d]pyrimidin-5-ylmethyl)-pyrimidin-2-yl]-(6-trifluoromethyl-pyridin-3-ylmethyl)-amine (P-0030), (6-Morpholin-4-yl-pyridin-2-ylmethyl)-[5-(7H-pyrrolo[2,3-d]pyrimidin-5-ylmethyl)-pyrimidin-2-yl]-amine (P-0031), (6-Pyrrolidin-1-yl-pyridin-2-ylmethyl)-[5-(7H-pyrrolo[2,3-d]pyrimidin-5-ylmethyl)-pyrimidin-2-yl]-amine (P-0032), (5-Ethyl-pyridin-2-ylmethyl)-[5-(7H-pyrrolo[2,3-d]pyrimidin-5-ylmethyl)-pyrimidin-2-yl]-amine (P-0033), (3-Methyl-pyridin-4-ylmethyl)-[5-(7H-pyrrolo[2,3-d]pyrimidin-5-ylmethyl)-pyrimidin-2-yl]-amine (P-0034), (2-Methyl-pyridin-4-ylmethyl)-[5-(7H-pyrrolo[2,3-d]pyrimidin-5-ylmethyl)-pyrimidin-2-yl]-amine (P-0035), (2-Morpholin-4-yl-pyridin-4-ylmethyl)-[5-(7H-pyrrolo[2,3-d]pyrimidin-5-ylmethyl)-pyrimidin-2-yl]-amine (P-0036), (2-Methoxy-pyridin-3-ylmethyl)-[5-(7H-pyrrolo[2,3-d]pyrimidin-5-ylmethyl)-pyrimidin-2-yl]-amine (P-0084), (2-Ethoxy-pyridin-3-ylmethyl)-[5-(7H-pyrrolo[2,3-d]pyrimidin-5-ylmethyl)-pyrimidin-2-yl]-amine (P-0085), (2-Cyclopentyloxy-pyridin-3-ylmethyl)-[5-(7H-pyrrolo[2,3-d]pyrimidin-5-ylmethyl)-pyrimidin-2-yl]-amine (P-0086), and (2-Cyclopentyloxy-pyridin-4-ylmethyl)-[5-(7H-pyrrolo[2,3-d]pyrimidin-5-ylmethyl)-pyrimidin-2-yl]-amine (P-0087).

The following table indicates the amine compound (column 2) used in step 5 to afford the desired compound (column 3). The compound number is provided in column 1, and the observed mass is in column 4

| Compound number | Amine structure | Compound structure | MS (ESI) [M + H$^+$]$^+$ |
|---|---|---|---|
| P-0029 | | 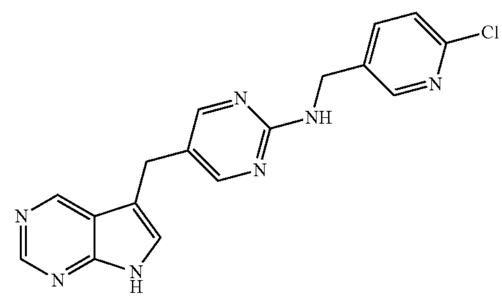 [SMILES: Clc1ccc(CNc2ncc(Cc3c[nH]c4ncncc34)cn2)cn1] | 352.3 |
| P-0030 | | 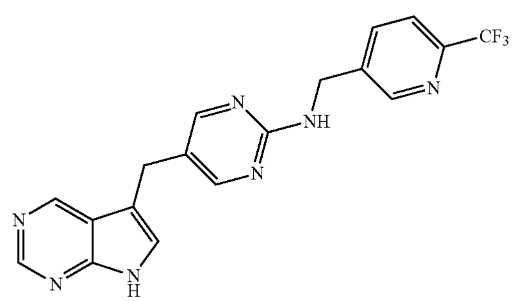 [SMILES: FC(F)(F)c1ccc(CNc2ncc(Cc3c[nH]c4ncncc34)cn2)cn1] | 386.3 |
| P-0031 | | 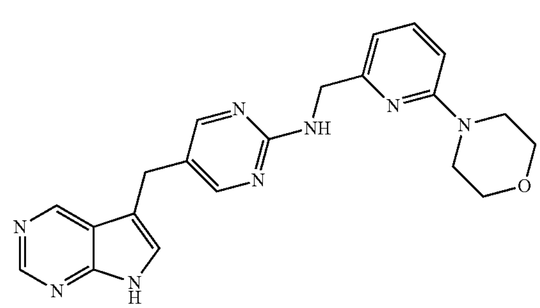 [SMILES: c1cc(CNc2ncc(Cc3c[nH]c4ncncc34)cn2)nc(N2CCOCC2)c1] | 403.5 |

-continued

| Compound number | Amine structure | Compound structure | MS (ESI) [M + H⁺]⁺ |
|---|---|---|---|
| P-0032 | | 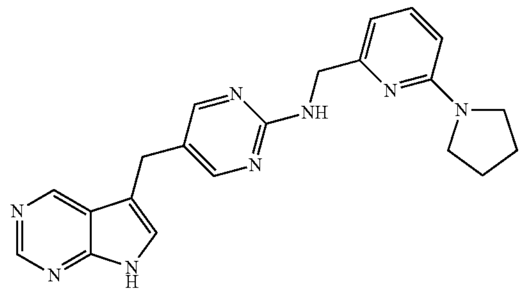 [SMILES: c1cc(CNc2ncc(Cc3c[nH]c4ncncc34)cn2)nc(N2CCCC2)c1] | 387.1 |
| P-0033 | | 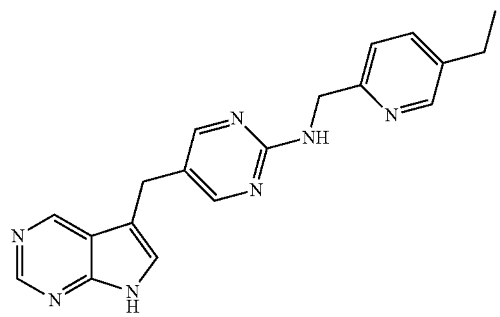 [SMILES: CCc1ccc(CNc2ncc(Cc3c[nH]c4ncncc34)cn2)nc1] | 346.3 |
| P-0034 | | 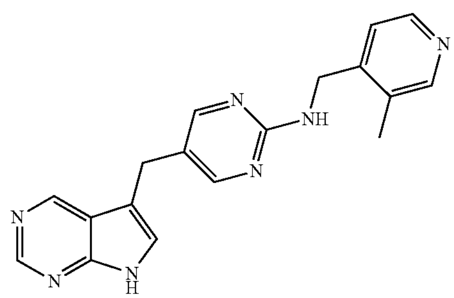 [SMILES: Cc1cnccc1CNc1ncc(Cc2c[nH]c3ncncc23)cn1] | 332.3 |
| P-0035 | | 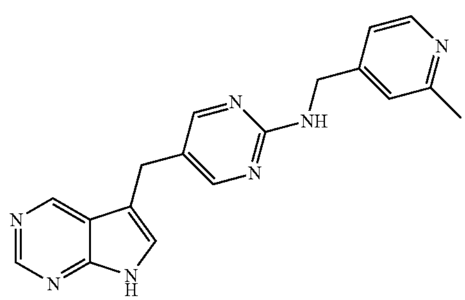 [SMILES: Cc1cc(CNc2ncc(Cc3c[nH]c4ncncc34)cn2)ccn1] | 332.3 |
| P-0036 | | 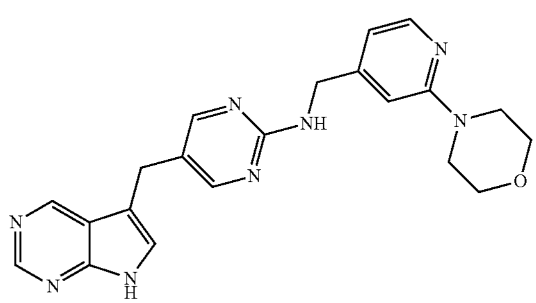 [SMILES: c1cc(CNc2ncc(Cc3c[nH]c4ncncc34)cn2)cc(N2CCOCC2)n1] | 403.1 |

| Compound number | Amine structure | Compound structure | MS (ESI) [M + H+]+ |
|---|---|---|---|
| P-0084 | 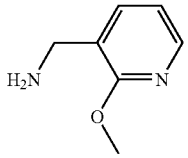 | 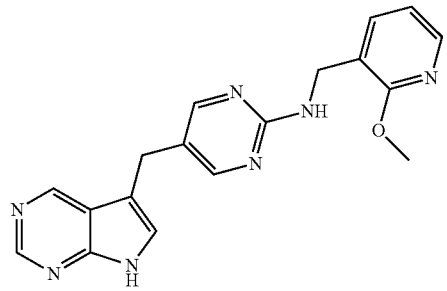 [SMILES: COc1ncccc1CNc1ncc(Cc2c[nH]c3ncncc23)cn1] | 348.3 |
| P-0085 | 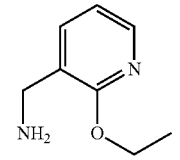 | 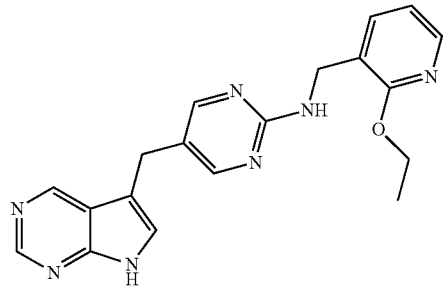 [SMILES: CCOc1ncccc1CNc1ncc(Cc2c[nH]c3ncncc23)cn1] | 362.3 |
| P-0086 | 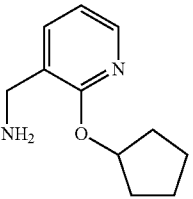 [SMILES: NCc1cccnc1OC1CCCC1] | 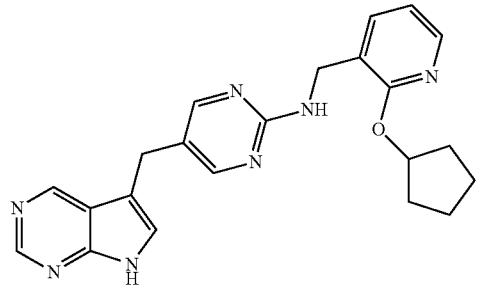 [SMILES: c1cnc(OC2CCCC2)c(CNc2ncc(Cc3c[nH]c4ncncc34)cn2)c1] | 402.3 |
| P-0087 | 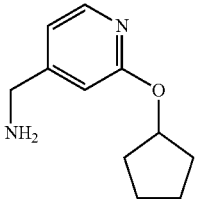 [SMILES: NCc1ccnc(OC2CCCC2)c1] | 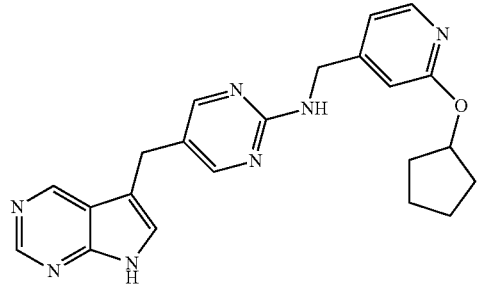 [SMILES: c1cc(CNc2ncc(Cc3c[nH]c4ncncc34)cn2)cc(OC2CCCC2)n1] | 402.3 |

Example 9
Synthesis of [6-fluoro-5-(7H-pyrrolo[2,3-d]pyrimidin-5-ylmethyl)-pyridin-2-yl]-(3,4,5-trimethoxy-benzyl)-amine P-0037
[6-Fluoro-5-(7H-pyrrolo[2,3-d]pyrimidin-5-ylmethyl)-pyridin-2-yl]-(3,4,5-trimethoxy-benzyl)-amine P-0037 was prepared in ten steps from 2,6-difluoro-pyridine 20 as shown in Scheme 12.
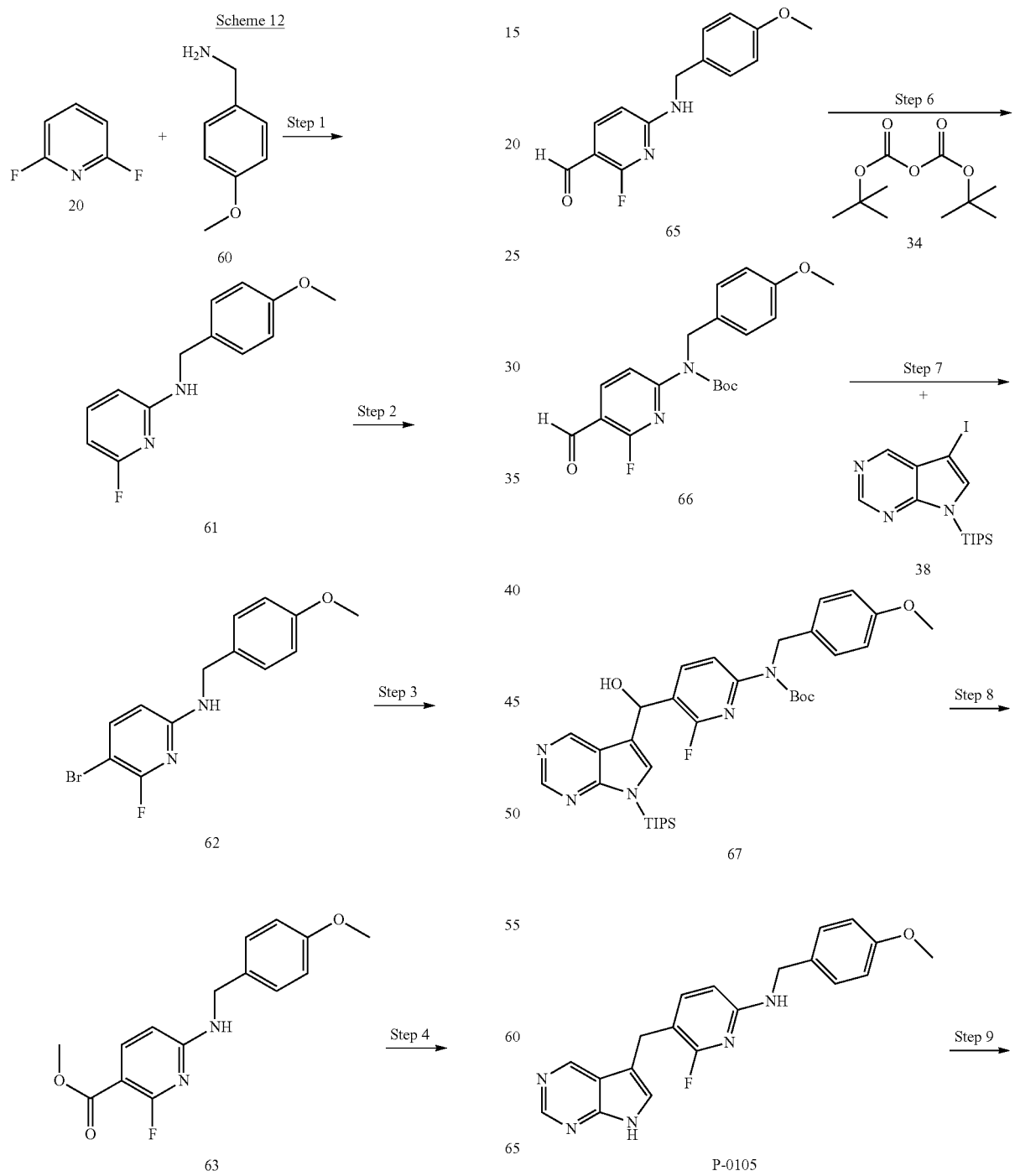

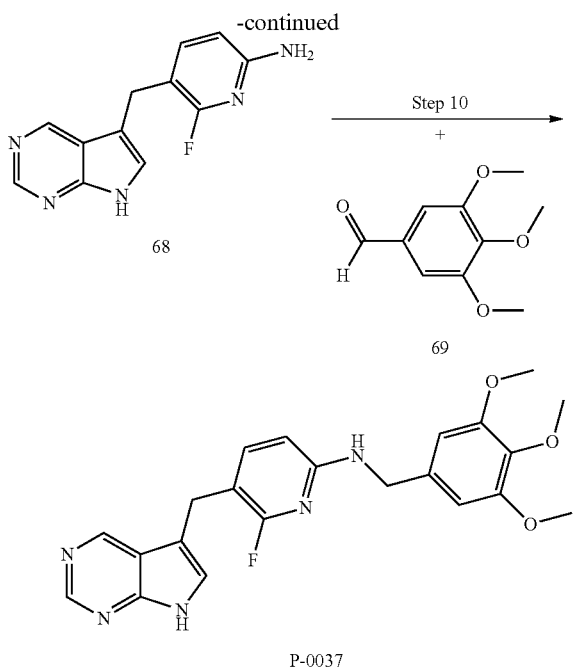

Step 1—Preparation of (6-fluoro-pyridin-2-yl)-(4-methoxy-benzyl)-amine (61)

To 2,6-difluoro-pyridine (20, 100 g, 869 mmol) in 500 mL of N-methylpyrrolidone, 4-methoxy-benzylamine (60, 136 mL, 1.043 mol) and N,N-diisopropylethylamine (304 mL, 1.738 mol) were added. The reaction was stirred at 90° C. overnight, then poured into 8 L of water. The precipitate was collected by filtration and washed with water, then taken up in ethyl acetate and washed with water. The organic layer was dried over sodium sulfate, filtered and the filtrate concentrated under vacuum. The resulting material was triturated with heptane and collected by filtration to provide the desired compound (61, 151 g, 650 mmol, 74.8% yield).

Step 2—Preparation of (5-bromo-6-fluoro-pyridin-2-yl)-(4-methoxy-benzyl)-amine (62)

To (6-fluoro-pyridin-2-yl)-(4-methoxy-benzyl)-amine (61, 151 g, 650 mmol) in 4 L of acetonitrile under an atmosphere of nitrogen, N-bromosuccinimide (116 g, 650 mmol) was added in portions. After reacting for 2 hours, the solvent was removed under vacuum and the residue taken up in ethyl acetate, then poured into aqueous sodium thiosulfate. The organic layer was washed with warm water, dried over sodium sulfate, filtered and the filtrate concentrated under vacuum. The resulting material was crystallized from heptane to provide the desired compound (62, 172 g, 553 mmol, 85% yield).

Step 3—Preparation of 2-fluoro-6-(4-methoxy-benzylamino)-nicotinic acid methyl ester (63)

To (5-bromo-6-fluoro-pyridin-2-yl)-(4-methoxy-benzyl)-amine (62, 85 g, 273 mmol) in 1.5 L methanol in a 2 L Parr flask, triethylamine (77 mL, 546 mmol) and [1,1'-bis(diphenylphosphino)ferrocene]dichloropalladium(II) (5.80 g, 7.10 mmol) were added. The reaction was heated at 100° C. under 100 psi of carbon monoxide overnight. The reaction was cooled and filtered through celite and the filtrate was concentrated under vacuum. The resulting material was dissolved in dichloromethane and passed through a plug of silica gel, eluting with ethyl acetate. The solvent was removed under vacuum to provide the desired compound as a peach colored solid (63, 70 g, 241 mmol, 88% yield).

Step 4—Preparation of [2-fluoro-6-(4-methoxy-benzylamino)-pyridin-3-yl]-methanol (64)

To 2-fluoro-6-(4-methoxy-benzylamino)-nicotinic acid methyl ester (63, 70 g, 241 mmol) in 350 mL of tetrahydrofuran, lithium aluminum hydride (362 mL, 1 M in tetrahydrofuran, 362 mmol) was added dropwise while cooling. The reaction was stirred at room temperature for 2 hours, then quenched with dropwise addition of 14 mL of water, 14 mL of 15% aqueous sodium hydroxide, and 42 mL of water, sequentially. Methyl tert-butyl ether (500 mL) was added and the solids removed by filtration. The filtrate was concentrated under vacuum and the resulting solid was dissolved in dichloromethane, passed through a plug of silica gel and eluted with 50-100% ethyl acetate in heptane. The solvent was removed under vacuum to provide the desired compound as an off-white solid (64, 63 g, 240 mmol, 100% yield).

Step 5—Preparation of 2-fluoro-6-(4-methoxy-benzylamino)-pyridine-3-carbaldehyde (65)

To [2-fluoro-6-(4-methoxy-benzylamino)-pyridin-3-yl]-methanol (64, 63 g, 240 mmol) in 1.25 L of ethyl acetate, manganese(IV) oxide (210 g, 2.416 mol) was added. The reaction was stirred overnight at room temperature, then filtered through celite and the celite rinsed with ethyl acetate. The combined filtrates were concentrated under vacuum and the resulting solid was triturated with heptane and collected by filtration to provide the desired compound as a white solid (65, 62 g, 238 mmol, 99% yield).

Step 6—Preparation of (6-fluoro-5-formyl-pyridin-2-yl)-(4-methoxy-benzyl)-carbamic acid tert-butyl ester (66)

2-Fluoro-6-(4-methoxy-benzylamino)-pyridine-3-carbaldehyde (65, 62 g, 238 mmol), 600 mL of tert-butyl alcohol, di-tert-butyldicarbonate (34, 83 mL, 357 mmol) and dimethylaminopyridine (2.91 g, 23.82 mmol) were combined in a round bottom flask. The reaction was stirred at 30° C. overnight and then concentrated under vacuum. The resulting material was purified by silica gel column chromatography, eluting with 0-20% ethyl acetate in hexane. Appropriate fractions were combined and the solvents removed under vacuum to provide the desired compound (66, 54 g, 150 mmol, 62.9% yield).

Step 7—Preparation of {6-fluoro-5-[hydroxy-(7-triisopropylsilanyl-7H-pyrrolo[2,3-d]pyrimidin-5-yl)-methyl]-pyridin-2-yl}-(4-methoxy-benzyl)-carbamic acid tert-butyl ester (67)

To 5-iodo-7-triisopropylsilanyl-7H-pyrrolo[2,3-d]pyrimidine (38, 30 g, 74.7 mmol) in 300 mL of tetrahydrofuran under an atmosphere of nitrogen at −20° C., isopropylmagnesium chloride (43.6 mL, 2 M in tetrahydrofuran, 87 mmol) was added and the reaction allowed to warm to 0° C. over 30 minutes. The reaction was cooled to −40° C. and (6-fluoro-5-formyl-pyridin-2-yl)-(4-methoxy-benzyl)-carbamic acid tert-butyl ester (66, 17.96 g, 49.8 mmol) in tetrahydrofuran was added. The reaction was allowed to warm to 0° C. over an hour, then quenched with brine and extracted with ethyl acetate. The organic layer was dried over sodium sulfate, filtered and the filtrate concentrated under vacuum. The resulting material was purified by silica gel column chromatography, eluting with 0-40% ethyl acetate in hexane. Appropriate fractions were combined and the solvents removed under vacuum to provide the desired compound (67, 27 g, 42.5 mmol, 85% yield).

Step 8—Preparation of [6-Fluoro-5-(7H-pyrrolo[2,3-d]pyrimidin-5-ylmethyl)-pyridin-2-yl]-(4-methoxy-benzyl)-amine (P-0105)

To {6-fluoro-5-[hydroxy-(7-triisopropylsilanyl-7H-pyrrolo[2,3-d]pyrimidin-5-yl)-methyl]-pyridin-2-yl}-(4-methoxy-benzyl)-carbamic acid tert-butyl ester (67, 27 g, 42.5 mmol) in 700 mL of acetonitrile, triethylsilane (67.8 mL, 425 mmol) and trifluoroacetic acid (32.7 mL, 425 mmol) were added. The reaction was stirred at 50° C. overnight, solvents removed under vacuum, and the residue taken up in ethyl acetate and poured into aqueous potassium carbonate. The organic layer was separated, concentrated under vacuum and purified by silica gel column chromatography, eluting with 0-10% methanol in dichloromethane. Appropriate fractions were combined and the solvents removed under vacuum to provide the desired compound (P-0105, 4.5 g, 12.38 mmol, 29.2% yield).

Step 9—Preparation of 6-fluoro-5-(7H-pyrrolo[2,3-d]pyrimidin-5-ylmethyl)-pyridin-2-ylamine (68)

To [6-fluoro-5-(7H-pyrrolo[2,3-d]pyrimidin-5-ylmethyl)-pyridin-2-yl]-(4-methoxy-benzyl)-amine (P-0105, 4.5 g, 12.38 mmol) in 100 mL of dichloromethane, trifluoroacetic acid (95 mL, 1.238 mol) was added. The reaction was stirred at reflux for several hours, then concentrated under vacuum. The resulting material was taken up in ethyl acetate and poured into aqueous potassium carbonate. The resulting solid was filtered, washed with water, azeotroped from toluene and triturated with dichloromethane. The solid was isolated by filtration to provide the desired compound as a white solid (68, 2.8 g, 11.51 mmol, 93% yield).

Steps 10—Preparation of [6-fluoro-5-(7H-pyrrolo[2,3-d]pyrimidin-5-ylmethyl)-pyridin-2-yl]-(3,4,5-trimethoxy-benzyl)-amine (P-0037)

In a 2 mL microwave vial, 6-fluoro-5-(7H-pyrrolo[2,3-d]pyrimidin-5-ylmethyl)-pyridin-2-ylamine (68, 9.72 mg, 0.04 mmol) and 3,4,5-trimethoxy-benzaldehyde (69, 15.7 mg, 0.08 mmol) were dissolved in 600 µL of 95:5 ethanol:acetic acid, and silica supported cyanoborohydride (50 mg, 1 mmol/g, 0.05 mmol) was added. The reaction was irradiated for 10 minutes at 160° C. in a microwave. The vial was centrifuged to condense the silica and the supernatant was removed by pipette into another vial. The residual silica was rinsed with 500 µL of ethanol, centrifuged and the supernatant added to the first supernatant. The solvents were removed under vacuum and the resulting material dissolved in dimethyl sulfoxide for purification by HPLC. Samples were purified on Phenomenex C18 column (50 mm×10 mm ID) with mobile phase A of 0.1% trifluoroacetic acid in water, mobile phase B of 0.1% trifluoroacetic acid in acetonitrile, 20-100% B over 16 minutes at a flow rate of 6 mL/min. Appropriate fractions were collected and solvents removed under vacuum to provide the desired compound. MS (ESI) [M+H$^+$]$^+$=424.3.

Additional compounds were prepared in following the protocol of Scheme 12, step 10, substituting 3,4,5-trimethoxy-benzaldehyde 69 with a suitable aldehyde. The following compounds were made using this procedure:

(2,5-Dimethoxy-benzyl)-[6-fluoro-5-(7H-pyrrolo[2,3-d]pyrimidin-5-ylmethyl)-pyridin-2-yl]-amine (P-0038),

[6-Fluoro-5-(7H-pyrrolo[2,3-d]pyrimidin-5-ylmethyl)-pyridin-2-yl]-(6-morpholin-4-yl-pyridin-3-ylmethyl)-amine (P-0039),

[6-Fluoro-5-(7H-pyrrolo[2,3-d]pyrimidin-5-ylmethyl)-pyridin-2-yl]-(5-methoxy-pyridin-3-ylmethyl)-amine (P-0040), (5-Fluoro-pyridin-2-ylmethyl)-[6-fluoro-5-(7H-pyrrolo[2,3-d]pyrimidin-5-ylmethyl)-pyridin-2-yl]-amine (P-0041), (5-{[6-Fluoro-5-(7H-pyrrolo[2,3-d]pyrimidin-5-ylmethyl)-pyridin-2-ylamino]-methyl}-pyrimidin-2-yl)-methyl-amine (P-0042), (2,6-Dimethoxy-pyridin-3-ylmethyl)-[6-fluoro-5-(7H-pyrrolo[2,3-d]pyrimidin-5-ylmethyl)-pyridin-2-yl]-amine (P-0043), (5-Chloro-pyridin-3-ylmethyl)-[6-fluoro-5-(7H-pyrrolo[2,3-d]pyrimidin-5-ylmethyl)-pyridin-2-yl]-amine (P-0044), (6-Chloro-pyridin-3-ylmethyl)-[6-fluoro-5-(7H-pyrrolo[2,3-d]pyrimidin-5-ylmethyl)-pyridin-2-yl]-amine (P-0045), (3-Bromo-pyridin-4-ylmethyl)-[6-fluoro-5-(7H-pyrrolo[2,3-d]pyrimidin-5-ylmethyl)-pyridin-2-yl]-amine (P-0046), (3-Chloro-pyridin-4-ylmethyl)-[6-fluoro-5-(7H-pyrrolo[2,3-d]pyrimidin-5-ylmethyl)-pyridin-2-yl]-amine (P-0047),

[6-Fluoro-5-(7H-pyrrolo[2,3-d]pyrimidin-5-ylmethyl)-pyridin-2-yl]-(2-methyl-pyrimidin-5-ylmethyl)-amine (P-0048), (3-Fluoro-pyridin-4-ylmethyl)-[6-fluoro-5-(7H-pyrrolo[2,3-d]pyrimidin-5-ylmethyl)-pyridin-2-yl]-amine (P-0049), (5-Fluoro-pyridin-3-ylmethyl)-[6-fluoro-5-(7H-pyrrolo[2,3-d]pyrimidin-5-ylmethyl)-pyridin-2-yl]-amine (P-0050),

[6-Fluoro-5-(7H-pyrrolo[2,3-d]pyrimidin-5-ylmethyl)-pyridin-2-yl]-[2-(2,2,2-trifluoro-ethoxy)-pyridin-3-ylmethyl]-amine (P-0051), (5-Fluoro-2-methane sulfonyl-benzyl)-[6-fluoro-5-(7H-pyrrolo[2,3-d]pyrimidin-5-ylmethyl)-pyridin-2-yl]-amine (P-0052), (5-Bromo-pyridin-2-ylmethyl)-[6-fluoro-5-(7H-pyrrolo[2,3-d]pyrimidin-5-ylmethyl)-pyridin-2-yl]-amine (P-0053), (3,5-Bis-trifluoromethyl-benzyl)-[6-fluoro-5-(7H-pyrrolo[2,3-d]pyrimidin-5-ylmethyl)-pyridin-2-yl]-amine (P-0054),

[6-Fluoro-5-(7H-pyrrolo[2,3-d]pyrimidin-5-ylmethyl)-pyridin-2-yl]-(3-methyl-pyridin-4-ylmethyl)-amine (P-0055),

[6-Fluoro-5-(7H-pyrrolo[2,3-d]pyrimidin-5-ylmethyl)-pyridin-2-yl]-(4-methoxy-pyridin-3-ylmethyl)-amine (P-0056),

[6-Fluoro-5-(7H-pyrrolo[2,3-d]pyrimidin-5-ylmethyl)-pyridin-2-yl]-(2-isopropoxy-pyridin-3-ylmethyl)-amine (P-0057),

[6-Fluoro-5-(7H-pyrrolo[2,3-d]pyrimidin-5-ylmethyl)-pyridin-2-yl]-(4-methyl-pyridin-2-ylmethyl)-amine (P-0058),

[6-Fluoro-5-(7H-pyrrolo[2,3-d]pyrimidin-5-ylmethyl)-pyridin-2-yl]-(2-pyrrolidin-1-yl-pyridin-4-ylmethyl)-amine (P-0059), (4-Chloro-2-methanesulfonyl-benzyl)-[6-fluoro-5-(7H-pyrrolo[2,3-d]pyrimidin-5-ylmethyl)-pyridin-2-yl]-amine (P-0060), (2-Dimethylamino-benzyl)-[6-fluoro-5-(7H-pyrrolo[2,3-d]pyrimidin-5-ylmethyl)-pyridin-2-yl]-amine (P-0061),

[6-Fluoro-5-(7H-pyrrolo[2,3-d]pyrimidin-5-ylmethyl)-pyridin-2-yl]-(5-methyl-pyridin-2-ylmethyl)-amine (P-0062),
(3,5-Dimethyl-benzyl)-[6-fluoro-5-(7H-pyrrolo[2,3-d]pyrimidin-5-ylmethyl)-pyridin-2-yl]-amine (P-0063),
(3-Fluoro-5-methyl-benzyl)-[6-fluoro-5-(7H-pyrrolo[2,3-d]pyrimidin-5-ylmethyl)-pyridin-2-yl]-amine (P-0064),
(3,5-Dimethoxy-benzyl)-[6-fluoro-5-(7H-pyrrolo[2,3-d]pyrimidin-5-ylmethyl)-pyridin-2-yl]-amine (P-0065),
[6-Fluoro-5-(7H-pyrrolo[2,3-d]pyrimidin-5-ylmethyl)-pyridin-2-yl]-(2-methylamino-pyridin-3-ylmethyl)-amine (P-0066),
(3-Chloro-5-fluoro-benzyl)-[6-fluoro-5-(7H-pyrrolo[2,3-d]pyrimidin-5-ylmethyl)-pyridin-2-yl]-amine (P-0067),
(2-Fluoro-pyridin-3-ylmethyl)-[6-fluoro-5-(7H-pyrrolo[2,3-d]pyrimidin-5-ylmethyl)-pyridin-2-yl]-amine (P-0068),
(2-Ethoxy-pyridin-3-ylmethyl)-[6-fluoro-5-(7H-pyrrolo[2,3-d]pyrimidin-5-ylmethyl)-pyridin-2-yl]-amine (P-0069),
(2-Cyclopentyloxy-pyridin-3-ylmethyl)-[6-fluoro-5-(7H-pyrrolo[2,3-d]pyrimidin-5-ylmethyl)-pyridin-2-yl]-amine (P-0070),
[6-Fluoro-5-(7H-pyrrolo[2,3-d]pyrimidin-5-ylmethyl)-pyridin-2-yl]-(2-trifluoromethyl-pyridin-3-ylmethyl)-amine (P-0071),
(2-Chloro-5-fluoro-pyridin-4-ylmethyl)-[6-fluoro-5-(7H-pyrrolo[2,3-d]pyrimidin-5-ylmethyl)-pyridin-2-yl]-amine (P-0072),
4-{[6-Fluoro-5-(7H-pyrrolo[2,3-d]pyrimidin-5-ylmethyl)-pyridin-2-ylamino]-methyl}-pyridine-2-carbonitrile (P-0073),
(2-Fluoro-pyridin-4-ylmethyl)-[6-fluoro-5-(7H-pyrrolo[2,3-d]pyrimidin-5-ylmethyl)-pyridin-2-yl]-amine (P-0074),
[6-Fluoro-5-(7H-pyrrolo[2,3-d]pyrimidin-5-ylmethyl)-pyridin-2-yl]-(2-trifluoromethyl-pyridin-4-ylmethyl)-amine (P-0075),
(2-Chloro-pyridin-4-ylmethyl)-[6-fluoro-5-(7H-pyrrolo[2,3-d]pyrimidin-5-ylmethyl)-pyridin-2-yl]-amine (P-0076),
(5-Chloro-2-fluoro-pyridin-3-ylmethyl)-[6-fluoro-5-(7H-pyrrolo[2,3-d]pyrimidin-5-ylmethyl)-pyridin-2-yl]-amine (P-0077),
(2-Ethyl-pyrimidin-5-ylmethyl)-[6-fluoro-5-(7H-pyrrolo[2,3-d]pyrimidin-5-ylmethyl)-pyridin-2-yl]-amine (P-0078),
[6-Fluoro-5-(7H-pyrrolo[2,3-d]pyrimidin-5-ylmethyl)-pyridin-2-yl]-(2-isopropyl-pyrimidin-5-ylmethyl)-amine (P-0079),
[6-Fluoro-5-(7H-pyrrolo[2,3-d]pyrimidin-5-ylmethyl)-pyridin-2-yl]-[2-(2-methoxy-ethyl)-pyrimidin-5-ylmethyl]-amine (P-0080),
(2-Butyl-pyrimidin-5-ylmethyl)-[6-fluoro-5-(7H-pyrrolo[2,3-d]pyrimidin-5-ylmethyl)-pyridin-2-yl]-amine (P-0081),
[6-Fluoro-5-(7H-pyrrolo[2,3-d]pyrimidin-5-ylmethyl)-pyridin-2-yl]-(3-methoxy-5-trifluoromethyl-benzyl)-amine (P-0082),
(3-Fluoro-5-methoxy-benzyl)-[6-fluoro-5-(7H-pyrrolo[2,3-d]pyrimidin-5-ylmethyl)-pyridin-2-yl]-amine (P-0083),
(2-Cyclohexyloxy-pyridin-3-ylmethyl)-[6-fluoro-5-(7H-pyrrolo[2,3-d]pyrimidin-5-ylmethyl)-pyridin-2-yl]-amine (P-0088), and
[6-Fluoro-5-(7H-pyrrolo[2,3-d]pyrimidin-5-ylmethyl)-pyridin-2-yl]-(5-pyrrolidin-1-yl-pyridin-2-ylmethyl)-amine (P-0089).

The following table indicates the aldehyde compound (column 2) used in step 10 to afford the desired compound (column 3). The compound number is provided in column 1, and the observed mass is in column 4

| Compound number | Aldehyde structure | Compound structure | MS (ESI) [M + H$^+$]$^+$ |
|---|---|---|---|
| P-0038 | | 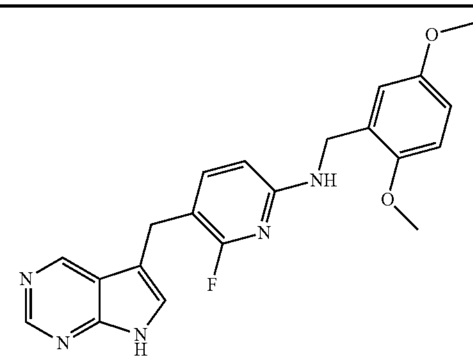 | 394.3 |
| P-0039 | | 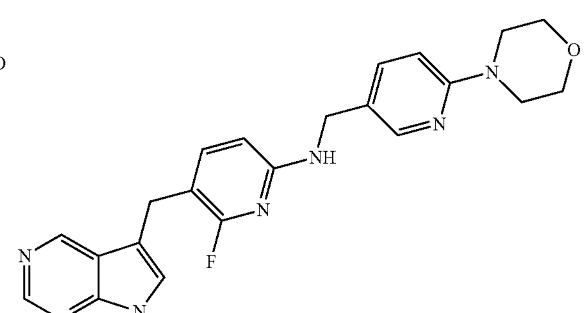 | 420.3 |

| Compound number | Aldehyde structure | Compound structure | MS (ESI) [M + H+]+ |
|---|---|---|---|
| P-0040 | | 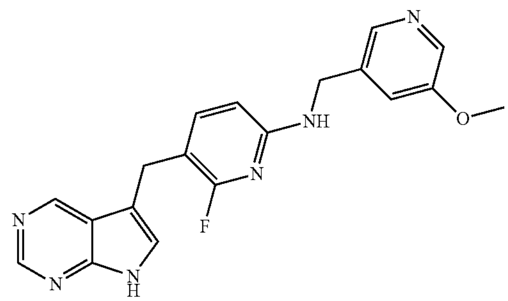 [SMILES: COc1cncc(CNc2ccc(Cc3c[nH]c4ncncc34)c(F)n2)c1] | 365.1 |
| P-0041 | | 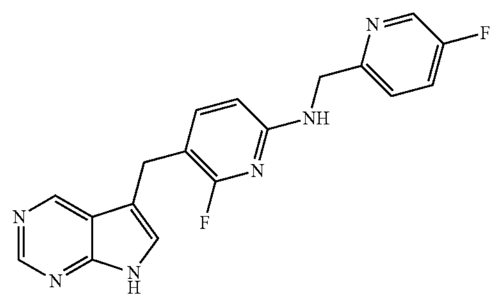 [SMILES: Fc1ccc(CNc2ccc(Cc3c[nH]c4ncncc34)c(F)n2)nc1] | 353.1 |
| P-0042 | | 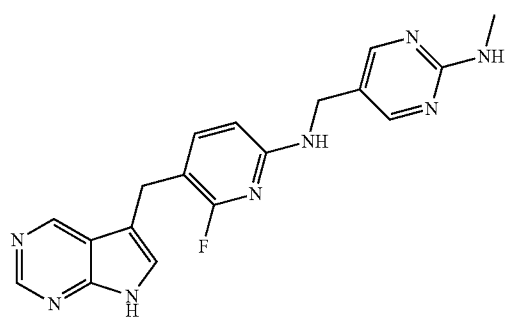 [SMILES: CNc1ncc(CNc2ccc(Cc3c[nH]c4ncncc34)c(F)n2)cn1] | 365.1 |
| P-0043 | | 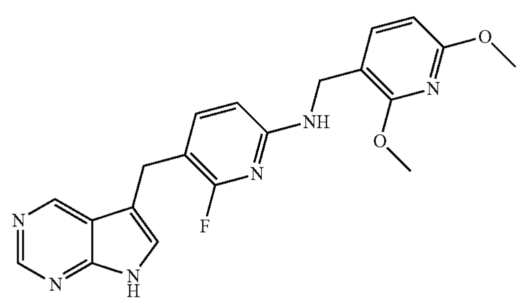 [SMILES: COc1ccc(CNc2ccc(Cc3c[nH]c4ncncc34)c(F)n2)c(OC)n1] | 395.1 |
| P-0044 | | 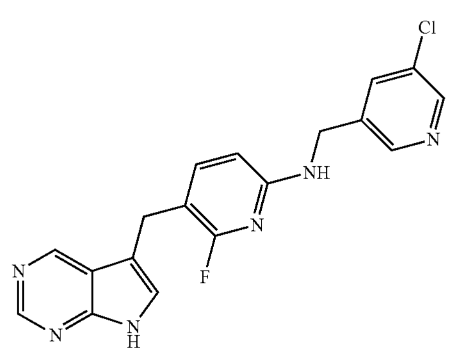 [SMILES: Fc1nc(NCc2cncc(Cl)c2)ccc1Cc1c[nH]c2ncncc12] | 369.1 |

-continued

| Compound number | Aldehyde structure | Compound structure | MS (ESI) [M + H⁺]⁺ |
|---|---|---|---|
| P-0045 | 6-chloropyridine-3-carbaldehyde | 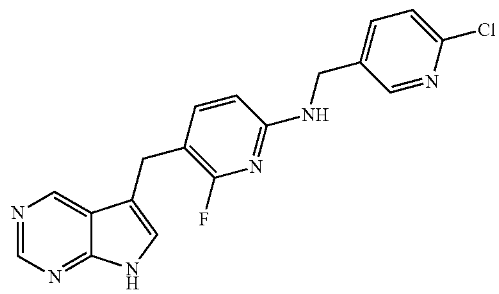 [SMILES: Fc1nc(NCc2ccc(Cl)nc2)ccc1Cc1c[nH]c2ncncc12] | 369.1 |
| P-0046 | 3-bromopyridine-4-carbaldehyde | 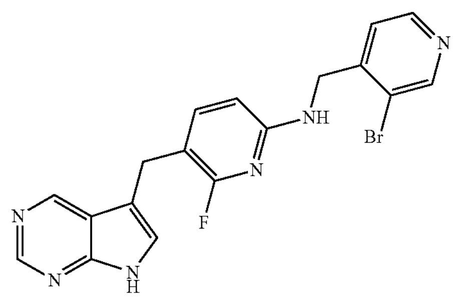 [SMILES: Fc1nc(NCc2ccncc2Br)ccc1Cc1c[nH]c2ncncc12] | 413.1 |
| P-0047 | 3-chloropyridine-4-carbaldehyde | 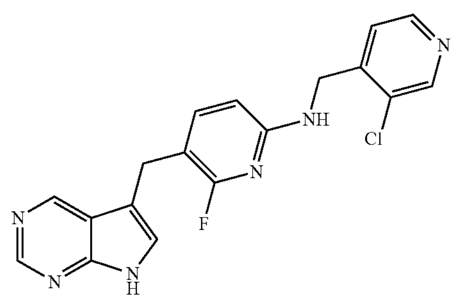 | 369.1 |
| P-0048 | 2-methylpyrimidine-5-carbaldehyde | 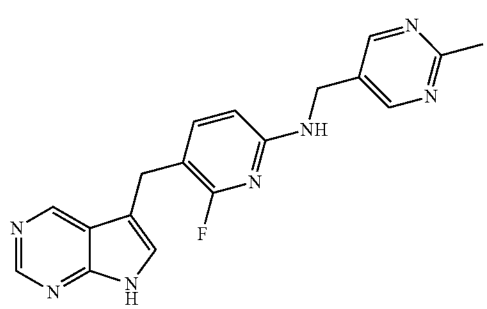 [SMILES: Cc1ncc(CNc2ccc(Cc3c[nH]c4ncncc34)c(F)n2)cn1] | 350.3 |
| P-0049 | 3-fluoropyridine-4-carbaldehyde | 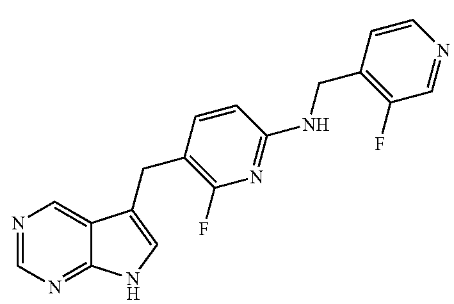 | 353.1 |

-continued

| Compound number | Aldehyde structure | Compound structure | MS (ESI) [M + H+]+ |
|---|---|---|---|
| P-0050 | | 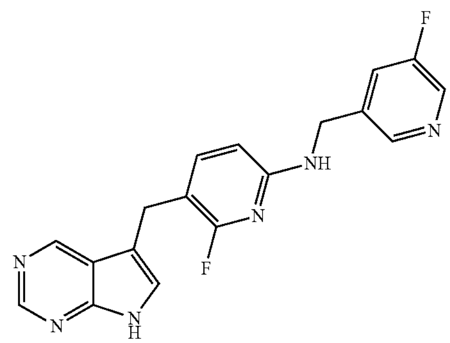 [SMILES: Fc1cncc(CNc2ccc(Cc3c[nH]c4ncncc34)c(F)n2)c1] | 353.1 |
| P-0051 | | 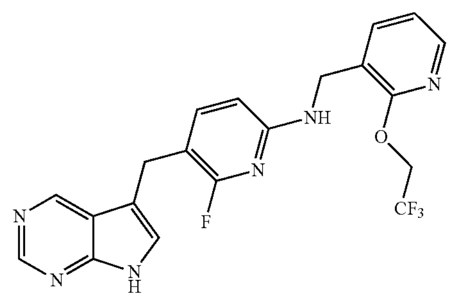 [SMILES: Fc1nc(NCc2cccnc2OCC(F)(F)F)ccc1Cc1c[nH]c2ncncc12] | 433.1 |
| P-0052 | | 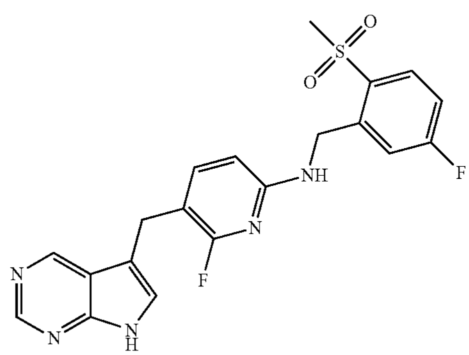 [SMILES: CS(=O)(=O)c1ccc(F)cc1CNc1ccc(Cc2c[nH]c3ncncc23)c(F)n1] | 430.3 |
| P-0053 | | 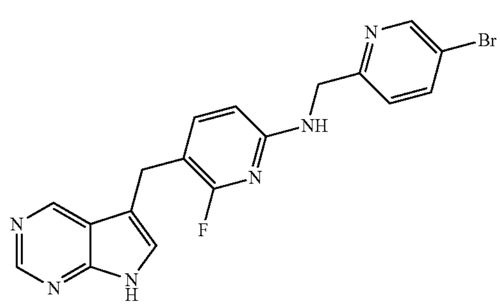 [SMILES: Fc1nc(NCc2ccc(Br)cn2)ccc1Cc1c[nH]c2ncncc12] | 413.1 |

-continued

| Compound number | Aldehyde structure | Compound structure | MS (ESI) [M + H+]+ |
|---|---|---|---|
| P-0054 | | 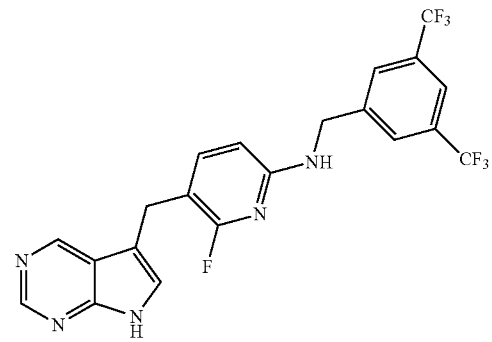 [SMILES: Fc1nc(NCc2cc(C(F)(F)F)cc(C(F)(F)F)c2)ccc1Cc1c[nH]c2ncncc12] | 470.3 |
| P-0055 | | 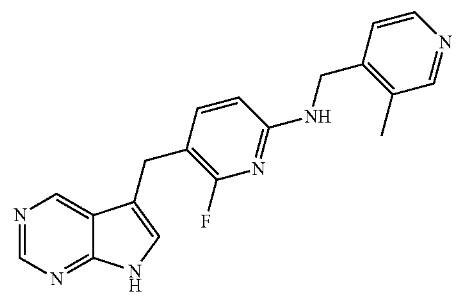 [SMILES: Cc1cnccc1CNc1ccc(Cc2c[nH]c3ncncc23)c(F)n1] | 349.1 |
| P-0056 | | 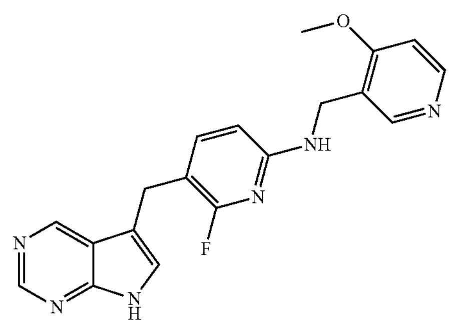 [SMILES: COc1ccncc1CNc1ccc(Cc2c[nH]c3ncncc23)c(F)n1] | 365.1 |
| P-0057 | | 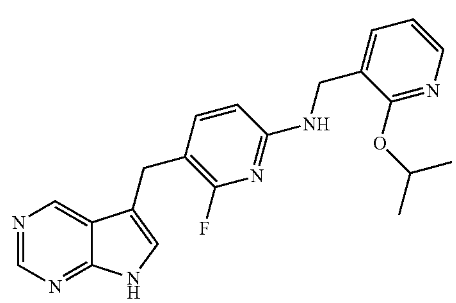 [SMILES: CC(C)Oc1ncccc1CNc1ccc(Cc2c[nH]c3ncncc23)c(F)n1] | 393.1 |
| P-0058 | | 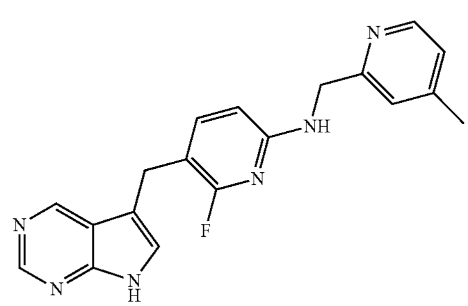 [SMILES: Cc1ccnc(CNc2ccc(Cc3c[nH]c4ncncc34)c(F)n2)c1] | 349.1 |

-continued
| Compound number | Aldehyde structure | Compound structure | MS (ESI) [M + H+]+ |
|---|---|---|---|
| P-0059 | 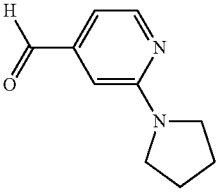 [SMILES: O=Cc1ccnc(N2CCCC2)c1] | 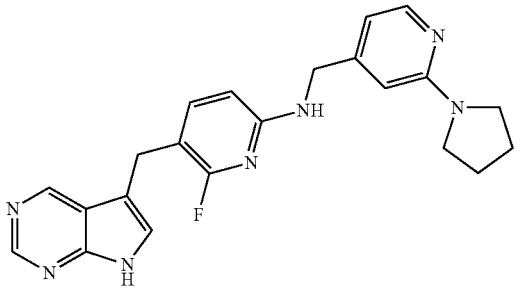 [SMILES: Fc1nc(NCc2ccnc(N3CCCC3)c2)ccc1Cc1c[nH]c2ncncc12] | 404.3 |
| P-0060 | 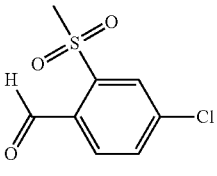 | 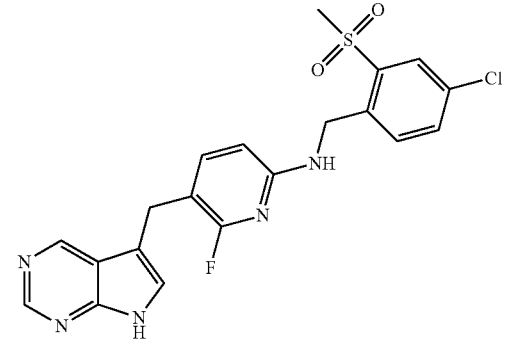 [SMILES: CS(=O)(=O)c1cc(Cl)ccc1CNc1ccc(Cc2c[nH]c3ncncc23)c(F)n1] | 445.9 |
| P-0061 | 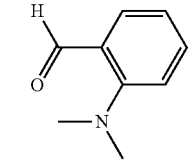 | 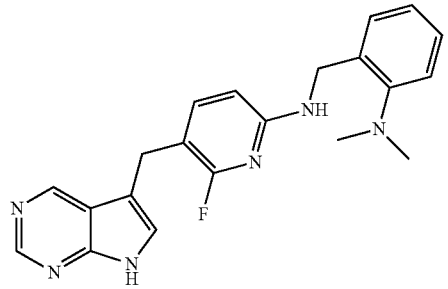 [SMILES: CN(C)c1ccccc1CNc1ccc(Cc2c[nH]c3ncncc23)c(F)n1] | 377.5 |
| P-0062 | 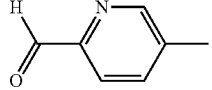 | 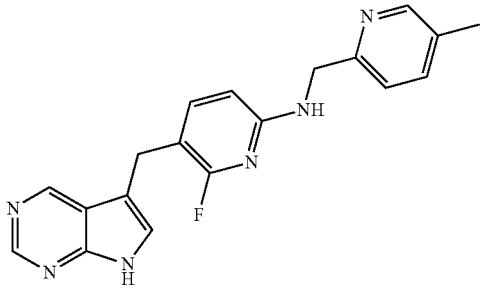 [SMILES: Cc1ccc(CNc2ccc(Cc3c[nH]c4ncncc34)c(F)n2)nc1] | 349.1 |
| P-0063 | 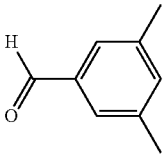 | 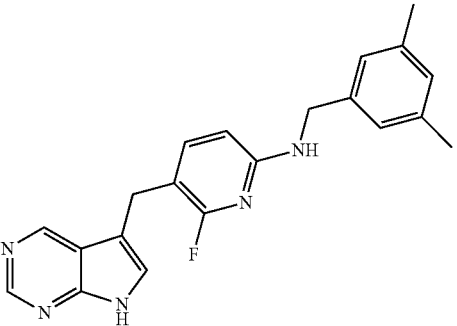 [SMILES: Cc1cc(C)cc(CNc2ccc(Cc3c[nH]c4ncncc34)c(F)n2)c1] | 362.3 |

-continued

| Compound number | Aldehyde structure | Compound structure | MS (ESI) [M + H⁺]⁺ |
|---|---|---|---|
| P-0064 | | 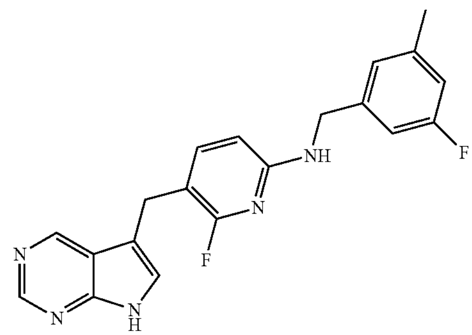 [SMILES: Cc1cc(F)cc(CNc2ccc(Cc3c[nH]c4ncncc34)c(F)n2)c1] | 366.3 |
| P-0065 | | 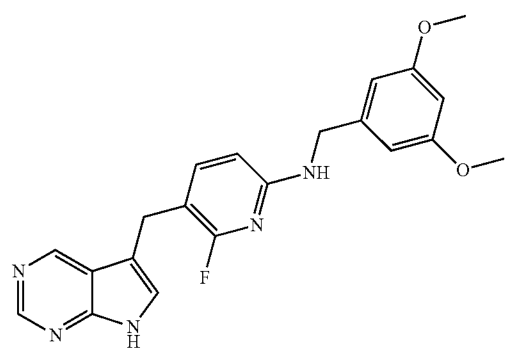 [SMILES: COc1cc(CNc2ccc(Cc3c[nH]c4ncncc34)c(F)n2)cc(OC)c1] | 394.3 |
| P-0066 | | 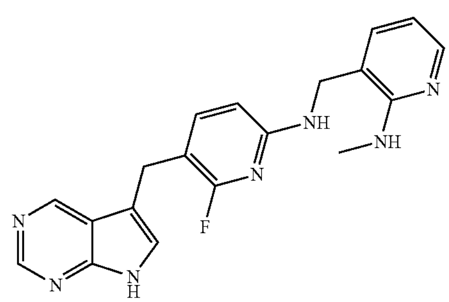 [SMILES: CNc1ncccc1CNc1ccc(Cc2c[nH]c3ncncc23)c(F)n1] | 364.3 |
| P-0067 | | 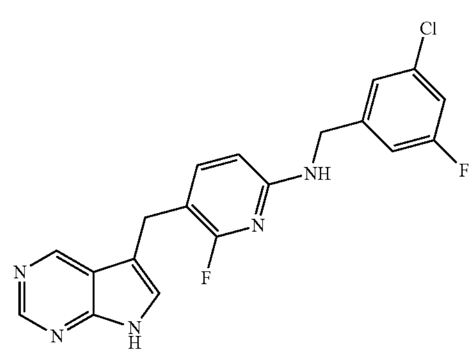 [SMILES: Fc1cc(Cl)cc(CNc2ccc(Cc3c[nH]c4ncncc34)c(F)n2)c1] | 386.3 |

-continued
| Compound number | Aldehyde structure | Compound structure | MS (ESI) [M + H⁺]⁺ |
|---|---|---|---|
| P-0068 | 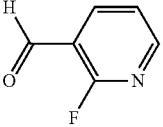 | 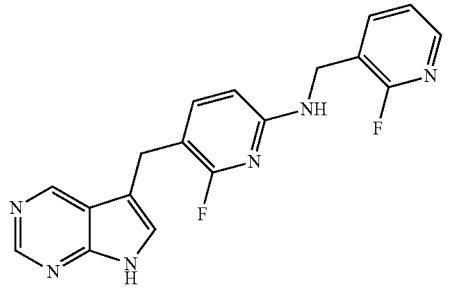 [SMILES: Fc1ncccc1CNc1ccc(Cc2c[nH]c3ncncc23)c(F)n1] | 353.1 |
| P-0069 | 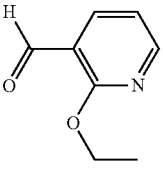 | 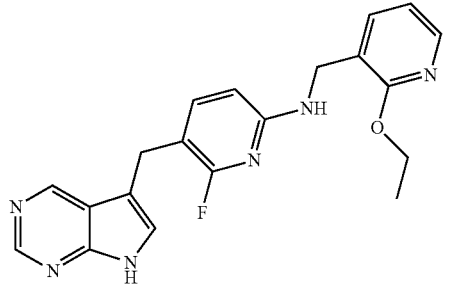 [SMILES: CCOc1ncccc1CNc1ccc(Cc2c[nH]c3ncncc23)c(F)n1] | 379.1 |
| P-0070 | 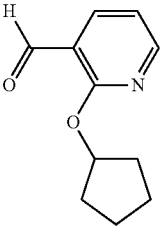 [SMILES: O=Cc1cccnc1OC1CCCC1] | 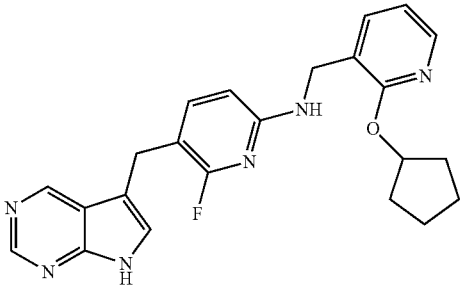 [SMILES: Fc1nc(NCc2cccnc2OC2CCCC2)ccc1Cc1c[nH]c2ncncc12] | 419.1 |
| P-0071 | 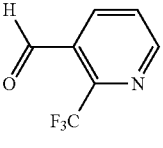 | 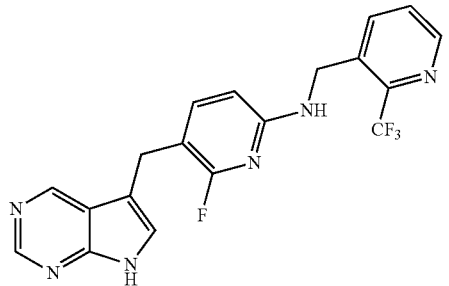 [SMILES: Fc1nc(NCc2cccnc2C(F)(F)F)ccc1Cc1c[nH]c2ncncc12] | 403.1 |
| P-0072 | 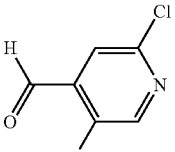 | 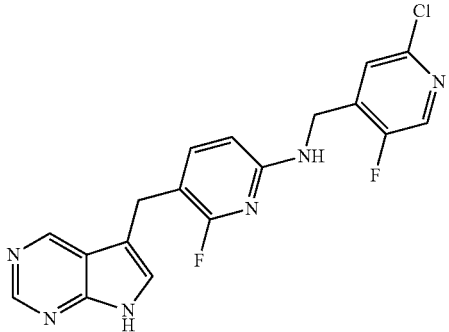 [SMILES: Fc1cnc(Cl)cc1CNc1ccc(Cc2c[nH]c3ncncc23)c(F)n1] | 387.1 |

-continued

| Compound number | Aldehyde structure | Compound structure | MS (ESI) [M + H+]+ |
|---|---|---|---|
| P-0073 | | 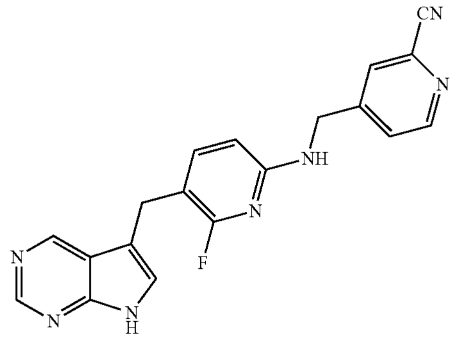 | 360.3 |
| P-0074 | | 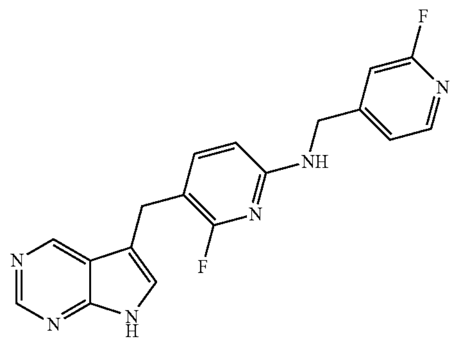 [SMILES: Fc1cc(CNc2ccc(Cc3c[nH]c4ncncc34)c(F)n2)ccn1] | 363.1 |
| P-0075 | | 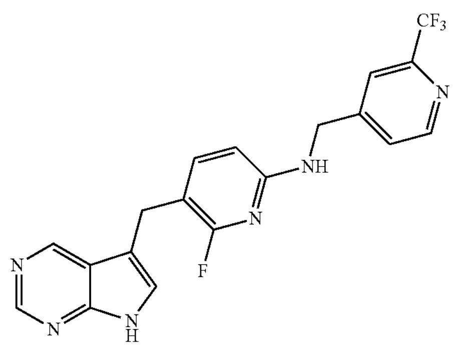 [SMILES: Fc1nc(NCc2ccnc(C(F)(F)F)c2)ccc1Cc1c[nH]c2ncncc12] | 403.1 |
| P-0076 | | 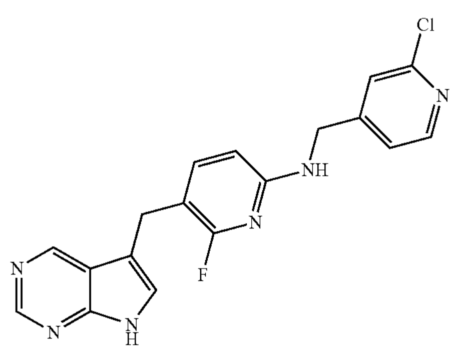 [SMILES: Fc1nc(NCc2ccnc(Cl)c2)ccc1Cc1c[nH]c2ncncc12] | 369.1 |

-continued
| Compound number | Aldehyde structure | Compound structure | MS (ESI) [M + H⁺]⁺ |
|---|---|---|---|
| P-0077 | 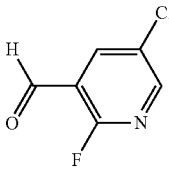 | 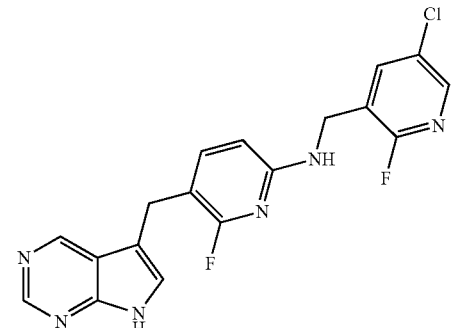 | 387.1 |
| P-0078 | 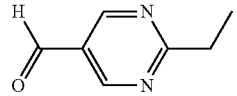 | 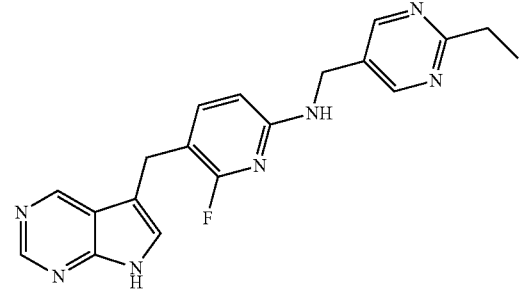 [SMILES: CCc1ncc(CNc2ccc(Cc3c[nH]c4ncncc34)c(F)n2)cn1] | 364.3 |
| P-0079 | 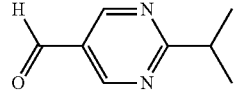 | 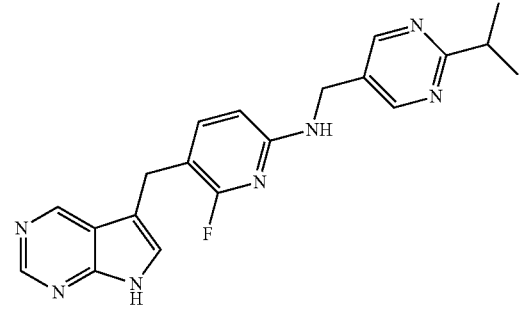 [SMILES: CC(C)c1ncc(CNc2ccc(Cc3c[nH]c4ncncc34)c(F)n2)cn1] | 378.3 |
| P-0080 | 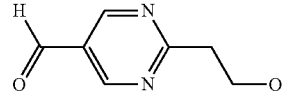 | 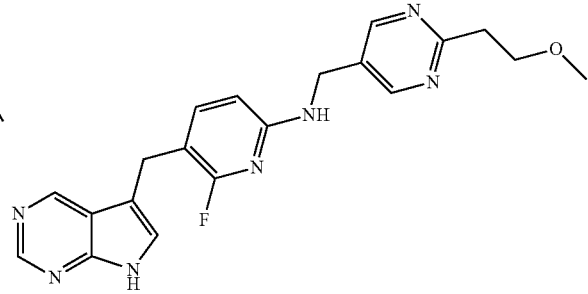 | 394.3 |
| P-0081 | 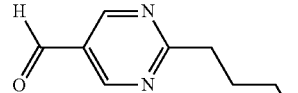 | 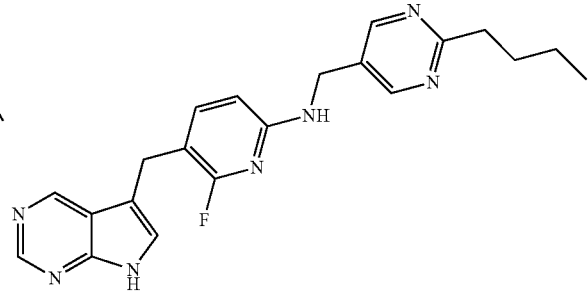 | 392.3 |

-continued

| Compound number | Aldehyde structure | Compound structure | MS (ESI) [M + H+]+ |
|---|---|---|---|
| P-0082 | | 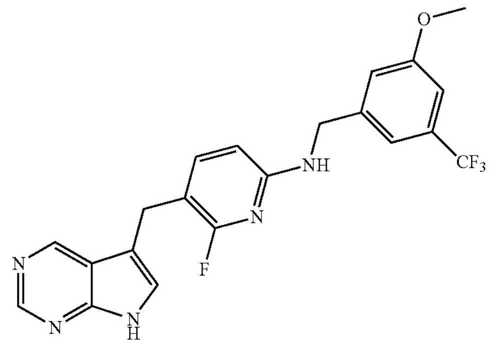 [SMILES: COc1cc(CNc2ccc(Cc3c[nH]c4ncncc34)c(F)n2)cc(C(F)(F)F)c1] | 432.3 |
| P-0083 | | 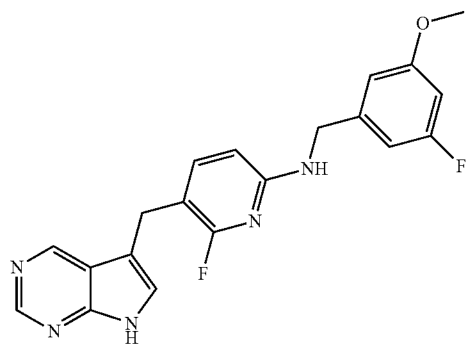 [SMILES: COc1cc(F)cc(CNc2ccc(Cc3c[nH]c4ncncc34)c(F)n2)c1] | 382.3 |
| P-0088 | | 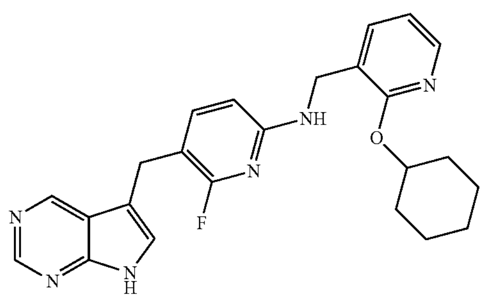 [SMILES: Fc1nc(NCc2cccnc2OC2CCCCC2)ccc1Cc1c[nH]c2ncncc12] | 433.5 |
| P-0089 | | 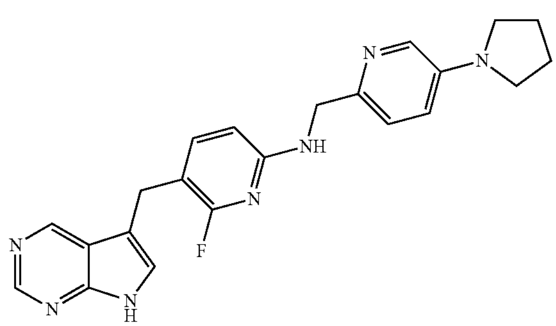 [SMILES: Fc1nc(NCc2ccc(N3CCCC3)cn2)ccc1Cc1c[nH]c2ncncc12] | 404.3 |

Example 10

Synthesis of {6-[(6-methoxy-pyridin-3-ylmethyl)-amino]-pyridin-3-yl}-(7H-pyrrolo[2,3-d]pyrimidin-5-yl)-methanone P-0008

{6-[(6-Methoxy-pyridin-3-ylmethyl)-amino]-pyridin-3-yl}-(7H-pyrrolo[2,3-d]pyrimidin-5-yl)-methanone P-0008 was prepared in three steps from 7H-pyrrolo[2,3-d]pyrimidine 6 and (5-formyl-pyridin-2-yl)-(6-methoxy-pyridin-3-ylmethyl)-carbamic acid tert-butyl ester 71 as shown in Scheme 13.

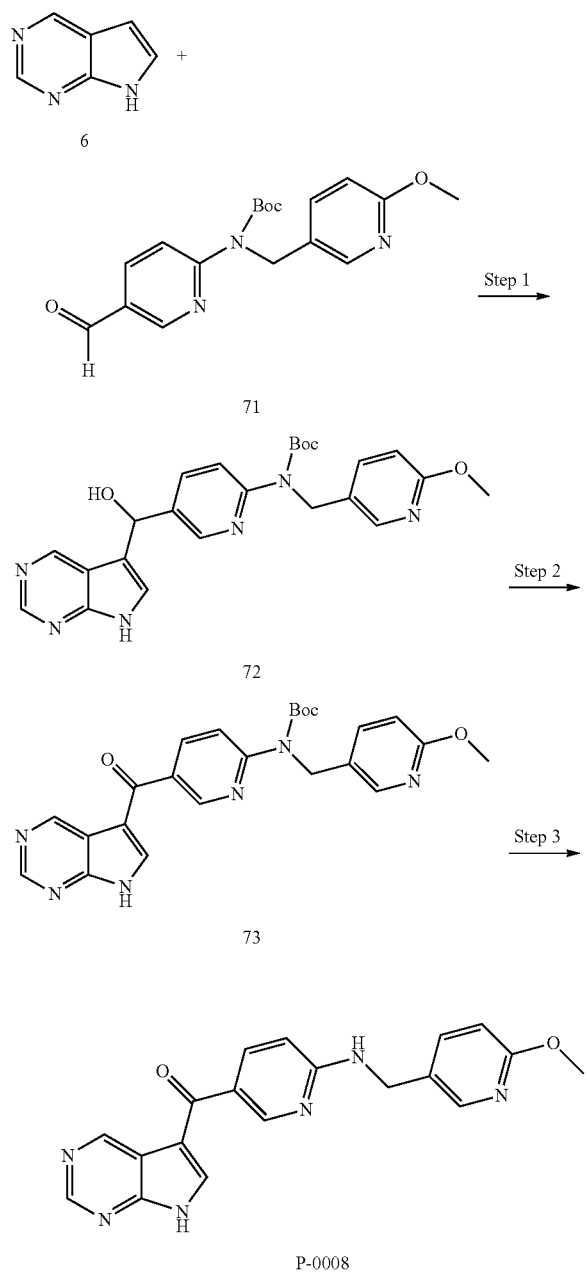

Scheme 13

Step 1—Preparation of {5-[hydroxy-(7H-pyrrolo[2,3-d]pyrimidin-5-yl)-methyl]-pyridin-2-yl}-(6-methoxy-pyridin-3-ylmethyl)-carbamic acid tert-butyl ester (72)

7H-Pyrrolo[2,3-d]pyrimidine (6, 0.450 g, 3.78 mmol), (5-formyl-pyridin-2-yl)-(6-methoxy-pyridin-3-ylmethyl)-carbamic acid tert-butyl ester (71, 1.43 g, 4.16 mmol), potassium hydroxide (0.689 g, 12.3 mmol) and 6.6 mL methanol were combined in a reaction vessel. The reaction mixture was allowed to stir at room temperature for 36 hours, then concentrated under vacuum to provide a thick brown slurry, which was combined with ethyl acetate and aqueous saturated sodium bicarbonate. The organic layer was dried with sodium sulfate, filtered and the filtrate adsorbed onto silica. This was purified by silica gel column chromatography, eluting with a gradient of 1-10% methanol in dichloromethane over 30 minutes. Appropriate fractions were combined and the solvents removed under vacuum to provide the desired compound (72, 380 mg). $^1$H NMR was consistent with the compound structure.

Step 2—Preparation of (6-methoxy-pyridin-3-ylmethyl)-[5-(7H-pyrrolo[2,3-d]pyrimidine-5-carbonyl)-pyridin-2-yl]carbamic acid tert-butyl ester (73)

To {5-[hydroxy-(7H-pyrrolo[2,3-d]pyrimidin-5-yl)-methyl]-pyridin-2-yl}-(6-methoxy-pyridin-3-ylmethyl)-carbamic acid tert-butyl ester (72, 0.189 g, 0.409 mmol) in 4.0 mL of dichloromethane, Dess-Martin periodinane (0.208 g, 0.490 mmol) was added. The reaction was stirred at room temperature for 1 hour, then poured into aqueous potassium carbonate and extracted with ethyl acetate. The organic layer was dried over sodium sulfate, filtered and the filtrate concentrated under vacuum. The resulting material was purified by silica gel column chromatography, eluting with methanol and dichloromethane. Appropriate fractions were combined and the solvents removed under vacuum to provide the desired compound (73, 66 mg). $^1$H NMR was consistent with the compound structure.

Step 3—Preparation of {6-[(6-methoxy-pyridin-3-ylmethyl)-amino]-pyridin-3-yl}-(7H-pyrrolo[2,3-d]pyrimidin-5-yl)-methanone (P-0008)

To (6-methoxy-pyridin-3-ylmethyl)-[5-(7H-pyrrolo[2,3-d]pyrimidine-5-carbonyl)-pyridin-2-yl]-carbamic acid tert-butyl ester (73, 66 mg, 0.14 mmol) in 5 mL of dichloromethane, trifluoroacetic acid (0.5 mL, 6.0 mmol) was added. The reaction was stirred at room temperature for 4 hours, then concentrated under vacuum, and combined with aqueous saturated sodium bicarbonate and ethyl acetate. The organic layer was dried over sodium sulfate, filtered and the filtrate adsorbed onto silica. This was purified by silica gel column chromatography eluting with methanol and dichloromethane. Appropriate fractions were combined, the solvents removed under vacuum, and the resulting solid washed with hexanes and ethyl acetate, with sonicating. The solid was collected by filtration to provide the desired compound as a white solid (P-0008, 4.8 mg). MS (ESI) [M+H$^+$]$^+$=360.9.

Example 11

Synthesis of {6-[(6-methoxy-pyridin-3-ylmethyl)-amino]-2-methyl-pyridin-3-yl}-(7H-pyrrolo[2,3-d]pyrimidin-5-yl)-methanone P-0019

{6-[(6-Methoxy-pyridin-3-ylmethyl)-amino]-2-methyl-pyridin-3-yl}-(7H-pyrrolo[2,3-d]pyrimidin-5-yl)-methanone P-0019 was prepared in two steps from 5-iodo-7-triisopropylsilanyl-7H-pyrrolo[2,3-d]pyrimidine 38 and (5-formyl-6-methyl-pyridin-2-yl)-(6-methoxy-pyridin-3-yl-methyl)-carbamic acid tert-butyl ester 74 as shown in Scheme 14.

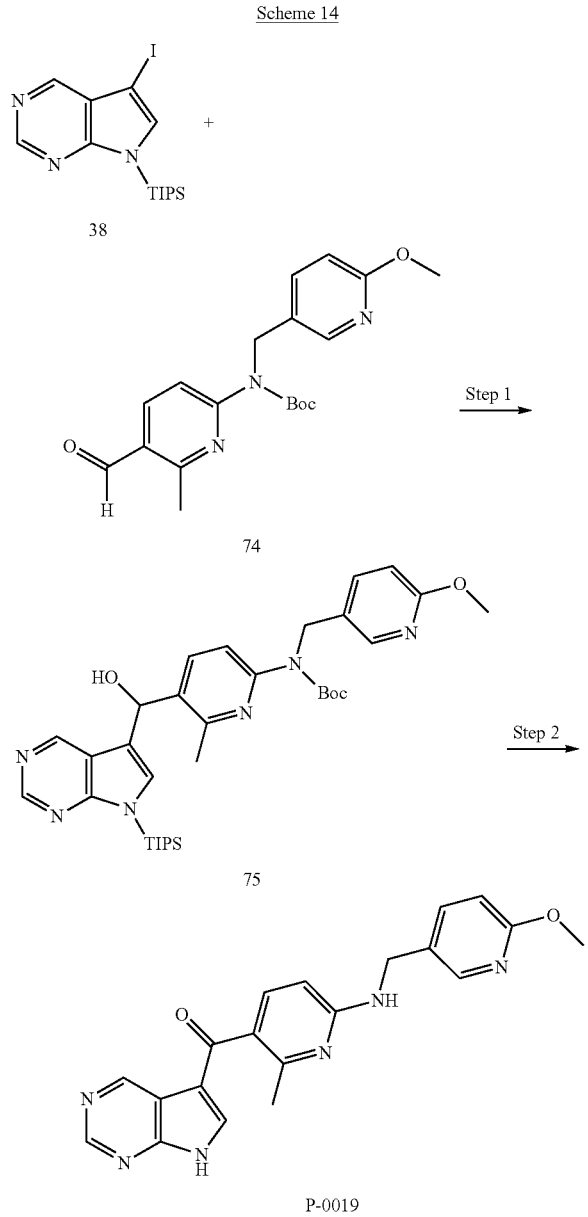

Step 1—Preparation of {5-[hydroxy-(7-triisopropyl-silanyl-7H-pyrrolo[2,3-d]pyrimidin-5-yl)-methyl]-6-methyl-pyridin-2-yl}-(6-methoxy-pyridin-3-ylmethyl)-carbamic acid tert-butyl ester (75)

To 5-iodo-7-triisopropylsilanyl-7H-pyrrolo[2,3-d]pyrimidine (38, 0.37 g, 0.92 mmol) in a round bottom flask, 1.1 mL of tetrahydrofuran was added and the mixture cooled to −25° C. Isopropylmagnesium chloride (0.49 mL, 2.0 M in tetrahydrofuran, 0.97 mmol) was added and the reaction stirred, coming to 0° C. The reaction was cooled to −25° C. and (5-formyl-6-methyl-pyridin-2-yl)-(6-methoxy-pyridin-3-yl-methyl)-carbamic acid tert-butyl ester (74, 0.300 g, 0.839 mmol) in 2.5 mL of tetrahydrofuran was added. The reaction was stirred, coming to 0° C., then poured into aqueous saturated sodium bicarbonate and ethyl acetate. The organic layer was washed with brine, then dried over sodium sulfate, filtered and the filtrate adsorbed onto silica. This was purified by silica gel column chromatography eluting with 10-80% ethyl acetate in hexanes. Appropriate fractions were combined and the solvents removed under vacuum to provide the desired compound (75, 317 mg). MS (ESI) [M+H$^+$]$^+$=634.09.

Step 2—Preparation of {6-[(6-methoxy-pyridin-3-ylmethyl)-amino]-2-methyl-pyridin-3-yl}-(7H-pyrrolo[2,3-d]pyrimidin-5-yl)-methanone (P-0019)

To {5-[hydroxy-(7-triisopropylsilanyl-7H-pyrrolo[2,3-d]pyrimidin-5-yl)-methyl]-6-methyl-pyridin-2-yl}-(6-methoxy-pyridin-3-ylmethyl)-carbamic acid tert-butyl ester (75, 0.317 g, 0.501 mmol) dissolved in 15.0 mL of 1,2-dichloroethane, triethylsilane (1.00 mL, 6.26 mmol) was added, followed by trifluoroacetic acid (0.482 mL, 6.26 mmol). The reaction was stirred at 70° C. overnight, then concentrated under vacuum and combined with 1 N aqueous potassium carbonate and extracted with ethyl acetate. The organic layer was washed with brine, then dried with sodium sulfate, filtered and the filtrate adsorbed onto silica. This was purified by silica gel column chromatography eluting with 50-100% ethyl acetate in hexanes. Appropriate fractions were combined and the solvents removed under vacuum to provide the desired compound (P-0019, 57.5 mg). $^1$H NMR was consistent with the compound structure.

Example 12

Synthesis of 5-{6-[(5-fluoro-2-methoxy-pyridin-3-ylmethyl)-amino]-pyridin-3-ylmethyl}-7H-pyrrolo[2,3-d]pyrimidin-4-ol P-0099

5-{6-[(5-Fluoro-2-methoxy-pyridin-3-ylmethyl)-amino]-pyridin-3-ylmethyl}-7H-pyrrolo[2,3-d]pyrimidin-4-ol P-0099 was prepared in two steps from 4-chloro-7H-pyrrolo[2,3-d]pyrimidine 1 and (5-fluoro-2-methoxy-pyridin-3-yl-methyl)-(5-formyl-pyridin-2-yl)-carbamic acid tert-butyl ester 77 as shown in Scheme 15.

Scheme 15

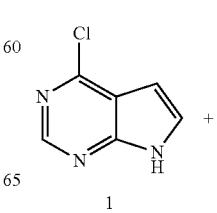

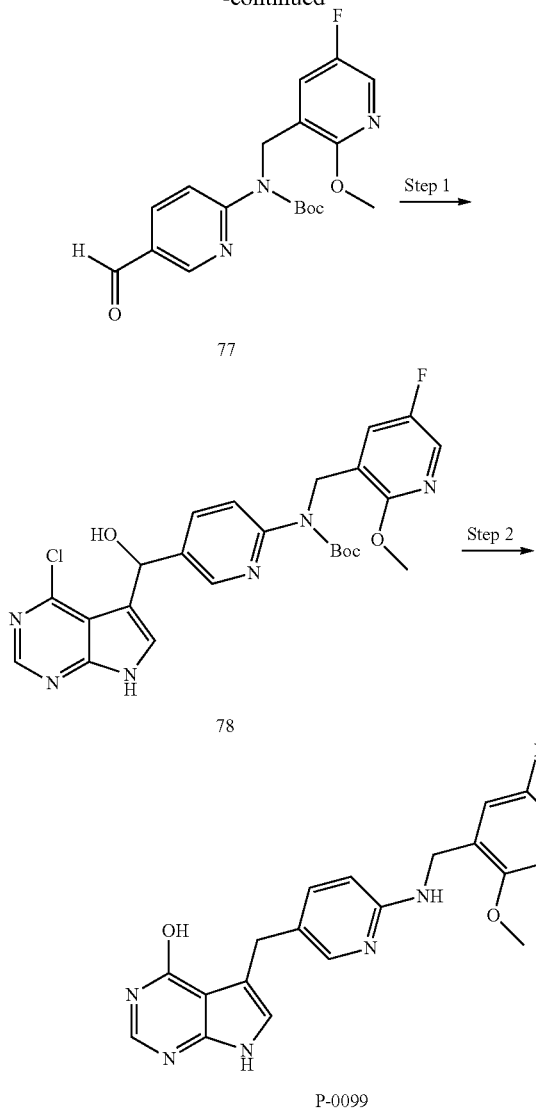

Step 1—Preparation of {5-[(4-chloro-7H-pyrrolo[2,3-d]pyrimidin-5-yl)-hydroxy-methyl]-pyridin-2-yl}-(5-fluoro-2-methoxy-pyridin-3-ylmethyl)-carbamic acid tert-butyl ester (78)

4-Chloro-7H-pyrrolo[2,3-d]pyrimidine (1, 0.121 g, 0.790 mmol), (5-fluoro-2-methoxy-pyridin-3-ylmethyl)-(5-formyl-pyridin-2-yl)-carbamic acid tert-butyl ester (77), 2.5 mL of N,N-dimethylformamide and cesium carbonate (0.751 g, 2.30 mmol) were combined in a round bottom flask. The reaction was stirred at room temperature for 6 days, then neutralized with 0.1N aqueous hydrochloric acid, then extracted 3× with ethyl acetate. The organic layers were combined, washed with brine, dried over sodium sulfate, filtered and the filtrate concentrated. The resulting material was purified by silica gel column chromatography, eluting with methanol and dichloromethane. Appropriate fractions were combined and solvents removed under vacuum to provide the desired compound (78, 0.023 g). MS (ESI) [M−H$^+$]$^-$=513.2, 515.2.

Step 2—Preparation of 5-{6-[(5-fluoro-2-methoxy-pyridin-3-ylmethyl)-amino]-pyridin-3-ylmethyl}-7H-pyrrolo[2,3-d]pyrimidin-4-ol (P-0099)

{5-[(4-Chloro-7H-pyrrolo[2,3-d]pyrimidin-5-yl)-hydroxy-methyl]-pyridin-2-yl}-(5-fluoro-2-methoxy-pyridin-3-ylmethyl)-carbamic acid tert-butyl ester (78, 0.022 g, 0.043 mmol), trifluoroacetic acid (0.062 mL, 0.80 mmol), triethylsilane (0.15 mL, 0.97 mmol) and 0.46 mL acetonitrile were combined in a round bottom flask. The reaction was heated at reflux for 3 hours, then poured into water and extracted with ethyl acetate. The organic layer was washed with brine, dried over sodium sulfate, filtered and the filtrate concentrated under vacuum. The resulting material was purified by silica gel column chromatography, eluting with methanol in dichloromethane. Appropriate fractions were combined and solvents removed under vacuum to provide the desired compound (P-0099, 0.0072 g). MS (ESI) [M+H$^+$]$^+$=380.8.

Example 13

Kinase Activity Assays

Assays for the activity of kinases, including, but not limited to, Fms, Kit, B-Raf, B-Raf V600E, c-Raf-1, and TrkA are known in the art, for example as described in US Patent Publication Number US20070032519 and U.S. patent application Ser. No. 11/473,347 (see also, PCT publication WO2007002433), the disclosures of which are hereby incorporated by reference with respect to such assays.

Compounds screened by at least one of the methods described in U.S. patent application Ser. No. 11/473,347, or by similar methods, having IC$_{50}$ of less than 10 μM are shown in tables 1a (A-Raf), 1b (B-Raf), 1c (B-Raf V600E), 1d (C-Raf), 1e (Btk), 1f (Flt-1), 1g (Flt-3), 1h (Fms), 1i (Kdr), 1j (Kit), 1k (Src), 1l (TEC), and 1m (TrkA).

TABLE 1a

Compounds with activity toward kinase A-Raf with IC$_{50}$ ≤ 10 μM.

| | |
|---|---|
| A-Raf | P-0001, P-0003, P-0006, P-0007, P-0009, P-0011, P-0013, P-0014 |

TABLE 1b

Compounds with activity toward kinase B-Raf with IC$_{50}$ ≤10 μM.

| | |
|---|---|
| B-Raf | P-0013, P-0043, P-0052, P-0070, P-0086, P-0088, P-0096, P-0100, P-0101, P-0102, P-0103 |

TABLE 1c

Compounds with activity toward kinase B-Raf V600E with IC$_{50}$ ≤ 10 μM.

| | |
|---|---|
| B-Raf V600E | P-0001, P-0002, P-0003, P-0004, P-0006, P-0007, P-0008, P-0009, P-0013, P-0014, P-0016, P-0021, P-0022, P-0037, P-0038, P-0039, P-0040, P-0041, P-0044, P-0045, P-0050, P-0051, P-0052, P-0053, P-0060, P-0062, P-0063, P-0067, P-0070, P-0072, |

TABLE 1c-continued

Compounds with activity toward kinase B-Raf V600E with IC$_{50}$ ≤ 10 μM.

P-0073, P-0076, P-0077, P-0078, P-0081, P-0086, P-0088, P-0089, P-0091, P-0095, P-0100, P-0101, P-0102, P-0103

TABLE 1d

Compounds with activity toward kinase C-Raf with IC$_{50}$ ≤ 10 μM.

C-Raf  P-0004, P-0039, P-0041, P-0044, P-0051, P-0052, P-0057, P-0070, P-0086, P-0088, P-0092, P-0093, P-0096, P-0100, P-0101, P-0102, P-0103

TABLE 1e

Compounds with activity toward kinase Btk with IC$_{50}$ ≤ 10 μM.

Btk  P-0009, P-0098, P-0101

TABLE 1f

Compounds with activity toward kinase Flt-1 with IC$_{50}$ ≤ 10 μM.

Flt-1  P-0001, P-0003, P-0006

TABLE 1g

Compounds with activity toward kinase Flt-3 with IC$_{50}$ ≤ 10 μM.

Flt-3  P-0001, P-0002, P-0003, P-0005, P-0006, P-0007, P-0008, P-0009, P-0010, P-0011, P-0013, P-0014, P-0104

TABLE 1h

Compounds with activity toward kinase Fms with IC$_{50}$ ≤ 10 μM.

Fms  P-0001, P-0002, P-0003, P-0004, P-0005, P-0006, P-0007, P-0009, P-0010, P-0011, P-0012, P-0013, P-0014, P-0015, P-0016, P-0017, P-0018, P-0019, P-0020, P-0021, P-0022, P-0023, P-0024, P-0025, P-0026, P-0027, P-0028, P-0029, P-0030, P-0031, P-0032, P-0033, P-0034, P-0035, P-0036, P-0037, P-0038, P-0039, P-0040, P-0041, P-0042, P-0043, P-0044, P-0045, P-0046, P-0047, P-0048, P-0049, P-0050, P-0051, P-0052, P-0053, P-0054, P-0055, P-0056, P-0057, P-0058, P-0059, P-0060, P-0061, P-0062, P-0063, P-0064, P-0065, P-0066, P-0067, P-0068, P-0069, P-0070, P-0071, P-0072, P-0073, P-0074, P-0075, P-0076, P-0077, P-0078, P-0079, P-0080, P-0081, P-0082, P-0083, P-0084, P-0085, P-0086, P-0087, P-0088, P-0089, P-0090, P-0091, P-0092, P-0093, P-0094, P-0095, P-0096, P-0097, P-0098, P-0099, P-0100, P-0101, P-0102, P-0103, P-0104

TABLE 1i

Compounds with activity toward kinase Kdr with IC$_{50}$ ≤ 10 μM.

Kdr  P-0001, P-0002, P-0004, P-0005, P-0006, P-0007, P-0008, P-0009, P-0010, P-0011, P-0012, P-0013, P-0014, P-0015, P-0016, P-0017, P-0018, P-0020, P-0021, P-0022, P-0023, P-0024, P-0025, P-0026, P-0027, P-0029, P-0030, P-0031, P-0032, P-0033, P-0036, P-0037, P-0039, P-0041, P-0043, P-0044, P-0045, P-0046, P-0047, P-0051, P-0053, P-0054, P-0057, P-0058, P-0059, P-0060, P-0061, P-0062, P-0063, P-0064, P-0065, P-0066, P-0067, P-0068, P-0069, P-0070, P-0071, P-0072, P-0073, P-0074, P-0075, P-0076, P-0078, P-0079, P-0081, P-0082, P-0083, P-0085, P-0086, P-0087, P-0088, P-0089, P-0091, P-0093, P-0094, P-0096, P-0100, P-0101, P-0102, P-0103

TABLE 1j

Compounds with activity toward kinase Kit with IC$_{50}$ ≤ 10 μM.

Kit  P-0001, P-0002, P-0003, P-0004, P-0005, P-0006, P-0007, P-0008, P-0009, P-0011, P-0012, P-0013, P-0014, P-0015, P-0016, P-0017, P-0018, P-0022, P-0023, P-0024, P-0026, P-0027, P-0029, P-0030, P-0031, P-0032, P-0033, P-0036, P-0038, P-0041, P-0043, P-0045, P-0051, P-0053, P-0054, P-0057, P-0061, P-0062, P-0063, P-0064, P-0067, P-0069, P-0070, P-0082, P-0083, P-0084, P-0085, P-0086, P-0087, P-0088, P-0089, P-0090, P-0091, P-0092, P-0093, P-0094, P-0095, P-0096, P-0097, P-0098, P-0099, P-0100, P-0101, P-0102, P-0103, P-0104

TABLE 1k

Compounds with activity toward kinase Src with IC$_{50}$ ≤ 10 μM.

Src  P-0005, P-0006, P-0014, P-0079, P-0088, P-0089, P-0090, P-0092, P-0095, P-0097,

TABLE 11

Compounds with activity toward kinase TEC with $IC_{50} \leq 10$ μM.

| | |
|---|---|
| TEC | P-0001, P-0003 |

TABLE 1m

Compounds with activity toward kinase TrkA with $IC_{50} \leq 10$ μM.

| | |
|---|---|
| TrkA | P-0001, P-0003, P-0005, P-0006, P-0007, P-0010, P-0011, P-0024, P-0051, P-0052, P-0054, P-0057, P-0061, P-0063, P-0064, P-0065, P-0067, P-0069, P-0070, P-0071, P-0075, P-0082, P-0090, P-0091, P-0094, P-0095, P-0097, P-0098, P-0099, P-0100, P-0101, P-0102, P-0103 |

Example 14

Efficacy of Compounds in Combination with Standard-of-Care Chemotherapeutic Agents in Four Human Cancer Cell Lines Compounds of the invention, such as compounds of Formula I, in combination with a standard chemotherapeutic agent, such as 5-fluorouracil, carboplatin, dacarbazine, gefitinib, oxaliplatin, paclitaxel, SN-38, temozolomide, or vinblastine, can be assessed for their effectiveness in killing human tumor cells. Such assays are known in the art, for example, as described in U.S. patent application Ser. No. 11/473,347, hereby incorporated by reference with respect to such assays.

Example 15

Pharmaceutical Properties of Compounds

Compounds of the invention, such as compounds of Formula I, demonstrate improved solubility and/or pharmacokinetics when compared to similarly substituted 1H-Pyrrolo[2,3-b]pyridine compounds. Typically, 1H-Pyrrolo[2,3-b]pyridine compounds with improved aqueous solubility may not have acceptable pharmacokinetics, assessed by measuring plasma levels in rats treated with the compounds. Improved solubility with improved exposure levels, as measured by area under the curve (AUC), is indicative of beneficial pharmaceutical properties of the compound, such as improved bioavailability.

As an indication of relative solubility, the turbidity of compounds in aqueous solutions may be assessed. Each compound is diluted into four different physiologically relevant buffers and solution turbidity was measured by spectrophotometry. The concentration of compound that demonstrated turbidity by forming enough insoluble suspension to raise the average optical density above 0.01 at three wavelengths (490, 535, and 650 nm) was used to define the limit of the compound solubility in that buffer. To assess possible compound properties in different physiological compartments, such as stomach, intestine and blood, a series of aqueous buffers with varying pH was used.

Compounds were dissolved at a concentration of 25 mM in dimethyl sulfoxide, then serially diluted 1:1 into a 96 well plate, diluting 10 times in pure dimethyl sulfoxide, with the final well of each row a dimethyl sulfoxide blank. In an assay plate, 99 μL of appropriate buffer was added to each well, and 1 μL of each sample dilution was added to the buffer, achieving a range of final total concentrations in aqueous solutions having different pH. The buffers used were Simulated Gastric Fluid (SGF-pH 1.5) 0.5M NaCl, pH 1.5; Simulated Intestinal fluid (SIF-pH 4.5 and pH 6.8) 0.05M $NaH_2PO_4$, pH 4.5 and 6.8; and Hepes Buffer (HEPES-pH 7.4) 10 mM HEPES, 150 mM NaCl, pH 7.4. Control compounds pyrene, estriol and propranolol HCl were also assessed. Plates were spun and then mixed for 1 minute, and the absorbance was read using a Tecan Safire II to read wavelengths in the visible range (490, 535, and 650 nm) at four locations per well, reflecting the degree of turbidity present. The average optical density for each wavelength in each well was graphed vs. compound concentration, and the concentration at which the curve crosses a threshold O.D. of 0.01 for each wavelength was reported as the endpoint turbidity assay result. The average of the three wavelengths is used to compare turbidity of compounds. Compounds are considered to have low solubility if the threshold concentration is <31.3 μM, moderate solubility if the threshold concentration is 31.3 μM to 250 μM, and high solubility if the threshold concentration is >250 μM.

Pharmacokinetic properties were assessed in male Sprague Dawley rats. Rats were dosed daily with compound either by IV injections via surgically implanted jugular catheters or by oral gavage (PO). Each compound was prepared as a 20 mg/mL stock solution in dimethyl sulfoxide, which was further diluted to provide the dosing stock at the desired concentration for the IV or PO formulations. For IV dosing, the dosing stock was diluted into a 1:1:8 mixture of Solutol®:ethanol:water. For PO dosing, the dosing stock was diluted into 1% methylcellulose. In a cassette format, 5 compounds were diluted to 0.5 mg/mL each for IV dosing and 0.4 mg/mL each for PO dosing and dosed at 1 mg/kg (2 mL/kg) or 2 mg/kg (5 mL/kg), respectively. For IV dosed animals, tail vein blood samples were collected with lithium heparin anticoagulant at 5, 15, 30, and 60 minutes and 4, 8, and 24 hours post dosing each day. For PO dosed animals, tail vein blood samples were collected with lithium heparin anticoagulant at 30 minutes, 1, 2, 4, 8 and 24 hours post dosing each day. Samples were processed to plasma and frozen for later analysis of each compound by LC/MS/MS. Plasma levels as a function of time were plotted to assess the AUC (ng*hr/mL).

All patents and other references cited in the specification are indicative of the level of skill of those skilled in the art to which the invention pertains, and are incorporated by reference in their entireties, including any tables and figures, to the same extent as if each reference had been incorporated by reference in its entirety individually.

One skilled in the art would readily appreciate that the present invention is well adapted to obtain the ends and advantages mentioned, as well as those inherent therein. The methods, variances, and compositions described herein as presently representative of preferred embodiments are exemplary and are not intended as limitations on the scope of the invention. Changes therein and other uses will occur to those skilled in the art, which are encompassed within the spirit of the invention, are defined by the scope of the claims.

The invention illustratively described herein suitably may be practiced in the absence of any element or elements, limitation or limitations which is not specifically disclosed herein.

Thus, for example, in each instance herein any of the terms "comprising", "consisting essentially of" and "consisting of" may be replaced with either of the other two terms. Thus, for an embodiment of the invention using one of the terms, the invention also includes another embodiment wherein one of these terms is replaced with another of these terms. In each embodiment, the terms have their established meaning. Thus, for example, one embodiment may encompass a method "comprising" a series of steps, another embodiment would encompass a method "consisting essentially of" the same steps, and a third embodiment would encompass a method "consisting of" the same steps. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

In addition, where features or aspects of the invention are described in terms of Markush groups or other grouping of alternatives, those skilled in the art will recognize that the invention is also thereby described in terms of any individual member or subgroup of members of the Markush group or other group.

Also, unless indicated to the contrary, where various numerical values are provided for embodiments, additional embodiments are described by taking any 2 different values as the endpoints of a range. Such ranges are also within the scope of the described invention.

Thus, additional embodiments are within the scope of the invention and within the following claims.

What is claimed is:

1. A compound having the chemical structure of Formula I,

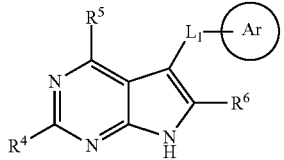

Formula I or a salt, a tautomer or a stereoisomer thereof,
wherein:
$L_1$ is selected from the group consisting of —C($R^7R^8$)—, —C(O)—, —C(S)—, —N($R^9$)—, —O—, —S—, —S(O)—, and —S(O)$_2$—;
Ar is selected from the group consisting of:

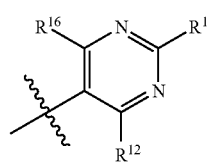 and 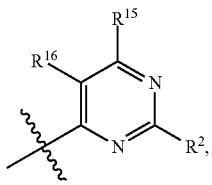

wherein

indicates the point of attachment of Ar to $L_1$ of Formula I;
$R^2$ is selected from the group consisting of —[C($R^{10}R^{11}$)]$_r$—$R^{19}$, —[C($R^{10}R^{11}$)]$_p$—N($R^{18}$)—[C($R^{10}R^{11}$)]$_q$—$R^{19}$, —[C($R^{10}R^{11}$)]$_p$—O—[C($R^{10}R^{11}$)]$_q$—$R^{19}$, —[O—[C($R^{10}R^{11}$)]$_2$]$_a$—$R^{21}$, —[C($R^{10}R^{11}$)]$_p$—S—[C($R^{10}R^{11}$)]$_q$—$R^{19}$, —[C($R^{10}R^{11}$)]$_p$—C(O)—[C($R^{10}R^{11}$)]$_q$—$R^{19}$, —[C($R^{10}R^{11}$)]$_p$—C(S)—[C($R^{10}R^{11}$)]$_q$—$R^{19}$, —[C($R^{10}R^{11}$)]$_p$—S(O)—[C($R^{10}R^{11}$)]$_q$—$R^{19}$, —[C($R^{10}R^{11}$)]$_p$—S(O)$_2$—[C($R^{10}R^{11}$)]$_q$—$R^{19}$, —[C($R^{10}R^{11}$)]$_p$—C(O)—N($R^{18}$)—[C($R^{10}R^{11}$)]$_q$—$R^{19}$, —[C($R^{10}R^{11}$)]$_p$—C(S)—N($R^{18}$)—[C($R^{10}R^{11}$)]$_q$—$R^{19}$, —[C($R^{10}R^{11}$)]$_p$—S(O)—N($R^{18}$)—[C($R^{10}R^{11}$)]$_q$—$R^{19}$, —[C($R^{10}R^{11}$)]$_p$—S(O)$_2$—N($R^{18}$)—[C($R^{10}R^{11}$)]$_q$$R^{19}$, and —N($R^{18}$)—$R^{20}$;
a is 1 or 2;
p, q and r are independently 0, 1, 2, or 3;
s is 1, 2, or 3;
$R^4$ is selected from the group consisting of hydrogen, optionally substituted lower alkyl, optionally substituted lower alkenyl, optionally substituted lower alkynyl, optionally substituted cycloalkyl, optionally substituted heterocycloalkyl, optionally substituted aryl, optionally substituted heteroaryl, —CN, —NO$_2$, —O—$R^{22}$, —S—$R^{24}$, —N($R^{22}$)—$R^{23}$, —C(O)—$R^{24}$, —C(S)—$R^{24}$, —C(O)—N($R^{22}$)—$R^{23}$, —C(S)—N($R^{22}$)—$R^{23}$, —C(O)—N($R^{25}$)—OR$^{22}$, —C(S)—N($R^{25}$)—OR$^{22}$, —C(O)—N($R^{25}$)—S(O)$_2$—$R^{24}$, —C(S)—N($R^{25}$)—S(O)$_2$—$R^{24}$, —C(O)—O—$R^{22}$, —S(O)—$R^{24}$, —S(O)$_2$—$R^{24}$, —S(O)—N($R^{22}$)—$R^{23}$, —S(O)$_2$—N($R^{22}$)—$R^{23}$, —S(O)$_2$—N($R^{25}$)—C(O)$R^{24}$, —S(O)$_2$—N($R^{25}$)—C(S)$R^{24}$, —N($R^{25}$)—C(O)—$R^{24}$, —N($R^{25}$)—C(S)—$R^{24}$, —N($R^{25}$)—S(O)—$R^{24}$, —N($R^{25}$)—S(O)$_2$—$R^{24}$, —N($R^{25}$)—C(O)—N($R^{22}$)—$R^{23}$, —N($R^{25}$)—C(S)—N($R^{22}$)—$R^{23}$, and —N($R^{25}$)—S(O)$_2$—N($R^{22}$)—$R^{23}$;
$R^5$ is selected from the group consisting of hydrogen, optionally substituted lower alkyl, optionally substituted lower alkenyl, optionally substituted lower alkynyl, optionally substituted cycloalkyl, optionally substituted heterocycloalkyl, optionally substituted aryl, optionally substituted heteroaryl, —CN, —NO$_2$, —O—$R^{28}$, —S—$R^{28}$, —C(O)—$R^{28}$, —C(S)—$R^{28}$, —C(O)—N($R^{26}$)—$R^{27}$, —C(S)—N($R^{26}$)—$R^{27}$, —C(O)—N($R^{29}$)—OR$^{26}$, —C(S)—N($R^{29}$)—OR$^{26}$, —C(O)—N($R^{29}$)—S(O)$_2$—$R^{28}$, —C(S)—N($R^{29}$)—S(O)$_2$—$R^{28}$, —C(O)—O—$R^{26}$, —S(O)—$R^{28}$, —S(O)$_2$—$R^{28}$, —S(O)—N($R^{26}$)—$R^{27}$, —S(O)$_2$—N($R^{26}$)—$R^{27}$, —S(O)$_2$—N($R^{29}$)—C(O)$R^{28}$, —S(O)$_2$—N($R^{29}$)—C(S)$R^{28}$, —N($R^{29}$)—C(O)—$R^{28}$, —N($R^{29}$)—C(S)—$R^{28}$, —N($R^{29}$)—S(O)—$R^{28}$, —N($R^{29}$)—S(O)$_2$—$R^{28}$, —N($R^{29}$)—C(O)—N($R^{26}$)—$R^{27}$, —N($R^{29}$)—C(S)—N($R^{26}$)—$R^{27}$, and —N($R^{29}$)—S(O)$_2$—N($R^{26}$)—$R^{27}$;
$R^6$ is selected from the group consisting of hydrogen, halogen, optionally substituted lower alkyl, optionally substituted lower alkenyl, optionally substituted lower alkynyl, optionally substituted cycloalkyl, optionally substituted heterocycloalkyl, optionally substituted aryl, optionally substituted heteroaryl, —CN, —NO$_2$, —O—$R^{30}$, —S—$R^{32}$, —N($R^{30}$)—$R^{31}$, —C(O)—$R^{32}$, —C(S)—$R^{32}$, —C(O)—N($R^{30}$)—$R^{31}$, —C(S)—N($R^{30}$)—$R^{31}$, —C(O)—N($R^{33}$)—O$R^{30}$, —C(S)—N($R^{33}$)—O$R^{30}$, —C(O)—N($R^{33}$)—S(O)$_2$—$R^{32}$, —C(S)—N($R^{33}$)—S(O)$_2$—$R^{32}$, —C(O)—O—$R^{30}$, —S(O)—$R^{32}$, —S(O)$_2$—$R^{32}$, —S(O)—N($R^{30}$)—$R^{31}$, —S(O)$_2$—N($R^{30}$)—$R^{31}$, —S(O)$_2$—N($R^{33}$)—C(O)$R^{32}$, —S(O)$_2$—N($R^{33}$)—C(S)$R^{32}$, —N($R^{33}$)—C(O)—$R^{32}$, —N($R^{33}$)—C(S)—$R^{32}$, —N($R^{33}$)—S(O)—$R^{32}$, —N($R^{33}$)—S(O)$_2$—$R^{32}$, —N($R^{33}$)—C(O)—N($R^{30}$)—$R^{31}$, —N($R^{33}$)—C(S)—N($R^{30}$)—$R^{31}$, and —N($R^{33}$)—S(O)$_2$—N($R^{30}$)—$R^{31}$;

$R^7$, $R^8$, $R^{10}$, and $R^{11}$, at each occurrence, are independently selected from the group consisting of hydrogen, fluoro, —OH, —NH$_2$, lower alkyl, lower alkoxy, lower alkylthio, mono-alkylamino, di-alkylamino, and —N($R^{34}$)—$R^{35}$, wherein the alkyl chain(s) of lower alkyl, lower alkoxy, lower alkylthio, mono-alkylamino, or di-alkylamino are optionally substituted with one or more substituents selected from the group consisting of fluoro, —OH, —NH$_2$, lower alkoxy, fluoro substituted lower alkoxy, lower alkylthio, fluoro substituted lower alkylthio, mono-alkylamino, di-alkylamino, and cycloalkylamino; or $R^7$ and $R^8$, or any two of $R^{10}$ and $R^{11}$ on the same or different carbons, combine to form a 3-7 membered monocyclic cycloalkyl or 5-7 membered monocyclic heterocycloalkyl and any others of $R^{10}$ and $R^{11}$ are independently selected from the group consisting of hydrogen, fluoro, —OH, —NH$_2$, lower alkyl, lower alkoxy, lower alklylthio, mono-alkylamino, di-alkylamino, and —N($R^{34}$)—$R^{35}$, wherein the alkyl chain(s) of lower alkyl, lower alkoxy, lower alkylthio, mono-alkylamino, or di-alkylamino are optionally substituted with one or more substituents selected from the group consisting of fluoro, —OH, —NH$_2$, lower alkoxy, fluoro substituted lower alkoxy, lower alkylthio, fluoro substituted lower alkylthio, mono-alkylamino, di-alkylamino, and cycloalkylamino, and wherein the 3-7 membered monocyclic cycloalkyl or 5-7 membered monocyclic heterocycloalkyl are optionally substituted with one or more substituents selected from the group consisting of halogen, —OH, —NH$_2$, lower alkyl, fluoro substituted lower alkyl, lower alkoxy, fluoro substituted lower alkoxy, lower alkylthio, fluoro substituted lower alkylthio, mono-alkylamino, di-alkylamino, and cycloalkylamino;

$R^9$, $R^{25}$, $R^{29}$, and $R^{33}$ are independently selected from the group consisting of hydrogen, optionally substituted lower alkyl, optionally substituted cycloalkyl, optionally substituted heterocycloalkyl, optionally substituted aryl, optionally substituted heteroaryl, —C(O)—$R^{36}$, —C(S)—$R^{36}$, —S(O)—$R^{36}$, —S(O)$_2$—$R^{36}$, —C(O)—N(H)—$R^{36}$, —C(S)—N(H)—$R^{36}$, and —S(O)$_2$—N(H)—$R^{36}$;

$R^{15}$ and $R^{16}$ are independently selected from the group consisting of hydrogen, halogen, optionally substituted lower alkyl, —N($R^{37}$)—$R^{38}$, —O—$R^{37}$, and —S—$R^{39}$;

$R^{18}$ at each occurrence is independently hydrogen, lower alkyl, or lower alkyl substituted with one or more substituents selected from the group consisting of fluoro, —OH, —NH$_{25}$ lower alkoxy, fluoro substituted lower alkoxy, lower alkylthio, fluoro substituted lower alkylthio, mono-alkylamino, fluoro substituted mono-alkylamino, di-alkylamino, fluoro substituted di-alkylamino, and —N($R^{34}$)—$R^{35}$;

$R^{19}$ is selected from the group consisting of optionally substituted cycloalkyl, optionally substituted heterocycloalkyl, optionally substituted aryl, and optionally substituted heteroaryl;

$R^{20}$ is selected from the group consisting of optionally substituted lower alkyl, optionally substituted lower alkenyl, and optionally substituted lower alkynyl;

$R^{21}$ is selected from the group consisting of hydrogen, optionally substituted lower alkyl, optionally substituted cycloalkyl, optionally substituted heterocycloalkyl, optionally substituted aryl, optionally substituted heteroaryl, and —O—$R^{40}$;

$R^{24}$, $R^{28}$ and $R^{32}$ are independently selected from the group consisting of optionally substituted lower alkyl, optionally substituted lower alkenyl, optionally substituted lower alkynyl, optionally substituted cycloalkyl, optionally substituted heterocycloalkyl, optionally substituted aryl, and optionally substituted heteroaryl;

$R^{22}$, $R^{23}$, $R^{26}$, $R^{27}$, $R^{30}$ and $R^{31}$ are independently selected from the group consisting of hydrogen, optionally substituted lower alkyl, optionally substituted lower alkenyl, optionally substituted lower alkynyl, optionally substituted cycloalkyl, optionally substituted heterocycloalkyl, optionally substituted aryl, and optionally substituted heteroaryl;

$R^{34}$ and $R^{35}$ at each occurrence combine with the nitrogen to which they are attached to form a 5-7 membered heterocycloalkyl optionally substituted with one or more substituents selected from the group consisting of fluoro, —OH, —NH$_2$, lower alkyl, fluoro substituted lower alkyl, lower alkoxy, fluoro substituted lower alkoxy, lower alkylthio, and fluoro substituted lower alkylthio;

$R^{36}$ at each occurrence is independently selected from the group consisting of optionally substituted lower alkyl, optionally substituted cycloalkyl, optionally substituted heterocycloalkyl, optionally substituted aryl, and optionally substituted heteroaryl;

$R^{37}$ and $R^{38}$ at each occurrence are independently hydrogen or optionally substituted lower alkyl; and $R^{39}$ and $R^{40}$ at each occurrence are independently optionally substituted lower alkyl.

2. The compound of claim 1, wherein:

$R^{20}$ is selected from the group consisting of lower alkyl, lower alkenyl, and lower alkynyl, wherein lower alkyl, lower alkenyl or lower alkynyl are optionally substituted with one or more substituents $R^{74}$;

$R^{21}$ is selected from the group consisting of hydrogen, lower alkyl optionally substituted with one or more substituents $R^{74}$, cycloalkyl, heterocycloalkyl, aryl, heteroaryl, and —O—$R^{73}$, wherein cycloalkyl, heterocycloalkyl, aryl or heteroaryl are optionally substituted with one or more substituents $R^{75}$;

$R^{19}$ is selected from the group consisting of cycloalkyl, heterocycloalkyl, aryl and heteroaryl, wherein cycloalkyl, heterocycloalkyl, aryl or heteroaryl are optionally substituted with one or more substituents $R^{75}$;

$R^{73}$ is lower alkyl optionally substituted with one or more substituents $R^{74}$;

$R^{74}$ at each occurrence is independently selected from the group consisting of —OH, —NH$_2$, —C(O)—OH, —S(O)—NH$_2$, —S(O)$_2$—NH$_2$, —C(O)—NH$_2$, —O—$R^{76}$, —S—$R^{76}$, —N($R^{77}$)—$R^{76}$, —N($R^{77}$)—C(O)—$R^{76}$, —N($R^{77}$)—S(O)—$R^{76}$, —N($R^{77}$)—S(O)$_2$—$R^{76}$, —C(O)—N($R^{77}$)—$R^{76}$, —C(O)—O—$R^{76}$, —C(O)—$R^{76}$, —S(O)—N($R^{77}$)—$R^{76}$, —S(O)$_2$—N($R^{77}$)—$R^{76}$, —S(O)—$R^{76}$, —S(O)$_2$—$R^{76}$, fluoro, cycloalkyl, heterocycloalkyl, aryl and heteroaryl, wherein cycloalkyl, heterocycloalkyl, aryl and heteroaryl are optionally substituted with one or more substituents $R^{75}$;

$R^{75}$ at each occurrence is independently selected from the group consisting of —OH, —NH$_2$, —NO$_2$, —CN, —C(O)—OH, —S(O)—NH$_2$, —S(O)$_2$—NH$_2$, —C(O)—NH$_2$, —O—R$^{76}$, —S—R$^{76}$, —N(R$^{77}$)—R$^{76}$, —N(R$^{77}$)—C(O)—R$^{76}$, —N(R$^{77}$)—S(O)—R$^{76}$, —N(R$^{77}$)—S(O)$_2$—R$^{76}$, —S(O)—R$^{76}$, —S(O)$_2$—R$^{76}$, —C(O)—R$^{76}$, —C(O)—O—R$^{76}$, —C(O)—N(R$^{77}$)—R$^{76}$, —S(O)—N(R$^{77}$)—R$^{76}$, —S(O)$_2$—N(R$^{77}$)—R$^{76}$, halogen, lower alkyl, cycloalkyl, heterocycloalkyl, aryl and heteroaryl, wherein lower alkyl is optionally substituted with one or more substituents selected from the group consisting of fluoro, lower alkoxy, fluoro substituted lower alkoxy, lower alkylthio, fluoro substituted lower alkylthio, mono-alkylamino, di-alkylamino, cycloalkyl, heterocycloalkyl, aryl, and heteroaryl, and wherein cycloalkyl, heterocycloalkyl, aryl, and heteroaryl as $R^{75}$, or as substituents of lower alkyl, are optionally substituted with one or more substituents selected from the group consisting of —OH, —NH$_2$, —NO$_2$, —CN, —C(O)—OH, —S(O)$_2$—NH$_2$, —C(O)—NH$_2$, —O—R$^{78}$, —S—R$^{78}$, —N(R$^{77}$)—R$^{78}$, —N(R$^{77}$)—C(O)—R$^{78}$, —N(R$^{77}$)—S(O)$_2$—R$^{78}$, —S(O)—R$^{78}$, —S(O)$_2$—R$^{78}$, —C(O)—R$^{78}$, —C(O)—O—R$^{78}$, —C(O)—N(R$^{77}$)—R$^{78}$, —S(O)$_2$—N(R$^{77}$)—R$^{78}$, halogen, lower alkyl, fluoro substituted lower alkyl, and cycloalkylamino;

$R^{76}$ at each occurrence is independently selected from the group consisting of lower alkyl, cycloalkyl, heterocycloalkyl, aryl and heteroaryl, wherein lower alkyl is optionally substituted with one or more substituents selected from the group consisting of fluoro, lower alkoxy, fluoro substituted lower alkoxy, lower alkylthio, fluoro substituted lower alkylthio, mono-alkylamino, di-alkylamino, cycloalkyl, heterocycloalkyl, aryl, and heteroaryl, and wherein cycloalkyl, heterocycloalkyl, aryl, and heteroaryl as $R^{76}$ or as substituents of lower alkyl are optionally substituted with one or more substituents selected from the group consisting of —OH, —NH$_2$, —CN, —NO$_2$, —C(O)—OH, —S(O)$_2$—NH$_2$, —C(O)—NH$_2$, —O—R$^{80}$, —S—R$^{80}$, —N(R$^{79}$)—R$^{80}$, —N(R$^{79}$)—C(O)—R$^{80}$, —N(R$^{79}$)—S(O)$_2$—R$^{80}$, —C(O)—R$^{80}$, —S(O)—R$^{80}$, —S(O)$_2$—R$^{80}$, —C(O)—O—R$^{80}$, —C(O)—N(R$^{79}$)—R$^{80}$, —S(O)$_2$—N(R$^{79}$)—R$^{80}$, halogen, lower alkyl, fluoro substituted lower alkyl, and cycloalkylamino;

$R^{77}$ and $R^{79}$ at each occurrence are independently hydrogen, lower alkyl, or lower alkyl substituted with one or more substituents selected from the group consisting of fluoro, —OH, —NH$_2$, lower alkoxy, fluoro substituted lower alkoxy, lower alkylthio, fluoro substituted lower alkylthio, mono-alkylamino, fluoro substituted mono-alkylamino, di-alkylamino, fluoro substituted di-alkylamino, and cycloalkylamino; and $R^{78}$ and $R^{80}$ at each occurrence are independently selected from the group consisting of lower alkyl, heterocycloalkyl and heteroaryl, wherein lower alkyl is optionally substituted with one or more substituents selected from the group consisting of fluoro, lower alkoxy, fluoro substituted lower alkoxy, lower alkylthio, fluoro substituted lower alkylthio, mono-alkylamino, di-alkylamino, and cycloalkylamino, and wherein heterocycloalkyl and heteroaryl are optionally substituted with one or more substituents selected from the group consisting of halogen, —CN, lower alkyl, fluoro substituted lower alkyl, lower alkoxy and fluoro substituted lower alkoxy.

3. The compound of claim 2, wherein:

$R^{75}$ at each occurrence is independently selected from the group consisting of —OH, —NH$_2$, —NO$_2$, —CN, —O—R$^{76}$, —S—R$^{76}$, —N(R$^{77}$)—R$^{76}$, —N(R$^{77}$)—C(O)—R$^{76}$, —N(R$^{77}$)—S(O)—R$^{76}$, —N(R$^{77}$)—S(O)$_2$—R$^{76}$, —C(O)—R$^{76}$, —S(O)—R$^{76}$, —S(O)$_2$—R$^{76}$, halogen, lower alkyl, cycloalkyl, heterocycloalkyl, aryl and heteroaryl, wherein lower alkyl is optionally substituted with one or more substituents selected from the group consisting of fluoro, lower alkoxy, fluoro substituted lower alkoxy, lower alkylthio, fluoro substituted lower alkylthio, mono-alkylamino, di-alkylamino, cycloalkyl, heterocycloalkyl, aryl, and heteroaryl, and wherein cycloalkyl, heterocycloalkyl, aryl, and heteroaryl as $R^{75}$, or as substituents of lower alkyl, are optionally substituted with one or more substituents selected from the group consisting of —OH, —NH$_2$, —NO$_2$, —CN, —O—R$^{78}$, —S—R$^{78}$, —N(R$^{77}$)—R$^{78}$, —N(R$^{77}$)—C(O)—R$^{78}$, —N(R$^{77}$)—S(O)$_2$—R$^{78}$, —S(O)—R$^{78}$, —S(O)$_2$—R$^{78}$, —C(O)—R$^{78}$, halogen, lower alkyl, fluoro substituted lower alkyl, and cycloalkylamino;

$R^{76}$ at each occurrence is independently selected from the group consisting of lower alkyl, cycloalkyl, heterocycloalkyl, aryl and heteroaryl, wherein lower alkyl is optionally substituted with one or more substituents selected from the group consisting of fluoro, lower alkoxy, fluoro substituted lower alkoxy, lower alkylthio, fluoro substituted lower alkylthio, mono-alkylamino, di-alkylamino, cycloalkyl, heterocycloalkyl, aryl, and heteroaryl, and wherein cycloalkyl, heterocycloalkyl, aryl, and heteroaryl as $R^{76}$ or as substituents of lower alkyl are optionally substituted with one or more substituents selected from the group consisting of —OH, —NH$_2$, —CN, —NO$_2$, —C(O)—OH, —S(O)$_2$—NH$_2$, —C(O)—NH$_2$, —O—R$^{80}$, —S—R$^{80}$, —N(R$^{79}$)—R$^{80}$, —N(R$^{79}$)—C(O)—R$^{80}$, —N(R$^{79}$)—S(O)$_2$—R$^{80}$, —C(O)—R$^{80}$, —S(O)—R$^{80}$, —S(O)$_2$—R$^{80}$, —C(O)—O—R$^{80}$, —C(O)—N(R$^{79}$)—R$^{80}$, —S(O)$_2$—N(R$^{79}$)—R$^{80}$, halogen, lower alkyl, fluoro substituted lower alkyl, and cycloalkylamino;

$R^{77}$ and $R^{79}$ at each occurrence are independently hydrogen, lower alkyl, or lower alkyl substituted with one or more substituents selected from the group consisting of fluoro, —OH, —NH$_2$, lower alkoxy, fluoro substituted lower alkoxy, lower alkylthio, fluoro substituted lower alkylthio, mono-alkylamino, fluoro substituted mono-alkylamino, di-alkylamino, fluoro substituted di-alkylamino, and cycloalkylamino; and $R^{78}$ and $R^{80}$ at each occurrence are independently selected from the group consisting of lower alkyl, heterocycloalkyl and heteroaryl, wherein lower alkyl is optionally substituted with one or more substituents selected from the group consisting of fluoro, lower alkoxy, fluoro substituted lower alkoxy, lower alkylthio, fluoro substituted lower alkylthio, mono-alkylamino, di-alkylamino, and cycloalkylamino, and wherein heterocycloalkyl and heteroaryl are optionally substituted with one or more substituents selected from the group consisting of halogen, —CN, lower alkyl, fluoro substituted lower alkyl, lower alkoxy and fluoro substituted lower alkoxy.

4. The compound of claim 3, wherein:

$R^4$ is selected from the group consisting of hydrogen, —CN, —O—R$^{100}$, —S—R$^{100}$, —N(R$^{101}$)—R$^{100}$, and lower alkyl, wherein lower alkyl is optionally substituted with one or more substituents selected from the group consisting of fluoro, lower alkoxy, fluoro substituted lower alkoxy, lower alkylthio, fluoro substituted lower alkylthio, mono-alkylamino, di-alkylamino, and cycloalkylamino;

$R^5$ is selected from the group consisting of hydrogen, —CN, —O—$R^{100}$, —S—$R^{100}$, and lower alkyl, wherein lower alkyl is optionally substituted with one or more substituents selected from the group consisting of fluoro, lower alkoxy, fluoro substituted lower alkoxy, lower alkylthio, fluoro substituted lower alkylthio, mono-alkylamino, di-alkylamino, and cycloalkylamino;

$R^6$ is hydrogen;

$R^{100}$ is lower alkyl optionally substituted with one or more substituents selected from the group consisting of fluoro, lower alkoxy, fluoro substituted lower alkoxy, lower alkylthio, fluoro substituted lower alkylthio, mono-alkylamino, di-alkylamino, and cycloalkylamino; and $R^{101}$ is hydrogen or lower alkyl optionally substituted with one or more substituents selected from the group consisting of fluoro, lower alkoxy, fluoro substituted lower alkoxy, lower alkylthio, fluoro substituted lower alkylthio, mono-alkylamino, di-alkylamino, and cycloalkylamino.

5. A compound having the chemical structure of Formula Ia,

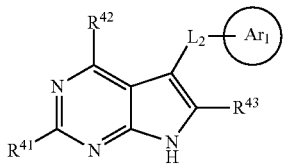

Formula Ia or a salt, a tautomer or a stereoisomer thereof,
wherein:
$L_2$ is selected from the group consisting of —C($R^{44}R^{45}$)—, —C(O)—, —C(S)—, —N($R^{46}$)—, —O—, —S—, —S(O)—, and —S(O)$_2$—;

$Ar_1$ is

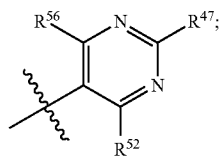

wherein

indicates the point of attachment of $Ar_1$ to $L_2$ of Formula Ia;
$R^{47}$ is selected from the group consisting of a bond, —C($R^{49}R^{50}$)—$R^{58}$, —[C($R^{49}R^{50}$)]$_2$—$R^{58}$, —N($R^{51}$)—C($R^{49}R^{50}$)—$R^{58}$, —N($R^{51}$)— [C($R^{49}R^{50}$)]$_2$—$R^{58}$, —N($R^{51}$)—[C($R^{49}R^{50}$)]$_3$—$R^{58}$, —C($R^{49}R^{50}$)—N($R^{51}$)—$R^{58}$, —O—, —O—C($R^{49}R^{50}$)—$R^{58}$, —O—[C($R^{49}R^{50}$)]$_2$—$R^{58}$, —O—[C($R^{49}R^{50}$)]$_3$—$R^{58}$, —C($R^{49}R^{50}$)—O—$R^{58}$, —S—$R^{58}$, —S—C($R^{49}R^{50}$)—$R^{58}$, —S—[C($R^{49}R^{50}$)]$_2$—$R^{58}$, —S—[C($R^{49}R^{50}$)]$_3$—$R^{58}$, —C($R^{49}R^{50}$)—S—$R^{58}$, —C(O)—N($R^{51}$)—$R^{58}$, —C(O)—N($R^{51}$)—C($R^{49}R^{50}$)—$R^{58}$, —C(O)—N($R^{51}$)—[C($R^{49}R^{50}$)]$_2$—$R^{58}$, —C(S)—N($R^{51}$)—$R^{58}$, —C(S)—N($R^{51}$)—C($R^{49}R^{50}$)—$R^{58}$, —C(S)—N($R^{51}$)—[C($R^{49}R^{50}$)]$_2$—$R^{58}$, —S(O)—N($R^{51}$)—$R^{58}$, —S(O)—N($R^{51}$)—C($R^{49}R^{50}$)—$R^{58}$, —S(O)—N($R^{51}$)—[C($R^{49}R^{50}$)]$_2$—$R^{58}$, —S(O)$_2$—N($R^{51}$)—$R^{58}$, —S(O)$_2$—N($R^{51}$)—C($R^{49}R^{50}$)—$R^{58}$, —S(O)$_2$—N($R^{51}$))—[C($R^{49}R^{50}$)]$_2$—$R^{58}$, —N($R^{51}$)—C(O)—$R^{58}$, —N($R^{51}$)—C(O)—C($R^{49}R^{50}$)—$R^{58}$, —N($R^{51}$)—C(O)—[C($R^{49}R^{50}$)]$_2$—$R^{58}$, —N($R^{51}$)—C(S)—$R^{58}$, —N($R^{51}$)—C(S)—C($R^{49}R^{50}$)—$R^{58}$, —N($R^{51}$)—C(S)—[C($R^{49}R^{50}$)]$_2$—$R^{58}$, —N($R^{51}$)—S(O)—$R^{58}$, —N($R^{51}$)—S(O)—C($R^{49}R^{50}$)—$R^{58}$, —N($R^{51}$)—S(O)—[C($R^{49}R^{50}$)]$_2$—$R^{58}$, —N($R^{51}$)—S(O)$_2$—$R^{58}$, —N($R^{51}$)—S(O)$_2$—C($R^{49}R^{50}$)—$R^{58}$, —N($R^{51}$)—S(O)$_2$—[C($R^{49}R^{50}$)]$_2$—$R^{58}$, —N($R^{51}$)—C(O)—N($R^{51}$)—$R^{58}$, —N($R^{51}$)—C(O)—N($R^{51}$)—C($R^{49}R^{50}$)—$R^{58}$, —N($R^{51}$)—C(O)—N($R^{51}$)—[C($R^{49}R^{50}$)]$_2$—$R^{58}$, —N($R^{51}$)—C(S)—N($R^{51}$)—$R^{58}$, —N($R^{51}$)—C(S)—N($R^{51}$)—C($R^{49}R^{50}$)—$R^{58}$, —N($R^{51}$)—C(S)—N($R^{51}$)—[C($R^{49}R^{50}$)]$_2$—$R^{58}$, —N($R^{51}$)—S(O)$_2$—N($R^{51}$)—$R^{58}$, —N($R^{51}$)—S(O)$_2$—N($R^{51}$)—)C($R^{49}R^{50}$)—$R^{58}$, and —N($R^{51}$)—S(O)$_2$—N($R^{51}$)—[C($R^{49}R^{50}$)]$_2$—$R^{58}$;

$R^{41}$ is selected from the group consisting of hydrogen, —OH, —NH$_2$, —CN, —NO$_2$, —C(O)—OH, —S(O)—NH$_2$, —S(O)$_2$—NH$_2$, —C(O)—NH$_2$, —O—$R^{59}$, —S—$R^{59}$, —N($R^{60}$)—$R^{59}$, —N($R^{60}$)—C(O)—$R^{59}$, —N($R^{60}$)—S(O)—$R^{59}$, —N($R^{60}$)—S(O)$_2$—$R^{59}$, —C(O)—N($R^{60}$)—$R^{59}$, —C(O)—O—$R^{59}$, —C(O)—$R^{59}$, —S(O)—N($R^{60}$)—$R^{59}$, —S(O)$_2$—N($R^{60}$)—$R^{59}$, —S(O)—$R^{59}$, —S(O)$_2$—$R^{59}$, lower alkyl, cycloalkyl, heterocycloalkyl, aryl and heteroaryl, wherein lower alkyl is optionally substituted with one or more substituents selected from the group consisting of fluoro, lower alkoxy, fluoro substituted lower alkoxy, lower alkylthio, fluoro substituted lower alkylthio, mono-alkylamino, di-alkylamino, cycloalkyl, heterocycloalkyl, aryl, and heteroaryl, wherein cycloalkyl, heterocycloalkyl, aryl, and heteroaryl as $R^{41}$ or as substituents of lower alkyl are optionally substituted with one or more substituents selected from the group consisting of —OH, —NH$_2$, —CN, —NO$_2$, —C(O)—OH, —S(O)—NH$_2$, —S(O)$_2$—NH$_2$, —C(O)—NH$_2$, —O—$R^{61}$, —S—$R^{61}$, —N($R^{60}$)—$R^{61}$, —N($R^{60}$)—C(O)—$R^{61}$, —N($R^{60}$)—S(O)—$R^{61}$, —N($R^{60}$)—S(O)$_2$—$R^{61}$, —C(O)—$R^{61}$, —S(O)—$R^{61}$, —S(O)$_2R^{61}$, —C(O)—O—$R^{61}$, —C(O)—N($R^{60}$)$R^{61}$, —S(O)—N($R^{60}$)—$R^{61}$, —S(O)$_2$—N($R^{60}$)—$R^{61}$, halogen, lower alkyl, fluoro substituted lower alkyl, and cycloalkylamino;

$R^{42}$ is selected from the group consisting of hydrogen, —CN, —NO$_2$, —C(O)—OH, —S(O)—NH$_2$, —S(O)$_2$—NH$_2$, —C(O)—NH$_2$, —O—$R^{62}$, —S—$R^{62}$, —N($R^{63}$)—C(O)—$R^{62}$, —N($R^{63}$)—S(O)—$R^{62}$, —N($R^{63}$)—S(O)$_2$—$R^{62}$, —C(O)—N($R^{63}$)—$R^{62}$, —C(O)—O—$R^{62}$, —C(O)—$R^{62}$, —S(O)—N($R^{63}$)—$R^{62}$, —S(O)$_2$—N($R^{63}$)—$R^{62}$, —S(O)—$R^{62}$, —S(O)$_2$—$R^{62}$, lower alkyl, cycloalkyl, heterocycloalkyl, aryl and heteroaryl, wherein lower alkyl is optionally substituted with one or more substituents selected from the group consisting of fluoro, lower alkoxy, fluoro substituted lower alkoxy, lower alkylthio, fluoro substituted lower alkylthio, mono-alkylamino, di-alkylamino, cycloalkyl, heterocycloalkyl, aryl, and heteroaryl, wherein cycloalkyl, heterocycloalkyl, aryl, and heteroaryl as $R^{42}$ or as substituents of lower alkyl are optionally substituted with one or more substituents selected from the group consisting of —OH, —NH$_2$, —CN, —NO$_2$, —C(O)—OH, —S(O)—NH$_2$, —S(O)$_2$—NH$_2$, —C(O)—NH$_2$, —O—R$^{64}$, —S—R$^{64}$, —N(R$^{63}$)—R$^{64}$, —N(R$^{63}$)—C(O)—R$^{64}$, —N(R$^{63}$)—S(O)—R$^{64}$, —N(R$^{63}$)—S(O)$_2$—R$^{64}$, —C(O)—R$^{64}$, —S(O)—R$^{64}$, —S(O)$_2$—R$^{64}$, —C(O)—O—R$^{64}$, —C(O)—N(R$^{63}$)—R$^{64}$, —S(O)—N(R$^{63}$)—R$^{64}$, —S(O)$_2$—N(R$^{63}$)—R$^{64}$, halogen, lower alkyl, fluoro substituted lower alkyl, and cycloalkylamino;

$R^{43}$ is independently selected from the group consisting of hydrogen, —OH, —NH$_2$, —CN, —NO$_2$, —C(O)—OH, —S(O)—NH$_2$, —S(O)$_2$—NH$_2$, —C(O)—NH$_2$, —O—R$^{65}$, —S—R$^{65}$, —N(R$^{66}$)—R$^{65}$, —N(R$^{66}$)—C(O)—R$^{65}$, —N(R$^{66}$)—S(O)—R$^{65}$, —N(R$^{66}$)—S(O)$_2$—R$^{65}$, —C(O)—N(R$^{66}$)—R$^{65}$, —C(O)—O—R$^{65}$, —C(O)—R$^{65}$, —S(O)—N(R$^{66}$)—R$^{65}$, —S(O)$_2$—N(R$^{66}$)—R$^{65}$, —S(O)—R$^{65}$, —S(O)$_2$—R$^{65}$, halogen, lower alkyl, cycloalkyl, heterocycloalkyl, aryl and heteroaryl, wherein lower alkyl is optionally substituted with one or more substituents selected from the group consisting of fluoro, lower alkoxy, fluoro substituted lower alkoxy, lower alkylthio, fluoro substituted lower alkylthio, mono-alkylamino, di-alkylamino, cycloalkyl, heterocycloalkyl, aryl, and heteroaryl, wherein cycloalkyl, heterocycloalkyl, aryl, and heteroaryl as $R^{43}$ or as substituents of lower alkyl are optionally substituted with one or more substituents selected from the group consisting of —OH, —NH$_2$, —CN, —NO$_2$, —C(O)—OH, —S(O)—NH$_2$, —S(O)$_2$—NH$_2$, —C(O)—NH$_2$, —O—R$^{67}$, —S—R$^{67}$, —N(R$^{66}$)—R$^{67}$, —N(R$^{66}$)—C(O)—R$^{67}$, —N(R$^{66}$)—S(O)—R$^{67}$, —N(R$^{66}$)—S(O)$_2$—R$^{67}$, —C(O)—R$^{67}$, —S(O)—R$^{67}$, —S(O)$_2$—R$^{67}$, —C(O)—O—R$^{67}$, —C(O)—N(R$^{66}$)—R$^{67}$, —S(O)—N(R$^{66}$)—R$^{67}$, —S(O)$_2$—N(R$^{66}$)—R$^{67}$, halogen, lower alkyl, fluoro substituted lower alkyl, and cycloalkylamino;

$R^{58}$ is selected from the group consisting of optionally substituted cycloalkyl, optionally substituted heterocycloalkyl, optionally substituted aryl or optionally substituted heteroaryl;

$R^{44}$, $R^{45}$, $R^{49}$ and $R^{50}$ at each occurrence are independently selected from the group consisting of hydrogen, fluoro, lower alkyl, fluoro substituted lower alkyl, lower alkoxy, fluoro substituted lower alkoxy, lower alkylthio, fluoro substituted lower alkylthio, mono-alkylamino, di-alkylamino, and cycloalkylamino; or $R^{44}$ and $R^{45}$, or any two of $R^{49}$ and $R^{50}$ on the same or different carbons, combine to form a 3-7 membered monocyclic cycloalkyl or 5-7 membered monocyclic heterocycloalkyl, and any others of $R^{49}$ and $R^{50}$ are independently selected from the group consisting of hydrogen, fluoro, lower alkyl, fluoro substituted lower alkyl, lower alkoxy, fluoro substituted lower alkoxy, lower alkylthio, fluoro substituted lower alkylthio, mono-alkylamino, di-alkylamino, and cycloalkylamino, wherein the 3-7 membered monocyclic cycloalkyl or 5-7 membered monocyclic heterocycloalkyl is optionally substituted with one or more substituents selected from the group consisting of halogen, —OH, —NH$_2$, lower alkyl, fluoro substituted lower alkyl, lower alkoxy, fluoro substituted lower alkoxy, lower alkylthio, fluoro substituted lower alkylthio, mono-alkylamino, di-alkylamino, and cycloalkylamino;

$R^{52}$, and $R^{56}$ are independently selected from the group consisting of halogen, lower alkyl, —N(R$^{70}$)—R$^{71}$, —O—R$^{70}$, and —S—R$^{72}$, wherein lower alkyl is optionally substituted with one or more substituents selected from the group consisting of fluoro, —OH, —NH$_2$, lower alkoxy, fluoro substituted lower alkoxy, lower alkylthio, fluoro substituted lower alkylthio, mono-alkylamino, fluoro substituted mono-alkylamino, di-alkylamino, fluoro substituted di-alkylamino, and cycloalkylamino;

$R^{59}$, $R^{62}$, and $R^{65}$ are independently selected from the group consisting of lower alkyl, cycloalkyl, heterocycloalkyl, aryl and heteroaryl, wherein lower alkyl is optionally substituted with one or more substituents selected from the group consisting of fluoro, lower alkoxy, fluoro substituted lower alkoxy, lower alkylthio, fluoro substituted lower alkylthio, mono-alkylamino, di-alkylamino, cycloalkyl, heterocycloalkyl, aryl, and heteroaryl, and wherein cycloalkyl, heterocycloalkyl, aryl, and heteroaryl as $R^{59}$, $R^{62}$, or $R^{65}$ or as substituents of lower alkyl are optionally substituted with one or more substituents selected from the group consisting of —OH, —NH$_2$, —CN, —NO$_2$, —C(O)—OH, —S(O)—NH$_2$, —S(O)$_2$—NH$_2$, —C(O)—NH$_2$, —O—R$^{69}$, —S—R$^{69}$, —N(R$^{68}$)—R$^{69}$, —N(R$^{68}$)—C(O)—R$^{69}$, —N(R$^{68}$)—S(O)—R$^{69}$, —N(R$^{68}$)—S(O)$_2$—R$^{69}$, —C(O)—R$^{69}$, —S(O)—R$^{69}$, —S(O)$_2$—R$^{69}$, —C(O)—O—R$^{69}$, —C(O)—N(R$^{68}$)—R$^{69}$, —S(O)—N(R$^{68}$)—R$^{69}$, —S(O)$_2$—N(R$^{68}$)—R$^{69}$, halogen, lower alkyl, fluoro substituted lower alkyl, and cycloalkylamino;

$R^{46}$, $R^{51}$, $R^{60}$, $R^{63}$, $R^{66}$ and $R^{68}$ at each occurrence are independently hydrogen, lower alkyl, or lower alkyl substituted with one or more substituents selected from the group consisting of fluoro, —OH, —NH$_2$, lower alkoxy, fluoro substituted lower alkoxy, lower alkylthio, fluoro substituted lower alkylthio, mono-alkylamino, fluoro substituted mono-alkylamino, di-alkylamino, fluoro substituted di-alkylamino, and cycloalkylamino;

$R^{61}$, $R^{64}$, $R^{67}$ and $R^{69}$ at each occurrence are independently selected from the group consisting of lower alkyl, heterocycloalkyl and heteroaryl, wherein lower alkyl is optionally substituted with one or more substituents selected from the group consisting of fluoro, lower alkoxy, fluoro substituted lower alkoxy, lower alkylthio, fluoro substituted lower alkylthio, mono-alkylamino, di-alkylamino, and cycloalkylamino, and wherein heterocycloalkyl and heteroaryl are optionally substituted with one or more substituents selected from the group consisting of halogen, —CN, lower alkyl, fluoro substituted lower alkyl, lower alkoxy and fluoro substituted lower alkoxy;

$R^{70}$ and $R^{71}$ at each occurrence are independently hydrogen, lower alkyl or lower alkyl substituted with one or more substituents selected from the group consisting of fluoro, —OH, —NH$_2$, lower alkoxy, fluoro substituted lower alkoxy, lower alkylthio, fluoro substituted lower alkylthio, mono-alkylamino, fluoro substituted mono-alkylamino, di-alkylamino, fluoro substituted di-alkylamino, and cycloalkylamino; and $R^{72}$ at each occurrence is lower alkyl or lower alkyl substituted with one or more substituents selected from the group consisting of fluoro, —OH, —NH$_2$, lower alkoxy, fluoro substituted lower alkoxy, lower alkylthio, fluoro substituted lower alkylthio, mono-alkylamino, fluoro substituted mono-alkylamino, di-alkylamino, fluoro substituted di-alkylamino, and cycloalkylamino.

6. The compound of claim 5, wherein:

$R^{58}$ is selected from the group consisting of cycloalkyl, heterocycloalkyl, aryl and heteroaryl, wherein cycloalkyl, heterocycloalkyl, aryl or heteroaryl are optionally substituted with one or more substituents $R^{75}$;

$R^{75}$ at each occurrence is independently selected from the group consisting of —OH, —NH$_2$, —NO$_2$, —CN, —C(O)—OH, —S(O)—NH$_2$, —S(O)$_2$—NH$_2$, —C(O)—NH$_2$, —O—R$^{76}$, —S—R$^{76}$, —N(R$^{77}$)—R$^{76}$, —N(R$^{77}$)—C(O)—R$^{76}$, —N(R$^{77}$)—S(O)—R$^{76}$, —N(R$^{77}$)—S(O)$_2$—R$^{76}$, —S(O)—R$^{76}$, —S(O)$_2$—R$^{76}$, —C(O)—R$^{76}$, —C(O)—O—R$^{76}$, —C(O)—N(R$^{77}$)—R$^{76}$, —S(O)—N(R$^{77}$)—R$^{76}$, —S(O)$_2$—N(R$^{77}$)—R$^{76}$, halogen, lower alkyl, cycloalkyl, heterocycloalkyl, aryl and heteroaryl, wherein lower alkyl is optionally substituted with one or more substituents selected from the group consisting of fluoro, lower alkoxy, fluoro substituted lower alkoxy, lower alkylthio, fluoro substituted lower alkylthio, mono-alkylamino, di-alkylamino, cycloalkyl, heterocycloalkyl, aryl, and heteroaryl, and wherein cycloalkyl, heterocycloalkyl, aryl, and heteroaryl as $R^{75}$, or as substituents of lower alkyl, are optionally substituted with one or more substituents selected from the group consisting of —OH, —NH$_2$, —NO$_2$, —CN, —C(O)—OH, —S(O)$_2$—NH$_2$, —C(O)—NH$_2$, —O—R$^{78}$, —S—R$^{78}$, —N(R$^{77}$)—R$^{78}$, —N(R$^{77}$)—C(O)—R$^{78}$, —N(R$^{77}$)—S(O)$_2$—R$^{78}$, —S(O)—R$^{78}$, —S(O)$_2$—R$^{78}$, —C(O)—R$^{78}$, —C(O)—O—R$^{78}$, —C(O)—N(R$^{77}$)—R$^{78}$, —S(O)$_2$—N(R$^{77}$)—R$^{78}$, halogen, lower alkyl, fluoro substituted lower alkyl, and cycloalkylamino;

$R^{76}$ at each occurrence is independently selected from the group consisting of lower alkyl, cycloalkyl, heterocycloalkyl, aryl and heteroaryl, wherein lower alkyl is optionally substituted with one or more substituents selected from the group consisting of fluoro, lower alkoxy, fluoro substituted lower alkoxy, lower alkylthio, fluoro substituted lower alkylthio, mono-alkylamino, di-alkylamino, cycloalkyl, heterocycloalkyl, aryl, and heteroaryl, and wherein cycloalkyl, heterocycloalkyl, aryl, and heteroaryl as $R^{76}$ or as substituents of lower alkyl are optionally substituted with one or more substituents selected from the group consisting of —OH, —NH$_2$, —CN, —NO$_2$, —C(O)—OH, —S(O)$_2$—NH$_2$, —C(O)—NH$_2$, —O—R$^{80}$, —S—R$^{80}$, —N(R$^{79}$)—R$^{80}$, —N(R$^{79}$)—C(O)—R$^{80}$, —N(R$^{79}$)—S(O)$_2$—R$^{80}$, —C(O)—R$^{80}$, —S(O)—R$^{80}$, —S(O)$_2$—R$^{80}$, —C(O)—O—R$^{80}$, —C(O)—N(R$^{79}$)—R$^{80}$, —S(O)$_2$—N(R$^{79}$)—R$^{80}$, halogen, lower alkyl, fluoro substituted lower alkyl, and cycloalkylamino;

$R^{77}$ and $R^{79}$ at each occurrence are independently hydrogen, lower alkyl, or lower alkyl substituted with one or more substituents selected from the group consisting of fluoro, —OH, —NH$_2$, lower alkoxy, fluoro substituted lower alkoxy, lower alkylthio, fluoro substituted lower alkylthio, mono-alkylamino, fluoro substituted mono-alkylamino, di-alkylamino, fluoro substituted di-alkylamino, and cycloalkylamino; and $R^{78}$ and $R^{80}$ at each occurrence are independently selected from the group consisting of lower alkyl, heterocycloalkyl and heteroaryl, wherein lower alkyl is optionally substituted with one or more substituents selected from the group consisting of fluoro, lower alkoxy, fluoro substituted lower alkoxy, lower alkylthio, fluoro substituted lower alkylthio, mono-alkylamino, di-alkylamino, and cycloalkylamino, and wherein heterocycloalkyl and heteroaryl are optionally substituted with one or more substituents selected from the group consisting of halogen, —CN, lower alkyl, fluoro substituted lower alkyl, lower alkoxy and fluoro substituted lower alkoxy.

7. The compound of claim 6, wherein:

$R^{75}$ at each occurrence is independently selected from the group consisting of —OH, —NH$_2$, —NO$_2$, —CN, —O—R$^{76}$, —S—R$^{76}$, —N(R$^{77}$)—R$^{76}$, —N(R$^{77}$)—C(O)—R$^{76}$, —N(R$^{77}$)—S(O)—R$^{76}$, —N(R$^{77}$)—S(O)$_2$—R$^{76}$, —C(O)—R$^{76}$, —S(O)—R$^{76}$, —S(O)$_2$—R$^{76}$, halogen, lower alkyl, cycloalkyl, heterocycloalkyl, aryl and heteroaryl, wherein lower alkyl is optionally substituted with one or more substituents selected from the group consisting of fluoro, lower alkoxy, fluoro substituted lower alkoxy, lower alkylthio, fluoro substituted lower alkylthio, mono-alkylamino, di-alkylamino, cycloalkyl, heterocycloalkyl, aryl, and heteroaryl, and wherein cycloalkyl, heterocycloalkyl, aryl, and heteroaryl as $R^{75}$, or as substituents of lower alkyl, are optionally substituted with one or more substituents selected from the group consisting of —OH, —NH$_2$, —NO$_2$, —CN, —O—R$^{78}$, —S—R$^{78}$, —N(R$^{77}$)—R$^{78}$, —N(R$^{77}$)—C(O)—R$^{78}$, —N(R$^{77}$)—S(O)$_2$—R$^{78}$, —S(O)—R$^{78}$, —S(O)$_2$—R$^{78}$, —C(O)—R$^{78}$, halogen, lower alkyl, fluoro substituted lower alkyl, and cycloalkylamino;

$R^{76}$ at each occurrence is independently selected from the group consisting of lower alkyl, cycloalkyl, heterocycloalkyl, aryl and heteroaryl, wherein lower alkyl is optionally substituted with one or more substituents selected from the group consisting of fluoro, lower alkoxy, fluoro substituted lower alkoxy, lower alkylthio, fluoro substituted lower alkylthio, mono-alkylamino, di-alkylamino, cycloalkyl, heterocycloalkyl, aryl, and heteroaryl, and wherein cycloalkyl, heterocycloalkyl, aryl, and heteroaryl as $R^{76}$ or as substituents of lower alkyl are optionally substituted with one or more substituents selected from the group consisting of —OH, —NH$_2$, —CN, —NO$_2$, —C(O)—OH, —S(O)$_2$—NH$_2$, —C(O)—NH$_2$, —O—R$^{80}$, —S—R$^{80}$, —N(R$^{79}$)—R$^{80}$, —N(R$^{79}$)—C(O)—R$^{80}$, —N(R$^{79}$)—S(O)$_2$—R$^{80}$, —C(O)—R$^{80}$, —S(O)—R$^{80}$, —S(O)$_2$—R$^{80}$, —C(O)—O—R$^{80}$, —C(O)—N(R$^{79}$)—R$^{80}$, —S(O)$_2$—N(R$^{79}$)—R$^{80}$, halogen, lower alkyl, fluoro substituted lower alkyl, and cycloalkylamino;

$R^{77}$ and $R^{79}$ at each occurrence are independently hydrogen, lower alkyl, or lower alkyl substituted with one or more substituents selected from the group consisting of fluoro, —OH, —NH$_2$, lower alkoxy, fluoro substituted lower alkoxy, lower alkylthio, fluoro substituted lower alkylthio, mono-alkylamino, fluoro substituted mono-alkylamino, di-alkylamino, fluoro substituted di-alkylamino, and cycloalkylamino; and $R^{78}$ and $R^{80}$ at each occurrence are independently selected from the group consisting of lower alkyl, heterocycloalkyl and heteroaryl, wherein lower alkyl is optionally substituted with one or more substituents selected from the group consisting of fluoro, lower alkoxy, fluoro substituted lower alkoxy, lower alkylthio, fluoro substituted lower alkylthio, mono-alkylamino, di-alkylamino, and cycloalkylamino, and wherein heterocycloalkyl and heteroaryl are optionally substituted with one or more substituents selected from the group consisting of halogen, —CN, lower alkyl, fluoro substituted lower alkyl, lower alkoxy and fluoro substituted lower alkoxy.

8. The compound of claim 7, wherein:

$R^{41}$ is selected from the group consisting of hydrogen, —CN, —O—R$^{100}$, —S—R$^{100}$, —N(R$^{101}$)—R$^{100}$, and lower alkyl, wherein lower alkyl is optionally substituted with one or more substituents selected from the group consisting of fluoro, lower alkoxy, fluoro substituted lower alkoxy, lower alkylthio, fluoro substituted lower alkylthio, mono-alkylamino, di-alkylamino, and cycloalkylamino;

$R^{42}$ is selected from the group consisting of hydrogen, —CN, —O—$R^{100}$, —S—$R^{100}$, and lower alkyl, wherein lower alkyl is optionally substituted with one or more substituents selected from the group consisting of fluoro, lower alkoxy, fluoro substituted lower alkoxy, lower alkylthio, fluoro substituted lower alkylthio, mono-alkylamino, di-alkylamino, and cycloalkylamino;

$R^{43}$ is hydrogen;

$R^{100}$ is lower alkyl optionally substituted with one or more substituents selected from the group consisting of fluoro, lower alkoxy, fluoro substituted lower alkoxy, lower alkylthio, fluoro substituted lower alkylthio, mono-alkylamino, di-alkylamino, and cycloalkylamino; and $R^{101}$ is hydrogen or lower alkyl optionally substituted with one or more substituents selected from the group consisting of fluoro, lower alkoxy, fluoro substituted lower alkoxy, lower alkylthio, fluoro substituted lower alkylthio, mono-alkylamino, di-alkylamino, and cycloalkylamino.

9. The compound of claim 8, wherein:
$Ar_1$ is

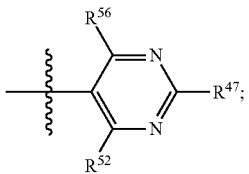

$R^{52}$, and $R^{56}$ are independently halogen, lower alkyl, fluoro substituted lower alkyl, —N($R^{82}$)—$R^{81}$, —O—$R^{81}$, or —S—$R^{83}$;

$R^{81}$ and $R^{82}$ are independently hydrogen, lower alkyl, or fluoro substituted lower alkyl; and $R^{83}$ is lower alkyl or fluoro substituted lower alkyl.

10. A compound having the chemical structure of Formula Ia,

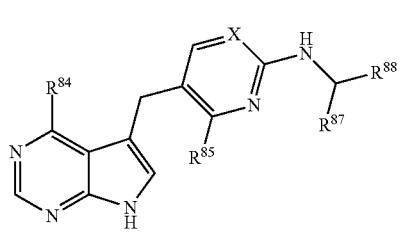

Formula Ib or a salt, a tautomer or a stereoisomer thereof,
wherein:
X is N;
$R^{84}$ is hydrogen, lower alkyl, fluoro substituted lower alkyl, lower alkoxy, fluoro substituted lower alkoxy, or cycloalkyl;
$R^{85}$ is fluoro, lower alkyl or lower alkoxy;
$R^{87}$ is hydrogen or lower alkyl; and $R^{88}$ is phenyl, pyridinyl or pyrimidinyl, wherein phenyl, pyridinyl or pyrimidinyl are optionally substituted with 1, 2 or 3 substituents independently selected from the group consisting of —CN, fluoro, chloro, bromo, lower alkyl, fluoro substituted lower alkyl, methoxy substituted lower alkyl, lower alkoxy, fluoro substituted lower alkoxy, cycloalkyloxy, alkylsulfonyl, mono-alkylamino, di-alkylamino, or cycloalkylamino.

11. A compound selected from the group consisting of:
(6-Methoxy-pyridin-3-ylmethyl)-[5-(7H-pyrrolo[2,3-d]pyrimidin-5-ylmethyl)-pyrimidin-2-yl]-amine (P-0015),
(5-Fluoro-2-methoxy-pyridin-3-ylmethyl)-[5-(7H-pyrrolo[2,3-d]pyrimidin-5-ylmethyl)-pyrimidin-2-yl]-amine (P-0022),
(5-Fluoro-6-methoxy-pyridin-3-ylmethyl)-[5-(7H-pyrrolo[2,3-d]pyrimidin-5-ylmethyl)-pyrimidin-2-yl]-amine (P-0024),
(5-Fluoro-2-methoxy-pyridin-4-ylmethyl)-[5-(7H-pyrrolo[2,3-d]pyrimidin-5-ylmethyl)-pyrimidin-2-yl]-amine (P-0025),
Pyridin-2-ylmethyl-[5-(7H-pyrrolo[2,3-d]pyrimidin-5-ylmethyl)-pyrimidin-2-yl]-amine (P-0028),
(6-Chloro-pyridin-3-ylmethyl)-[5-(7H-pyrrolo[2,3-d]pyrimidin-5-ylmethyl)-pyrimidin-2-yl]-amine (P-0029),
[5-(7H-Pyrrolo[2,3-d]pyrimidin-5-ylmethyl)-pyrimidin-2-yl]-(6-trifluoromethyl-pyridin-3-ylmethyl)-amine (P-0030),
(6-Morpholin-4-yl-pyridin-2-ylmethyl)-[5-(7H-pyrrolo[2,3-d]pyrimidin-5-ylmethyl)-pyrimidin-2-yl]-amine (P-0031),
(6-Pyrrolidin-1-yl-pyridin-2-ylmethyl)-[5-(7H-pyrrolo[2,3-d]pyrimidin-5-ylmethyl)-pyrimidin-2-yl]-amine (P-0032),
(5-Ethyl-pyridin-2-ylmethyl)-[5-(7H-pyrrolo[2,3-d]pyrimidin-5-ylmethyl)-pyrimidin-2-yl]-amine (P-0033),
(3-Methyl-pyridin-4-ylmethyl)-[5-(7H-pyrrolo[2,3-d]pyrimidin-5-ylmethyl)-pyrimidin-2-yl]-amine (P-0034),
(2-Methyl-pyridin-4-ylmethyl)-[5-(7H-pyrrolo[2,3-d]pyrimidin-5-ylmethyl)-pyrimidin-2-yl]-amine (P-0035),
(2-Morpholin-4-yl-pyridin-4-ylmethyl)-[5-(7H-pyrrolo[2,3-d]pyrimidin-5-ylmethyl)-pyrimidin-2-yl]-amine (P-0036),
(2-Methoxy-pyridin-3-ylmethyl)-[5-(7H-pyrrolo[2,3-d]pyrimidin-5-ylmethyl)-pyrimidin-2-yl]-amine (P-0084),
(2-Ethoxy-pyridin-3-ylmethyl)-[5-(7H-pyrrolo[2,3-d]pyrimidin-5-ylmethyl)-pyrimidin-2-yl]-amine (P-0085),
(2-Cyclopentyloxy-pyridin-3-ylmethyl)-[5-(7H-pyrrolo[2,3-d]pyrimidin-5-ylmethyl)-pyrimidin-2-yl]-amine (P-0086),
(2-Cyclopentyloxy-pyridin-4-ylmethyl)-[5-(7H-pyrrolo[2,3-d]pyrimidin-5-ylmethyl)-pyrimidin-2-yl]-amine (P-0087),
(5-Fluoro-6-methoxy-pyridin-3-ylmethyl)-[5-(4-methoxy-7H-pyrrolo[2,3-d]pyrimidin-5-ylmethyl)-pyrimidin-2-yl]-amine (P-0092),
(5-Fluoro-2-methoxy-pyridin-3-ylmethyl)-[5-(4-methoxy-7H-pyrrolo[2,3-d]pyrimidin-5-ylmethyl)-pyrimidin-2-yl]-amine (P-0093),
(5-Fluoro-pyridin-3-ylmethyl)-[5-(4-methoxy-7H-pyrrolo[2,3-d]pyrimidin-5-ylmethyl)-pyrimidin-2-yl]-amine (P-0098) and
[5-(4-Methoxy-7H-pyrrolo[2,3-d]pyrimidin-5-ylmethyl)-pyrimidin-2-yl]-(6-trifluoromethyl-pyridin-3-ylmethyl)-amine (P-0102),
or a salt, a tautomer or a stereoisomer thereof.

12. A composition comprising a pharmaceutically acceptable carrier; and a compound according to claim 1.

13. A composition comprising a pharmaceutically acceptable carrier; and a compound according to claim 5.

14. A composition comprising a pharmaceutically acceptable carrier; and a compound according to claim 10.

15. A composition comprising a pharmaceutically acceptable carrier; and a compound according to claim 12.

* * * * *

UNITED STATES PATENT AND TRADEMARK OFFICE
CERTIFICATE OF CORRECTION

PATENT NO. : 8,912,204 B2  
APPLICATION NO. : 13/411919  
DATED : December 16, 2014  
INVENTOR(S) : Prabha N. Ibrahim et al.

Page 1 of 1

It is certified that error appears in the above-identified patent and that said Letters Patent is hereby corrected as shown below:

IN THE CLAIMS

In Claim 1, Column 191, Line 57, please replace "Ar is selected from the group consisting of:" with --Ar is:--.

In Claim 1, Column 191, Lines 58-65, please replace " 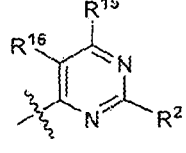 ,"

with the following: -- 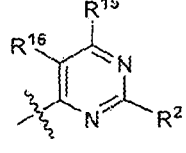 ;--.

In Claim 1, Column 193, Line 63, please replace "–NH$_{25}$" with -- –NH$_2$,--.

In Claim 10, Column 203, Lines 45-46, please replace "Formula Ia" with --Formula Ib--.

In Claim 15, Column 205, Line 8, please replace "claim 12" with --claim 11--.

Signed and Sealed this  
Sixth Day of October, 2015

Michelle K. Lee  
*Director of the United States Patent and Trademark Office*